US010322150B2

(12) United States Patent
Honda et al.

(10) Patent No.: US 10,322,150 B2
(45) **Date of Patent: *Jun. 18, 2019**

(54) COMPOSITION FOR INDUCING PROLIFERATION OR ACCUMULATION OF REGULATORY T CELLS

(71) Applicant: The University of Tokyo, Tokyo (JP)

(72) Inventors: Kenya Honda, Tokyo (JP); Koji Atarashi, Tokyo (JP); Kikuji Itoh, Tokyo (JP); Takeshi Tanoue, Tokyo (JP)

(73) Assignee: The University of Tokyo, Tokyo (JP)

( * ) Notice: Subject to any disclaimer, the term of this patent is extended or adjusted under 35 U.S.C. 154(b) by 0 days.

This patent is subject to a terminal disclaimer.

(21) Appl. No.: 16/117,054

(22) Filed: Aug. 30, 2018

(65) Prior Publication Data

US 2019/0030093 A1 Jan. 31, 2019

Related U.S. Application Data

(63) Continuation of application No. 15/730,203, filed on Oct. 11, 2017, now Pat. No. 10,092,603, which is a continuation of application No. 15/216,015, filed on Jul. 21, 2016, now Pat. No. 9,801,933, which is a continuation of application No. 14/492,850, filed on Sep. 22, 2014, now Pat. No. 9,433,652, which is a continuation of application No. 13/701,467, filed as application No. PCT/JP2011/063302 on Jun. 3, 2011, now abandoned.

(30) Foreign Application Priority Data

Jun. 4, 2010 (JP) ................................ 2010-129134
Dec. 3, 2010 (WO) .................. PCT/JP2010/071746

(51) Int. Cl.

| | |
|---|---|
| ***A61K 9/00*** | (2006.01) |
| ***A61K 9/48*** | (2006.01) |
| ***A61K 35/00*** | (2006.01) |
| ***A61K 35/74*** | (2015.01) |
| ***A61K 39/00*** | (2006.01) |
| ***A61K 39/08*** | (2006.01) |
| ***A61K 39/39*** | (2006.01) |
| ***A61K 45/00*** | (2006.01) |
| ***A61K 45/06*** | (2006.01) |
| ***C12Q 1/689*** | (2018.01) |
| ***G01N 33/50*** | (2006.01) |
| ***A01K 67/027*** | (2006.01) |
| ***A61K 35/742*** | (2015.01) |

(52) U.S. Cl.

CPC ........ *A61K 35/742* (2013.01); *A01K 67/0275* (2013.01); *A61K 9/0053* (2013.01); *A61K 9/48* (2013.01); *A61K 35/74* (2013.01); *A61K 39/0008* (2013.01); *A61K 39/08* (2013.01); *A61K 39/39* (2013.01); *A61K 45/00* (2013.01); *A61K 45/06* (2013.01); *C12Q 1/689* (2013.01); *G01N 33/505* (2013.01); *A01K 2267/0325* (2013.01); *A61K 35/00* (2013.01); *A61K 2039/52* (2013.01); *A61K 2039/542* (2013.01); *A61K 2039/55594* (2013.01); *A61K 2039/57* (2013.01); *C12Q 2600/158* (2013.01); *G01N 2333/33* (2013.01); *G01N 2500/10* (2013.01)

(58) Field of Classification Search

None

See application file for complete search history.

(56) References Cited

U.S. PATENT DOCUMENTS

| | | | |
|---|---|---|---|
| 4,576,936 | A | 3/1986 | MacDonald |
| 5,599,795 | A | 2/1997 | McCann et al. |
| 5,700,787 | A | 12/1997 | Tzianabos et al. |
| 6,348,452 | B1 | 2/2002 | Brown et al. |
| 6,551,632 | B2 | 4/2003 | Borody |
| 6,645,530 | B1 | 11/2003 | Borody |
| 7,629,330 | B2 | 12/2009 | Wang et al. |
| 7,749,494 | B2 | 7/2010 | Renaud et al. |
| 8,586,029 | B2 | 11/2013 | Kasper et al. |
| 8,906,668 | B2 | 12/2014 | Henn et al. |
| 9,011,834 | B1 | 4/2015 | McKenzie et al. |
| 9,028,841 | B2 | 5/2015 | Henn et al. |
| 9,180,147 | B2 | 11/2015 | McKenzie et al. |
| 9,415,079 | B2 | 8/2016 | Honda et al. |
| 9,421,230 | B2 | 8/2016 | Honda et al. |

(Continued)

FOREIGN PATENT DOCUMENTS

| | | | |
|---|---|---|---|
| CA | 2850000 | A1 | 4/2013 |
| CN | 101310730 | A | 11/2008 |

(Continued)

OTHER PUBLICATIONS

[No Author Listed] Japanese Journal of Bacteriology. 2008;63(1): 166, 3-E-27/P43.

[No Author Listed] Ruminococcus. Microbe Wiki. Aug. 2010 Last accessed at https://microbewild.kenyon.edu/index.php/Ruminococcus on Apr. 19, 2016.

AAS et al., Recurrent Clostridium difficile colitis: case series involving 18 patients treated with donor stool administered via a nasogastric tube. Clin Infect Dis. Mar. 1, 2003;36(5):580-5. Epub Feb. 14, 2003.

(Continued)

*Primary Examiner* — Brian Gangle

(74) *Attorney, Agent, or Firm* — Wolf, Greenfield & Sacks, P.C.

(57) ABSTRACT

It was found that bacteria belonging to the genus *Clostridium* induce accumulation of regulatory T cells (Treg cells) in the colon. Moreover, the present inventors found that regulatory T cells (Treg cells) induced by from these bacteria suppressed proliferation of effector T-cells. From these findings, the present inventors found that the use of bacteria belonging to the genus *Clostridium* or a physiologically active substance derived therefrom made it possible to induce proliferation or accumulation of regulatory T cells (Treg cells), and further to suppress immune functions.

29 Claims, 41 Drawing Sheets

Specification includes a Sequence Listing.

(56) References Cited

U.S. PATENT DOCUMENTS

| | | | |
|---|---|---|---|
| 9,433,652 | B2 | 9/2016 | Honda et al. |
| 9,446,080 | B2 | 9/2016 | McKenzie et al. |
| 9,533,014 | B2 | 1/2017 | Henn et al. |
| 9,585,921 | B2 | 3/2017 | McKenzie et al. |
| 9,603,878 | B2 | 3/2017 | Berry et al. |
| 9,610,307 | B2 | 4/2017 | Berry et al. |
| 9,642,281 | B1 | 5/2017 | Chen |
| 9,642,881 | B2 | 5/2017 | Honda et al. |
| 9,642,882 | B2 | 5/2017 | Honda et al. |
| 9,649,345 | B2 | 5/2017 | Honda et al. |
| 9,662,381 | B2 | 5/2017 | Honda et al. |
| 9,764,019 | B2 | 9/2017 | Honda et al. |
| 9,801,933 | B2 | 10/2017 | Honda et al. |
| 9,808,519 | B2 | 11/2017 | Honda et al. |
| 9,827,276 | B2 | 11/2017 | Honda et al. |
| 9,833,483 | B2 | 12/2017 | Honda et al. |
| 9,855,303 | B2 | 1/2018 | McKenzie et al. |
| 9,987,312 | B2 | 6/2018 | Miyamoto et al. |
| 10,052,353 | B2 | 8/2018 | Honda et al. |
| 10,058,578 | B2 | 8/2018 | Honda et al. |
| 10,092,603 | B2 | 10/2018 | Honda et al. |
| 10,130,695 | B2 | 11/2018 | Honda et al. |
| 10,183,045 | B2 | 1/2019 | Honda et al. |
| 2003/0113306 | A1 | 6/2003 | Collins et al. |
| 2004/0028689 | A1 | 2/2004 | Borody |
| 2004/0170617 | A1 | 9/2004 | Finegold |
| 2004/0219160 | A1 | 11/2004 | Tzianabos et al. |
| 2006/0067924 | A1 | 3/2006 | Lee et al. |
| 2006/0240482 | A1 | 10/2006 | Kwok et al. |
| 2007/0258953 | A1 | 11/2007 | Duncan et al. |
| 2008/0003207 | A1 | 1/2008 | Cui |
| 2008/0305089 | A1 | 12/2008 | Bufe et al. |
| 2008/0311080 | A1 | 12/2008 | Collins et al. |
| 2009/0124573 | A1 | 5/2009 | Mazmanian et al. |
| 2009/0317427 | A1 | 12/2009 | Kasper et al. |
| 2010/0119488 | A1 | 5/2010 | Huber-Haag et al. |
| 2010/0275282 | A1 | 10/2010 | Round et al. |
| 2011/0009360 | A1 | 1/2011 | Kasper et al. |
| 2012/0020941 | A1 | 1/2012 | Wacklin et al. |
| 2012/0027734 | A1 | 2/2012 | Van Immerseel et al. |
| 2012/0276149 | A1 | 11/2012 | Littman et al. |
| 2013/0149339 | A1 | 6/2013 | Honda et al. |
| 2014/0147425 | A1 | 5/2014 | Henn et al. |
| 2014/0171339 | A1 | 6/2014 | Keku et al. |
| 2014/0199281 | A1 | 7/2014 | Henn et al. |
| 2014/0341921 | A1 | 11/2014 | Honda et al. |
| 2015/0143557 | A1 | 5/2015 | Honda et al. |
| 2015/0190435 | A1 | 7/2015 | Henn et al. |
| 2015/0224152 | A1 | 8/2015 | Littman et al. |
| 2015/0297642 | A1 | 10/2015 | Borody |
| 2015/0320805 | A9 | 11/2015 | Honda et al. |
| 2016/0040215 | A1 | 2/2016 | Henn et al. |
| 2016/0143960 | A1 | 5/2016 | Honda et al. |
| 2016/0143962 | A1 | 5/2016 | Berry et al. |
| 2016/0151430 | A1 | 6/2016 | Honda et al. |
| 2016/0158294 | A1 | 6/2016 | Von Maltzahn et al. |
| 2016/0193256 | A1 | 7/2016 | Honda et al. |
| 2016/0193257 | A1 | 7/2016 | Honda et al. |
| 2016/0199423 | A1 | 7/2016 | McKenzie et al. |
| 2016/0199424 | A1 | 7/2016 | Berry et al. |
| 2016/0235792 | A1 | 8/2016 | Berry et al. |
| 2016/0243172 | A1 | 8/2016 | Cook et al. |
| 2016/0271188 | A1 | 9/2016 | Berry et al. |
| 2016/0279177 | A1 | 9/2016 | Kelly et al. |
| 2017/0007691 | A1 | 1/2017 | Riken et al. |
| 2017/0028061 | A1 | 2/2017 | Riken et al. |
| 2017/0087197 | A1 | 3/2017 | Honda et al. |
| 2017/0105977 | A1 | 4/2017 | Golden et al. |
| 2017/0112915 | A1 | 4/2017 | Honda et al. |
| 2017/0142775 | A1 | 5/2017 | Kanesalingam et al. |
| 2017/0143775 | A1 | 5/2017 | Mulder et al. |
| 2017/0165302 | A1 | 6/2017 | Henn et al. |
| 2017/0209502 | A1 | 7/2017 | Honda et al. |
| 2017/0216378 | A1 | 8/2017 | Honda et al. |
| 2017/0232044 | A1 | 8/2017 | Honda et al. |
| 2017/0232045 | A1 | 8/2017 | Honda et al. |
| 2017/0354697 | A1 | 12/2017 | Schneider et al. |
| 2018/0000921 | A1 | 1/2018 | Honda et al. |
| 2018/0015130 | A1 | 1/2018 | Berry et al. |
| 2018/0153981 | A1 | 6/2018 | Honda et al. |
| 2018/0243348 | A1 | 8/2018 | Honda et al. |
| 2019/0030092 | A1 | 1/2019 | Honda et al. |
| 2019/0046591 | A1 | 2/2019 | Honda et al. |
| 2019/0046592 | A1 | 2/2019 | Honda et al. |

FOREIGN PATENT DOCUMENTS

| | | | |
|---|---|---|---|
| CN | 101496819 | A | 8/2009 |
| DE | 102006062250 | A1 | 6/2008 |
| EP | 1749538 | A1 | 2/2007 |
| EP | 1955706 | A1 | 8/2008 |
| EP | 2 823 822 | A1 | 10/2016 |
| JP | 2009-084215 | A | 4/2009 |
| JP | 2010-129134 | | 6/2010 |
| KR | 10-0913405 | B1 | 8/2009 |
| WO | WO 02/07741 | A1 | 1/2002 |
| WO | WO 2009/050486 | A2 | 4/2009 |
| WO | WO 2009/149149 | A1 | 12/2009 |
| WO | WO 2011/005756 | A1 | 1/2011 |
| WO | WO 2011/022542 | A2 | 2/2011 |
| WO | WO 2011/022660 | A1 | 2/2011 |
| WO | WO 2011/027990 | A2 | 3/2011 |
| WO | WO 2011/151941 | A1 | 12/2011 |
| WO | WO 2011/152566 | A2 | 12/2011 |
| WO | WO 2012/013861 | A2 | 2/2012 |
| WO | WO 2013/080561 | A1 | 6/2013 |
| WO | WO 2015/156419 | A1 | 10/2015 |
| WO | WO 2016/194427 | A1 | 12/2016 |
| WO | WO 2018/084172 | A1 | 5/2018 |

OTHER PUBLICATIONS

Abraham et al., Molecular mechanisms of IL-2 gene regulation following costimulation through LFA-1. J Immunol. Nov. 1, 2001;167(9):5193-201.

Abrams, Open-Label, Uncontrolled Trial of Bowel Sterilization and Repopulation With Normal Bowel Flora for Treatment Of Inflammatory Bowel Disease. Current Therapeutic Research. Dec. 1997;58(12):1001-1012.

Andoh et al., Terminal restriction fragment polymorphism analyses of fecal microbiota in five siblings including two with ulcerative colitis. Clin J Gastroenterol. Oct. 2009;2(5):343-345. doi:10.1007/s12328-009-0106-8. Epub Sep. 19, 2009.

Andoh et al., Faecal microbiota profile of Crohn's disease determined by terminal restriction fragment length polymorphism analysis. Aliment Pharmacol Ther. Jan. 2009;29(1):75-82. doi: 10.1111/j.1365-2036.2008.03860.x. Epub Sep. 26, 2008.

Atarashi et al., ATP drives lamina propria T(H)17 cell differentiation. Nature. Oct. 9, 2008;455(7214):808-12. doi: 10.1038/nature07240. Epub Aug. 20, 2008.

Atarashi et al., Induction of Colonic Regulatory T Cells by Indigenous *clostridium* Species *Science* 331 (2011) 337-341.

Atarashi et al., Induction of Colonic Regulatory T Cells by Indigenous *clostridium* Species Science 331 (2011) 337-341. Supporting Online Material.

Atarashi et al., Microbiota in autoimmunity and tolerance. Curr Opin Immunol. Dec. 2011;23(6):761-8. doi: 10.1016/j.coi.2011.11.002. Epub Nov. 22, 2011.

Atarashi et al., Microbiotal influence on T cell subset development Seminars in Immunology. Apr. 4, 2011;23(2):146-153.

Atarashi et al., Regulation of colonic regulatory T cells by *clostridium* species. Poster 064-03. Aug. 25, 2010.

Atarashi et al., Regulation of colonic regulatory T cells by *clostridium* species. WS/PP-064-03 abstract. $14^{th}$ International Congress of Immunology. iii132. Aug. 25, 2010.

Atarashi et al., Treg induction by a rationally selected mixture of Clostridia strains from the human microbiota. Nature. Aug. 8, 2013;500(7461):232-6. doi: 10.1038/nature12331. Epub Jul. 10, 2013.

Autoimmune Disease List. American Autoimmune Related Diseases Association. 2017.

(56) References Cited

OTHER PUBLICATIONS

Bakken, Fecal bacteriotherapy for recurrent Clostridium difficile infection. Anaerobe. Dec. 2009;15(6):285-9. doi: 10.1016/j.anaerobe.2009.09.007. Epub Sep. 22, 2009.
Barnes et al., Regulatory T cells reinforce intestinal homeostasis. Immunity. Sep. 18, 2009;31(3):401-11. doi: 10.1016/j.immuni.2009.08.011.
Bassaganya-Riera et al., Punicic acid modulates mucosal immune responses and prevents gut inflammation through PPAR gamma and delta-dependent mechanisms. FASEB J. 2010; 24 (Meeting Abstract Supplement). Abstract.
Bassaganya-Riera et al., Soluble fibers and resistant starch ameliorate disease activity in an experimental model of inflammatory bowel disease. FASEB J. 2010; 24 (Meeting Abstract Supplement). Abstract.
Belkaid et al., Natural regulatory T cells in infectious disease. Nat Immunol. Apr. 2005;6(4):353-60.
Borody et al., Treatment of ulcerative colitis using fecal bacteriotherapy. J Clin Gastroenterol. Jul. 2003;37(1):42-7.
Bouskra et al., Lymphoid tissue genesis induced by commensals through NOD1 regulates intestinal homeostasis. Nature. Nov. 27, 2008;456(7221):507-10. doi: 10.1038/nature07450. Epub Nov. 5, 2008.
Browne et al., Culturing of 'unculturable' human microbiota reveals novel taxa and extensive sporulation. Nature. May 4, 2016. doi: 10.1038/nature17645.
Bueche et al., Quantification of endospore-forming firmicutes by quantitative PCR with the functional gene spo0A. Appl Environ Microbiol. Sep. 2013;79(17):5302-12. doi: 10.1128/AEM.01376-13. Epub Jun. 28, 2013.
Cai Miaoying et al, Names of Bacteria. the 2nd edition, Science Press, 1996-06, p. 179.
Cato et al., Clostridium Oroticum Comb. Nov. Int. J. Syst. Bact. Jan. 1968;17(1):9-13.
Cebra, Influences of microbiota on intestinal immune system development. Am J Clin Nutr. May 1999;69(5):1046S-1051S.
Chandrasekaran et al., Clostridium difficile Toxin B blocks effector T cells proliferation by inhibiting PLD signaling. J. Immunol. Apr. 2010; 184(1): 49.19. Abstract.
Clavel et al., Survival of Bacillus cereus spores and vegetative cells in acid media simulating human stomach. J Appl Microbiol. 2004;97(1):214-9.
Collins et al., The phylogeny of the genus *Clostridium*: proposal of five new genera and eleven new species combinations. Int J Syst Bacteriol. Oct. 1994;44(4):812-26.
Curotto De Lafaille et al., Natural and adaptive foxp3+ regulatory T cells: more of the same or a division of labor? Immunity. May 2009;30(5):626-35. doi: 10.1016/j.immuni.2009.05.002.
Dewhirst et al., Phylogeny of the defined murine microbiota: altered Schaedler flora. Appl Environ Microbiol. Aug. 1999;65(8):3287-92.
Di Giacinto et al., Probiotics ameliorate recurrent Th1-mediated murine colitis by inducing IL-10 and IL-10-dependent TGF-beta-bearing regulatory cells. J Immunol. Mar. 15, 2005;174(6):3237-46.
Eeckhaut et al. The anaerobic butyrate-producing strain Butyricicoccus pullicaecorum decreases colonic inflammation and ulceration in a TNBS-induced colitis rat model. In, 5th Probiotics, Prebiotics and New Foods Congress, Rome, Italy (2009).
Ellis et al., Molecular characterization of stool microbiota in HIV-infected subjects by panbacterial and order-level 16S ribosomal DNA (rDNA) quantification and correlations with immune activation. J Acquir Immune Defic Syndr. Aug. 15, 2011;57(5):363-70. doi: 10.1097/QAI.0b013e31821a603c.
European Office Action for Application No. 11 728 077.6, dated Sep. 18, 2015.
Favier et al., Development of bacterial and bifidobacterial communities in feces of newborn babies. Anaerobe. Oct. 2003;9(5):219-29.
Foditsch et al., Isolation and characterization of Faecalibacterium prausnitzii from calves and piglets. PLoS One. Dec. 31, 2014;9(12):e116465. doi: 10.1371/journal.pone.0116465. eCollection 2014.
Foligne et al., A key role of dendritic cells in probiotic functionality. PLoS One. Mar. 21, 2007;2(3):e313.
Foligne et al., Correlation between in vitro and in vivo immunomodulatory properties of lactic acid bacteria. World J Gastroenterol. Jan. 14, 2007;13(2):236-43.
Frank et al., Molecular-phylogenetic characterization of microbial community imbalances in human inflammatory bowel diseases. Proc Natl Acad Sci U S A. Aug. 21, 2007;104(34):13780-5. Epub Aug. 15, 2007.
Gaboriau-Routhiau et al., The key role of segmented filamentous bacteria in the coordinated maturation of gut helper T cell responses. Immunity. Oct. 16, 2009;31(4):677-89. doi: 10.1016/j.immuni.2009.08.020.
Garrett et al., Communicable ulcerative colitis induced by T-bet deficiency in the innate immune system. Cell. Oct. 5, 2007;131(1):33-45.
Geuking et al., Intestinal bacterial colonization induces mutualistic regulatory T cell responses. Immunity. May 27, 2011;34(5):794-806. doi: 10.1016/j.immuni.2011.03.021. Epub May 19, 2011.
Grehan et al., Durable alteration of the colonic microbiota by the administration of donor fecal flora. J Clin Gastroenterol. Sep. 2010;44(8):551-61. doi: 10.1097/MCG.0b013e3181e5d06b.
Hart et al., Modulation of human dendritic cell phenotype and function by probiotic bacteria. Gut. Nov. 2004;53(11):1602-9.
Hata et al., Blood group B degrading activity of Ruminococcus gnavus alpha-galactosidase. Artif Cells Blood Substit Immobil Biotechnol. May 2004;32(2):263-74.
Hayashi et al., Fecal microbial diversity in a strict vegetarian as determined by molecular analysis and cultivation. Microbiol Immunol. 2002;46(12):819-31.
Hayashi et al., Phylogenetic analysis of the human gut microbiota using 16S rDNA clone libraries and strictly anaerobic culture-based methods. Microbiol Immunol. 2002;46(8):535-48.
Hazenberg et al., Effects of the human intestinal flora on germ-free mice. J Appl Bacteriol. Feb. 1981;50(1):95-106.
Honda et al., Regulation of T Cell Responses by Intestinal Commensal Bacteria. J Intestinal Microbiol. 2011;25(2):103-104.
ICI Wrap-Up Report. 14$^{th}$ International Congress of Immunology. Aug. 22-27, 2010.
Iizuka et al., Novel evidence suggesting Clostridium difficile is present in human gut microbiota more frequently than previously suspected. Microbiol Immunol. 2004;48(11):889-92.
International Statistical Classification of Diseases and Related Health Problems 10$^{th}$ Revision. WHO (ICD-10). 2016. Chapter 1. Certain infectious and parasitic diseases (A00-B99).
Itoh et al., Characterization of clostridia isolated from faeces of limited flora mice and their effect on caecal size when associated with germ-free mice. Lab Anim. Apr. 1985;19(2):111-8.
Itoh et al., Colonization resistance against Pseudomonas aeruginosa in gnotobiotic mice. Lab Anim. Jul. 1986;20(3):197-201.
Itoh et al., Intestinal bacteria antagonistic to Clostridium difficile in mice. Lab Anim. Jan. 1987;21(1):20-5.
Itoh et al., Production of gnotobiotic mice with normal physiological functions. I. Selection of useful bacteria from feces of conventional mice. Z Versuchstierkd. 1980;22(3):173-8.
Ivanov et al., Induction of intestinal Th17 cells by segmented filamentous bacteria. Cell. Oct. 30, 2009;139(3):485-98. doi: 10.1016/j.cell.2009.09.033.
Ivanov et al., Specific microbiota direct the differentiation of IL-17-producing T-helper cells in the mucosa of the small intestine. Cell Host Microbe. Oct. 16, 2008;4(4):337-49. doi: 10.1016/j.chom.2008.09.009.
Janeway et al., Autoimmune responses are directed against self antigens. Immunobiology: The Immune System in Health and Disease. 5$^{th}$ edition. 2001. New York: Garland Science.
Janeway et al., Immunobiology: The Immune System in Health and Disease. 6$^{th}$ edition 2005. Chapter 10. 414. Figure 10.4.
Jarry et al., Mucosal IL-10 and TGF-beta play crucial roles in preventing LPS-driven, IFN-gamma-mediated epithelial damage in human colon explants. J Clin Invest. Mar. 2008;118(3):1132-42.
Jawetz et al., Spore-forming gram-positive bacilli: *bacillus* and *clostridium* species. Medical Microbiology. Chapter 11. Nov. 2011.

(56) References Cited

OTHER PUBLICATIONS

Kakihana et al., Fecal microbiota transplantation for patients with steroid-resistant acute graft-versus-host disease of the gut. Blood. Oct. 20, 2016;128(16):2083-2088. doi: 10.1182/blood-2016-05-717652. Epub Jul. 26, 2016.
Kamanaka et al., Expression of interleukin-10 in intestinal lymphocytes detected by an interleukin-10 reporter knockin tiger mouse. Immunity. Dec. 2006;25(6):941-52. Epub Nov. 30, 2006.
Karimi et al., Lactobacillus reuteri-induced regulatory T cells protect against an allergic airway response in mice. Am J Respir Crit Care Med. Feb. 1, 2009;179(3):186-93. doi: 10.1164/rccm.200806-951OC. Epub Nov. 21, 2008.
Kelly et al., Commensal gut bacteria: mechanisms of immune modulation. Trends Immunol. Jun. 2005;26(6):326-33.
Keynan et al., The role of regulatory T cells in chronic and acute viral infections. Clin Infect Dis. Apr. 1, 2008;46(7):1046-52. doi: 10.1086/529379.
Khoruts et al., Changes in the composition of the human fecal microbiome after bacteriotherapy for recurrent Clostridium difficile-associated diarrhea. J Clin Gastroenterol. May-Jun. 2010;44(5):354-60. doi: 10.1097/MCG.0b013e3181c87e02.
Kita, Intestinal colonization and transmission of Clostridium difficile among students as a community. J Antibact Antifung Agents. 2004;32(3):105-113.
Krogius-Kurikka et al., Sequence analysis of percent G+C fraction libraries of human faecal bacterial DNA reveals a high number of Actinobacteria. BMC Microbiol. Apr. 8, 2009;9:68. doi: 10.1186/1471-2180-9-68.
Kwon et al., Generation of regulatory dendritic cells and CD4+ Foxp3+ T cells by probiotics administration suppresses immune disorders. Proc Natl Acad Sci U S A. Feb. 2, 2010;107(5):2159-64. doi: 10.1073/pnas.0904055107. Epub Jan. 13, 2010.
Latvala et al., Potentially probiotic bacteria induce efficient maturation but differential cytokine production in human monocyte-derived dendritic cells. World J Gastroenterol. Sep. 28, 2008;14(36):5570-83; discussion 5581-2.
Lau et al., Bacteraemia caused by Anaerotruncus colihominis and emended description of the species. J Clin Pathol. Jul. 2006;59(7):748-52. Epub Feb. 7, 2006.
Lawley et al., Targeted restoration of the intestinal microbiota with a simple, defined bacteriotherapy resolves relapsing Clostridium difficile disease in mice. PLoS Pathog. 2012;8(10):e1002995. doi: 10.1371/journal.ppat.1002995. Epub Oct. 25, 2012.
Lawson et al., *Anaerotruncus colihominis* gen. nov., sp. nov., from human faeces. Int J Syst Evol Microbiol. Mar. 2004;54(Pt 2):413-7.
Lawson, Anaerotruncus. Bergey's Manual of Systematics of Archaea and Bacteria. Sep. 14, 2015;1-4.
Li et al., Effect of oral feeding with Clostridium leptum on regulatory T-cell responses and allergic airway inflammation in mice. Ann Allergy Asthma Immunol. Sep. 2012;109(3):201-7. doi: 10.1016/j.anai.2012.06.017. Epub Jul. 17, 2012.
Li et al., Symbiotic gut microbes modulate human metabolic phenotypes. Proc Natl Acad Sci U S A. Feb. 12, 2008;105(6):2117-22. doi: 10.1073/pnas.0712038105.
Liu et al., Reclassification of Clostridium coccoides, Ruminococcus hansenii, Ruminococcus hydrogenotrophicus, Ruminococcus luti, Ruminococcus productus and Ruminococcus schinkii as *Blautia coccoides* gen. nov., comb. nov., *Blautia hansenii* comb. nov., *Blautia hydrogenotrophica* comb. nov., *Blautia luti* comb. nov., *Blautia producta* comb. nov., *Blautia schinkii* comb. nov. and description of *Blautia wexlerae* sp. nov., isolated from human faeces. Int J Syst Evol Microbiol. Aug. 2008;58(Pt 8):1896-902. doi: 10.1099/ijs.0.65208-0.
Livingston et al., Gut commensal Lactobacillus reuteri 100-23 stimulates an immunoregulatory response. Immunol Cell Biol. Jan. 2010;88(1):99-102. doi: 10.1038/icb.2009.71. Epub Sep. 29, 2009.
Lopetuso et al., Commensal Clostridia:leading players in the maintenance of gut homeostasis. Gut Pathog. Aug. 13, 2013;5(1):23. doi: 10.1186/1757-4749-5-23.
Louis et al., Diversity, metabolism and microbial ecology of butyrate-producing bacteria from the human large intestine. FEMS Microbiol Lett. May 2009;294(1):1-8. doi: 10.1111/j.1574-6968.2009.01514.x. Epub Feb. 13, 2009.
Lu et al., Molecular orchestration of differentiation and function of regulatory T cells. Genes Dev. Jun. 1, 2009;23(11):1270-82. doi:10.1101/gad.1791009.
Macpherson et al., Interactions between commensal intestinal bacteria and the immune system. Nat Rev Immunol. Jun. 2004;4(6):478-85.
Maizels et al., Regulatory T cells in infection. Adv Immunol. 2011;112:73-136. doi: 10.1016/B978-0-12-387827-4.00003-6.
Mandalari et al., In vitro evaluation of the prebiotic properties of almond skins (*Amygdalus communis* L.). FEMS Microbiol Lett. Mar. 2010;304(2):116-22. doi: 10.1111/j.1574-6968.2010.01898.x. Epub Jan. 11, 2010.
Mangin et al., Molecular inventory of faecal microflora in patients with Crohn's disease. FEMS Microbiol Ecol. Oct. 1, 2004;50(1):25-36. doi: 10.1016/j.femsec.2004.05.005.
Maslowski et al., Regulation of inflammatory responses by gut microbiota and chemoattractant receptor GPR43. Nature. Oct. 29, 2009;461(7268):1282-6. doi: 10.1038/nature08530.
Maynard et al., Regulatory T cells expressing interleukin 10 develop from Foxp3+ and Foxp3− precursor cells in the absence of interleukin 10. Nat Immunol. Sep. 2007;8(9):931-41. Epub Aug. 12, 2007.
Mazmanian et al., A microbial symbiosis factor prevents intestinal inflammatory disease. Nature. May 29, 2008;453(7195):620-5. doi:10.1038/nature07008.
Mazmanian, Gut immune balance is as easy as S-F-B. Immunity. Oct. 16, 2009;31(4):536-8. doi: 10.1016/j.immuni.2009.09.005.
Miquel et al., Faecalibacterium prausnitzii and human intestinal health. Curr Opin Microbiol. Jun. 2013;16(3):255-61. doi:10.1016/j.mib.2013.06.003. Epub Jul. 3, 2013. Review.
Miyake et al., Dysbiosis in the Gut Microbiota of Patients with Multiple Sclerosis, with a Striking Depletion of Species Belonging to Clostridia XIVa and IV Clusters. PLoS One. Sep. 14. 2015;10(9):e0137429. doi: 10.1371/journal.pone.0137429. eCollection 2015.
Momose et al., 16S rRNA gene sequence-based analysis of clostridia related to conversion of germfree mice to the normal state. J Appl Microbiol. Dec. 1, 2009;107(6):2088-97. doi:10.1111/j.1365-2672.2009.04431.x. Epub Jul. 15, 2009.
Narushima et al., Characterization of the 17 strains of regulatory T cell-inducing human-derived Clostridia. Gut Microbes. May-Jun. 2014;5(3):333-9. doi: 10.4161/gmic.28572. Epub Mar. 18, 2014.
Office Action for Japanese application No. 2017-049543.
O'Garra et al., IL-10-producing and naturally occurring CD4+ Tregs: limiting collateral damage. J Clin Invest. Nov. 2004;114(10):1372-8.
Okada et al., Effects of fecal microorganisms and their chloroform-resistant variants derived from mice, rats, and humans on immunological and physiological characteristics of the intestines of ex-germfree mice. Infect Immun. Dec. 1994;62(12):5442-6.
O'Mahony et al., Commensal-induced regulatory T cells mediate protection against pathogen-stimulated NF-kappaB activation. PLoS Pathog. Aug. 1, 2008;4(8):e1000112. doi: 10.1371/journal.ppat.1000112.
Opposition against EP Patent 2 575 835 B1 dated Apr. 25, 2017. 35 pages. Seres Therapeutics.
Opposition against EP Patent 2 575 835 B1 dated Jul. 18, 2017. 23 pages. Strawman Limited.
Opposition against EP Patent 2 575 835 B1 dated Jul. 18, 2017. 4 pages. Mr. Lars Manke.
Opposition against EP Patent 2 575 835 B1 dated Jul. 19, 2017. 20 pages. Dr. Martin Grund.
Opposition against EP Patent 2 575 835 B1 dated Jul. 19, 2017. 27 pages. Muller Fottner Steineke Part mbB.
Opposition against EP Patent 2 575 835 B1. Seres Therapeutics, Inc. Annexure; dated May 25, 2018.
Opposition against EP Patent 2 575 835 B1. Summary of File History for Information; dated Jun. 7, 2018.
Opposition against EP Patent No. 2 575 835 B1 dated Jul. 19, 2017. 37 pages. Nestec S.A.

(56) References Cited

OTHER PUBLICATIONS

Paredes-Sabja et al., Clostridium difficile spore biology:sporulation, germination, and spore structural proteins. Trends Microbiol. Jul. 2014;22(7):406-16. doi: 10.1016/j.tim.2014.04.003. Epub May 7, 2014.
Qin et al., A human gut microbial gene catalogue established by metagenomic sequencing. Nature. Mar. 4, 2010;464(7285):59-65. doi: 10.1038/nature08821.
Qiu et al., C. Faecalibacterium prausnitzii upregulates regulatory T cells and anti-inflammatory cytokines in treating TNBS-induced colitis. J Crohns Colitis. Dec. 1, 2013;7(11):e558-68. doi: 10.1016/j.crohns.2013.04.002. Epub May 2, 2013.
Reeck et al., "Homology" in proteins and nucleic acids: a terminology muddle and a way out of it. Cell. Aug. 28, 1987;50(5):667.
Reexamination Decision for Chinese application No. 201180037900.8 dated Mar. 19, 2018.
Rehman et al., Transcriptional activity of the dominant gut mucosal microbiota in chronic inflammatory bowel disease patients. J Med Microbiol. Sep. 2010;59(Pt 9):1114-22. doi:10.1099/jmm.0.021170-0. Epub Jun. 3, 2010.
Response to European Office Action for Application No. 11 728 077.6, dated Feb. 25, 2014.
Response to European Office Action for Application No. 11 728 077.6, dated Jan. 28, 2015.
Response to European Office Action for Application No. 11 728 077.6, dated Nov. 18, 2015.
Roberts, CSO Vedanta Biosciences Presentation. 1st Microbiome Drug Development Summit. Jun. 28, 2016.
Rohlke et al., Fecal flora reconstitution for recurrent Clostridium difficile infection: results and methodology. J Clin Gastroenterol. Sep. 2010;44(8):567-70. doi: 10.1097/MCG.0b013e3181dadb10.
Rosero et al., Reclassification of Eubacterium rectale (Prévot et al., 1967) in a new genus *Agathobacter* gen. nov., as *Agathobacter rectalis* comb. nov., within the family Lachnospiraceae, and description of *Agathobacter ruminis* sp. nov., from the rumen. Int J Syst Evol Microbiol. Nov. 30, 2015. doi: 10.1099/ijsem.0.000788.
Rossi et al., Faecalibacterium prausnitzii A2-165 has a high capacity to induce IL-10 in human and murine dendritic cells and modulates T cell responses. Sci Rep. Jan. 4, 2016;6:18507. doi:10.1038/srep18507.
Round et al., Inducible Foxp3+ regulatory T-cell development by a commensal bacterium of the intestinal microbiota. Proc Natl Acad Sci U S A. Jul. 6, 2010;107(27):12204-9. doi: 10.1073/pnas.0909122107. Epub Jun. 21, 2010.
Round et al., The gut microbiota shapes intestinal immune responses during health and disease. Nat Rev Immunol. May 2009;9(5):313-23. doi:10.1038/nri2515. Review. Erratum in: Nat Rev Immunol. Aug. 2009;9(8):600.
Rubtsov et al., Regulatory T cell-derived interleukin-10 limits inflammation at environmental interfaces. Immunity. Apr. 2008;28(4):546-58. doi: 10.1016/j.immuni.2008.02.017.
Sakaguchi et al., Regulatory T cells and immune tolerance. Cell. May 30, 2008;133(5):77587. doi: 10.1016/j.ce11.2008.05.009.
Salzman et al., Enteric defensins are essential regulators of intestinal microbial ecology. Nat Immunol. Jan. 2010;11(1):76-83. doi:10.1038/ni.1825. Epub Oct. 22, 2009.
Sanchez et al., The role of natural regulatory T cells in infection. Immunol Res. Apr. 2011;49(1-3):124-34. doi: 10.1007/s12026-010-8176-8.
Sanos et al., RORgammat and commensal microflora are required for the differentiation of mucosal interleukin 22-producing NKp46+ cells. Nat Immunol. Jan. 2009;10(1):83-91. doi: 10.1038/ni.1684. Epub Nov. 23, 2008.
Sartor, Therapeutic correction of bacterial dysbiosis discovered by molecular techniques. Proc Natl Acad Sci U S A. Oct. 28, 2008;105(43):16413-4. doi:10.1073/pnas.0809363105. Epub Oct. 23, 2008.
Schloss et al., The dynamics of a family's gut microbiota reveal variations on a theme. Microbiome. Jul. 21, 2014;2:25. doi:10.1186/2049-2618-2-25. eCollection 2014.
Schouten et al., Oligosaccharide-induced whey-specific CD25(+) regulatory T-cells are involved in the suppression of cow milk allergy in mice. J Nutr. Apr. 2010;140(4):835-41. doi: 10.3945/jn.109.116061. Epub Feb. 17, 2010.
Screenshot of https://academic.oup.com/intimm/issue/22/Suppl_1_Pt3 showing the publication of Warren et al. at the Workshop abstract WS64 of XIVth International congress of Immunology held in Kobe in Japan on Aug. 2010.
Segain et al., Butyrate inhibits inflammatory responses through NFkappaB inhibition: implications for Crohn's disease. Gut. Sep. 2000;47(3):397-403.
Sequence listing of WO 2011/152566.
Sghir et al., Quantification of bacterial groups within human fecal flora by oligonucleotide probe hybridization. Appl Environ Microbiol. May 2000;66(5):2263-6.
Shen et al., Molecular profiling of the Clostridium leptum subgroup in human fecal microflora by PCR-denaturing gradient gel electrophoresis and clone library analysis. Appl Environ Microbiol. Aug. 2006;72(8):5232-8.
So et al., Lactobacillus casei potentiates induction of oral tolerance in experimental arthritis. Mol Immunol. Nov. 2008;46(1):172-80. doi: 10.1016/j.molimm.2008.07.038. Epub Sep. 19, 2008.
So et al., Lactobacillus casei suppresses experimental arthritis by down-regulating T helper 1 effector functions. Mol Immunol. May 2008;45(9):2690-9. doi:10.1016/j.molimm.2007.12.010. Epub Feb. 19, 2008.
Sokol et al., *Faecalibacterium prausnitzii* is an anti-inflammatory commensal bacterium identified by gut microbiota analysis of Crohn disease patients. Proc Natl Acad Sci U S A. Oct. 28, 2008;105(43):16731-6. doi: 10.1073/pnas.0804812105. Epub Oct. 20, 2008.
Sokol et al., Low counts of Faecalibacterium prausnitzii in colitis microbiota. Inflamm Bowel Dis. Aug. 2009;15(8):1183-9. doi:10.1002/ibd.20903.
Song et al., *Clostridium bartlettii* sp. nov., isolated from human faeces. Anaerobe. Jun. 2004;10(3):179-84.
Sydora et al. CD4+CD25+ regulatory T cells have divergent effects on intestinal inflammation in IL-10 gene-deficient mice. Dig Dis Sci. Jun. 2008;53(6):1544-52.
Takaishi et al., Imbalance in intestinal microflora constitution could be involved in the pathogenesis of inflammatory bowel disease. Int J Med Microbiol. Jul. 2008;298(5-6):463-72. Epub Sep. 25, 2007.
Tanoue et al., Immune responses to gut microbiota-commensals and pathogens *Gut Microbes*. Jul.-Aug. 2010; 1(4): 224-233.
Tanoue et al., Regulation of intestinal Th17 and Treg cells by gut microbiota. Inflammation Regeneration. May 2015;35(3):99-105.
Tao et al., Deacetylase inhibition promotes the generation and function of regulatory T cells. Nat Med. Nov. 2007;13(11):1299-307. Epub Oct. 7, 2007.
Thibault et al., Butyrate utilization by the colonic mucosa in inflammatory bowel diseases: a transport deficiency. Inflamm Bowel Dis. Apr. 2010;16(4):684-95. doi:10.1002/ibd.21108.
Third Party Observations filed in European Patent Application No. 11728077.6 on Jan. 29, 2016.
Umesaki et al., Differential roles of segmented filamentous bacteria and clostridia in development of the intestinal immune system. Infect Immun. Jul. 1999;67(7):3504-11.
Valcheva et al., Prebiotics Prevent Loss Of Intestinal Biodiversity And Reduce Colitis In Hla-B27 Transgenic Rats. Canadian Digestive Diseases Week. Feb. 2009. Poster Session 2-Immunology and Inflammatory Bowel Disease. Abstract 168.
Van Immerseel et al., Butyric acid-producing anaerobic bacteria as a novel probiotic treatment approach for inflammatory bowel disease. J Med Microbiol. Feb. 2010;59(Pt 2):141-3. doi: 10.1099/jmm.0.017541-0. Epub Nov. 26, 2009.
Van't Land et al., Regulatory T-cells have a prominent role in the immune modulated vaccine response by specific oligosaccharides. Vaccine. Aug. 9, 2010;28(35):5711-7. doi: 10.1016/j.vaccine.2010.06.046. Epub Jun. 26, 2010.
Wachsman et al., Characterization of an orotic acid fermenting bacterium, *Zymobacterium oroticum*, nov. gen., nov. spec. J Bacteriol. Oct. 1954;68(4):400-4.

(56) References Cited

OTHER PUBLICATIONS

Wang et al., Analysis of the germination of individual Clostridium perfringens spores and its heterogeneity. J Appl Microbiol. Nov. 2011;111(5):1212-23. doi:10.1111/j.1365-2672.2011.05135.x. Epub Sep. 14, 2011.

Warren et al., *Clostridium aldenense* sp. nov. and *Clostridium citroniae* sp. nov. isolated from human clinical infections. J Clin Microbiol. Jul. 2006;44(7):2416-22.

Wells et al., Clostridia: Sporeforming Anaerobic Bacilli. Medical Microbiology.4$^{th}$ edition. Ed:Baron. 1996. University of Texas Medical Branch at Galveston. Mar. 7, 2017.

Zhang et al., Therapeutic effects of Clostridium butyricum on experimental colitis induced by oxazolone in rats. World J Gastroenterol. Apr. 21, 2009;15(15):1821-8.

Zhou et al., Total fecal microbiota transplantation alleviates high-fat diet-induced steatohepatitis in mice via beneficial regulation of gut microbiota. Sci Rep. May 8, 2017;7(1):1529. doi: 10.1038/s41598-017-01751-y.

[No Author Listed] Poster Presentation Schedule 14$^{th}$ International Congress of Immunology. Aug. 25, 2010. Kyoto, Japan.

[No Author Listed] Screenshot—pre-conference itinerary tool for the XIVth International Congress of Immunology held in Kobe on Aug. 2010 as "D98" in EP Opposition 2575835.

Abbas et al., Regulatory T cells: recommendations to simplify the nomenclature. Nat Immunol. Apr. 2013;14(4):307-8. doi: 10.1038/ni.2554.

Arpaia et al., A Distinct Function of Regulatory T Cells in Tissue Protection. Cell. Aug. 27, 2015;162(5):1078-89. doi: 10.1016/j.cell.2015.08.021. Supplemental Information.

Bag et al., Complete Genome Sequence of *Faecalibacterium prausnitzii* Isolated from the Gut of a Healthy Indian Adult. Genome Announc. Nov. 16, 2017;5(46). pii: e01286-17. doi: 10.1128/genomeA.01286-17.

Bergey et al., (2009). Bergey's manual of systematic bacteriology: vol. 3. New York: Springer. 795, 814-815 and 820. (17 pages).

Declaration by Marin Vuliè, Ph.D. Concerning European Patent 2575835. Dec. 17, 2018.

Declaration of Alexander Rudensky, Ph.D. Concerning European Patent 2575835. Dec. 16, 2018.

Declaration of Dr. James Dooley regarding abstracts of the XIVth International Congress of Immunology in Kobe in Aug. 2010, cited in EP Opposition 2575835.

Declaration of Joseph Sorg, Ph.D. Concerning European Patent 2575835. Dec. 16, 2018.

Eiseman B et al.; Fecal Enema as an Adjunct in the Treatment of Pseudomembranous Enterocolitis; Surgery vol. 44 No. 5; Nov. 1958.

Fontenot et al., Regulatory T Cell Lineage Specification by the Forkhead Transcription Factor Foxp3. Immunity. Mar. 2005;22(3):329-41.

Hattori et al., Bunchi Shokakibyo, 2011, 8/2:116-121, abstract only (Year: 2011).

Hattori et al., Bunshi Shokakibyo, 2012, 9/2:130-137, abstract only (Year: 2012).

Hattori et al., Kagaku Ryoho no Ryoiki, 2011, 27/9:1989-1997, abstract only (Year: 2011).

Hattori et al., Rinsho Kensa, 2011, 55/2:135-141, abstract only (Year: 2011).

Hsu et al., IL-10 Potentiates Differentiation of Human Induced Regulatory T Cells via STAT3 and Foxo1. J Immunol. Oct. 15, 2015;195(8):3665-74. doi: 10.4049/jimmunol.1402898. Epub Sep. 11, 2015.

Jordan et al., Thymic selection of CD4+CD25+ regulatory T cells induced by an agonist self-peptide. Nat Immunol. Apr. 2001;2(4):301-6.

Kuswanto et al., Poor Repair of Skeletal Muscle in Aging Mice Reflects a Defect in Local, Interleukin-33-Dependent Accumulation of Regulatory T Cells. Immunity. Feb. 16, 2016;44(2):355-67. doi: 10.1016/j.immuni.2016.01.009. Epub Feb. 9, 2016. Supplemental Information.

Lafaille et al., High Incidence of Spontaneous Autoimmune Encephalomyelitis in Immunodeficient Anti-Myelin Basic Protein T cell Receptor Transgenic Mice. Cell. Aug. 12, 1994;78(3):399-408.

Leber et al., Systems Modeling of Interactions between Mucosal Immunity and the Gut Microbiome during *Clostridium difficile* Infection. PLoS One. Jul. 31, 2015;10(7):e0134849. doi: 10.1371/journal.pone.0134849. eCollection 2015.

Levine et al., Continuous requirement for the TCR in regulatory T cell function. Nat Immunol. Nov. 2014;15(11):1070-8. doi: 10.1038/ni.3004. Epub Sep. 28, 2014.

Levine et al., Suppression of lethal autoimmunity by regulatory T cells with a single TCR specificity. J Exp Med. Mar. 6, 2017;214(3):609-622. doi: 10.1084/jem.20161318. Epub Jan. 27, 2017.

Martín et al., The Commensal Bacterium *Faecalibacterium prausnitzii* Is Protective in DNBS-induced Chronic Moderate and Severe Colitis Models; Inflamm Bowel Dis 2014;20:417-430.

Murai et al., Interleukin 10 acts on regulatory T cells to maintain expression of the transcription factor Foxp3 and suppressive function in mice with colitis. Nat Immunol. Nov. 2009;10(11):1178-84. doi: 10.1038/ni.1791. Epub Sep. 27, 2009.

Opposition against European Patent No. 2575835/The University of Tokyo dated Dec. 18, 2018. Muller Fottner Steinecke.

Opposition to European Patent No. 2575835 dated Dec. 18, 2018. Mathys & Squire.

Panduro et al., Tissue Tregs. Annu Rev Immunol. May 20, 2016;34:609-33. doi: 10.1146/annurev-immunol-032712-095948. Author manuscript.

Povoleri et al., Human retinoic acid-regulated CD161+ regulatory T cells support wound repair in intestinal mucosa. Nat Immunol. Dec. 2018;19(12):1403-1414. doi: 10.1038/s41590-018-0230-z. Epub Nov. 5, 2018.

Pre-Hearing Submission Opponent 5 for EP Patent 2575835. Dec. 18, 2018.

Rautava, Potential uses of probiotics in the neonate. Semin Fetal Neonatal Med. Feb. 2007;12(1):45-53. Epub Nov. 29, 2006.

Response to the Summons to attend oral proceedings pursuant to Rule 115(1) EPC, dated Jun. 7, 2018. Mailed Nov. 16, 2018. EP Patent 2575835.

Solomon et al., Mortality in patients with *Clostridium difficile* infection correlates with host pro-inflammatory and humoral immune responses. J Med Microbiol. Sep. 2013;62(Pt 9):1453-60. doi: 10.1099/jmm.0.058479-0. Epub May 30, 2013.

Stackebrandt et al., Phylogenetic basis for a taxonomic dissection of the genus *Clostridium*. FEMS Immunol Med Microbiol. Jul. 1999;24(3):253-8.

Steer et al., *Clostridium hathewayi* sp. nov., from human faeces. Syst Appl Microbiol. Nov. 2001;24(3):353-7. Abstract only.

Van Den Elsen et al., Embracing the gut microbiota: the new frontier for inflammatory and infectious diseases. Clin Transl Immunology. Jan. 20, 2017;6(1):e125. doi: 10.1038/cti.2016.91. eCollection Jan. 2017.

Varanasi et al., Role of IL-18 induced Amphiregulin expression on virus induced ocular lesions. Mucosal Immunol. Nov. 2018;11(6):1705-1715. doi: 10.1038/s41385-018-0058-8. Epub Aug. 7, 2018.

Vidhyalakshmi et al.; Encapsulation "The Future of Probiotics"—A Review; Advances in Biological Research 3 (3-4): 96-103, 2009.

Wan et al., Identifying Foxp3-expressing suppressor T cells with a bicistronic reporter. Proc Natl Acad Sci U S A. Apr. 5, 2005;102(14):5126-31. Epub Mar. 28, 2005.

Workman et al.; The Development and Function of Regulatory T Cells. Cell Mol Life Sci., 66(16), 2603-2622.

Written Submission for EP 2575835 on behalf of proprietor dated Dec. 18, 2018. Hoffmann Eitle.

Large intestine
21.4
4.03
74.4
0.22
Small intestine
37.7
5.35
55
2.02
Mesenteric lymph nodes
31.3
0.54
68.1
0.069
Peyer's patches
19.3
0.55
79.8
0.32
Spleen
18.5
0.38
81
0.13
Thymus
97.7
0.024
2.3
3.73e-3
CD4
Foxp3

```
SEQUENCE LISTING

<160> NUMBER OF SEQ ID NOS: 69

<210> SEQ ID NO 1
<211> LENGTH: 23
<212> TYPE: DNA
<213> ORGANISM: Artificial
<220> FEATURE:
<223> OTHER INFORMATION: Artificially synthesized primer sequence

<400> SEQUENCE: 1

ggcaatagtt ccttcccaga gtt                                          23


<210> SEQ ID NO 2
<211> LENGTH: 22
<212> TYPE: DNA
<213> ORGANISM: Artificial
<220> FEATURE:
<223> OTHER INFORMATION: Artificially synthesized primer sequence

<400> SEQUENCE: 2

gggtcgcata ttgtggtact tg                                           22


<210> SEQ ID NO 3
<211> LENGTH: 23
<212> TYPE: DNA
<213> ORGANISM: Artificial
<220> FEATURE:
<223> OTHER INFORMATION: Artificially synthesized primer sequence

<400> SEQUENCE: 3

ccttttgtag ccctgctcac tct                                          23


<210> SEQ ID NO 4
<211> LENGTH: 21
<212> TYPE: DNA
<213> ORGANISM: Artificial
<220> FEATURE:
<223> OTHER INFORMATION: Artificially synthesized primer sequence

<400> SEQUENCE: 4

gggtcacctg tatggcttca g                                            21


<210> SEQ ID NO 5
<211> LENGTH: 21
<212> TYPE: DNA
<213> ORGANISM: Artificial
<220> FEATURE:
<223> OTHER INFORMATION: Artificially synthesized primer sequence

<400> SEQUENCE: 5

tcagtgcaag atctgcaagc a                                            21
```

<210> SEQ ID NO 6
<211> LENGTH: 19
<212> TYPE: DNA
<213> ORGANISM: Artificial
<220> FEATURE:
<223> OTHER INFORMATION: Artificially synthesized primer sequence

<400> SEQUENCE: 6
acaccggaag ccaaacaca 19

<210> SEQ ID NO 7
<211> LENGTH: 27
<212> TYPE: DNA
<213> ORGANISM: Artificial
<220> FEATURE:
<223> OTHER INFORMATION: Artificially synthesized primer sequence

<400> SEQUENCE: 7
gattttaata agctccaaga ccaaggt 27

<210> SEQ ID NO 8
<211> LENGTH: 27
<212> TYPE: DNA
<213> ORGANISM: Artificial
<220> FEATURE:
<223> OTHER INFORMATION: Artificially synthesized primer sequence

<400> SEQUENCE: 8
cttctatgca gttgatgaag atgtcaa 27

<210> SEQ ID NO 9
<211> LENGTH: 21
<212> TYPE: DNA
<213> ORGANISM: Artificial
<220> FEATURE:
<223> OTHER INFORMATION: Artificially synthesized primer sequence

<400> SEQUENCE: 9
cctcgtcccg tagacaaaat g 21

<210> SEQ ID NO 10
<211> LENGTH: 20
<212> TYPE: DNA
<213> ORGANISM: Artificial
<220> FEATURE:
<223> OTHER INFORMATION: Artificially synthesized primer sequence

<400> SEQUENCE: 10
tctccacttt gccactgcaa 20

<210> SEQ ID NO 11
<211> LENGTH: 20
<212> TYPE: DNA
<213> ORGANISM: Artificial
<220> FEATURE:
<223> OTHER INFORMATION: Artificially synthesized primer sequence

<400> SEQUENCE: 11
ggacattgtc tttgatggca 20

<210> SEQ ID NO 12
<211> LENGTH: 20
<212> TYPE: DNA
<213> ORGANISM: Artificial
<220> FEATURE:
<223> OTHER INFORMATION: Artificially synthesized primer sequence

<400> SEQUENCE: 12
cttgtcacgt ggtgtcactg 20

<210> SEQ ID NO 13
<211> LENGTH: 20
<212> TYPE: DNA
<213> ORGANISM: Artificial
<220> FEATURE:
<223> OTHER INFORMATION: Artificially synthesized primer sequence

<400> SEQUENCE: 13
tctctggacg tcaaatgtgg 20

<210> SEQ ID NO 14
<211> LENGTH: 19
<212> TYPE: DNA
<213> ORGANISM: Artificial
<220> FEATURE:
<223> OTHER INFORMATION: Artificially synthesized primer sequence

<400> SEQUENCE: 14
gctgaacagc agagccttc 19

<210> SEQ ID NO 15
<211> LENGTH: 20
<212> TYPE: DNA
<213> ORGANISM: Artificial
<220> FEATURE:
<223> OTHER INFORMATION: Artificially synthesized primer sequence

<400> SEQUENCE: 15
aggtctggat cactccaagg 20

<210> SEQ ID NO 16
<211> LENGTH: 19
<212> TYPE: DNA
<213> ORGANISM: Artificial
<220> FEATURE:
<223> OTHER INFORMATION: Artificially synthesized primer sequence

<400> SEQUENCE: 16
tcgcctggac cataaagaa 19

<210> SEQ ID NO 17
<211> LENGTH: 20
<212> TYPE: DNA
<213> ORGANISM: Artificial
<220> FEATURE:
<223> OTHER INFORMATION: Artificially synthesized primer sequence

<400> SEQUENCE: 17
agaggatgcg tgactttgtg 20

<210> SEQ ID NO 18
<211> LENGTH: 20
<212> TYPE: DNA
<213> ORGANISM: Artificial
<220> FEATURE:
<223> OTHER INFORMATION: Artificially synthesized primer sequence

<400> SEQUENCE: 18
atacagcaga ccttctggca 20

<210> SEQ ID NO 19

```
<211> LENGTH: 20
<212> TYPE: DNA
<213> ORGANISM: Artificial
<220> FEATURE:
<223> OTHER INFORMATION: Artificially synthesized primer sequence

<400> SEQUENCE: 19

agagtttgat cmtggctcag                                              20


<210> SEQ ID NO 20
<211> LENGTH: 16
<212> TYPE: DNA
<213> ORGANISM: Artificial
<220> FEATURE:
<223> OTHER INFORMATION: Artificially synthesized primer sequence

<400> SEQUENCE: 20

attaccgcgg ckgctg                                                  16


<210> SEQ ID NO 21
<211> LENGTH: 1460
<212> TYPE: DNA
<213> ORGANISM: Clostridium leptum
<220> FEATURE:
<221> NAME/KEY: rRNA
<222> LOCATION: (1)..(1460)
<223> OTHER INFORMATION: 16S rRNA coding gene sequence of Clostridium
      strain 1

<400> SEQUENCE: 21

agagtttgat cctggctcag gatgaacgct ggcggcgtgc ttaacacatg caagtcgaac     60

gagaaccatt ggatcgagga ttcgtccaag tgaaggtggg gaaagtggcg gacgggtgag    120

taacgcgtga gcaatctgcc ttggagtggg gaataacggc tggaaacagc cgctaatacc    180

gcatgataca gctgggaggc atctccctgg ctgtcaaaga tttatcgctc tgagatgagc    240

tcgcgtctga ttagctagtt ggcggggtaa cggcccacca aggcgacgat cagtagccgg    300

actgagaggt tggccggcca cattgggact gagacacggc ccagactcct acgggaggca    360

gcagtgggga atattgggca atgggcgcaa gcctgaccca gcaacgccgc gtgaaggaag    420

aaggctttcg ggttgtaaac ttcttttgtc agggacgaag caagtgacgg tacctgacac    480

ggctactacg gtcagcagcg cgtatacgta ggtgccagcg tatccggaat tacctgggtt    540

aaggcgtgtt agccggactg cagtcagatg tgaatcacgg gctcaacttg tgctgcattg    600

gaactgtagt tctgagtact gagagcagac ggaattctag gtagcggtga atgcgtagat    660

ataggaggac acagtgcgag gcgtctgctg acagcaactg acgctgaggc gggaagcgtg    720

ggggagccaa caggattaga tacctggtag ttcacgcctg gtaaaacgat ggatactagg    780

tgtgggggga ctgacccct cgtggccgcc agttaacacc aataaagtat cccacctggg     840

agtacgatcg caaggttgaa actcaaagga attgacgggg cccgcacaag cggtggagta    900

tgtggtttaa ttcgaagcaa cgcgaagaac cttaccaggg cttgacatcc cgaggaccgg    960

actagagata gtcttttctc ttcggagacc tcggtgacag gtggtgcatg gttgtcgtca   1020

gctcgtgtcg taagatgttg ggttaagtcc cgcaacgagc gcaaccctta ttgttagttg   1080

ctacgcaaga gcactctagc gagactgccg ttgacaaaac ggaggaaggt ggggacgacg   1140

tcaaatcatc atgcccctta tgtcctgggc cacacacgta ctacaatggt ggtcaacaga   1200

gggaagcaat accgcgaggt ggagcaaatc cctaaaagcc atcccagttc ggatcgcagg   1260

ctgcaacccg cctgcgtgaa gttggaatcg ctagtaatcg cggatcagca tgccgcggtg   1320
```

```
aatacgttcc cgggccttgt acacaccgcc cgtcacacca tgagagtcgg gaacacccga   1380

agtccgtagc ctaaccgcaa ggggggcgc ggccgaaggt gggttcgata attggggtga   1440

agtcgtaaca aggtagccgt                                               1460


<210> SEQ ID NO 22
<211> LENGTH: 1485
<212> TYPE: DNA
<213> ORGANISM: Clostridium leptum
<220> FEATURE:
<221> NAME/KEY: rRNA
<222> LOCATION: (1)..(1485)
<223> OTHER INFORMATION: 16S rRNA coding gene sequence of Clostridium
      strain 2

<400> SEQUENCE: 22

agagtttgat cctggctcag gatgaacgct ggcggcgtgc ttaacacatg caagtcgaac     60

ggagcacccc tgaaggagtt ttcggacaac ggaagggact gcttagtggc ggacgggtga    120

gtaacgcgtg aggaacctgc cttggagtgg ggaataacag ctggaaacag ctgctaatac    180

cgcataatat atctgggccg catggctctg gatatcaaag atttatcgct ctgagatgga    240

ctcgcgtctg attagctagt tggcggggta acggcccacc aaggcgacga tcagtagccg    300

gactgagagg ttggccggcc acattgggac tgagacacgg cccagactcc tacgggaggc    360

agcagtgggg aatattgggc aatgggcgca agcctgaccc agcaacgccg cgtgaaggaa    420

gaaggctttc gggttgtaaa cttcttttgt cagggacgaa gcaagtgacg gtacctgacg    480

aataagccac ggctaactac gtgccagcag ccgcggtaat acgtaggtgg caagcgttat    540

ccggatttac tgggtgtaaa gggcgtgtag gcgggactgc aagtcagatg tgaaaaccac    600

gggctcaacc tgtgggcctg catttgaaac tgtagttctt gagtactgga gaggcagacg    660

gaattctagt tgtagcgtga aatgcgtaga tatagaagaa cacagttgcg gagccggtct    720

gcaactgacg ctgagcgcga aagcgtgggg agcaaacagg attagatacc ctggtagtcc    780

acgctgtaaa cgatggatta ctaggtgtgg ggggactgac cccctccgtg ccgcagttaa    840

cacaataagt atcccacctg gggagtacga tcgcaaggtt gaaactcaaa aggaattgac    900

gggggcccgc acaagcggtg gagtatgtgg tttaaattcg aagcaacgcg aagaacctta    960

ccagggcttg acatcccggt gaccgtccta gagataggat ttcccttcg gggacactgg   1020

agacaggtgg tgcatggttg tcgtcagctc gtgtcgtgag atgttgggtt aagtcccgca   1080

acgagcgcaa cccttattgt tagttgctac gcaagagcac tctagcgaga ctgccgttga   1140

caaaacggag gaaggtgggg acgacgtcaa atcatcatgc cccttatgtc ctgggccaca   1200

cacgtactac aatggtggtc aacagaggga agcaaagccg cgaggtggag caaatcccta   1260

aaagccatcc cagttcggat cgcaggctgc aacccgcctg cgtgaagttg gaatcgctag   1320

taatcgcgga tcagaatgcc gcggtgaata cgttcccggg ccttgtacac accgcccgtc   1380

acaccatgag agtcgggaac acccgaagtc cgtagcctaa ccgcaagggg ggcgcggccg   1440

aaggtgggtt cgataattgg ggtgaagtcg taacaaggta gccgt                   1485


<210> SEQ ID NO 23
<211> LENGTH: 1491
<212> TYPE: DNA
<213> ORGANISM: Clostridium leptum
<220> FEATURE:
<221> NAME/KEY: rRNA
<222> LOCATION: (1)..(1491)
<223> OTHER INFORMATION: 16S rRNA coding gene sequence of Clostridium
      strain 3
```

<400> SEQUENCE: 23

```
agagtttgat cctggctcag gacgaacgct ggcggcgtgc ttaacacatg caagtcgaac     60
ggagcacctt cgaaagagac ttcggtcaat ggaaaagaat gcttagtggc ggacgggtga    120
gtaacgcgtg aggaacctgc ctttcagtgg gggacaacag ttggaaacga ctgctaatac    180
cgcataacgt acgggtatcg catggtatct gtaccaaaga tttatcgctg agagatggcc    240
tcgcgtctga ttagctagtt ggtagggtaa cggcctacca aggcgacgat cagtagccgg    300
actgagaggt tggccggcca cattgggact gagatacggc ccagactcct acgggaggca    360
gcagtgggga atattgggca atgggcgaaa gcctgaccca gcaacgccgc gtgaaggaag    420
aaggctttcg ggttgtaaac ttcttttgac ggggaagagc agaagacggt acctgtcgaa    480
taagccacgg ctaactacgt gccagcagcc gcggtaatac gtaggtggca agcgttgtcc    540
ggatttactg ggtgtaaagg gcgtgtagcc gggctgacaa gtcagatgtg aaatccgggg    600
gctcaacccc cgaactgcat ttgaaactgt tggtcttgag tatcggagag gcaggcggaa    660
ttcctagtgt agcggtgaaa tgcgtagata ttagggggaa caccagtggc gaagcggcct    720
gctggacgac aactgacggt gaggcgcgaa agcgtgggga gcaaacagga ttagataccc    780
tggtagtcca cgctgtaaac gatggatact aggtgtgcgg ggactgaccc ctgcgtgccg    840
cagctaacgc aataagtatc ccacctgggg agtacgatcg caaggttgaa actcaaagga    900
attgacgggg gcccgcacaa gcggtggatt atgtggttta attcgatgca acgcgaagaa    960
ccttaccagg gcttgacatc ctactaacga agtagagata cattaggtac ccttcggggg   1020
aagtagagac aggtggtgca tggttgtcgt cagctcgtgt cgtgagatgt tgggttaagt   1080
cccgcaacga gcgcaaccct tattgttagt tgctacgcaa gagcactcta gcgagactgc   1140
cgttgacaaa acggaggaag gtggggacga cgtcaaatca tcatgcccct tatgtcctgg   1200
gctacacacg taatacaatg gcggtcaaca gagggatgca aaaccgcgag gtggagcgaa   1260
cccctaaaag ccgtcccagt tcagatcgca gtctgcaacc cgactgcgtg aagtcggaat   1320
cgctagtaat cgcggatcag catgccgcgg tgaatacgtt cccgggcctt gtacacaccg   1380
cccgtcacac catgagagtc gggaacaccc gaagtccgta gcctaaccgc aaggagggcg   1440
cggccgaagg tgggttcgat aattggggtg aagtcgtaac aaggtagccg t            1491
```

<210> SEQ ID NO 24
<211> LENGTH: 1491
<212> TYPE: DNA
<213> ORGANISM: Clostridium coccoides
<220> FEATURE:
<221> NAME/KEY: rRNA
<222> LOCATION: (1)..(1491)
<223> OTHER INFORMATION: 16S rRNA coding gene sequence of Clostridium strain 4

<400> SEQUENCE: 24

```
agagtttgat cctggctcag gatgaacgct ggcggcgtgc ctaacacatg caagtcgaac     60
gggtgtacgg ggaggaaggc ttcggccgga aaacctgtgc atgagtggcg gacgggtgag    120
taacgcgtgg gcaacctggc ctgtacaggg ggataacact tagaaatagg tgctaatacc    180
gcataacggg ggaagccgca tggcttttcc ctgaaaactc cggtggtaca ggatgggccc    240
gcgtctgatt agccagttgg cagggtaacg gcctaccaaa gcgacgatca gtagccggcc    300
tgagagggcg gacggccaca ctgggactga gacacggccc agactcctac gggaggcagc    360
agtgggggat attgcacaat gggggaaac cctgatgcag cgacgccgcg tgagtgaaga    420
```

```
agtatttcgg tatgtaaagc tctatcagca gggaagaaaa tgacggtacc tgactaagaa    480

gccccggcta actacgtgcc agcagccgcg gtaatacgta gggggcaagc gttatccgga    540

tttactgggt gtaaagggag cgtagacggc agcgcaagtc tgagtgaaat cccatggctt    600

aaccatggaa ctgctttgga aactgtgcag ctggagtgca ggagagtaag cggaattcct    660

agtgtagcgt gaaatgcgta gattatagga ggaacaccag tggcgaaggc ggctaactga    720

actgtaactg acgttgaggc tcgaaagcgt ggggagcaaa caggattaga taccctggta    780

gtccacgccg taaacgatga ttactaggtg ttggggggacc aaggtcttcg gtgccggcgc    840

aaacgcatta agtaatccac ctggggagta cgttcgcaag aatgaaactc aaaggaattg    900

acggggaccc gcacaagcgg tggagcatgt ggtttaattc gaagcaacgc gaagaacctt    960

acctggtctt gacatcccga tgacgagtga gcaaagtcac tttcccttcg ggcattgga    1020

gacaggtggt gcatggttgt cgtcagctcg tgtcgtgaga tgttgggtta agtcccgcaa   1080

cgagcgcaac ccctatttcc agtagccagc aggtagagct gggcactctg gagagactgc   1140

ccgggataac cgggaggaag gcggggatga cgtcaaatca tcatgcccct tatgatcagg   1200

gctacacacg tgctacaatg gcgtaaacaa agggaagcga gacggtgacg ttgagcaaat   1260

cccaaaaata acgtcccagt tcggattgta gtctgcaact cgactacatg aagctggaat   1320

cgctagtaat cgcgaatcag aatgtcgcgg tgaatacgtt cccgggtctt gtacacaccg   1380

cccgtcacac catgggagtc ggaaatgccc gaagtcagtg acctaaccga aaggaaggag   1440

ctgccgaagg tggagccggt aactggggtg aagtcgtaac aaggtagccg t             1491
```

```
<210> SEQ ID NO 25
<211> LENGTH: 1467
<212> TYPE: DNA
<213> ORGANISM: Clostridium leptum
<220> FEATURE:
<221> NAME/KEY: rRNA
<222> LOCATION: (1)..(1467)
<223> OTHER INFORMATION: 16S rRNA coding gene sequence of Clostridium
      strain 5

<400> SEQUENCE: 25

agagtttgat cctggctcag gacgaacgct ggcggcacgc ctaacacatg caagtcgaac     60

ggagtgaaga tgctcgcatc tgaacttagt ggcggacggg tgagtaacac gtgagcaacc    120

tgcctttcag agggggatta cgtttggaaa cgaacgctaa taccgcataa aatatcggag    180

tcgcatggca ctgatatcaa aggagcaatc cgctgaaaga tgggctcgcg tccgattagg    240

cagttggcgg ggtatcggcc caccaaaccg acaatcggta gccggactga gaggttgaac    300

ggccacattg ggactgagac gcggcccaga ctcctacggg aggcagcagt gggggatatt    360

gcacaatggg ggaaaccctg atgcagcgat gccgcgtgaa tgaagacggc cttcgggttg    420

taaagttctg tcgcagggga cgaaaatgac ggtaccctgc aagaaagctc cggctaacta    480

cgtgccagca gccgcggtaa tacgtaggga gcaagcgttg tccggaatta ctgggtgtaa    540

agggagcgta ggcgggagga taagttgaat gtgaaatcta tgggctcaac ccatagctgc    600

gttcaaactg ttcttcttga gtgaagtaga ggcaggcgga attcctagtg tagcggtgaa    660

atgcgtagat attaggagga caccagtggc gaaggcgggc tgctgggctt tactgacgct    720

gaggctcgaa agcgtgggta gcaaacagga ttagataccc tggtagtcca cgcggtaaac    780

gatgattact aggtgtgggt ggactgaccc catccgtgcc ggagttaaca caataagtaa    840

tccacctggg gagtacggcc gcaaggttga aactcaaagg aattgacggg ggcccgcaca    900
```

```
agcagtggag tatgtggttt aattcgacgc aacgcgaaga accttaccag gtcttgacat     960

cgagtgacgg acatagagat atgtctttcc ttcgggacac gaagacaggt ggtgcatggt    1020

tgtcgtcagc tcgtgtcgtg agatgttggg ttaagtcccg caacgagcgc aacccttacc    1080

attagttgct acgcaagagc actctaatgg gactgccgtt gacaaaacgg aggaaggtgg    1140

ggatgacgtc aaatcatcat gccccttatg acctgggcga cacacgtact acaatggcgg    1200

tcaacagagg gaggcaaagc cgcgaggcag agcaaacccc taaaagccgt ctcagttcgg    1260

attgcaggct gcaactcgcc tgcatgaagt cggaattgct agtaatcgcg gatcagcatg    1320

ccgcggtgaa tacgttcccg ggccttgtac acaccgcccg tcacaccatg agagccggta    1380

acacccgaag tcaatagtct aaccgcaagg aggacattgc cgaaggtggg attggtaatt    1440

ggggtgaagt cgtaacaagg tagccgt                                        1467


<210> SEQ ID NO 26
<211> LENGTH: 1474
<212> TYPE: DNA
<213> ORGANISM: Clostridium coccoides
<220> FEATURE:
<221> NAME/KEY: rRNA
<222> LOCATION: (1)..(1474)
<223> OTHER INFORMATION: 16S rRNA coding gene sequence of Clostridium
      strain 6

<400> SEQUENCE: 26

agagtttgat catggctcag gatgaacgct ggcggcgtgc ctaacacatg caagtcgaac      60

gggtgtacgg gaaggaaggc ttcggccgga aaacctgtgc atgagtggcg gacgggtgag     120

taacgcgtgg gcaacctggc ctgtacaggg ggataacact tagaaatagg tgctaatacc     180

gcataacggg ggaagccgca tggcttttcc ctgaaaactc cggtggtaca ggatgggccc     240

gcgtctgatt agccagttgg cagggtaacg gcctaccaaa gcgacgatca gtagccggcc     300

tgagagggcg gacggccaca ctgggactga gacacggccc agactcctac gggaggcagc     360

agtgggggat attgcacaat gggggaaacc ctgatgcagc gacgccgcgt gggtgaagaa     420

gcgcctcggc gcgtaaagcc ctgtcagcag ggaagaaaat gacggtacct gaagaagaag     480

ccccggctaa ctacgtgcca gcagccgcgg taatacgtag ggggcaagcg ttatccggga     540

tttactgggt gtaaaggggg cgcagacggc gatgcaagcc aggagtgaaa gcccggggcc     600

caaccccggg actgctcttg ggaactgcgt ggctggagtg cagagggcag cggaattcct     660

ggtgaaatgc gtagatatca gaagacacgg tgcgaggcgg cctgctgact gcactgacgt     720

tgagccgaag cgtggggagc aaacaggatt agataccgtg gtagtcacgc cgtaaacgat     780

gattactagg tgtcggggag cagagactgc ccggtgccgc agccaacgca ttaagtaatc     840

cacctgggga gtacgttcgc aagaatgaaa ctcaaaggaa ttgacgggga cccgcacaag     900

cggtggagca tgtggtttaa ttcgaagcaa cgcgaagaac cttacctggt cttgacatcc     960

cgatgacgag tgagcaaagt cactttccct tcggggcatt ggagacaggt ggtgcatggt    1020

tgtcgtcagc tcgtgtcgtg agatgttggg ttaagtcccg caacgagcgc aacccctatt    1080

tccagtagcc agcaggtaga gctgggcact ctggagagac tgcccgggat aaccgggagg    1140

aaggcgggga tgacgtcaaa tcatcatgcc ccttatgatc agggctacac acgtgctaca    1200

atggcgtaaa caaagggaag cgagacggtg acgttaagca aatcccaaaa ataacgtccc    1260

agttcggatt gtagtctgca actcgactac atgaagctgg aatcgctagt aatcgcgaat    1320

cagaatgtcg cggtgaatac gttcccgggt cttgtacaca ccgcccgtca caccatggga    1380
```

```
gtcggaaatg cccgaagtca gtgacctaac cgaaaggaag gagctgccga aggtggagcc   1440

ggtaactggg gtgaagtcgt aacaaggtag ccgt                               1474


<210> SEQ ID NO 27
<211> LENGTH: 1484
<212> TYPE: DNA
<213> ORGANISM: Clostridium leptum
<220> FEATURE:
<221> NAME/KEY: rRNA
<222> LOCATION: (1)..(1484)
<223> OTHER INFORMATION: 16S rRNA coding gene sequence of Clostridium
      strain 7

<400> SEQUENCE: 27

agagtttgat cctggctcag gatgaacgct ggcggcgtgc ttaacacatg caagtcgaac     60

gagaatccag tgaaggagtt ttcggacaac ggatctggag gaaagtggcg gacgggtgag    120

taacgcgtga gcaatctgcc ttggagtggg gaataacggt tggaaacagc cgctaatacc    180

gcatgatgcg tctgggaggc atctctctgg acgccaaaga tttatcgctc tgagatgagc    240

tcgcgtctga ttagcttgtt ggcggggtaa aggcccacca aggcgacgat cagtagccgg    300

actgagaggt tggccggcca cattgggact gagacacggc ccagactcct acgggaggca    360

gcagtgggga atattgggca atgggcgcaa gcctgaccca gcaacgccgc gtgaaggaag    420

aaggctttcg ggttgtaaac ttcttttctg agggacgaag aaagtgacgg tacctcagga    480

ataagccacg gctaactacg tgccagcagc cgcggtaata cgtaggtggc aagcgttatc    540

cggatttatt gggtgtaaag ggcgtgtagg cgggaaagca agtcagatgt gaaaactcag    600

ggctcaaccc tgagcctgca tttgaaactg tttttcttga gtgctggaga ggcaatcgga    660

attccgtgtg tagcggtgaa atgcgtagat atacggagga caccagtggc gagcggattg    720

ctggacagta ctgacgctga agcgcgaaag cgtgggagca aacagataga tacctggtag    780

tcacgcgtaa acgatggata ctaggtgtgg ggggactgac cccctccgtg ccgcagctaa    840

cgcaataagt atcccacctg gggagtacga tcgcaaggtt gaaactcaaa ggaattgacg    900

ggggcccgca caagcggtgg agtatgtggt ttaattcgaa gcaacgcgaa gaaccttacc    960

agggcttgac atcctgctaa cgaaccagag atggattagg tgcccttcgg ggaaagcaga   1020

gacaggtggt gcatggttgt cgtcagctcg tgtcgtgaga tgttgggtta agtcccgcaa   1080

cgagcgcaac ccttattgtt agttgctacg caagagcact ctagcgagac tgccgttgac   1140

aaaacggagg aaggtgggga cgacgtcaaa tcatcatgcc ccttacgtcc tgggccacac   1200

acgtactaca atggcggcca acaaagagag gcaagaccgc gaggtggagc aaatctcaaa   1260

aagccgtccc agttcggatc gcaggctgca acccgcctgc gtgaagttgg aatcgctagt   1320

aatcgcggat cagcatgccg cggtgaatac gttcccgggc cttgtacaca ccgcccgtca   1380

caccatgaga gtcgggaaca cccgaagtcc gtagcctaac cgcaaggggg gcgcggccga   1440

aggtgggttc gataattggg gtgaagtcgt aacaaggtag ccgt                   1484


<210> SEQ ID NO 28
<211> LENGTH: 1483
<212> TYPE: DNA
<213> ORGANISM: Clostridium leptum
<220> FEATURE:
<221> NAME/KEY: rRNA
<222> LOCATION: (1)..(1483)
<223> OTHER INFORMATION: 16S rRNA coding gene sequence of Clostridium
      strain 8
```

<400> SEQUENCE: 28
agagtttgat cctggctcag gacgaacgct ggcggcgtgc ttaacacatg caagtcgaac 60
ggagcacccc tgaaggagtt ttcggacaac ggatgggaat gcttagtggc ggactggtga 120
gtaacgcgtg aggaacctgc cttccagagg gggacaacag ttggaaacga ctgctaatac 180
cgcatgatgc gttggagccg catgactccg acgtcaaaga tttatcgctg gaagatggcc 240
tcgcgtctga ttagctagtt ggtgaggtaa cggcccacca aggcgacgat cagtagccgg 300
actgagaggt tggccggcca cattgggact gagatacggc ccagactcct acgggaggca 360
gcagtgggga atattgggca atggacgcaa gtctgaccca gcaacgccgc gtgaaggaag 420
aaggctttcg ggttgtaaac ttcttttaag ggggaagagc agaagacggt accccttgaa 480
taagccacgg ctaactacgt gccagcagcc gcggtaatac gtaggtggca agcgttgtcc 540
ggatttactg ggtgtaaagg gcgtgcagcc ggagagacaa gtcagatgtg aaatccacgg 600
gctcaacccg tgaactgcat ttgaaactgt ttcctttgag tgtcggagag gtaatcggga 660
ttccttgtgt agcggtgaat gcgtagatat agagaccaca gtgccgacgc cgaatactga 720
cgatactgac ggtgagcgcg aaagcgtggg gagcaaacag gattagatac cctggtagtc 780
cacgctgtaa acgatcgata ctaggtgtgc ggggactgac ccctgcgtgc cggagttaac 840
acaataagta tcgcacctgg ggagtacgat cgcaaggttg aaactcaaag gaattgacgg 900
gggcccgcac aagcggtgga ttatgtggtt taattcgaag caacgcgaag aaccttacca 960
gggcttgaca tcctgctaac gaagtagaga tacattaggt gcccttcggg gaaagcagag 1020
acaggtggtg catggttgtc gtcagctcgt gtcgtgagat gttgggttaa gtcccgcaac 1080
gagcgcaacc cctattgtta gttgctacgc aagagcactc tagcgagact gccgttgaca 1140
aaacggagga aggcggggac gacgtcaaat catcatgccc cttatgtcct gggctacaca 1200
cgtaatacaa tggcggttaa caaagggatg caaagccgcg aggcagagcg aaccccaaaa 1260
agccgtccca gttcggatcg caggctgcaa cccgcctgcg tgaagtcgga atcgctagta 1320
atcgcggatc agcatgccgc ggtgaatacg ttcccgggcc ttgtacacac cgcccgtcac 1380
accatgagag tcgggaacac ccgaagtccg tagcctaacc gcaaggaggg cgcggccgaa 1440
ggtgggttcg ataattgggg tgaagtcgta acaaggtagc cgt 1483

<210> SEQ ID NO 29
<211> LENGTH: 1480
<212> TYPE: DNA
<213> ORGANISM: Clostridium coccoides
<220> FEATURE:
<221> NAME/KEY: rRNA
<222> LOCATION: (1)..(1480)
<223> OTHER INFORMATION: 16S rRNA coding gene sequence of Clostridium strain 9

<400> SEQUENCE: 29
ggagtttgat cctggctcag gatgaacgct ggcggcgtgc ttaacacatg caagtcgaac 60
gggctcatat tgaaacctag tgatgtatga gttagtggcg gacgggtgag taacgcgtgg 120
agaacctgcc gtatactggg ggataacact tagaaatagg tgctaatacc gcataagcgc 180
acagcttcgc atgaagcagt gtgaaaaact ccggtggtat acgatggatc cgcgtctgat 240
tagctggttg gcggggtaac agcccaccaa ggcgacgatc agtagccggc ctgagagggt 300
gaacggccac attgggactg agacacggcc caaactccta cgggaggcag cagtggggaa 360
tattgcacaa tgggggaaac cctgatgcag cgacgccgcg tgagtgaaga agtatttcgg 420

```
tatgtaaagc tctatcagca gggaagaaat actgacctta cggtcagcag acggtacctg    480

actaagaagc cccgggctaa ctacgtgcca gcagccgcgg taatacgtag ggcaagcgt     540

tatccggatt tactgggtgt aaagggggcg cagacggcga tgcaagccag gagtgaaagc    600

cggggcccaa ccccgggact gctcttggac tgcgtggctg gagtgcagag ggcagcgaat    660

tcctgtgtag cgtgaatgcg tagattcaga ggacacgtgc gagcgcctgc tgactgcact    720

gacgtgagcc cgaagcgtgg ggagcaaaca ggattagata cctggtagtc cacgccgtaa    780

acgatgatta ctaggtgtcg gggagcagag actgcccggt gccgcagcca acgcattaag    840

taatccacct ggggagtacg ttcgcaagaa tgaaactcaa aggaattgac ggggacccgc    900

acaagcggtg gagcatgtgg tttaattcga agcaacgcga agaaccttac caggccttga    960

catccccctg gatggcccgt aacggggtca gcctttcggg gcaggggaga caggtggtgc   1020

atggttgtcg tcagctcgtg tcgtgagatg ttgggttaag tcccgcaacg agcgcaaccc   1080

ctgcccgcag tagccagcat tttagatggg gactctgcgg ggactgccgg ggacaacccg   1140

gaggaaggcg gggatgacgt caaatcatca tgccccttat ggcctgggct acacacgtgc   1200

tacaatggcg ccgacagagg gaggcgaagc ggcgacgcgg agcgaacccc aaaaacggcg   1260

tcccagttcg gattgtagtc tgcaacccga ctacatgaag ccggaatcgc tagtaatcgc   1320

ggatcagaat gccgcggtga atacgttccc gggtcttgta cacaccgccc gtcacaccat   1380

gggagccggg aatgcccgaa gtctgtgacc gaacccgtaa ggggaggggc agccgaaggc   1440

aggcccggtg actggggtga agtcgtaaca aggtagccgt                         1480
```

```
<210> SEQ ID NO 30
<211> LENGTH: 1489
<212> TYPE: DNA
<213> ORGANISM: Clostridium leptum
<220> FEATURE:
<221> NAME/KEY: rRNA
<222> LOCATION: (1)..(1489)
<223> OTHER INFORMATION: 16S rRNA coding gene sequence of Clostridium
      strain 10

<400> SEQUENCE: 30

agagtttgat cctggctcag gatgaacgct ggcggcgtgc ttaacacatg caagtcgagc     60

gaagcacttt tttagaactc ttcggaggga agagagggtg acttagcggc ggacgggtga    120

gtaacgcgtg ggcaacctgc cttacacagg gggataacaa ttagaaatga ttgctaatac    180

cgcataagac cacggtactg catggtacag tggtaaaaac tgaggtggtg taagatgggc    240

ccgcgtctga ttaggtagtt ggtggggtag aagcctacca agccgacgat cagtagccga    300

cctgagaggg cgaccggcca cattgggact gagacacggc ccaaactcct acgggaggca    360

gcagtgggga atattgcaca atgggggaaa ccctgatgca gcgacgccgc gtgagtgagg    420

aagtatttcg gtatgtaaag ctctatcagc agggaagaaa atgacggtac ctgactaaga    480

agccccggc taactacgtg ccagcagccg cggtaatacg tagggggcaa gcgttatccg     540

gatttactgg gtgtaaaggg agcgtagacg gacttgcaag tctgatgtga aaatccgggg    600

cccaacccgg gactgcattg aaactgtatt ttttggaggg gtccgaggag gcaagtggaa    660

tcctgggtag cggtgaaatg gcgtagaatt cagggaggaa caccagtggc ggaaggcgaa    720

ttactggacg ataactgacg gtgaggcgcg aagcgtggga gcaaacaaga attagatacc    780

ctggtagtca cgctgtaacg atcgatacta ggtgtgcggg gactgacccc tgcgtgccgg    840

agttaacaca ataagtatcg cactggggag tacgatcgca aggttgaaac tcaaaggaat    900
```

```
tgacgggggc ccgcacaagc ggtggattat gtggtttaat tcgaagcaac gcgaagaacc    960

ttaccagggc ttgacatcct gctaacgaag tagagataca ttaggtgccc ttcggggaaa   1020

gcagagacag gtggtgcatg gttgtcgtca gctcgtgtcg tgagatgttg ggttaagtcc   1080

cgcaacgagc gcaaccccta ttgttagttg ctacgcaaga gcactctagc gagactgccg   1140

ttgacaaaac ggaggaaggc ggggacgacg tcaaatcatc atgcccctta tgtcctgggc   1200

tacacacgta atacaatggc ggttaacaaa gggatgcaaa gccgcgaggc agagcgaacc   1260

ccaaaaagcc gtcccagttc ggatcgcagg ctgcaacccg cctgcgtgaa gtcggaatcg   1320

ctagtaatcg cggatcagca tgccgcggtg aatacgttcc cgggccttgt acacaccgcc   1380

cgtcacacca tgagagtcgg gaacacccga agtccgtagc ctaaccgcaa ggagggcgcg   1440

gccgaaggtg ggttcgataa ttggggtgaa gtcgtaacaa ggtagccgt                1489


<210> SEQ ID NO 31
<211> LENGTH: 1490
<212> TYPE: DNA
<213> ORGANISM: Clostridium leptum
<220> FEATURE:
<221> NAME/KEY: rRNA
<222> LOCATION: (1)..(1490)
<223> OTHER INFORMATION: 16S rRNA coding gene sequence of Clostridium
      strain 11

<400> SEQUENCE: 31

agagtttgat cctggctcag gatgaacgct ggcggcgtgc ttaacacatg caagtcgaac     60

gagaatccag tgaaggagtt ttcggacaac ggatctggag gaaagtggcg gacgggtgag    120

taacgcgtga gcaatctgcc ttggagtggg gaataacggt tggaaacagc cgctaatacc    180

gcatgatgcg tctgggaggc atctctctgg acgccaaaga tttatcgctc tgagatgagc    240

tcgcgtctga ttagcttgtt ggcggggtaa aggcccacca aggcgacgat cagtagccgg    300

actgagaggt tggccggcca cattgggact gagacacggc ccagactcct acgggaggca    360

gcagtgggga atattgggca atgggcgcaa gcctgaccca gcaacgccgc gtgaaggaag    420

aaggctttcg ggttgtaaac ttcttttctg agggacgaag aaagtgacgg tacctcagga    480

ataagccacg gctaactacg tgccagcagc cgcggtaata cgtaggtggc aagcgttatc    540

cggatttatt gggtgtaaag ggcgtgtagg cgggaaagca agtcagatgt gaaaactcag    600

ggctcaaccc tgagcctgca tttgaaactg tttttcttga gtgctggaga ggcaatcgga    660

attccgtgtt gtagcggtga aatgcgtaga ttataccgga ggaaccacca gtggcggaag    720

gcggattgct ggaacagtaa ctgacgctga ggcgccgaaa gcgtggggag caaacaggat    780

agataccctg gtagtccacg ccgtaaacga tggatactaa gtgtggggga ctgacccctt    840

cgtgcccagc taagcaataa gtttcccacc tggggagtac gatcgcaggt gaaactcaaa    900

ggaattgacg gggcccgcc caagcgggtg gagtaggggt taattggagc aacgggaaga     960

accttaccag ggcttgacat cctgtaacga accagaagag ggattaggtg ccttcgggga   1020

aagcagagac aggtggtgca tggttgtcgt cagctcgtgt cgtgagatgt gggtaaagtc   1080

ccgcaacgag cgcaaccctt attgttagtt gctacgcaag agcactctag cgagactgcc   1140

gttgacaaaa cggaggaagg tggggacgac gtcaaatcat catgcccctt acgtcctggg   1200

ccacacacgt actacaatgg cggccaacaa agagaggcaa gaccgcgagg tggagaaaat   1260

ctcaaaaagc cgtcccagtt cggatcgcag gctgcaaccc gcctgcgtga agttggaatc   1320

gctagtaatc gcggatcagc atgccgcggt gaatacgttc ccgggccttg tacacaccgc   1380
```

```
ccgtcacacc atgagagtcg ggaacacccg aagtccgtag cctaaccgca agggggcgc   1440

ggccgaaggt gggttcgata attggggtga agtcgtaaca aggtagccgt             1490
```

<210> SEQ ID NO 32
<211> LENGTH: 1489
<212> TYPE: DNA
<213> ORGANISM: Clostridium coccoides
<220> FEATURE:
<221> NAME/KEY: rRNA
<222> LOCATION: (1)..(1489)
<223> OTHER INFORMATION: 16S rRNA coding gene sequence of Clostridium strain 12

<400> SEQUENCE: 32

```
agagtttgat catggctcag gatgaacgct ggcggcgtgc ttaacacatg caagtcgaac     60

gggctcatat tgaaacctag tgatgtatga gttagtggcg gacgggtgag taacgcgtgg    120

agaacctgcc gtatactggg ggataacact tagaaatagg tgctaatacc gcataagcgc    180

acagcttcgc atgaagcagt gtgaaaaact ccggtggtat acgatggatc cgcgtctgat    240

tagctggttg gcggggtaac agcccaccaa ggcgacgatc agtagccggc ctgagagggt    300

gaacggccac attgggactg agacacggcc caaactccta cgggaggcag cagtggggaa    360

tattgcacaa tgggggaaac cctgatgcag cgacgccgcg tgagtgaaga agtatttcgg    420

tatgtaaagc tctatcagca gggaagaaat actgacctta cggtcagcag acggtacctg    480

actaagaagc cccggctaac tacgtgccag cagccgcggt aatacgtagg gggcaagcgt    540

tatccggatt tactgggtgt aaagggagcg tagacggcag cgcaagtctg aagtgaaatc    600

ccatggctta accatggaac tgctttggaa actgtgcagc tggagtgcag gagaggtaag    660

cggaattcct agtgtagcgg tgaatgcgta gatattagag gacaccagtg gcgatgcggc    720

ttactggact gtactgacgt tgagctcgaa agcgtgggga gcaccagaat tagaatactg    780

tagtcacgcc gtaaccgatg atactaggtg tgggggacca aggtctcgtg ccggcggcaa    840

acgcattaag taatccacct ggggagtacg ttcgcaagaa tgaaactcaa aggaattgac    900

ggggacccgc acaagcggtg gagcatgtgg tttaattcga agcaacgcga agaaccttac    960

ctggtcttga catcccgatg acgagtgagc aaagtcactt tcccttcggg gcattggaga   1020

caggtggtgc atggttgtcg tcagctcgtg tcgtgagatg ttgggttaag tcccgcaacg   1080

agcgcaaccc ctatttccag tagccagcag gtagagctgg gcactctgga gagactgccc   1140

gggataaccg ggaggaaggc ggggatgacg tcaaatcatc atgcccctta tgatcagggc   1200

tacacacgtg ctacaatggc gtaaacaaag ggaagcgaga cggtgacgtt aagcaaatcc   1260

caaaaataac gtcccagttc ggattgtagt ctgcaactcg actacatgaa gctggaatcg   1320

ctagtaatcg cgaatcagaa tgtcgcggtg aatacgttcc cgggtcttgt acacaccgcc   1380

cgtcacacca tgggagtcgg aaatgcccga agtcagtgac ctaaccgaaa ggaaggagct   1440

gccgaaggtg gagccggtaa ctggggtgaa gtcgtaacaa ggtagccgt              1489
```

<210> SEQ ID NO 33
<211> LENGTH: 1456
<212> TYPE: DNA
<213> ORGANISM: Clostridium coccoides
<220> FEATURE:
<221> NAME/KEY: rRNA
<222> LOCATION: (1)..(1456)
<223> OTHER INFORMATION: 16S rRNA coding gene sequence of Clostridium strain 13

<400> SEQUENCE: 33

```
agagtttgat catggctcag gatgaacgct ggcggcgtgc ttaacacatg caagtcgaac      60

gaagcacttg agaacgattc ttcggatgag gacttttgtg actgagtggc ggacgggtga     120

gtaacgcgtg ggtaacctgc cctatacagg gggataacag ttagaaatga ctgctaatac     180

cgcataagcg cactaaaacc gcatggttcg gtgtgaaaaa ctgaggtggt ataggatgga     240

cccgcgtctg attagcttgt tggtggggta acggctcacc aaggcgacga tcagtagccg     300

gcctgagagg gcgaccggcc acattgggac tgagacacgg cccaaactcc tacgggaggc     360

agcagtgggg gatattgcac aatgggggga accctgatgc agcgacgccg cgtgggtgaa     420

gaagcgcctc ggcgcgtaaa gccctgtcag cagggaagaa aatgacggta cctgaagaag     480

aagccccggc taactacgtg ccagcagccg cggtaatacg taggggcaag cgttattccg     540

ggatttactg ggtgtaaagg gggcgcagac ggcgatgcaa gccaggagtg aagcccgggg     600

cccacccggg actgctcttg gactgcgtgc tggagtgcag aaggggcagc gatcctgtgt     660

accgtgaatt gcgtagatat cagagacacg ttgcgagcgc tgctgactgc actgacgtga     720

gcgaagctgg agcacagata gatactgtag tcagcgtaac gatgatacta gtgtcgggag     780

cagagactgc ccgttgcggc agcccaacgc attagtattc cacttgggga gtacgtttcg     840

cagaatgaac ttcaaggaaa tgacggggac ccgcacaagg cggtggagca tgtggtttaa     900

ttcgaagcaa cgcgaagaac cttaccaggc cttgacatcc cccctggatg gcccgtaacg     960

gggtcagcct ttcggggcag gggagacagg tggtgcatgg ttgtcgtcag ctcgtgtcgt    1020

gagatgttgg gttaagtccc gcaacgagcg caacccctgc ccgcagtagc cagcatttta    1080

gatggggact ctgcggggac tgccggggac aacccggagg aaggcgggga tgacgtcaaa    1140

tcatcatgcc ccttatggcc tgggctacac acgtgctaca atggcgccga cagagggagg    1200

cgaagcggcg acgcggagcg aaccccaaaa acggcgtccc agttcggatt gtagtctgca    1260

acccgactac atgaagccgg aatcgctagt aatcgcggat cagaatgccg cggtgaatac    1320

gttcccgggt cttgtacaca ccgcccgtca caccatggga gccgggaatg cccgaagtct    1380

gtgaccgaac ccgtaagggg aggggcagcc gaaggcaggc tcggtgactg ggtgaagtc     1440

gtaacaaggt agccgt                                                    1456
```

<210> SEQ ID NO 34
<211> LENGTH: 1475
<212> TYPE: DNA
<213> ORGANISM: Clostridium leptum
<220> FEATURE:
<221> NAME/KEY: rRNA
<222> LOCATION: (1)..(1475)
<223> OTHER INFORMATION: 16S rRNA coding gene sequence of Clostridium strain 14

<400> SEQUENCE: 34

```
agagtttgat cctggctcag gacgaacgct ggcggcgtgc ttaacacatg caagtcgaac      60

ggagcacccc tgaaggagtt ttcggacaac ggatgggaat gcttagtggc ggactggtga     120

gtaacgcgtg aggaacctgc cttccagagg gggacaacag ttggaaacga ctgctaatac     180

cgcatgatgc gttggagccg catgactccg acgtcaaaga tttatcgctg gaagatggcc     240

tcgcgtctga ttagctagtt ggtgaggtaa cggcccacca aggcgacgat cagtagccgg     300

actgagaggt tggccggcca cattgggact gagatacggc ccagactcct acgggaggca     360

gcagtgggga atattgggca atggacgcaa gtctgaccca gcaacgccgc gtgaaggaag     420

aaggctttcg ggttgtaaac ttcttttaag gggaagagc agaagacggt accccttgaa      480
```

```
taagccacgg ctaactacgt gccagcagcc gcggtaatac gtaggtggca agcgttgtcc    540

ggatttactg ggtgtaaagg gcgtgcagcc ggagagacaa gtcagatgtg aaatccacgg    600

gctcaacccg tgaactgcat ttgaaactgt ttcccttgag tgtcggagag gtaatcggaa    660

tttccttgtg tagcggtgaa tgcgtagata taaggaagga cacagtggcg agcggattac    720

tggacgatac tgacgtgagc gcgaaagcgt gggggagcaa cagaaattag atactgtagt    780

gcagctgtaa cgatcgatac tagttgcggg actgacccct tgcgtgcgag ttacacaata    840

agtatcgcac ctgggagtac gatcgcaagg ttggaactca aaggaattga cggggcccgc    900

acaagcgttg gattatgtgg tttaattcga agcaacgcga agaaccttac cagggcttga    960

catcctgcta acgaagtaga gatacattag gtgcccttcg ggaaagtag agacaggtgg   1020

tgcatggttg tcgtcagctc gtgtcgtgag atgttgggtt aagtcccgca acgagcgcaa   1080

cccctattgt tagttgctac gcaagagcac tctagcgaga ctgccgttga caaaacggag   1140

gaaggcgggg acgacgtcaa atcatcatgc cccttatgtc ctgggctaca cacgtaatac   1200

aatggcggtt aacaaaggga tgcaaagccg cgaggcagag cgaaccccaa aaagccgtcc   1260

cagttcggat cgcaggctgc aacccgcctg cgtgaagtcg gaatcgctag taatcgcgga   1320

tcagcatgcc gcggtgaata cgttcccggg ccttgtacac accgcccgtc acaccatgag   1380

agtcgggaac acccgaagtc cgtagcctaa ccgcaaggag ggcgcggccg aaggtgggtt   1440

cgataattgg ggtgaagtcg taacaaggta gccgt                              1475
```

```
<210> SEQ ID NO 35
<211> LENGTH: 1480
<212> TYPE: DNA
<213> ORGANISM: Clostridium coccoides
<220> FEATURE:
<221> NAME/KEY: rRNA
<222> LOCATION: (1)..(1480)
<223> OTHER INFORMATION: 16S rRNA coding gene sequence of Clostridium
      strain 15

<400> SEQUENCE: 35

agagtttgat cctggctcag gatgaacgct ggcggcgtgc ttaacacatg caagtcgaac     60

gggctcatat tgaaacctag tgatgtatga gttagtggcg gacgggtgag taacgcgtgg    120

agaacctgcc gtatactggg ggataacact tagaaatagg tgctaatacc gcataagcgc    180

acagcttcgc atgaagcagt gtgaaaaact ccggtggtat acgatggatc cgcgtctgat    240

tagctggttg gcggggtaac agcccaccaa ggcgacgatc agtagccggc ctgagagggt    300

gaacggccac attgggactg agacacggcc caaactccta cgggaggcag cagtggggaa    360

tattgcacaa tgggggaaac cctgatgcag cgacgccgcg tgagtgaaga agtatttcgg    420

tatgtaaagc tctatcagca gggaagaaat actgacctta cggtcagcag acggtacctg    480

actaagaagc cccggctaac tacgtgccag cagccgcggt aatacgtagg ggcaagcgtt    540

atccggattt actgggtgta aagggagcgt agacggcagc gcaagtctga agtgaaatcc    600

catggcttaa cccatggaac tgctttggaa actgtgcagc tggagtgcag gagaggtaag    660

cggaattcct agtgtagcgt gaaatgcgta gattattagg aggacaacag tgcgagcgct    720

actgacgtga ggctcgaagc gtgggagcaa acaggattag atacctggta gtcacgcgta    780

aacgatgatt actagggtgt tgggggacca aggtcttcgg tgccggcgca aacgcattaa    840

gtaatccacc tggggagtac gttcgcaaga atgaaactca aaggaattga cggggacccg    900

cacaagcggt ggagcatgtg gtttaattcg aagcaacgcg aagaacctta cctggtcttg    960
```

```
acatcccgat gacgagtgag caaagtcact ttcccttcgg ggcattggag acaggtggtg   1020

catggttgtc gtcagctcgt gtcgtgagat gttgggttaa gtcccgcaac gagcgcaacc   1080

cctatttcca gtagccagca ggtagagctg ggcactctgg agagactgcc cgggataacc   1140

gggaggaagg cggggatgac gtcaaatcat catgcccctt atgatcaggg ctacacacgt   1200

gctacaatgg cgtaaacaaa gggaagcgag acggtgacgt taagcaaatc ccaaaaataa   1260

cgtcccagtt cggattgtag tctgcaactc gactacatga agctggaatc gctagtaatc   1320

gcgaatcaga atgtcgcggt gaatacgttc ccgggtcttg tacacaccgc ccgtcacacc   1380

atgggagtcg gaaatgcccg aagtcagtga cctaaccgaa aggaaggagc tgccgaaggt   1440

ggagccggta actggggtga agtcgtaaca aggtagccgt                         1480


<210> SEQ ID NO 36
<211> LENGTH: 1486
<212> TYPE: DNA
<213> ORGANISM: Clostridium papyrosolvens
<220> FEATURE:
<221> NAME/KEY: rRNA
<222> LOCATION: (1)..(1486)
<223> OTHER INFORMATION: 16S rRNA coding gene sequence of Clostridium
      strain 16

<400> SEQUENCE: 36

agagtttgat cctggctcag gataaacgct ggcggcgcac ataagacatg caagtcgaac     60

ggacttaact cattctttta gattgagagc ggttagtggc ggactggtga gtaacacgta    120

agcaacctgc ctatcagagg ggaataacag tgagaaatca ttgctaatac cgcatatgct    180

cacagtatca catgatacag tgaggaaagg agcaatccgc tgatagatgg gcttgcgcct    240

gattagttag ttggtggggt aacggcctac caagacgacg atcagtagcc ggactgagag    300

gttgaacggc cacattggga ctgagatacg gcccagactc ctacgggagg cagcagtcgg    360

gaatattgcg caatggagga aactctgacg cagtgacgcc gcgtatagga agaaggtttt    420

cggattgtaa actattgtcg ttagggaaga taaaagactg tacctaagga ggaagccccg    480

gctaactatg tgccagcagc cgcggtaata catagggggc aagcgttatc cggaattatt    540

gggtgtaaag ggtgcgtaga cggaagaaca agttggttgt gaaatccctc ggctcaactg    600

aggaactgca accaaaacta ttctccttga gtgtcggaga ggaaagtgga attcctagtg    660

tagcggtgaa atgcgtagat attaggagga acaccagtgg cgaaggcgac tttctggacg    720

ataactgacg ttgaggcacg aaagtgtggg gagcaaacag gattagatac cctggtagtc    780

cacactgtaa acgatggata ctaggtgtag ggtgtattaa gcactctgtg ccgccgctaa    840

cgcattaagt atcccacctg gggagtacga ccgcaaggtt gaaactcaaa ggaattgacg    900

ggggcccgca caagcagtgg agtatgtggt ttaattcgaa gcaacgcgaa gaaccttacc    960

agggcttgac atataccgga atatactaga gatagtatag tccttcggga ctggtataca   1020

ggtggtgcat ggttgtcgtc agctcgtgtc gtgagatgtt gggttaagtc ccgcaacgag   1080

cgcaacccct atcgttagtt gctagcaggt aatgctgaga actctagcga gactgccggt   1140

gataaatcgg aggaaggtgg ggatgacgtc aaatcatcat gccctttatg tcctgggcta   1200

cacacgtact acaatggccg taacagaggg aagcaatata gtgatatgga gcaaaaccct   1260

aaaagcggtc tcagttcgga ttgaaggctg aaattcgcct tcatgaagcc ggaattgcta   1320

gtaatggcag gtcagcatac tgccgtgaat acgttcccgg gccttgtaca caccgcccgt   1380

cacaccatga gagttggaaa tacccgaagc ctgtgagcta actgtaaaga ggcagcagtc   1440
```

```
gaaggtagag ccaatgattg gggtgaagtc gtaacaaggt agccgt                1486


<210> SEQ ID NO 37
<211> LENGTH: 1493
<212> TYPE: DNA
<213> ORGANISM: Clostridium leptum
<220> FEATURE:
<221> NAME/KEY: rRNA
<222> LOCATION: (1)..(1493)
<223> OTHER INFORMATION: 16S rRNA coding gene sequence of Clostridium
      strain 17

<400> SEQUENCE: 37

agagtttgat catggctcag gatgaacgct ggcggcgtgc ttaacacatg caagtcgaac     60

gagaaccaac ggattgagga ttcgtccaaa tgaagttggg gaaagtggcg gacgggtgag    120

taacgcgtga gcaatctgcc ttggagtggg gaataacggt tggaaacagc cgctaatacc    180

gcatgatgcg tctgggaggc atctctctgg acgccaaaga tttatcgctc tgagatgagc    240

tcgcgtctga ttagctagtt ggcggggcaa cggcccacca aggcgacgat cagtagccgg    300

actgagaggt tggccggcca cattgggact gagacacggc ccagactcct acgggaggca    360

gcagtgggga atattgggca atgggcgcaa gcctgaccca gcaacgccgc gtgaaggaag    420

aaggctttcg ggttgtaaac ttcttttaag gggacgaac aaatgacggt accccttgaa     480

taagccacgg ctaactacgt gccagcagcc gcggtaatac gtaggtggca agcgttatcc    540

ggatttattg ggtgtaaagg gcgtgtaggc gggaatgcaa gtcagatgtg aaaactatgg    600

gctcaaccca tagcctgcat ttgaaactgt atttcttgag tgctggagag gcaatcggaa    660

ttccgtgtgt agcggtgaaa tgcgtagata tacggaggaa caccagtggc gaagcggatt    720

gctggacagt aactgacgct gaggcgcgaa agcgtgggga gcaaacaggg attagatacc    780

ctggtagtca cgccgtaaac gatggatact aggtgtgggg ggactgaccc cctccgtgcc    840

gcagctaacg caataagtat cccacctggg gagtacgatc gcaagggttg aaactcaaag    900

gaattgacgg gggcccgcac aagcggtgga gtatgtggtt taattcgaag caacgcgaag    960

aaccttacca gggcttgaca tcctgctaac gaaccagaga tggatcaggt gcccttcggg   1020

gaaagcagag acaggtggtg catggttgtc gtcagctcgt gtcgtgagat gttgggttaa   1080

gtcccgcaac gagcgcaacc cctattgtta gttgctacgc aagagcactc tagcgagact   1140

gccgttgaca aaacggagga aggtggggac gacgtcaaat catcatgccc cttacgtcct   1200

gggccacaca cgtactacaa tggcggccaa caaagagagg caagaccgcg aggtggagca   1260

aatctcaaaa agccgtccca gttcggatcg caggctgcaa cccgcctgcg tgaagttgga   1320

atcgctagta atcgcggatc agcatgccgc ggtgaatacg ttcccgggcc ttgtacacac   1380

cgcccgtcac accatgagag tcgggaacac ccgaagtccg tagcctgacc gcaagggggg   1440

cgcggccgaa ggtgggttcg ataattgggg tgaagtagta acaaggtagc cgt          1493


<210> SEQ ID NO 38
<211> LENGTH: 1493
<212> TYPE: DNA
<213> ORGANISM: Clostridium leptum
<220> FEATURE:
<221> NAME/KEY: rRNA
<222> LOCATION: (1)..(1493)
<223> OTHER INFORMATION: 16S rRNA coding gene sequence of Clostridium
      strain 18

<400> SEQUENCE: 38
```

```
agagtttgat cctggctcag gacgaacgct ggcggcgcgc ctaacacatg caagtcgaac      60

ggagcttata tttcagaagt tttcggatgg acgagagata agcttagtgg cggacgggtg     120

agtaacacgt gagcaacctg cctttcagag ggggataaca gttggaaacg actgctaata     180

ccgcataacg ctgcgatggg gcatcccgat gcagccaaag gagcaatccg ctgaaagatg     240

ggctcgcggc cgattagcta gttggtgggg caacggccca ccaaggcgac gatcggtagc     300

cggactgaga ggttgatcgg ccacattggg actgagacac ggcccagact cctacgggag     360

gcagcagtgg gggatattgc acaatggagg aaactctgat gcagcgacgc cgcgtgaggg     420

aagacggtct tcggattgta aacctctgtc tttggggaag aaaatgacgg tacccaaaga     480

ggaagctccg gctaactacg tgccagcagc cgcggtaata cgtacggagc gagcgttgtc     540

cggaattact gggtgtaaag ggagcgtacg cgggcgagaa agttgaatgt taaatctacc     600

ggcttaactg gtagctgcgt tcaaaacttc ttgtcttgag tgaagtagag gcaggcggaa     660

ttcctagtgt agcggtgaaa tgcgtagata taggaggaca ccagtgggcg aagccgcctg     720

ctgggcttta actgacgctg aggctcgaaa gcgtggggag caaaccagga ttagataccc     780

tggtagtcaa cgctgtaaac gatgattact aggtgtgggg gggactgacc ccctccgtgc     840

cgcagttaac acaataagta tccacctggg gagtacggcc gcaaagtttg aaaactcaaa     900

aggaatgacg gggcccgca caaagcagtg gagtatgtgg tttaatttcg aagcaacgcg      960

aagaacctta ccaggtcttg acatcgtgcg catagcctag agataggtga agcccttcgg    1020

ggcgcacaga caggtggtgc atggttgtcg tcagctcgtg tcgtgagatg ttgggttaag    1080

tcccgcaacg agcgcaaccc ttattattag ttgctacgca agagcactct aatgagactg    1140

ccgttgacaa aacggaggaa ggtggggatg acgtcaaatc atcatgcccc ttatgacctg    1200

ggctacacac gtactacaat ggcactgaaa cagagggaag cgacatcgcg aggtgaagcg    1260

aatcccaaaa aagtgtccca gttcggattg caggctgcaa ctcgcctgca tgaagtcgga    1320

attgctagta atcgcggatc agcatgccgc ggtgaatacg ttcccgggcc ttgtacacac    1380

cgcccgtcac accatgggag tcggtaacac ccgaagccag tagcctaacc gcaaggaggg    1440

cgctgtcgaa ggtgggattg atgactgggg tgaagtcgta acaaggtagc cgt           1493
```

```
<210> SEQ ID NO 39
<211> LENGTH: 1483
<212> TYPE: DNA
<213> ORGANISM: Clostridium leptum
<220> FEATURE:
<221> NAME/KEY: misc_feature
<222> LOCATION: (1)..(1483)
<223> OTHER INFORMATION: 16S rRNA coding gene sequence of Clostridium
      strain 19

<400> SEQUENCE: 39
```

```
agagtttgat cctggctcag gacgaacgct ggcggcacgc ctaacacatg caagtcgaac      60

ggagtgaaga tgcttgcatc tgaacttagt ggcggacggg tgagtaacac gtgagcaacc     120

tgcctttcag agggggataa cgtttggaaa cgaacgctaa taccgcataa aatatcggag     180

tcgcatggca ctgatatcaa aggagcaatc cgctgaaaga tgggctcgcg tccgattagg     240

cagttggcgg ggtaacggcc caccaaaccg acaatcggta gccggactga gaggttgaac     300

ggccacattg ggactgagac acggcccaga ctcctacggg aggcagcagt gggggatatt     360

gcacaatggg ggaaaccctg atgcagcgat gccgcgtgaa tgaagacggc cttcgggttg     420

taaagttctg tcgcagggga cgaaaatgac ggtaccctgc aagaaagctc cggctaacta     480
```

```
cgtgccagca gccgcggtaa tacgtaggga gcaagcgttg tccggaatta ctgggtgtaa    540

agggagcgta ggcgggagga taaagttgaa tgtgaaatct atgggctcaa cccatagctg    600

cgttcaaaac tgttcttctt gagtgaagta gaggcaggcg gaattcctag tgtagcggtg    660

aaatgcgtag atattaggag gaacaccagt ggcgaaagcg gcctgctggg cttttactga    720

cgctgaggct cgaaagcgtg ggtagcaaac agaattagat accctgtta ttcacggcgg    780

taaacgatga ttactaggtt tgggttgacc tgacccccat tcgtgccgga agtaacacca    840

taaagtaatc cacctggggg agtacggccg ccaggttgaa acttcaaaag gaattgacgg    900

gggcccgcac aagcagtgga ggtatgtggt ttaatttcga cgcaaacgcg aagaacctta    960

ccagggtctt gacatcgagt gacggacata gagatatgtc tttcctttcg ggacacgaag   1020

acaggtggtg catggttgtc gtcagctcgt gtcgtgagat gttgggttaa gtcccgcaac   1080

gagcgcaacc cttaccatta gttgctacgc aagagcactc tgatgggact gccgttgaca   1140

aaacggagga aggtggggat gacgtcaaat catcatgccc cttatgacct gggcgacaca   1200

cgtactacaa tggcggtcaa cagagggagg caaagccgcg aggcagagca aacccctaaa   1260

agccgtctca gttcggattg caggctgcaa ctcgcctgca tgaagtcgga attgctagta   1320

atcgcggatc agcatgccgc ggtgaatacg ttcccgggcc ttgtacacac cgcccgtcac   1380

accatgagag ccggtaacac ccgaagtcaa tagtctaacc gcaaggagga cattgccgaa   1440

ggtgggattg gtaattgggg tgaagtcgta acaaggtagc cgt                     1483
```

<210> SEQ ID NO 40
<211> LENGTH: 1511
<212> TYPE: DNA
<213> ORGANISM: Clostridium coccoides
<220> FEATURE:
<221> NAME/KEY: rRNA
<222> LOCATION: (1)..(1511)
<223> OTHER INFORMATION: 16S rRNA coding gene sequence of Clostridium strain 20

<400> SEQUENCE: 40

```
agagtttgat cctggctcag gatgaacgct ggcggcgtgc ttaacacatg caagtcgaac     60

gggctcatat tgaaacctag tgatgtatga gttagtggcg gacgggtgag taacgcgtgg    120

agaacctgcc gtatactggg ggataacact tagaaatagg tgctaatacc gcataagcgc    180

acagcttcgc atgaaacagt gtgaaaaact ccggtggtat acgatggatc cgcgtctgat    240

tagctggttg gcggggtaac agcccaccaa ggcgacgatc agtagccggc ctgagagggt    300

gaacggccac attgggactg agacacggcc caaactccta cgggaggcag cagtggggaa    360

tattgcacaa tgggggaaac cctgatgcag cgacgccgcg tgagtgaaga agtatttcgg    420

tatgtaaagc tctatcagca gggaagaaat actgacctta cggtcagcag acggtacctg    480

actaagaagc cccggctaac tacgtgccag cagccgcggt aatacgtagg ggcaagcgtt    540

atccggattt actgggtgta aagggagcgt agacggcagc gcaagtctga gtgaaatccc    600

atggcttaac catggaactg ctttggaaac tgtgcagctg gagtgcagga gaggtaaagc    660

ggaattccta gtgtagcggg tgaaatgcgt agatatagga ggaacaacag tggcggaagg    720

cggctactgg gactgtaact gacgttgagg ctcgaaagcg tggggagcaa acaggattag    780

ataccctggt agtcacgccg taaacgatga ttactaggtg ttgggggacc ataggtcttc    840

ggtgccggcg caaacgcaat taagtaatcc acctggggga gtacgttcgc aagaatgaaa    900

ctcaaaggaa ttgacgggga cccgcacaaa gcggtggagc atgtggttta attcgaaagc    960
```

```
aaacgcgaag aaaccttacc tggtcttgac atcccgatga cgagtgagca aagtcacttt   1020

cccttcgggg caattggaga caggtggtgc atgggttgtc gtcagctcgt gtcgtgagat   1080

gttgggttaa gtcccgcaac gagcgcaacc cctatttcca gtagccagca ggtagagctg   1140

ggcactctgg agagactgcc cgggataacc gggaggaagg cggggatgac gtcaaatcat   1200

catgcccctt atgatcaggg ctacacacgt gctacaatgg cgtaaacaaa gggaagcgag   1260

acggtgacgt taagcaaatc ccaaaaataa cgtcccagtt cggattgtag tctgcaactc   1320

gattacatga agctggaatc gctagtaatc gcgaatcaga atgtcgcggt gaatacgttc   1380

ccgggtcttg tacacaccgc ccgtcacacc atgggagtcg gaaatgcccg aagtcagtga   1440

cctaaccgaa aggaaggagc tgccgaaggt ggagccggta actggggtga agtagataac   1500

aaggtagccg t                                                        1511
```

<210> SEQ ID NO 41
<211> LENGTH: 1495
<212> TYPE: DNA
<213> ORGANISM: Clostridium leptum
<220> FEATURE:
<221> NAME/KEY: rRNA
<222> LOCATION: (1)..(1495)
<223> OTHER INFORMATION: 16S rRNA coding gene sequence of Clostridium strain 21

<400> SEQUENCE: 41

```
agagtttgat cctgcgctca ggacgaacgc tggcggcgcg cctaacacat gcaagtcgaa     60

cgggactatt ttgggagaag ttttcggatg gatctcggga tagtttagtg gcggacgggt    120

gagtaacgcg tgggcaacct gccttacaca gggggataac aattagaaat gattgctaat    180

accgcataag accacggtac tgcatggtac agtggtaaaa actgaggtgg tgtaagatgg    240

gcccgcgtct gattaggtag ttggtggggt agaagcctac caagccgacg atcagtagcc    300

gacctgagag ggcgaccggc cacattggga ctgagacacg gcccaaactc ctacgggagg    360

cagcagtggg gaatattgca caatggggga aaccctgatg cagcgacgcc gcgtgagtga    420

ggaagtattt cggtatgtaa agctctatca gcagggaaga aaatgacggt acctgactaa    480

gaagccccgg ctaactacgt gccagcagcc gcggtaatac gtagggggca agcgttatcc    540

ggatttactg ggtgtaaagg gagcgtagac ggacttgcaa gtctgatgtg aaaatccggg    600

ggcccaaccc cggaactgca ttggaaactg tatatctaga gtgtcggaga ggcaagtgga    660

atttcctggt gtagcggtga aatgcgtaga tatcagagga acaccagtgg cgaaggcgct    720

tgcctgacga tgactgacgt tgaagctcga aagcgtgggg tagcaaacag aattagatac    780

cctggtaagt caacccggta aacgatgatt actaggtttt ggttggactg accccatccg    840

tgccggagta acaccaataa gttatccaac ctgggaagta cggccggcag gttgaaactc    900

aaaaggaaat gacgggggcc cgcacaagca gttgaagtat gtgggttaat tcgacgcaaa    960

cgcgaagaac cttaccaggt cttgacatcg agtgacggac atagagatat gtctttcctt   1020

cgggacacga agacaggtgg tgcatggttg tcgtcagctc gtgtcgtgag atgttgggtt   1080

aagtcccgca acgagcgcaa cccttaccat tagttgctac gcaagagcac tctgatggga   1140

ctgccgttga caaaacggag gaaggtgggg atgacgtcaa atcatcatgc cccttatgac   1200

ctgggcgaca cacgtactac aatggcggtc aacagaggga ggcaaagccg cgaggcagag   1260

caaaccccta aaagccgtct cagttcggat tgcaggctgc aactcgcctg catgaagtcg   1320

gaattgctag taatcgcgga tcagcatgcc gcggtgaata cgttcccggg ccttgtacac   1380
```

```
accgcccgtc acaccatgag agccggtaac acccgaagtc aatagtctaa ccgcaaggag   1440

gacattgccg aaggtgggat tggtaattgg ggtgaagtcg taacaaggta gccgt        1495


<210> SEQ ID NO 42
<211> LENGTH: 1491
<212> TYPE: DNA
<213> ORGANISM: Clostridium leptum
<220> FEATURE:
<221> NAME/KEY: rRNA
<222> LOCATION: (1)..(1491)
<223> OTHER INFORMATION: 16S rRNA coding gene sequence of Clostridium
      strain 22

<400> SEQUENCE: 42

agagtttgat cctggctcag gatgaacgct ggcggcgtgc ttaacacatg caagtcgaac     60

gagaatccag tgaaggagtt ttcggacaac ggatctggag gaaagtggcg gacgggtgag    120

taacgcgtga gcaatctgcc ttggagtggg gaataacggt tggaaacagc cgctaatacc    180

gcatgatgcg tctgggaggc atctctctgg acgccaaaga tttatcgctc tgagatgagc    240

tcgcgtctga ttagcttgtt ggcggggtaa aggcccacca aggcgacgat cagtagccgg    300

actgagaggt tggccggcca cattgggact gagacacggc ccagactcct acgggaggca    360

gcagtgggga atattgggca atgggcgcaa gcctgaccca gcaacgccgc gtgaaggaag    420

aaggctttcg ggttgtaaac ttcttttctg agggacgaag aaagtgacgg tacctcagga    480

ataagccacg gctaactacg tgccagcagc cgcggtaata cgtaggtggc aagcgttatc    540

cggatttatt gggtgtaaag ggcgtgtagg cgggaaagca agtcagatgt gaaaactcag    600

ggctcaaccc tgagcctgca tttgaaactg tttttcttga gtgctggaga ggcaatcgga    660

attccgtgtg tagcggtgaa atgcgtagat atacggagga caccagtggc gaagcggatt    720

gctggacagt aactgacgct gaggcgcgaa gcgtggggag caaacaggat tagataccct    780

ggtagtccac gccgtaaacg atggatacta ggtgtggggg gactgacccc ctccgtgccg    840

cagctaacgc aataagtatc ccacctgggg agtacgatcg caaggttgaa actcaaagga    900

attgacgggg gcccgcacaa gcggtggagt atgtggttta attcgaagca acgcgaagaa    960

ccttaccagg gcttgacatc ctgctaacga accagagatg gattaggtgc ccttcgggga   1020

aagcagagac aggtggtgca tggttgtcgt cagctcgtgt cgtgagatgt tgggttaagt   1080

cccgcaacga gcgcaacccct tattgttagt tgctacgcaa gagcactcta gcgagactgc   1140

cgttgacaaa acggaggaag gtggggacga cgtcaaatca tcatgcccct tacgtcctgg   1200

gccacacacg tactacaatg gcggccaaca aagagaggca agaccgcgag gtggagcaaa   1260

tctcaaaaag ccgtcccagt tcggatcgca ggctgcaacc cgcctgcgtg aagttggaat   1320

cgctagtaat cgcggatcag catgccgcgg tgaatacgtt cccgggcctt gtacacaccg   1380

cccgtcacac catgagagtc gggaacaccc gaagtccgta gcctaaccgc aagggggcg    1440

cggccgaagg tgggttcgat aattggggtg aagtcgtaac aaggtagccg t            1491


<210> SEQ ID NO 43
<211> LENGTH: 1495
<212> TYPE: DNA
<213> ORGANISM: Clostridium leptum
<220> FEATURE:
<221> NAME/KEY: rRNA
<222> LOCATION: (1)..(1495)
<223> OTHER INFORMATION: 16S rRNA coding gene sequence of Clostridium
      strain 23

<400> SEQUENCE: 43
```

```
agagtttgat cctgtgcctc aggatgaacg ctggcggcgt gcttaacaca tgcaagtcga     60

acgagaacca acggattgag gattcgtcca aatgaagttg gggaaagtgg cggacgggtg    120

agtaacgcgt gagcaatctg ccttggagtg gggaataacg gttggaaaca gccgctaata    180

ccgcatgatg cgtctgggag gcatctctct ggacgccaaa gatttatcgc tctgagatga    240

gctcgcgtct gattagctag ttggcggggc aacggcccac caaggcgacg atcagtagcc    300

ggactgagag gttggccggc cacattggga ctgagacacg gcccagactc ctacgggagg    360

cagcagtggg gaatattggg caatgggcgc aagcctgacc cagcaacgcc gcgtgaagga    420

agaaggcttt cgggttgtaa acttctttta agggggacga acaaatgacg gtaccccttg    480

aataagccac ggctaactac gtgccagcag ccgcggtaat acgtaggtgg caagcgttat    540

ccggatttat tgggtgtaaa gggcgtgtag gcgggaatgc aagtcagatg tgaaaactat    600

gggctcaacc catagcctgc atttgaaact gtatttcttg agtgctggag aggcaatcgg    660

aattccgtgt gtagcggtga aatgcgtaga tatacggagg aacaccagtg gcgaaggcgg    720

attgctggac agtaactgac gctgaggcgc gaaagcgtgg ggagcaaaca ggattagata    780

ccctggtagt ccacgccgta aacgatggat actaagtgtg gggggactga ccccctccgt    840

gccgcagcta acgcaataag tatcccacct ggggagtacg atcgcaaggt tgaaactcaa    900

aggaattgac gggggcccgc acaagcggtg gagtatgtgg tttaattcga agcaacgcga    960

agaaccttac cagggcttga catcctgcta acgaaccaga gatggatcag gtgcccttcg   1020

gggaaagcag agacaggtgg tgcatggttg tcgtcagctc gtgtcgtgag atgttgggtt   1080

aagtcccgca acgagcgcaa cccctattgt tagttgctac gcaagagcac tctagcgaga   1140

ctgccgttga caaaacggag gaaggtgggg acgacgtcaa atcatcatgc cccttacgtc   1200

ctgggccaca cacgtactac aatggcggcc aacaaagaga ggcaagaccg cgaggtggag   1260

caaatctcaa aaagccgtcc cagttcggat cgcaggctgc aacccgcctg cgtgaagttg   1320

gaatcgctag taatcgcgga tcagcatgcc gcggtgaata cgttcccggg ccttgtacac   1380

accgcccgtc acaccatgag agtcgggaac acccgaagtc cgtagcctga ccgcaagggg   1440

ggcgcggccg aaggtgggtt cgataattgg ggtgaagtcg taacaaggta gccgt        1495
```

```
<210> SEQ ID NO 44
<211> LENGTH: 1440
<212> TYPE: DNA
<213> ORGANISM: Clostridium leptum
<220> FEATURE:
<221> NAME/KEY: rRNA
<222> LOCATION: (1)..(1440)
<223> OTHER INFORMATION: 16S rRNA coding gene sequence of Clostridium
      strain 24

<400> SEQUENCE: 44

agagtttgat cctggctcag gacgaacgct ggcggcacgc ctaacacatg caagtcgaac     60

ggagtgaaga tgctcgcatc tgaacttagt ggcggacggg tgagtaacac gtgagcaacc    120

tgcctttcag agggggataa cgtttggaaa cgaacgctaa taccgcataa aatatcggag    180

tcgcatggca ctgatatcaa aggagtaatc cgctgaaaga tgggctcgcg tccgattagg    240

cagttggcgg ggtaacggcc caccaaaccg acaatcggta gccggactga gaggttgaac    300

ggccacattg ggactgagac acggcccaga ctcctacggg aggcagcagt gggggatatt    360

gcacaatggg ggaaaccctg atgcagcgat gccgcgtgaa tgaagacggc cttcgggttg    420

taaagttctg tcgcagggga cgaaaatgac ggtaccctgc aagaaagctc cggctaacta    480
```

```
cgtgccagca gccgcggtaa tacgtaggga gcaagcgttg tccggaatta ctgggtgtaa    540

agggagcgta ggcgggagga taagttgaat gtgaaatcta tgggctcaac ccatagttgc    600

gttcaaaact gttcttcttg agtgaagtag aggcaggcgg aattcctagt gtagcggtga    660

aatgcgtaga tattagagga acaccagtgg cgaagcggcc tgctgggctt ttactgacgc    720

tgagctcgaa agcgtgggta gcaacaggat tagataccct ggtagtccac gcggtaaacg    780

atgattacta gtgtgggtgg actgacccat ccatgccgga gttaacacaa tagtaatcca    840

cctggggagt acgcgcagtg aactcaaagg attgacgggg cccgcacaag cagtgagtat    900

gtggtttatt cgacgcacgc gagactacag tcttgacatc gatgacggac tagagatatg    960

tctttctcgg acacgaagac aggtggtgca tggttgtcgt cagctcgtgt cgtgagatgt   1020

tgggttaagt cccgcaacga gcgcaaccct taccattagt tgttacgcaa gagcactcta   1080

atgggactgc cgttgacaaa acggaggaag gtggggatga cgtcaaatca tcatgcccct   1140

tatgacctgg gcgacacacg tactacaatg gcggtcaaca gagggaggca aagccgcgag   1200

gcagagcaaa cccctaaaag ccgtctcagt tcggattgca ggctgcaact cgcctgcatg   1260

aagtcggaat tgctagtaat cgcggatcag catgccgcgg tgaatacgtt cccgggcctt   1320

gtacacaccg cccgtcacac catgagagcc ggtaacaccc gaagtcaata gtctaaccgc   1380

aaggaggaca ttgccgaagg tgggatggta attggggtga agtagtaaca aggtagccgt   1440
```

```
<210> SEQ ID NO 45
<211> LENGTH: 1495
<212> TYPE: DNA
<213> ORGANISM: Clostridium leptum
<220> FEATURE:
<221> NAME/KEY: rRNA
<222> LOCATION: (1)..(1495)
<223> OTHER INFORMATION: 16S rRNA coding gene sequence of Clostridium
      strain 25

<400> SEQUENCE: 45

agagtttgat cctggctcag gatgaacgct ggcggcgtgc ttaacacatg caagtcgaac     60

gagaaccatt ggatcgagga ttcgtccaag tgaaggtggg gaaagtggcg gacgggtgag    120

taacgcgtga gcaatctgcc ttggagtggg gaataacggc tggaaacagc cgctaatacc    180

gcatgataca gctgggaggc atctccctgg ctgtcaaaga tttatcgctc tgagatgagc    240

tcgcgtctga ttagctagtt ggcggggtaa cggcccacca aggcgacgat cagtagccgg    300

actgagaggt tggccggcca cattgggact gagacacggc ccagactcct acgggaggca    360

gcagtgggga atattgggca atgggcgcaa gcctgaccca gcaacgccgc gtgaaggaag    420

aaggctttcg ggttgtaaac ttcttttgtc agggacgaag caagtgacgg tacctgacga    480

ataagccacg gctaactacg tgccagcagc cgcggtaata cgtagtggca agcgttatcc    540

ggatttattg ggtgtaaagg gcgtgtaggc gggaatgca agtcagatgt gaaaactatg     600

gggctcaacc catagcctgc atttgaaact gtatttcttg agtgctggag aggcaatcga    660

attccgtgtg tagcgggtga aatgcgtaga tatacggagg aacaccagtg gcgaagcgga    720

ttgctggaca agtaactgac gctgaggcgc gaaagcgtgg ggagcaaaca ggattagata    780

ccctggtagt ccacgccgta aacgatggat actaggtgtg gggggactga ccccctccgt    840

gccgcagcta acgcaataag tatcccacct ggggagtacg atcgcaaggt tgaaactcaa    900

aggaattgac gggggcccgc acaagcggtg gagtatgtgg tttaattcga cgcaacgcga    960

agaaccttac cagggcttga catcctacta acgaaccaga gatggattag gtgcccttcg   1020
```

```
gggaaagtag agacaggtgg tgcatggttg tcgtcagctc gtgtcgtgag atgttgggtt   1080

aagtcccgca acgagcgcaa cccctattgt tagttgctac gcaagagcac tctagcgaga   1140

ctgccgttga caaaacggag gaaggtgggg acgacgtcaa atcatcatgc cccttacgtc   1200

ctgggccaca cacgtactac aatggcggcc aacaaagaga ggcaaagccg cgaggtggag   1260

caaatctcaa aaagccgtcc cagttcggat cgcaggctgc aacccgcctg cgtgaagttg   1320

gaatcgctag taatcgcgga tcagcatgcc gcggtgaata cgttcccggg ccttgtacac   1380

accgcccgtc acaccatgag agtcgggaac acccgaagtc cgtagcctaa ccgcaagggg   1440

ggcgcggccg aaggtgggtt cgataattgg ggtgaagtcg taacaaggta gccgt        1495
```

```
<210> SEQ ID NO 46
<211> LENGTH: 1495
<212> TYPE: DNA
<213> ORGANISM: Clostridium leptum
<220> FEATURE:
<221> NAME/KEY: rRNA
<222> LOCATION: (1)..(1495)
<223> OTHER INFORMATION: 16S rRNA coding gene sequence of Clostridium
      strain 26

<400> SEQUENCE: 46

agagtttgat catggctcag gacgaacgct ggcggcgtgc ttaacacatg caagtcgaac     60

ggagcacccc tgaaggagtt ttcggacaac ggatgggaat gcttagtggc ggactggtga    120

gtaacgcgtg aggaacctgc cttccagagg gggacaacag ttggaaacga ctgctaatac    180

cgcatgatgc gttggagccg catgactccg acgtcaaaga tttatcgctg gaagatggcc    240

tcgcgtctga ttagctagtt ggtgaggtaa cggcccacca aggcgacgat cagtagccgg    300

actgagaggt tggccggcca cattgggact gagatacggc ccagactcct acgggaggca    360

gcagtgggga atattgggca atggacgcaa gtctgaccca gcaacgccgc gtgaaggaag    420

aaggctttcg ggttgtaaac ttcttttaag gggaagagc agaagacggt accccttgaa    480

taagccacgg ctaactacgt gccagcagcc gcggtaatac gtaggtggca agcgttgtcc    540

ggatttactg ggtgtaaagg gcgtgcagcc ggagagacaa gtcagatgtg aaatccacgg    600

gctcaacccg tgaactgcat ttgaaactgt ttcccttgag tgtcggagag ggtaatcgga    660

attcctttgt gtagcggtga aatgcgtaga tataagaaga acaccagtgg cgaaggcgga    720

ttactggacg ataactgacg gtgaggcgcg aaagcgtggg ggagcaacag attaaatacc    780

ctggtagtcc acgctgttaa cgatcgatac taggtgtgcc gggactgacc ccctgcgtgc    840

ccggagttaa ccacaataag tatcgcacct ggggagtacg atcgcaaggt gaacttcaaa    900

ggaattgacg ggggcccgcc ccaagccgtg gattatgtgg ttaattcgaa gcaacgcgaa    960

gaacctaccc agggcttgac atcctgctaa cgaagtagag atacattagg tgccctttcg   1020

gggaaagcag agacaggtgg tgcatggttg tcgtcagctc gtgtcgtgag atgttgggtt   1080

aagtcccgca acgagcgcaa cccctattgt tagttgctac gcaagagcac tctagcgaga   1140

ctgccgttga caaaacggag gaaggcgggg acgacgtcaa atcatcatgc cccttatgtc   1200

ctgggctaca cacgtaatac aatggcggtt aacaaaggga tgcaaagccg cgaggcagag   1260

cgaaccccaa aaagccgtcc cagttcggat cgcaggctgc aacccgcctg cgtgaagtcg   1320

gaatcgctag taatcgcgga tcagcatgcc gcggtgaata cgttcccggg ccttgtacac   1380

accgcccgtc acaccatgag agtcgggaac acccgaagtc cgtagcctaa ccgcaaggag   1440

ggcgcggccg aaggtgggtt cgataattgg ggtgaagtcg taacaaggta gccgt        1495
```

<210> SEQ ID NO 47
<211> LENGTH: 1509
<212> TYPE: DNA
<213> ORGANISM: Clostridium leptum
<220> FEATURE:
<221> NAME/KEY: rRNA
<222> LOCATION: (1)..(1509)
<223> OTHER INFORMATION: 16S rRNA coding gene sequence of Clostridium strain 27

<400> SEQUENCE: 47

```
agagtttgat cctggctcag gatgaacgct ggcggcgtgc ttaacacatg caagtcgaac      60
ggagtacccc tgaaggagtt ttcggacaac tgatgggact acttagtggc ggacgggtga     120
gtaacgcgtg agtaacctgc cttggagtgg ggaataacag ctggaaacag ctgctaatac     180
cgcataatat gtctgtgtcg catggcactg gacatcaaag atttatcgct ctgagatgga     240
ctcgcgtctg attagctagt tggcggggta acggcccacc aaggcgacga tcagtagccg     300
gactgagagg ttggccggcc acattgggac tgagacacgg cccagactcc tacgggaggc     360
agcagtgggg aatattgggc aatgggcgca agcctgaccc agcaacgccg cgtgaaggaa     420
gaaggctttc gggttgtaaa cttcttttaa gggggaagag cagaagacgg taccccttga     480
ataagccacg gctaactacg tgccagcagc cgcggtaata cgtaggtggc aagcgttgtc     540
cggatttact gggtgtaaag ggcgtgcagc cggagagaca agtcagatgt gaaatccacg     600
ggctcaaccc gtgaactgca tttgaaactg tttcctggag ttcggagggt atggaattct     660
tgttagcggt gaaatgctgt agatatggga gaaccaccag tgcgaggggg cttccgggac     720
tgtacttgac tgtagaggtc tcaaagctgg gggagcaccg aggaatgaga taccgtgata     780
gtcccacgcg gtaacggatg attactaggt gttggggga cccaggctct ttcggtgccg      840
ggcgcaaacc ctttaggaat tccacctggg gaattacgtt tggcaagaaa ggaacttcaa     900
agaaattgaa cgggggaccc ccccaaccgg tggaggcatg gtgttttatt tcggaggaac     960
gggaagaacc tttaccttgt tctgaccttc cggatgacga agtgagcaaa gtcaacttcc    1020
cttcggggcc atggaggaca ggtggtggca tggttggtcg tcagctcgtg tcgtgagatg    1080
ttgggttaag tcccgcaacg agcgcaaccc ctatttccag tagccagcag gtagagctgg    1140
gcactctgga gagactgccc gggataaccg ggaggaaggc ggggatgacg tcaaatcatc    1200
atgcccctta tgatcagggc tacacacgtg ctacaatggc gtaaacaaag ggaagcgaga    1260
cggtgacgtt aagcaaatcc caaaaataac gtcccagttc ggattgtagt ctgcaactcg    1320
actacatgaa gctggaatcg ctagtaatcg cgaatcagaa tgtcgcggtg aatacgttcc    1380
cgggtcttgt acacaccgcc cgtcacacca tgggagtcgg aaatgcccga agtcagtgac    1440
ctaaccgaaa ggaaggagct gccgaaggtg gagccggtaa ctggggtgaa gtcgtaacaa    1500
ggtagccgt                                                            1509
```

<210> SEQ ID NO 48
<211> LENGTH: 1583
<212> TYPE: DNA
<213> ORGANISM: Clostridium leptum
<220> FEATURE:
<221> NAME/KEY: rRNA
<222> LOCATION: (1)..(1583)
<223> OTHER INFORMATION: 16S rRNA coding gene sequence of Clostridium strain 28

<400> SEQUENCE: 48

-continued

```
agagtttgat cctggctcag gacgaacgct ggcggcgcgc ctaacacatg caagtcgaac     60

ggagcttata tttcagaagt tttcggatgg acgagagata agcttagtgg cggacgggtg    120

agtaacacgt gagcaacctg cctttcagag ggggataaca gttggaaacg actgctaata    180

ccgcataacg ctgcgatggg gcatcccgat gcagccaaag gagcaatccg ctgaaagatg    240

ggctcgcggc cgattagcta gttggtgggg caacggccca ccaaggcgac gatcggtagc    300

cggactgaga ggttgatcgg ccacattggg actgagacac ggcccagact cctacgggag    360

gcagcagtgg gggatattgc acaatggagg aaactctgat gcagcgacgc cgcgtgaggg    420

aagacggtct tcggattgta aacctctgtc tttggggaag aaaatgacgg tacccaaaga    480

ggaagctccg gctaactacg tgccagcagc cgcggtaata cgtaggggag cgagcgttgt    540

ccggaattac tgggtgtaaa gggagcgtag cgggcgagaa agttgaatgt taaatctacc    600

ggcttaactg gtagctgcgt ccaaaacttc ttggtcttga gtgaaagtaa gaggccaggg    660

cggaaattct tagtgtaagc gggtgaaaat gcgttagata ttagggagga accaccaggt    720

gggcgaaggg cggcttgctg ggctttaact ggacggctgg aggcttggaa aaggcgtggg    780

gagagcaaac acagggaatt aagtataccc tggtatatgt cacacgcttg taaagagtat    840

gattaactta gggtggtggg gggaacttga ccctttcgtg tgcgcgcagg ttaacacaca    900

tttagagtat atccaacttg gggagagtac ggccggcaaa gtttgaaact tcaaaaggga    960

aattgagacc ggggggcccg gccaccaagc acagtggaga gtatggtggg tttaatttcg   1020

agaagcaacc ggcggaagag aaactttacc agtccttgac atcggtggcg gcataagccc   1080

tagagattag gtgaagccct tcgggggccc caccagacag gtggtgcatg gttgtcgtca   1140

gctcgtgtcg tgagatgttg ggttaagtcc ccgcaaacga gcgcaaccct tattattagt   1200

ttgctacgca agagcactct aatgagactg ccgttgacaa aacggaggaa ggtggggatg   1260

acgtcaaatc atcatgcccc ttatgacctg ggctacacac gtactacaat ggcactgaaa   1320

cagagggaag cgacatcgcg aggtgaagcg aatcccaaaa aagtgtccca gttcggattg   1380

caggctgcaa ctcgcctgca tgaagtcgga attgctagta atcgcggatc agcatgccgc   1440

ggtgaatacg ttcccgggcc ttgtacacac cgcccgtcac accatgggag tcggtaacac   1500

ccgaagccag tagcctaacc gcaaggaggg cgctgtcgaa ggtgggattg atgactgggg   1560

tgaagtcgta acaaggtagc cgt                                           1583
```

<210> SEQ ID NO 49
<211> LENGTH: 1519
<212> TYPE: DNA
<213> ORGANISM: Clostridium coccoides
<220> FEATURE:
<221> NAME/KEY: rRNA
<222> LOCATION: (1)..(1519)
<223> OTHER INFORMATION: 16S rRNA coding gene sequence of Clostridium strain 29

<400> SEQUENCE: 49

```
agagtttgat catggctcag gatgaacgct ggcggcgtgc ctaacacatg caagtcgaac     60

gggtgtacgg gaaggaaggc ttcggccgga aaacctgtgc atgagtggcg gacgggtgag    120

taacgcgtgg gcaacctggc ctgtacaggg ggataacact tagaaatagg tgctaatacc    180

gcataacggg ggaagccgca tggcttttcc ctgaaaactc cggtggtaca ggatgggccc    240

gcgtctgatt agccagttgg cagggtaacg gcctaccaaa gcgacgatca gtagccggcc    300

tgagagggcg gacggccaca ctgggactga gacacggccc agactcctac gggaggcagc    360
```

```
agtgggggat attgcacaat ggggggaacc ctgatgcagc gacgccgcgt gggtgaagaa    420
gcgcctcggc gcgtaaagcc ctgtcagcag ggaaagaaaa tgacggtacc tgaagaagaa    480
gccccgggct aactacgtgc cagcagccgg cggtaattac gtagggggc aggcgttatc    540
cggatttact gggtggtaaa ggggggcgca aacggcgatg gcaggccagg aatggaaagc    600
ccgggggccc aaccccggga cttgctcttg ggaaactggc ttggctggga gtggcaggag    660
gggcaggcgg aaattcctgg tggtagcggt ggaaaatggc taaaaatcaa gaagaaaaac    720
cggtggggaa aggcggcctg gtgggactgc gaactgacgt tgaaggcccg aaagcgtggg    780
gaacaaacag gatagattcc ctggtagttc cacgccgtaa acgatgatta ctaggtgtcg    840
gggagcagag actgcccggt gccgcagcca acgcattaag taatccacct ggggagtacg    900
ttcgcaagaa tgaaactcaa aggaattgac ggggacccgc acaagcggtg gagcatgtgg    960
tttaattcga agcaacgcga agaaccttac ctggtcttga catcccgatg acgagtgagc   1020
aaagtcactt tcccttcggg gcattggaga caggtggtgc atggttgtcg tcagctcgtg   1080
tcgtgagatg ttgggttaag tcccgcaacg agcgcaaccc ctatttccag tagccagcag   1140
gtagagctgg gcactctgga gagactgccc gggataaccg ggaggaaggc ggggatgacg   1200
tcaaatcatc atgcccctta tgatcagggc tacacacgtg ctacaatggc gtaaacaaag   1260
ggaagcgaga cggtgacgtt aagcaaatcc caaaaataac gtcccagttc ggattgtagt   1320
ctgcaactcg actacatgaa gctggaatcg ctagtaatcg cgaatcagaa tgtcgcggtg   1380
aatacgttcc cgggtcttgt acacaccgcc cgtcacacca tgggagtcgg aaatgcccga   1440
agtcagtgac ctaaccgaaa ggaaggagct gccgaaggtg gagccggtaa ctggggtgaa   1500
gtcgtaacaa ggtagccgt                                                1519
```

```
<210> SEQ ID NO 50
<211> LENGTH: 1497
<212> TYPE: DNA
<213> ORGANISM: Clostridium coccoides
<220> FEATURE:
<221> NAME/KEY: rRNA
<222> LOCATION: (1)..(1497)
<223> OTHER INFORMATION: 16S rRNA coding gene sequence of Clostridium
      strain 30

<400> SEQUENCE: 50

agagtttgat cctggctcag gatgaacgct ggcggcgtgc ctaacacatg caagtcgaac     60
ggggtatata agcggaagtt tacggatgga aggttatata cttagtggcg gacgggtgag    120
taacgcgtgg gcaacctgcc ccgtgccggg ggataccgcc tggaaacagg cgctaatacc    180
gcataagcgc atacagccgc atgggtgtat gcggaaagct ccggcggcac gggatgggcc    240
cgcgcccgat tagccagttg gcggggtaac ggcccaccaa agcgacgatc ggtagccggc    300
ctgagagggc ggacggccac attgggactg agacacggcc caaactccta cgggaggcag    360
cagtggggaa tattgcacaa tgggggaaac cctgatgcag caacgccgcg tgggtgaagg    420
agcgtttcgg cgcgtaaagc cctgtcagcg gggaagaaga aagacggtac ccgaccaaga    480
agccccggct aactacgtgc cagcagccgc ggtaatacgt agggggcgag cgttatccgg    540
aattactggg tgtaaaggga gcgtagacgg cgaggtaagc ctgaagtgga agcccgcggc    600
ccaaccgcgg aactgctttg ggaactgttt tgctggagta tgggaggggt aagcggaatt    660
cctggtgtag cggtgaaatg cgtagatatc aggaggaaca ccggtggcga aggcggctta    720
ctggaccata actgacgttg aggctcgaaa gcgtggggag cgaacaggat tagataccct    780
```

```
ggtagtccac gcgtaaacga tgattaccag gtgtcgggtg tcgaaggacg gcccggtgcc    840
gcagcgaacg cagtaagtaa tccacctggg gagtacgttc gcaagaatga aactcaaagg    900
aattgacggg gacccgcaca agcggtggag catgtggttt aattcgaagc aacgcgaaga    960
accttacccg gccttgacat cccctggaca gcatatgtaa tgtatgtttc cttcgggacc   1020
agggagacag gtggtgcatg gttgtcgtca gctcgtgtcg tgagatgttg ggtcaagtcc   1080
cgcaacgagc gcaacccctg cccccagtag ccagcattta agatgggcac tctgggggga   1140
ctgccgggga taacccggag gaaggcgggg atgacgtcaa atcatcatgc cccttatggc   1200
cggggctaca cacgtgctac aatggcgtaa acagagggag gcgagacagc gatgttaagc   1260
gaaccccaaa aataacgtcc cagttcggat tgcagcctgc aactcggctg catgaagctg   1320
gaatcgctag taatcgcgga tcagaatgcc gcggtgaata cgttcccggg tcttgtacac   1380
accgcccgtc acaccatggg agtcgggaac gcccgaagcc ggtgaccgaa cccgaaaggg   1440
gaggagccgt cgaaggcggg cctggtgact ggggtgaagt cgtaacaagg tagccgt      1497
```

```
<210> SEQ ID NO 51
<211> LENGTH: 1475
<212> TYPE: DNA
<213> ORGANISM: Clostridium leptum
<220> FEATURE:
<221> NAME/KEY: rRNA
<222> LOCATION: (1)..(1475)
<223> OTHER INFORMATION: 16S rRNA coding gene sequence of Clostridium
      strain 31

<400> SEQUENCE: 51

gagtttgatc ctggctcagg ataaacgctg gcggcgcaca taagacatgc aagtcgaacg     60
aacttaatac cttgcttgca aggtaagcgg ttagtggcgg actggtgagt aacacgtaag    120
aaatctgcct atcagagggg aataacagtg agaaatcact gctaataccg catatgccat    180
agttatcgca tgataatagt gggaaagaag caattcgctg atagatgagc ttgcggctga    240
ttagctagtt ggtggggtaa cggcctacca aggcgacgat cagtagccgg cctgagaggg    300
tgaacggcca cattgggact gagacacggc ccaaactcct acgggaggca gcagtgggga    360
atattgcaca atgggggaaa ccctgatgca gcgacgccgc gtgagtgaag aagtatttcg    420
gtatgtaaag ctctatcagc agggaagaaa atgacggtac ctgactaaga aagccccggc    480
taactacgtg ccagcagccg cggtaatacg tagggggcaa gcgttatccg gatttactgg    540
tgtaaaggga gcgtagacgg cagcgcaagt ctgagtgaaa tcccatggct tacccatgaa    600
actgctttgg aaactgtgca gctggagtgc aggagaggta agcggaatcc tagtgtagcg    660
gttgaaatgc gtagattatc agaaggaaca ccggtggccg aggcggcctg ctgggctttt    720
actgacgctg aggctcgaag cgtgggtagc aaacaggatt agataccctg gtagtccacg    780
cggtaaacga tgattactag gtgtgggtgg actgacccca tccgtgccgg agttaacaca    840
ataagtaatc cacctgggga gtacggccgc aaggttgaaa ctcaaaggaa ttgacggggg    900
cccgcacaag cagtggagta tgtggtttaa ttcgacgcaa cgcgaagaac cttaccaggt    960
cttgacatcg agtgacggac atagagatat gtctttcctt cgggacacga agacaggtgg   1020
tgcatggttg tcgtcagctc gtgtcgtgag atgttgggtt aagtcccgca acgagcgcaa   1080
cccttaccat tagttgctac gcaagagcac tctaatggga ctgccgttga caaaacggag   1140
gaaggtgggg atgacgtcaa atcatcatgc cccttatgac ctgggcgaca cacgtactac   1200
aatggcggtc aacagaggga ggcaaagccg cgaggcagag caaaccccta aaagccgtct   1260
```

```
cagttcggat tgcaggctgc aactcgcctg catgaagtcg gaattgctag taatcgcgga   1320

tcagcatgcc gcggtgaata cgttcccggg ccttgtacac accgcccgtc acaccatgag   1380

agccggtaac acccgaagtc aatagtctaa ccgcaaggag gacattgccg aaggtgggat   1440

tggtaattgg ggtgaagtcg taacaaggta gccgt                              1475


<210> SEQ ID NO 52
<211> LENGTH: 1491
<212> TYPE: DNA
<213> ORGANISM: Clostridium leptum
<220> FEATURE:
<221> NAME/KEY: rRNA
<222> LOCATION: (1)..(1491)
<223> OTHER INFORMATION: 16S rRNA coding gene sequence of Clostridium
      strain 32

<400> SEQUENCE: 52

agagtttgat cctggctcag gatgaacgct ggcggcgtgc ttaacacatg caagtcgaac     60

gagaatcagt ggattgagga ttcgtccaaa tgaaactgag gaaagtggcg gacgggtgag    120

taacgcgtga gcaatctgcc ttggagtggg gaataacggc tggaaacagc cgctaatacc    180

gcatgataca gttgggaggc atctctctga ctgtcaaaga tttatcgctc tgagatgagc    240

tcgcgtctga ttagctagtt ggcggggtaa cggcccacca aggcgacgat cagtagccgg    300

actgagaggt tggccggcca cattgggact gagacacggc ccagactcct acgggaggca    360

gcagtgggga atattgggca atgggcgcaa gcctgaccca gcaacgccgc gtgaaggaag    420

aaggctttcg ggttgtaaac ttcttttctg gggacgaac aaatgacggt accccaggaa    480

taagccacgg ctaactacgt gccagcagcc gcggtaatac gtaggtggca agcgttatcc    540

ggatttattg ggtgtaaagg gcgtgtaggc gggaatgcaa gtcagatgtg aaaactatgg    600

gctcaaccca tagcctgcat ttgaaactgt atttcttgag tgctggagag gcaatcggaa    660

ttccgtgtgt agcggtgaaa tgcgtagata tacggaggaa caccagtggc gaagcggatt    720

gctggacagt aactgacgct gaggcgcgaa agcgtgggga gcaaacagga ttagataccc    780

tggtagtcca cgccgtaacg atggatacta gtgtgggggg actgaccccc tccgtgccgc    840

agctaacgca ataagtatcc ccacctgggg agtacgatcg caaggttgaa actcaaagga    900

attgacgggg gcccgcacaa gcggtggagt atgtggttta attcgaagca acgcgaagaa    960

ccttaccagg gcttgacatc ctgctaacga accagagatg gattaggtgc ccttcgggga   1020

aagcagagac aggtggtgca tggttgtcgt cagctcgtgt cgtgagatgt tgggttaagt   1080

cccgcaacga gcgcaacccc tattgttagt tgctacgcaa gagcactcta gcgagactgc   1140

cgttgacaaa acggaggaag gtggggacga cgtcaaatca tcatgcccct tacgtcctgg   1200

gccacacacg tactacaatg gcggttaaca aagagaggca agaccgcgag gtggagcaaa   1260

tctcaaaaag ccgtcccagt tcggatcgca ggctgcaacc cgcctgcgtg aagttggaat   1320

cgctagtaat cgcggatcag catgccgcgg tgaatacgtt cccgggcctt gtacacaccg   1380

cccgtcacac catgagagtc gggaacaccc gaagtccgta gcctaaccgc aagggggcg    1440

cggccgaagg tgggttcgat aattggggtg aagtcgtaac aaggtagccg t            1491


<210> SEQ ID NO 53
<211> LENGTH: 1495
<212> TYPE: DNA
<213> ORGANISM: Clostridium coccoides
<220> FEATURE:
<221> NAME/KEY: rRNA
<222> LOCATION: (1)..(1495)
```

<223> OTHER INFORMATION: 16S rRNA coding gene sequence of Clostridium strain 33

<400> SEQUENCE: 53

```
agagtttgat cctggctcag gatgaacgct ggcggcgtgc ctaacacatg caagtcgaac     60

gggtgtacgg ggaggaaggc ttcggccgga aaacctgtgc atgagtggcg gacgggtgag    120

taacgcgtgg gcaacctggc ctgtacaggg ggataacact tagaaatagg tgctaatacc    180

gcataacggg ggaagccgca tggcttttcc ctgaaaactc cggtggtaca ggatgggccc    240

gcgtctgatt agccagttgg cagggtaacg gcctaccaaa gcgacgatca gtagccggcc    300

tgagagggcg gacggccaca ctgggactga gacacggccc agactcctac gggaggcagc    360

agtgggggat attgcacaat gggggggaacc ctgatgcagc gacgccgcgt gggtgaagaa    420

gcgcctcggc gcgtaaagcc ctgtcagcag ggaagaaaat gacggtacct gaagaagaag    480

ccccggctaa ctacgtgcca gcagccgcgg taatacgtag ggggcaagcg ttatccggat    540

ttactgggtg taaagggggc gcagacggcg atgcaagcca ggagtgaaag cccggggccc    600

aaccccggga ctgctcttgg aactgcgtgg ctggagtgca ggaggggcag gcggaattcc    660

tggtgtagcg gtgaaatgcg tagatatcag aggaacaccg gtggcgaaag cggcctgctg    720

gactgcaact gacgttgagg cccgaaagcg gtgggagcaa acaggattag ataccctggt    780

agtccacgcc gtaaacgatg attactaggt gtcggggagc agagactgcc cggtgccgca    840

gcccaacgca ttaagtatcc acctggggag tacgttcgca agaatgaaac tcaaaggaat    900

tgacggggac ccgcacaagc ggtggagcat gtggtttaat tcgaagcaac gcgaagaacc    960

ttaccaggcc ttgacatccc cctggatggc ccgtaacggg gccagccctt tttgggcagg   1020

ggagacaggt ggtgcatggt tgtcgtcagc tcgtgtcgtg agatgttggg ttaagtcccg   1080

caacgagcgc aacccctgcc cgcagtagcc agcattttag atggggactc tgcggggact   1140

gccggggaca acccggagga aggcggggat gacgtcaaat catcatgccc cttatggcct   1200

gggctacaca cgtgctacaa tggcgccgac agagggagga gaagcggcga cgcggagcga   1260

accccaaaaa cggcgtccca gttcggattg tagtctgcaa cccgactaca tgaagccgga   1320

atcgctagta atcgcggatc agaatgccgc ggtgaatacg ttcccgggtc ttgtacacac   1380

cgcccgtcac accatgggag ccgggaatgc ccgaagtctg tgaccgaacc cgtaagggga   1440

ggggcagccg aaggcaggcc cggtgactgg ggtgaagtcg taacaaggta gccgt        1495
```

<210> SEQ ID NO 54
<211> LENGTH: 1493
<212> TYPE: DNA
<213> ORGANISM: Clostridium leptum
<220> FEATURE:
<221> NAME/KEY: rRNA
<222> LOCATION: (1)..(1493)
<223> OTHER INFORMATION: 16S rRNA coding gene sequence of Clostridium strain 34

<400> SEQUENCE: 54

```
agagtttgat cctggctcag gacgaacgct ggcggcgtgc ttaacacatg caagtcgaac     60

ggagcacccc tgaaggagtt ttcggacaac ggatgggaat gcttagtgtc ggactggtga    120

gtaacgcgtg aggaacctgc cttccagagg gggacaacag ttggaaacga ctgctaatac    180

cgcatgatgc gttggagccg catgactccg acgtcaaaga tttatcgctg gaagatggcc    240

tcgcgtctga tttgttagtt ggtgaggtaa cggcccacca aggcgacgat cagtagccgg    300

actgagaggt tggccggcca cattgggact gagatacggc ccagactcct acgggaggca    360
```

```
gcagtgggga atattgggca atggacgcaa gtctgaccca gcaacgccgc gtgaaggaag    420

aaggctttcg ggttgtaaac ttcttttaag ggggaagagc agaagacggt accccttgaa    480

taagccacgg ctaactacgt gccagcagcc gcggtaatac gtaggtggca agcgttgtcc    540

ggatttactg ggtgtaaagg gcgtgcagcc ggagagacaa gtcagatgtg aaatccacgg    600

gctcaacccg tgaactgcat ttgaaactgt ttcccttgag tgtcggagag gtaatcggaa    660

ttccttgtgt agcggtgaaa tgcgtagata taaggaagaa caccagtggc gaaggcggat    720

tactggacga taactgacgg tgaggcgcga aagcgtgggg agcaaacagg attagatacc    780

ctggtagtcc acgctgtaaa cgatcgatac taggtgtgcg gggactgacc ccctgcgtgc    840

cggagttaac acaataagta tcgcacctgg ggagtacgat cgcaaggttg aaactcaaag    900

gaattgacgg gggcccgcac aagcggtgga ttatgtggtt taattcgaag caacgcgaag    960

aaccttacca gggcttgaca tcctgctaac gaagtagaga tacattaggt gcccttcggg   1020

gaaagcagag acaggtggtg catggttgtc gtcagctcgt gtcgtgagat gttgggttaa   1080

gtcccgcaac gagcgcaacc cctattgtta gttgctacgc aagagcactc tagcgagact   1140

gccgttgaca aaacggagga aggcggggac gacgtcaaat catcatgccc cttatgtcct   1200

gggctacaca cgtaatacaa tggcggttaa caaagggatg caaagccgcg aggcagagcg   1260

aaccccaaaa agccgtccca gttcggatcg caggctgcaa cccgcctgcg tgaagtcgga   1320

atcgctagta atcgcggatc agcatgccgc ggtgaatacg ttcccgggcc ttgtacacac   1380

cgcccgtcac accatgagag tcgggaacac ccgaagtccg tagcctaacc gcaaggaggg   1440

cgcggccgaa ggtgggttcg ataattgggg tgaagtcgta acaaggtagc cgt          1493
```

```
<210> SEQ ID NO 55
<211> LENGTH: 1498
<212> TYPE: DNA
<213> ORGANISM: Clostridium coccoides
<220> FEATURE:
<221> NAME/KEY: rRNA
<222> LOCATION: (1)..(1498)
<223> OTHER INFORMATION: 16S rRNA coding gene sequence of Clostridium
      strain 35

<400> SEQUENCE: 55
```

```
agagtttgat cctggctcag gatgaacgct ggcggcgtgc ctaacacatg caagtcgaac     60

gggtgtacag aagggaagat tacggtcgga aggtctgtgc atgagtggcg gacgggtgag    120

taacgcgtgg gcaacctggc ctgtacaggg ggataacact tagaaatagg tgctaatacc    180

gcataacggg ggaagccgca tggcttttcc ctgaaaactc cggtggtaca ggatgggccc    240

gcgtctgatt attttttttg tcagggtaac ggcctaccaa agcgacgatc agtagccggc    300

ctgagagggc ggacggccac actgggactg agacacggcc cagactccta cgggaggcag    360

cagtggggga tattgcacaa tgggggaaac cctgatgcag cgacgccgcg tgggtgaaga    420

agcgcctcgg cgcgtaaagc cctgtcagca gggaagaaaa tgacggtacc tgaagaagaa    480

gccccggcta actacgtgcc agcagccgcg gtaatacgta aggggcaagc gttatccgga    540

tttactgggt gtaaaggggg cgcagacggc gatgcaagcc aggagtgaaa gcccggggcc    600

caaccccggg actgctcttg ggaactgcgg tggctggagt gcaggagggg caggccggaa    660

ttcctggtgt agcggtgaaa tgcgtagata tcaggaggaa caccggtggc gaaggcggcc    720

tgctggactg caactgacgt tgaggcccga aagcgtgggg agcaaacagg attagatacc    780

ctggtagtca cgccgtaaac gatgattact aggtgtcggg gagcagagac tgcccggtgc    840
```

```
cgcagccaac gcattaagta atccacctgg ggagtacgtt cgcaagaatg aaactcaaag    900

gaattgacgg ggacccgcac aagcggtgga gcatgtggtt taattcgaag caacgcgaag    960

aaccttacca ggccttgaca tccccctgga tggcccgtaa cggggtcagc ctttcggggc   1020

aggggagaca ggtggtgcat ggttgtcgtc agctcgtgtc gtgagatgtt gggttaagtc   1080

ccgcaacgag cgcaacccct gcccgcagta gccagcattt tagatgggga ctctgcgggg   1140

actgccgggg acaacccgga ggaaggcggg gatgacgtca aatcatcatg ccccttatgg   1200

cctgggctac acacgtgcta caatggcgcc gacagaggga ggcgaagcgg cgacgcggag   1260

cgaaccccaa aaacggcgtc ccagttcgga ttgtagtctg caacccgact acatgaagcc   1320

ggaatcgcta gtaatcgcgg atcagaatgc cgcggtgaat acgttcccgg gtcttgtaca   1380

caccgcccgt cacaccatgg gagccgggaa tgcccgaagt ctgtgaccga acccgtaagg   1440

ggaggggcag ccgaaggcag gcccggtgac tggggtgaag tcgtaacaag gtagccgt     1498
```

<210> SEQ ID NO 56
<211> LENGTH: 1491
<212> TYPE: DNA
<213> ORGANISM: Clostridium leptum
<220> FEATURE:
<221> NAME/KEY: rRNA
<222> LOCATION: (1)..(1491)
<223> OTHER INFORMATION: 16S rRNA coding gene sequence of Clostridium strain 36

<400> SEQUENCE: 56

```
agagtttgat catggctcag gacgaacgct ggcggcaagc ttaacacatg caagtcgaac     60

ggagcgccta tgaaggagat ttcggtcaac ggaataggct gcttagtggc tgacgggtga    120

gtaacgcgtg aggaacctgc ctttcagagg gggacaacag ttggaaacga ctgctaatac    180

cgcataacac ataggtgtcg catggcattt atgtcaaaga tttatcgctg aaagatggcc    240

tcgcgtctga ttagctagtt ggtgaggtaa cggctcacca aggcgacgat cagtagccgg    300

actgagaggt tagccggcca cattgggact gagatacggc ccagactcct acgggaggca    360

gcagtgggga atattgggca atggacgcaa gtctgaccca gcaacgccgc gtgaaggaag    420

aaggctttcg ggttgtaaac ttcttttaag agggaagagc agaagacggt acctcttgaa    480

taagccacgg ctaactacgt gccagcagcc gcggtaatac gtagtggcaa gcgttgtccg    540

gatttactgg gtgtaaaggg cgtgtagccg ggctgacagt cagatgtgaa attccggggc    600

tcaaccccgg acctgcattt gaaactgttg gtcttgagta tcggagaggc aggcggaatt    660

cctagtgtag cggtgaaatg cgtagatatt aggaggaaca ccagtggcga aggcggcctg    720

ctggacgaca actgacggtg aggcgcgaaa gcgtggggag caaacaggat tagataccct    780

ggtagtccac gctgtaaacg atggatacta ggtgtgcggg gactgacccc ctgcgtgccg    840

cagttaacac aataagtatc ccacctgggg agtacgatcg caaggttgaa actcaaagga    900

attgacgggg gcccgcacaa gcggtggatt atgtggttta attcgatgca acgcgaagaa    960

ccttaccagg gcttgacatc ctgctaacga ggtagagata cgtcaggtgc ccttcgggga   1020

aagcagagac aggtggtgca tggttgtcgt cagctcgtgt cgtgagatgt tgggttaagt   1080

cccgcaacga gcgcaaccct tattgttagt tgctacgcaa gagcactcta gcgagactgc   1140

cgttgacaaa acggaggaag gtggggacga cgtcaaatca tcatgcccct tatgtcctgg   1200

gctacacacg taatacaatg gcggtaaaca gagggatgca atactgcgaa gtggagcgaa   1260

cccctaaaag ccgtcccagt tcagattgca gtctgcaact cgactgcatg aagtcggaat   1320
```

```
cgctagtaat cgcggatcag catgccgcgg tgaatacgtt cccgggcctt gtacacaccg   1380

cccgtcacac catgagagtc gggaacaccc gaagtccgta gcctaaccgc aaggagggcg   1440

cggccgaagg tgggttcgat aattggggtg aagtcgtaac aaggtagccg t            1491


<210> SEQ ID NO 57
<211> LENGTH: 1493
<212> TYPE: DNA
<213> ORGANISM: Clostridium coccoides
<220> FEATURE:
<221> NAME/KEY: rRNA
<222> LOCATION: (1)..(1493)
<223> OTHER INFORMATION: 16S rRNA coding gene sequence of Clostridium
      strain 37

<400> SEQUENCE: 57

agagtttgat cctggctcag gatgaacgct ggcggcgtgc ctaacacatg caagtcgaac     60

gggtgtacgg ggaggaaggc ttcggccgga aaacctgtgc atgagtggcg gacgggtgag    120

taacgcgtgg gcaacctggc ctgtacaggg ggataacact tagaaatagg tgctaatacc    180

gcataacggg ggaagccgca tggcttttcc ctgaaaactc cggtggtaca ggatgggccc    240

gcgtctgatt agccagttgg cagggtaacg gcctaccaaa gcgacgatca gtagccggcc    300

tgagagggcg gacggccaca ctgggactga gacacggccc agactcctac gggaggcagc    360

agtgggggat attgcacaat ggggggaaac cctgatgcag cgacgccgcg tgagtgaaga    420

agtatttcgg tatgtaaagc tctatcagca gggaagaaaa tgacggtacc tgactaagaa    480

gccccggcta actacgtgcc agcagccgcg gtaatacgta gggggcaagc gttatccgga    540

tttactgggt gtaaagggag cgtagacggc agcgcaagtc tgaagtgaaa tcccatggct    600

taaccatgga actgctttgg aaactgtgca gctggagtgc aggagaggta agcggaattc    660

ctagtgtagc ggtgaaatgc gtagatatta ggaggaacac cagtggcgaa ggcggcttac    720

tggactgtac tgacgttgag gctcgaaagc gtggggagca aacaggatta gataccctgg    780

tagtccacgc cgtaaacgat gattactagg tgttgggga ccaaggtctt cggtgccggc    840

gcaaacgcat taagtaatcc acctggggag tacgttcgca agaatgaaac tcaaaggaat    900

tgacggggac ccgcacaagc ggtggagcat gtggtttaat tcgaagcaac gcgaagaacc    960

ttacctggtc ttgacatccc gatgacgagt gagcaaagtc actttccctt cggggcattg   1020

gagacaggtg gtgcatggtt gtcgtcagct cgtgtcgtga gatgttgggt taagtcccgc   1080

aacgagcgca acccctattt ccagtagcca gcaggtagag ctgggcactc tggagagact   1140

gcccgggata accgggagga aggcggggat gacgtcaaat catcatgccc cttatgatca   1200

gggctacaca cgtgctacaa tggcgtaaac aaagggaagc gagacggtga cgttgagcaa   1260

atcccaaaaa taacgtccca gttcggattg tagtctgcaa ctcgactaca tgaagctgga   1320

atcgctagta atcgcgaatc agaatgtcgc ggtgaatacg ttcccgggtc ttgtacacac   1380

cgcccgtcac accatgggag tcggaaatgc ccgaagtcag tgacctaacc gaaaggaagg   1440

agctgccgaa ggtggagccg gtaactgggg tgaagtcgta acaaggtagc cgt          1493


<210> SEQ ID NO 58
<211> LENGTH: 1493
<212> TYPE: DNA
<213> ORGANISM: Clostridium leptum
<220> FEATURE:
<221> NAME/KEY: rRNA
<222> LOCATION: (1)..(1493)
<223> OTHER INFORMATION: 16S rRNA coding gene sequence of Clostridium
```

strain 38

<400> SEQUENCE: 58

```
aaagtttgat cctggctcag gacgaacgct ggcggcgtgc ttaacacatg caagtcgaac     60
ggagcacccc tgaaggagtt ttcggacaac ggatgggaat gcttagtggc ggactggtga    120
gtaacgcgtg aggaacctgc cttccagagg gggacaacag ttggaaacga ctgctaatac    180
cgcatgatgc gttggagccg catgactccg acgtcaaaga tttatcgctg gaagatggcc    240
tcgcgtctga ttagctagtt ggtgaggtaa cggcccacca aggcgacgat cagtagccgg    300
actgagaggt tggccggcca cattgggact gagatacggc ccagactcct acgggaggca    360
gcagtgggga atattgggca atggacgcaa gtctgaccca gcaacgccgc gtgaaggaag    420
aaggctttcg ggttgtaaac ttcttttaag gggaagagc agaagacggt accccttgaa    480
taagccacgg ctaactacgt gccagcagcc gcggtaatac gtagtggcaa gcgttgtccg    540
gatttactgg gtgtaaaggg cgtgcagccg gagagacaag tcagatgtga aatccacggg    600
ctcaacccgt gaactgcatt tgaaactgtt tcccttgagt gtcggagagg taatcggaat    660
tccttgtgta gcggtgaaat gcgtagatat aaggaagaac accagtggcg aaggcggatt    720
actggacgat aaactgacgg tgaggcgcga aagcgtgggg agcaaacagg attagatacc    780
ctggtagtcc acgctgtaaa cgatcgatac taggtgtgcg gggactgacc ccctgcgtgc    840
cggagttaac acaataagta tcgcacctgg ggagtacgat cgcaaggttg aaactcaaag    900
gaattgacgg gggcccgcac aagcggtgga ttatgtggtt taattcgaag caacgcgaag    960
aaccttacca gggcttgaca tcctgctaac gaagtagaga tacattaggt gcccttcggg   1020
gaaagtagag acaggtggtg catggttgtc gtcagctcgt gtcgtgagat gttgggttaa   1080
gtcccgcaac gagcgcaacc cctattgtta gttgctacgc aagagcactc tagcgagact   1140
gccgttgaca aaacggagga aggcggggac gacgtcaaat catcatgccc cttatgtcct   1200
gggctacaca cgtaatacaa tggcggttaa caaagggatg caaagccgcg aggcagagcg   1260
aaccccaaaa agccgtccca gttcggatcg caggctgcaa cccgcctgcg tgaagtcgga   1320
atcgctagta atcgcggatc agcatgccgc ggtgaatacg ttcccgggcc ttgtacacac   1380
cgcccgtcac accatgagag tcgggaacac ccgaagtccg tagcctaacc gcaaggaggg   1440
cgcggccgaa ggtgggttcg ataattgggg tgaagtcgta acaaggtagc cgt          1493
```

<210> SEQ ID NO 59
<211> LENGTH: 1511
<212> TYPE: DNA
<213> ORGANISM: Clostridium leptum
<220> FEATURE:
<221> NAME/KEY: rRNA
<222> LOCATION: (1)..(1511)
<223> OTHER INFORMATION: 16S rRNA coding gene sequence of Clostridium
strain 39

<400> SEQUENCE: 59

```
agagtttgat cctggctcag gacgaacgct ggcggcgtgc ttaacacatg caagtcgaac     60
ggagcacccc tgaaggagtt ttcggacaac ggatgggaat gcttagtggc ggactggtga    120
gtaacgcgtg aggaacctgc cttccagagg gggacaacag ttggaaacga ctgctaatac    180
cgcatgatgc gttggagccg catgactccg acgtcaaaga tttatcgctg gaagatggcc    240
tcgcgtctga ttagctagtt ggtgaggtaa cggcccacca aggcgacgat cagtagccgg    300
actgagaggt tggccggcca cattgggact gagatacggc ccagactcct acgggaggca    360
```

```
gcagtgggga atattgggca atggacgcaa gtctgaccca gcaacgccgc gtgaaggaag    420

aaggctttcg ggttgtaaac ttcttttaag gggaagagc agaagacggt accccttgaa    480

taagccacgg ctaactacgt gccagcagcc gcggtaatac gtaggtggca agcgttgtcc    540

ggatttactg ggtgtaaagg gcgtgcagcc ggagagacaa gtcagatgtg aaatccacgg    600

gctcaacccg tgaactgcat ttgaaactgt ttcccttgag tgtcggagag gtaatcggaa    660

ttccttgtgt agcggtgaaa tgcgtagata taaggaagac accagtggcg aagcggatta    720

ctggacgata actgacggtg aggcgcgaaa gcgtggggag caaacaggat tagatacctg    780

ggtagtcaac gctgtaaacg atcgatacta ggtggtgcgg gggacttgac cccctgccgt    840

tgccggagtt aacaccaata aagtattcgg caccctgggg agtacgatcg caaaggttga    900

aaactcaaaa gaaatggacg gggggccccg ccccaagcgg gtgggattat gttggtttat    960

ttcgaaagca acgcgaagaa ccctaacagg gcttgacatc ctgctaacga agtagagata   1020

cattaggtgc ccttcgggga aagtagagac aggtggtgca tggttgtcgt cagctcgtgt   1080

cgtgagatgt tgggttaagt cccgcaacga gcgcaacccc tattgttagt tgctacgcaa   1140

gagcactcta gcgagactgc cgttgacaaa acggaggaag gcggggacga cgtcaaatca   1200

tcatgcccct tatgtcctgg gctacacacg taatacaatg gcggttaaca aagggatgca   1260

aagccgcgag gcagagcgaa ccccaaaaag ccgtcccagt tcggatcgca ggctgcaacc   1320

cgcctgcgtg aagtcggaat cgctagtaat cgcggatcag catgccgcgg tgaatacgtt   1380

cccgggcctt gtacacaccg cccgtcacac catgagagtc gggaacaccc gaagtccgta   1440

gcctaaccgc aaggagggcg cggccgaagg tgggttcgat aattggggtg aagtcgtaac   1500

aaggtagccg t                                                        1511
```

```
<210> SEQ ID NO 60
<211> LENGTH: 1499
<212> TYPE: DNA
<213> ORGANISM: Clostridium leptum
<220> FEATURE:
<221> NAME/KEY: rRNA
<222> LOCATION: (1)..(1499)
<223> OTHER INFORMATION: 16S rRNA coding gene sequence of Clostridium
      strain 40

<400> SEQUENCE: 60

agagtttgat cctggctcag gataaacgct ggcggcatgc ctaacacatg caagtcgaac     60

ggagcgcctt ggaaggagac ttcggtcaac ggaagaggag gcttagtggc ggacgggtga    120

gtaacgcgtg aggaacctgc ctcagagagg gggataacac accgaaaggt gtgctaatac    180

cgcataacat atgagagggg catccctttc atatcaaaga tttattgctt tgagatggcc    240

tcgcgtccaa ttagctagtt ggtgaggtaa cggcccacca aggcgacgat tggtagccgg    300

actgagaggt tgaacggcca cattgggact gagacacggc ccagactcct acgggaggca    360

gcagtgggga atattgcaca atgggggaa ccctgatgca gcaatgccgc gtgaaggatg    420

aaggttttcg gattgtaaac ttcttttgta cgggacgaag aaagtgacgg taccgtaaga    480

ataagccacg gctaactacg tgccagcagc cgcggtaata cgtaggtggc aagcgttatc    540

cggatttact gggtgtaaag ggcgagtagg cgggattgca agtcagatgt gaaaactatg    600

ggctcaaccg atagagtgca tttgaaactg cagttcttga gtgatggaga ggcaggcgga    660

attcccggtg tagcggtgga atgcgtagat atcgggaggg aacaccagtg gcgaaggcgg    720

cctgctggac attaactgac gctgatgcgc gaaagcgtgg ggagcaaaca ggattagata    780
```

```
ccctggtagt cacgctgtaa acgatgatta ctaggtgtgg ggggtactga ccccccttccc    840

gtgccggagt taacacaata agtaatccac ctggggagta cggccgcaag gttgaaactc    900

aaaggaattg acgggggccc gcacaagcag tggagtatgt ggttttaatt cgaagcaacg    960

cgaagaacct taccagggct tgacatgggg atgaccgctt tagagataga gctttctctt   1020

cggagacatc ccacacaggt ggtgcatggt tgtcgtcagc tcgtgtcgtg agatgttggg   1080

ttaagtcccg caacgagcgc aacccttatt gttagttgct acgcaagagc actctagcga   1140

gactgccgtt gacaaaacgg aggaaggtgg ggacgacgtc aaatcatcat gccctttatg   1200

tcctgggcta cacacgtact acaatggcgg acatacagag ggaagcaaga cagcgatgtg   1260

gagcaaatcc ctaaaagccg tctcagttca gattgcaggc tgcaacccgc ctgcatgaag   1320

tcggaattgc tagtaatcgc ggatcagcat gccgcggtga atacgttccc gggccttgta   1380

cacaccgccc gtcacaccat gagagtcgga aacacccgaa gcctgtagcc caaccgcaag   1440

gggggcgcag tcgaaggtgg gtctgataat tggggtgaag tcgtaacaaa ggtagccgt    1499
```

```
<210> SEQ ID NO 61
<211> LENGTH: 1512
<212> TYPE: DNA
<213> ORGANISM: Clostridium coccoides
<220> FEATURE:
<221> NAME/KEY: rRNA
<222> LOCATION: (1)..(1512)
<223> OTHER INFORMATION: 16S rRNA coding gene sequence of Clostridium
      strain 41

<400> SEQUENCE: 61

agagtttgat cctggctcag gatgaacgct ggcggcgtgc ttaacacatg caagtcgaac     60

ggagatatca ttttcgaagc gattagttta ctaagagcgg agatgttgct atcttagtgg    120

cggacgggtg agtaacgcgt gggtaacctg ccttgcactg gggataaca cttagaaata    180

ggtgctaata ccgcataaca gtaggagacg catgtctttt acttgaaaac tccggtggtg    240

taagatggac ccgcgtctga ttagcttgtt ggcggggtaa cggcccacca aggcaacgat    300

cagtagccgg cctgagaggg tgaacggcca cattgggact gagacacggc ccaaactcct    360

acgggaggca gcagtgggga atattggaca atggggggaa ccctgatcca gcgacgccgc    420

gtgagtgaag aagtatttcg gtatgtaaag ctctatcagc agggaagaaa gaaatgacgg    480

tacctgacta agaagccccg gctaactacg tgccagcagc cgcggtaata cgtagggggc    540

aagcgttatc cggatttact gggtgtaaag ggagcgtaga cggcgatgca agtctgaagt    600

gaaaggcggg ggcccaaccc ccggactgct ttggaaactg tatggctgga gtgcaggaga    660

ggtaagtgga attcctagtg tagcggtgaa atgcgtagat attaggagga acaccagtgg    720

cgaaagcggc ttactggact gtaactgacg ttgaggctcg aaagcgtggg gagcaaacaa    780

gattagatac ctggtagtca cgccgtaaac gatgatcacc ggtttcggtg ggttatggac    840

ccatcggttg cgcagcaaac gcagtagtga tccacctggg gagtaacgtt cgcaagaatg    900

aaacttcaaa ggaaatgacg gggacccgg cacaagcggt ggaggcatgt gtttaattcg    960

aagcaacgcg aagaacctta cccaagtctt gacatcccgt gacgagtgag taacgtcact   1020

ttcccttcgg ggcagcggag acaggtggtg catggttgtc gtcagctcgt gtcgtgagat   1080

gttgggttaa gtcccgcaac gagcgcaacc cctatcctta gtagccagcg agttaggtcg   1140

ggcactctag ggagactgcc ggggacaacc cggaggaagg tggggatgac gtcaaatcat   1200

catgcccctt atgatttggg ctacacacgt gctacaatgg cgtaaacaaa gggaagcgag   1260
```

```
cctgtgaagg taagcgaatc ccagaaataa cgtctcagtt cggattgtag tctgcaactc   1320

gactacatga agctggaatc gctagtaatc gcggatcaga atgccgcggt gaatacgttc   1380

ccgggtcttg tacacaccgc ccgtcacacc atgggagtcg gaaatgcccg aagtctgtga   1440

cccaacctga gaaggaggga gcagccgaag gcaggtcgga tgactggggt gaagtcgtaa   1500

caaggtagcc gt                                                       1512
```

```
<210> SEQ ID NO 62
<211> LENGTH: 17
<212> TYPE: DNA
<213> ORGANISM: Artificial
<220> FEATURE:
<223> OTHER INFORMATION: Artificially synthesized primer sequence

<400> SEQUENCE: 62

ggtgaatacg ttcccgg                                                    17


<210> SEQ ID NO 63
<211> LENGTH: 22
<212> TYPE: DNA
<213> ORGANISM: Artificial
<220> FEATURE:
<223> OTHER INFORMATION: Artificially synthesized primer sequence

<400> SEQUENCE: 63

tacggctacc ttgttacgac tt                                              22


<210> SEQ ID NO 64
<211> LENGTH: 20
<212> TYPE: DNA
<213> ORGANISM: Artificial
<220> FEATURE:
<223> OTHER INFORMATION: Artificially synthesized primer sequence

<400> SEQUENCE: 64

aaatgacggt acctgactaa                                                 20


<210> SEQ ID NO 65
<211> LENGTH: 22
<212> TYPE: DNA
<213> ORGANISM: Artificial
<220> FEATURE:
<223> OTHER INFORMATION: Artificially synthesized primer sequence

<400> SEQUENCE: 65

ctttgagttt cattcttgcg aa                                              22


<210> SEQ ID NO 66
<211> LENGTH: 16
<212> TYPE: DNA
<213> ORGANISM: Artificial
<220> FEATURE:
<223> OTHER INFORMATION: Artificially synthesized primer sequence

<400> SEQUENCE: 66

gcacaagcag tggagt                                                     16


<210> SEQ ID NO 67
<211> LENGTH: 18
<212> TYPE: DNA
<213> ORGANISM: Artificial
<220> FEATURE:
<223> OTHER INFORMATION: Artificially synthesized primer sequence

<400> SEQUENCE: 67
```

```
cttcctccgt tttgtcaa                                                18


<210> SEQ ID NO 68
<211> LENGTH: 18
<212> TYPE: DNA
<213> ORGANISM: Artificial
<220> FEATURE:
<223> OTHER INFORMATION: Artificially synthesized primer sequence

<400> SEQUENCE: 68

gagaggaagg tcccccac                                                18


<210> SEQ ID NO 69
<211> LENGTH: 19
<212> TYPE: DNA
<213> ORGANISM: Artificial
<220> FEATURE:
<223> OTHER INFORMATION: Artificially synthesized primer sequence

<400> SEQUENCE: 69

cgctacttgg ctggttcag                                               19
```

COMPOSITION FOR INDUCING PROLIFERATION OR ACCUMULATION OF REGULATORY T CELLS

RELATED APPLICATIONS

This application is a continuation of U.S. application Ser. No. 15/730,203, filed Oct. 11, 2017, now issued as U.S. Pat. No. 10,092,603, which is a continuation of U.S. application Ser. No. 15/216,015, filed Jul. 21, 2016, now issued as U.S. Pat. No. 9,801,933, which is a continuation of U.S. application Ser. No. 14/492,850, filed Sep. 22, 2014, now issued as U.S. Pat. No. 9,433,652, which is a continuation of U.S. application Ser. No. 13/701,467, filed Feb. 11, 2013, which is a national stage filing under 35 U.S.C. 371 of International Application PCT/JP2011/063302, filed Jun. 3, 2011, which claims the benefit of and priority to JP 2010-129134, filed Jun. 4, 2010 and PCT/JP2010/071746, filed Dec. 3, 2010. The entire teachings of the referenced applications are incorporated by reference herein.

TECHNICAL FIELD

The present invention relates to a composition which has an effect of inducing proliferation or accumulation of regulatory T cells, and which comprises, as an active ingredient, bacteria belonging to the genus *Clostridium*, a physiologically active substance derived from the bacteria, bacterial spores, or the like. The present invention also relates to a method for inducing proliferation or accumulation of regulatory T cells, as well as a method for inhibiting such proliferation or accumulation. Moreover, the present invention relates to a vaccine composition containing at least one strain of bacteria belonging to the genus *Clostridium* or a spore of bacteria, as well as a method for treating or preventing at least one disease or condition selected from infectious diseases and autoimmune diseases by administering the vaccine composition to an individual in need thereof. The present invention also relates to a method for screening for a compound that promotes proliferation or accumulation of regulatory T cells, as well as a non-human mammal which is used in this method, and in which a reporter gene is expressed under control of IL-10 gene expression.

BACKGROUND ART

Hundreds of species of commensal microorganisms are harbored in gastrointestinal tracts of mammals, and intimately interact with the host immune systems. Results of researches using germ-free (GF) animals have shown that the commensal microorganisms exert great influences on the development of mucosal immune systems such as histogenesis of Peyer's patches (PPs) and isolated lymphoid follicles (ILFs), secretion of antimicrobial peptides from epithelium, and accumulation of unique lymphocytes in mucosal tissues, the unique lymphocytes including immunoglobulin A-producing plasma cells, intraepithelial lymphocytes, IL-17-producing CD4-positive T cells (Th 17), and IL-22-producing NK-like cells (Non-Patent Documents 1 to 7). Consequently, the presence of intestinal bacteria enhances protective functions of the mucous membranes, providing the hosts with robust immune responses against pathogenic microbes invading the bodies. On the other hand, the mucosal immune systems maintain unresponsiveness to dietary antigens and harmless microbes (Non-Patent Document 3). For this reason, abnormality in the regulation of cross-talk between commensal bacteria and an immune system (intestinal dysbiosis) may lead to overly robust immune response to environmental antigens, so that inflammatory bowel disease (IBD) is caused (Non-Patent Documents 8 to 10).

Results of Recent studies have shown that individual commensal bacteria control differentiation of their specific immune cells in the mucosal immune system. For example, *Bacteroides fragilis*, which is a commensal bacterium in humans, specifically induces a systemic Th1 cell response and a mucosal IL-10-producing T cell response in mice, and plays a role in protecting the host from colitis, which would otherwise be caused by a pathogen (Non-Patent Document 3). Segmented filamentous bacteria, which are intestinal commensal bacteria in mice, are shown to induce mucosal Th17 cell response and thereby to enhance resistance against infection of gastrointestinal tracts of the host with a pathogen (Non-Patent Documents 11 to 13). In addition, short-chain fatty acids derived from several commensal bacteria are known to suppress intestinal inflammation (Non-Patent Document 14). Moreover, it is presumed that the presence of some species of intestinal microbiota exerts a great influence on the differentiation of regulatory T cells (hereafter referred to as "Treg cells") which maintain homeostasis of the immune system.

Meanwhile, regulatory T cells which have been identified as a subset suppressing immunity are $CD4^+$ T cells in which a transcription factor Foxp3 is expressed, and are known to play an important role in maintaining immunological homeostasis (Non-Patent Documents 8, 9, 15, and 16). Moreover, it has been known that the Foxp3-expressing cells are present in a large number especially in the colon, and only Treg cells present locally in the colon constantly expresses IL-10, which is an immunosuppressive cytokine, at a high level (Non-Patent Document 17). It is also known that animals having $CD4^+$ $Foxp3^+$ cells from which IL-10 is specifically removed develop inflammatory bowel disease (Non-Patent Document 18).

Accordingly, if the mechanism of the induction of Treg cells which produce IL-10 in the colon at a high level is elucidated, immunosuppression can be enhanced, which in turn can be applied to treatment of autoimmune diseases such as inflammatory bowel disease, as well as to organ transplantation.

However, mechanisms of how a large number of Treg cells come to be present in the colon and how the Treg cells produce IL-10 in the colon at a high level are still unclear. Moreover, it is also still unclear what species of bacteria constituting the intestinal commensal bacterial flora exerts the influence on the induction of regulatory T cells.

CITATION LIST

Non Patent Literature

[NPL 1] J. J. Cebra, "Am J Clin Nutr", May, 1999, 69, 1046S

[NPL 2] A. J. Macpherson, N. L. Harris, "Nat Rev Immunol", June 2004, 4, 478

[NPL 3] J. L. Round, S. K. Mazmanian, "Nat Rev Immunol", May 2009, 9, 313

[NPL 4] D. Bouskra et al., "Nature", Nov. 27, 2008, 456, 507

[NPL 5]K. Atarashi et al., "Nature", Oct. 9, 2008, 455, 808

[NPL 6] Ivanov, I I et al., "Cell Host Microbe", Oct. 16, 2008, 4, 337

[NPL 7]S. L. Sanos et al., "Nat Immunol", January 2009, 10, 83

[NPL 8]M. A. Curotto de Lafaille, J. J. Lafaille, "Immunity", May 2009, 30, 626

[NPL 9]M. J. Barnes, F. Powrie, "Immunity", Sep. 18, 2009, 31, 401

[NPL 10]W. S. Garrett et al., "Cell", Oct. 5, 2007, 131, 33

[NPL 11] Ivanov, I I et al., "Cell", Oct. 30, 2009, 139, 485.

[NPL 12]V. Gaboriau-Routhiau et al., "Immunity", Oct. 16, 2009, 31, 677

[NPL 13]N. H. Salzman et al., "Nat Immunol", 11, 76.

[NPL 14]K. M. Maslowski et al., "Nature", Oct. 29, 2009, 461, 1282

[NPL 15]L. F. Lu, A. Rudensky, "Genes Dev", Jun. 1, 2009, 23, 1270

[NPL 16]S. Sakaguchi, T. Yamaguchi, T. Nomura, M. Ono, "Cell", May 30, 2008, 133, 775

[NPL 17]C. L. Maynard et al., "Nat Immunol", September 2007, 8, 931

[NPL 18]Y. P. Rubtsov et al., "Immunity", April 2008, 28, 546

SUMMARY OF INVENTION

Technical Problem

The present invention has been made in view of the above-described problems of the conventional techniques. Accordingly, an object of the present invention is to identify intestinal commensal bacteria which induce the proliferation or accumulation of regulatory T cells. Another object of the present invention is to provide compositions or the like which comprise the identified intestinal commensal bacteria or a physiologically active substance derived therefrom, and which thus have induce the proliferation or accumulation of regulatory T cells (Treg cells).

Solution to Problem

The present inventors have made earnest studies to solve the above-described problems. As a result, the present inventors have found that a chloroform-treated fraction and a spore-forming fraction of a fecal sample obtained from a mammal induces accumulation of regulatory T cells (Treg cells) in the colon. Moreover, the present inventors have found that bacteria belonging to the genus *Clostridium* induce proliferation or accumulation of regulatory T cells in the colon. The present inventors have also found that the regulatory T cells induced by these bacteria suppress proliferation of effector T cells. Furthermore, the present inventors have also found that colonization of bacteria belonging to the genus *Clostridium* and resultant proliferation or accumulation of Treg cells regulate local and systemic immune responses.

From these findings, the present inventors have found that the use of bacteria belonging to the genus *Clostridium*, spores thereof, or a physiologically active substance derived therefrom makes it possible to induce the proliferation or accumulation of regulatory T cells (Treg cells), and further to suppress immune functions.

More specifically, the present invention has the following aspects:

(1) A composition that induces proliferation or accumulation of regulatory T cells, the composition comprising, as an active ingredient, at least one substance selected from the group consisting of the following (a) to (c):

(a) bacteria belonging to the genus *Clostridium* or a physiologically active substance derived from the bacteria;

(b) a spore-forming fraction of a fecal sample obtained from a mammal or a culture supernatant of the fraction; and (c) a chloroform-treated fraction of a fecal sample obtained from a mammal or a culture supernatant of the fraction.

(2) Any of the compositions described herein wherein the regulatory T cells are transcription factor Foxp3-positive regulatory T cells or IL-10-producing regulatory T cells.

(3) The composition according to any one of (1) and (2), wherein the composition has an immunosuppressive effect.

(4) The composition according to any one of (1) to (3), wherein the composition is a pharmaceutical composition.

(5) A method for inducing proliferation or accumulation of regulatory T cells in an individual (e.g., an individual in need thereof, such as an individual in need of induction of proliferation or accumulation of regulatory T cells), the method comprising a step of administering, to the individual, at least one substance selected from the group consisting of the following (a) to (c):

(a) bacteria belonging to the genus *Clostridium* or a physiologically active substance derived from the bacteria;

(b) a spore-forming fraction of a fecal sample obtained from a mammal or a culture supernatant of the fraction; and (c) a chloroform-treated fraction of a fecal sample obtained from a mammal or a culture supernatant of the fraction.

(6) A method for inducing proliferation or accumulation of regulatory T cells in an individual (e.g., an individual in need thereof, such as an individual in need of induction of proliferation or accumulation of regulatory T cells), the method comprising a step of administering an antibiotic against Gram-negative bacteria to the individual. And the antibiotic can be administered alone or in combination with at least one substance selected from the group consisting of the following (a) to (c):

(a) bacteria belonging to the genus *Clostridium* or a physiologically active substance derived from the bacteria;

(b) a spore-forming fraction of a fecal sample obtained from a mammal or a culture supernatant of the fraction; and (c) a chloroform-treated fraction of a fecal sample obtained from a mammal or a culture supernatant of the fraction.

(7) A method for inducing proliferation or accumulation of regulatory T cells in an individual, the method comprising a step of administering, to the individual, at least one substance selected from the group consisting of almond skin, inulin, oligofructose, raffinose, lactulose, pectin, hemicellulose, amylopectin, acetyl-Co A, biotin, beet molasses, yeast extracts, and resistant starch.

(8) The method according to any one of (5) to (7), wherein a therapeutic composition is further administered to the individual.

Note that, the "therapeutic composition" here is meant to be something other than (a)-(c) described in (5) and (6), the antibiotic against Gram-negative bacteria described in (6), or the substances described in (7).

(9) The method according to (8), wherein the therapeutic composition is at least one composition selected from the group consisting of corticosteroids, mesalazine, mesalamine, sulfasalazine, sulfasalazine derivatives, immunosuppressive drugs, cyclosporin A, mercaptopurine, azathiopurine, prednisone, methotrexate, antihistamines, glucocorticoids, epinephrine, theophylline, cromolyn sodium, anti-leukotrienes, anti-cholinergic drugs for rhinitis, anti-cholinergic decongestants, mast-cell stabilizers, monoclonal anti-IgE antibodies, vaccines, and combinations thereof.

(10) The method according to any one of (5) to (9), wherein one measurement selected from the group consisting of promotion of IL-10 expression, promotion of CTLA4 expression, promotion of IDO expression, and suppression of IL-4 expression is used as an index of the induction of proliferation or accumulation of regulatory T cells in the individual.

(11) A method for inhibiting proliferation or accumulation of regulatory T cells in an individual (e.g., an individual thereof), the method comprising a step of administering an antibiotic against Gram-positive bacteria to the individual.

(12) The composition according to any one of (5) to (11), wherein the regulatory T cells are transcription factor Foxp3-positive regulatory T cells or IL-10-producing regulatory T cells.

(13) A vaccine composition comprising at least one substance selected from the group consisting of the following (a) to (c):

(a) bacteria belonging to the genus *Clostridium;*

(b) a spore of bacteria in a spore-forming fraction of a fecal sample obtained from a mammal; and (c) bacteria in a chloroform-treated fraction of a fecal sample obtained from a mammal.

(14) A method for treating aiding in treating, reducing the severity of, or preventing at least one disease selected from infectious diseases and autoimmune diseases in an individual (e.g., an individual in need thereof, such as an individual in need of treatment, reduction in the severity of or prevention of at least one such disease), the method comprising administering the vaccine composition according to (13) to the individual.

(15) A method for screening for a compound having an activity to promote proliferation or accumulation of regulatory T cells, the method comprising:

(I) preparing a test substance from at least one substance selected from the group consisting of the following (a) to (c):

(a) bacteria belonging to the genus *Clostridium* or a physiologically active substance derived from the bacteria;

(b) a spore-forming fraction of a fecal sample obtained from a mammal or a culture supernatant of the fraction; and (c) a chloroform-treated fraction of a fecal sample obtained from a mammal or a culture supernatant of the fraction.

(II) preparing non-human mammals in which a reporter gene is to be expressed under control of IL-10 gene expression;

(III) bringing the test substance into contact with the non-human mammal;

(IV) after the contact with the test substance, detecting cells expressing the reporter gene in a $CD4^+$ $Foxp3^+$ cell group of the non-human mammal, and determining the number of cells in the $CD4^+$ $Foxp3^+$ cell group expressing the reporter gene or a ratio of cells in the $CD4^+$ $Foxp3^+$ cell group expressing the reporter gene to cells in the $CD4^+$ $Foxp3^+$ cell group not expressing the reporter gene;

(V) detecting cells expressing the reporter gene in a $CD4^+$ $Foxp3^+$ cell group of the non-human mammal which has not been in contact with the test substance, and determining the number of cells in the $CD4^+$ $Foxp3^+$ cell group expressing the reporter gene or a ratio of cells in the $CD4^+$ $Foxp3^+$ cell group expressing the reporter gene to cells in the $CD4^+$ $Foxp3^+$ cell group not expressing the reporter gene; and (VI) comparing the number or the ratio determined in (IV) with the number or the ratio determined in (V), and determining, when the number or the ratio determined in (IV) is greater than that determined in (V), that the test substance is a compound that promotes proliferation or accumulation of Treg cells.

(16) A non-human mammal which is used for the method according to (15), and in which the reporter gene is expressed under the control of the IL-10 gene expression.

(17) A method for isolating, from a sample of bacteria belonging to the genus *Clostridium*, a compound having an activity to promote proliferation or accumulation of regulatory T cells, the method comprising (I) to (III):

(I) preparing a genomic DNA from the sample of bacteria belonging to the genus *Clostridium;*

(II) inserting the genomic DNA into a cloning system, and preparing a gene library derived from the sample of bacteria belonging to the genus *Clostridium*; and (III) isolating a compound having an activity to promote proliferation or accumulation of regulatory T cells, by use of the gene library obtained in step (II).

(18) A method of treatment comprising (I) to (III):

(I) measuring the percentage and/or absolute amounts of *Clostridium* Clusters IV and XIV in the microbiota of a subject, (II) comparing them to the same measurements in a healthy individual; and (III) administering a substance to the subject, if a statistically significant decrease in the number/amounts of *Clostridium* cluster IV, XIV in the subject compared to the healthy individual is detected, wherein the substance is at least one substance selected from the group consisting of the following (a) to (c):

(a) any of the substances described herein;

(b) an antibiotic against Gram-negative bacteria; and (c) the substance selected from the group consisting of almond skin, inulin, oligofructose, raffinose, lactulose, pectin, hemicellulose, amylopectin, acetyl-CoA, biotin, beet molasses, yeast extracts, and resistant starch.

(19) A method of monitoring, comprising (I) to (II):

(I) measuring level of *Clostridium* cluster IV, XIV in a subject after administering at least one substance selected from the group consisting of the following (a) to (c):

(a) any of the substances described herein;

(b) an antibiotic against Gram-negative bacteria; and (c) the substance selected from the group consisting of almond skin, inulin, oligofructose, raffinose, lactulose, pectin, hemicellulose, amylopectin, acetyl-Co A, biotin, beet molasses, yeast extracts, and resistant starch; and (II) if the level increases, it is judged to be a sign that the subject is responding favorably.

Advantageous Effects of Invention

The compositions of the present invention containing as an active ingredient bacteria belonging to the genus *Clostridium* or a physiologically active substance derived from the bacteria serves as an excellent composition for inducing the proliferation or accumulation of regulatory T cells (Treg cells). Immunity in a living organism can be suppressed through administration of the composition of the present invention as a pharmaceutical product or ingestion of the composition as a food or beverage. Accordingly, the composition of the present invention can be used, for example, to prevent or treat autoimmune diseases or allergic diseases, as well as to suppress immunological rejection in organ transplantation or the like. In addition, if a food or beverage such as a health food comprises the composition of the present invention, healthy individuals can ingest the composition easily and routinely. As a result, it is possible to induce the proliferation or accumulation of regulatory T cells and thereby to improve immune functions.

DESCRIPTION OF EMBODIMENTS

Figure 1:
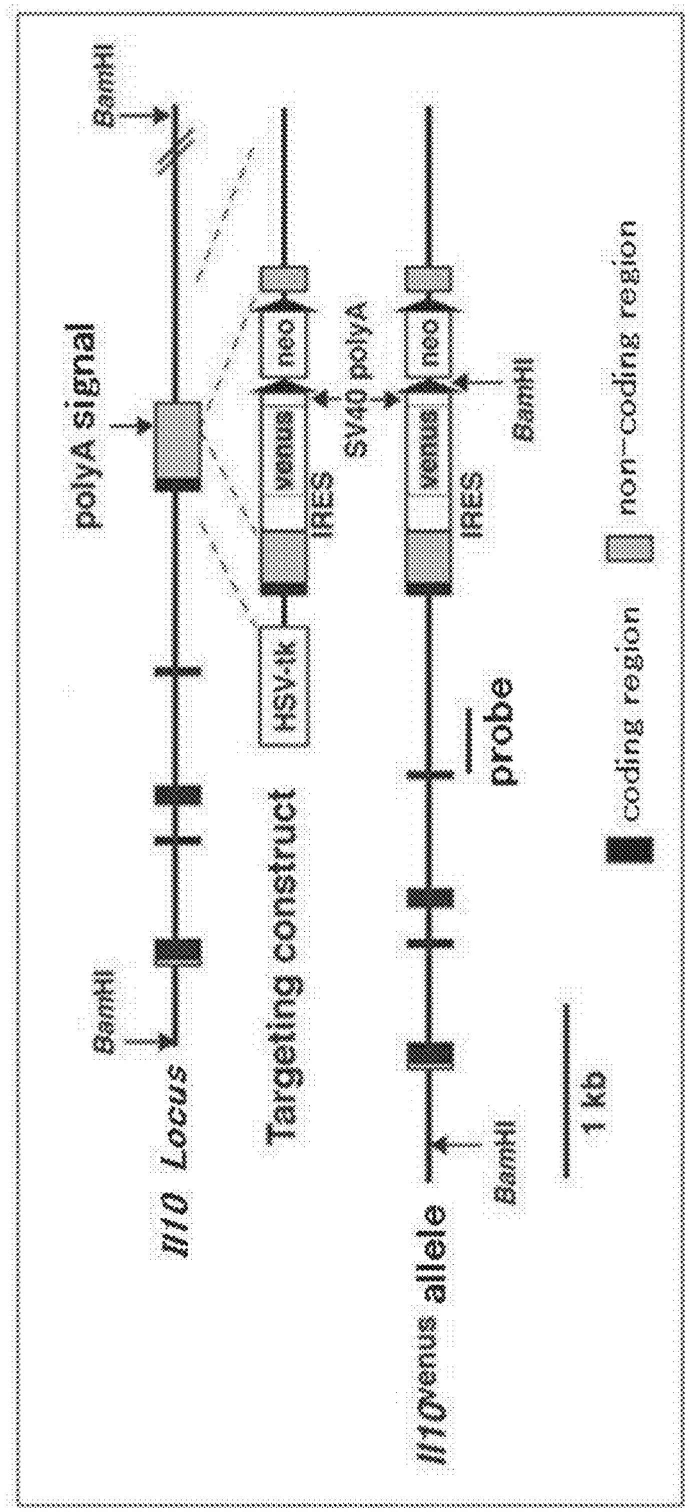
FIG. 1 is a schematic diagram showing a method of producing Il10$^{venus}$ mouse.

<Composition Having Effect of Inducing Proliferation or Accumulation of Regulatory T Cells>

The present invention provides a composition that induces proliferation or accumulation of regulatory T cells, the composition comprising, as an active ingredient, at least one substance selected from the group consisting of the following (a) to (c):

(a) bacteria belonging to the genus *Clostridium* or a physiologically active substance derived from the bacteria;

(b) a spore-forming fraction of a fecal sample obtained from a mammal or a culture supernatant of the fraction; and (c) a chloroform-treated fraction of a fecal sample obtained from a mammal or a culture supernatant of the fraction.

In the present invention "regulatory T cells" mean T cells which have a function of suppressing an abnormal or excessive immune response, and which play a role in immune tolerance. The regulatory T cells are typically transcription factor Foxp3-positive CD4-positive T cells. However, the regulatory T cells of the present invention also include transcription factor Foxp3-negative regulatory T cells, as long as the regulatory T cells are IL-10-producing CD4-positive T cells.

The meaning of the "induces proliferation or accumulation of regulatory T cells" in the present invention includes an effect of inducing the differentiation of immature T cells into regulatory T cells, which differentiation leads to the proliferation or the accumulation of regulatory T cells. In addition, the meaning of the "induces proliferation or accumulation of regulatory T cells" in the present invention includes in-vivo effects, in vitro effects, and ex vivo effects. Accordingly, all of the following effects are included: an effect of inducing in vivo proliferation or accumulation of regulatory T cells through administration or ingestion of the bacteria belonging to the genus *Clostridium* or the physiologically active substance or the like derived from the bacteria; an effect of inducing proliferation or accumulation of cultured regulatory T cells by causing the bacteria belonging to the genus *Clostridium* or the physiologically active substance or the like derived from the bacteria to act on the cultured regulatory T cells; and an effect of inducing proliferation or accumulation of regulatory T cells which are collected from a living organism and which are intended to be subsequently introduced into a living organism, such as the organism from which they were obtained or another organism, by causing the bacteria belonging to the genus *Clostridium* or the physiologically active substance or the like derived from the bacteria to act on the regulatory T cells. The effect of inducing proliferation or accumulation of regulatory T cells can be evaluated, for example, as follows. Specifically, the bacteria belonging to the genus *Clostridium* or the physiologically active substance or the like derived from the bacteria is orally administered to an experimental animal such as a germ-free mouse, then CD4-positive cells in the colon are isolated, and the ratio of regulatory T cells contained in the CD4-positive cells is measured by flow cytometry (refer to Example 7).

The regulatory T cells of which proliferation or accumulation is induced by the composition of the present invention are preferably transcription factor Foxp3-positive regulatory T cells or IL-10-producing regulatory T cells.

The "bacteria belonging to the genus *Clostridium*," which are the active ingredient in the composition of the present invention, is not particularly limited as long as the bacteria have the effect of inducing proliferation or accumulation of regulatory T cells. The bacteria preferably belong to the cluster XIVa or the cluster IV. One strain of the bacteria alone can be used for the composition of the present invention, but two or more strains of the bacteria can be used together for the composition of the present invention. The use of multiple strains of bacteria belonging to the cluster XIVa or the cluster IV in combination can bring about an excellent effect on regulatory T cells. In addition to the bacteria belonging to these clusters, bacteria belonging to other clusters (for example, bacteria belonging to the cluster III) can also be used in combination. If more than one strain of bacteria is used (e.g., one or more strain belonging to cluster XIVa, one or more strain belonging to cluster IV, one or more strain belonging to a cluster other than cluster XIVa or cluster IV, such as one or more strain belonging to cluster III), the type and number of strains used can vary widely. The type and number to be used can be determined based on a variety of factors (e.g., the desired effect, such as induction or inhibition of proliferation or accumulation of regulatory T cells; the disease or condition to be treated, prevented or reduced in severity; the age or gender of the recipient) The strains can be present in a single composition, in which case they will be consumed or ingested together, or can be present in more than one composition (e.g., each can be in a separate composition), in which case they can be consumed individually or the compositions can be combined and the resulting combination (combined compositions) consumed or ingested. Any number or combination of strains that proves effective (e.g., any number from one to 200, such as 1 to 100, 1 to 50, 1 to 40, 1 to 30, 1 to 20, 1 to 10, 1 to 5 and any number therebetween) can be administered. In certain embodiments of the present invention, a combination of some or all of the 46 strains described in Document (Itoh, K., and Mitsuoka, T. Characterization of clostridia isolated from faeces of limited flora mice and their effect on caecal size when associated with germ-free mice. Lab. Animals 19: 111-118 (1985)) is used. For example, at least one, two or more, three, three or more, four, four or more, five, five or more, six, six or more or any other number of the 46 described strains, including 46 strains, can be used. They can be used in combination with one another and in combination with strains not described in the cited reference (e.g., in combination with one or more strains belonging to cluster III). Note that, the cluster of "bacteria belonging to the genus *Clostridium*" can be identified, for example, as follows. Specifically, the bacteria belonging to the genus *Clostridium* are classified by PCR using a primer set consisting of SEQ ID NOs 64 and 65 (for *Clostridium* spp. belonging to the cluster XIVa) or a primer set consisting of SEQ ID NOs 66 and 67 (for *Clostridium* spp. belonging to the cluster IV) (refer to Example 18). In addition, the bacteria belonging to the genus *Clostridium* are classified by sequencing of 16S rRNA gene amplified using a primer set consisting of SEQ ID NOs 19 and 20 (refer to Example 7).

Viable cells of the bacteria belonging to the genus *Clostridium* can be used for the composition of the present invention, and killed cells thereof may also be used for the composition. In addition, from the viewpoint of stability to heat, resistance to antibiotics and the like, and long storage period, the bacteria belonging to the genus *Clostridium* are preferably in the form of spore.

The meaning of the "physiologically active substance derived from bacteria belonging to the genus *Clostridium*" of the present invention includes substances contained in the bacteria, secretion products of the bacteria, and metabolites of the bacteria. Such a physiologically active substance can be identified by purifying an active component from the bacteria, a culture supernatant thereof, or intestinal tract contents in the intestinal tract of a mouse in which only bacteria belonging to the genus *Clostridium* are colonized by an already known purification method.

The active ingredient "spore-forming fraction of a fecal sample obtained from a mammal" in the composition of the present invention is not particularly limited, as long as the fraction includes spore-forming bacteria present in feces of a mammal, and has the effect of inducing proliferation or accumulation of regulatory T cells.

The active ingredient "chloroform-treated fraction of a fecal sample obtained from a mammal" in the composition of the present invention is not particularly limited, as long as the fraction is obtained by treating feces of a mammal with chloroform (for example, 3% chloroform), and has the effect of inducing proliferation or accumulation of regulatory T cells.

Note that the "mammal" in the present invention is not particularly limited, and examples thereof include humans, mice, rats, cattle, horses, pigs, sheep, monkeys, dogs, and cats.

Meanwhile, when the "spore-forming fraction of a fecal sample obtained from a mammal" or the "chloroform-treated fraction of a fecal sample obtained from a mammal" is cultured in a medium, substances contained in the bacteria, secretion products of the bacteria, metabolites of the bacteria are released from the bacteria and the like contained in the fraction. The meaning of the active ingredient "culture supernatant of the fraction" in the composition of the present invention includes such substances, secretion products, and metabolites. The culture supernatant is not particularly limited, as long as the culture supernatant has the effect of inducing proliferation or accumulation of regulatory T cells. Examples of the culture supernatant include a protein fraction of the culture supernatant, a polysaccharide fraction of the culture supernatant, a lipid fraction of the culture supernatant, and a low-molecular weight metabolite fraction of the culture supernatant.

The composition of the present invention may be in the form of a pharmaceutical composition, a food or beverage (which may also be an animal feed), or a reagent used for an animal model experiment, the pharmaceutical composition, the food or beverage, and the reagent having the effect of inducing proliferation or accumulation of regulatory T cells. An example of the present invention revealed that regulatory T cells (Treg cells) induced by bacteria or the like belonging to the genus *Clostridium* suppressed the proliferation of effector T-cells. Accordingly, the composition of the present invention can be used suitably as a composition having an immunosuppressive effect. The immunosuppressive effect can be evaluated, for example, as follows. Specifically, regulatory T cells isolated from an experimental animal, such as a mouse, to which the composition of the present invention is orally administered are caused to act on effector T-cells ($CD4^+$ $CD25^-$ cells) isolated from the spleen, and then proliferation ability thereof is measured by using the intake amount of [$^3$H]-thymidine as an index (refer to Example 14).

The composition of the present invention can be used, for example, as a pharmaceutical composition for preventing or treating an autoimmune disease such as chronic inflammatory bowel disease, systemic lupus erythematosus, rheumatoid arthritis, multiple sclerosis, or Hashimoto's disease, or an allergic disease such as pollenosis or asthma; a pharmaceutical composition for suppressing rejection in organ transplantation or the like; a food or beverage for improving immune functions; or a reagent for suppressing the proliferation or function of effector T-cells.

More specific examples of target diseases of the composition of the present invention include autoimmune diseases, allergic diseases, and rejection in organ transplantations and the like, such as inflammatory bowel disease (IBD), ulcerative colitis, Crohn's disease, sprue, autoimmune arthritis, rheumatoid arthritis, Type I diabetes, multiple sclerosis, graft vs. host disease following bone marrow transplantation, osteoarthritis, juvenile chronic arthritis, Lyme arthritis, psoriatic arthritis, reactive arthritis, spondy loarthropathy, systemic lupus erythematosus, insulin dependent diabetes mellitus, thyroiditis, asthma, psoriasis, dermatitis scleroderma, atopic dermatitis, graft versus host disease, acute or chronic immune disease associated with organ transplantation, sarcoidosis, atherosclerosis, disseminated intravascular coagulation, Kawasaki's disease, Grave's disease, nephrotic syndrome, chronic fatigue syndrome, Wegener's granulomatosis, Henoch-Schoenle jn purpurea, microscopic vasculitis of the kidneys, chronic active hepatitis, uveitis, septic shock, toxic shock syndrome, sepsis syndrome, cachexia, acquired immunodeficiency syndrome, acute transverse myelitis, Huntington's chorea, Parkinson's disease, Alzheimer's disease, stroke, primary biliary cirrhosis, hemolytic anemia, polyglandular deficiency type I syndrome and polyglandular deficiency type II syndrome, Schmidt's syndrome, adult (acute) respiratory distress syndrome, alopecia, alopecia areata, seronegative arthopathy, arthropathy, Reiter's disease, psoriatic arthropathy, *chlamydia, yersinia* and *salmonella* associated arthropathy spondyloarhopathy, atheromatous disease/arteriosclerosis, atopic allergy, food allergies, autoimmune bullous disease, pemphigus vulgaris, pemphigus *foliaceus*, pemphigoid, linear IgA disease, autoimmune haemolytic anaemia, Coombs positive haemolytic anaemia, acquired pernicious anaemia, juvenile pernicious anaemia, myalgic encephalitis/Royal Free Disease, chronic mucocutaneous candidiasis, giant cell arteritis, primary sclerosing hepatitis, cryptogenic autoimmune hepatitis, Acquired Immunodeficiency Disease Syndrome, Acquired Immunodeficiency Related Diseases, Hepatitis C, common varied immunodeficiency (common variable hypogammaglobulinaemia), dilated cardiomyopathy, fibrotic lung disease, cryptogenic fibrosing alveolitis, postinflammatory interstitial lung disease, interstitial pneumonitis, connective tissue disease associated interstitial lung disease, mixed connective tissue disease associated lung disease, systemic sclerosis associated interstitial lung disease, rheumatoid arthritis associated interstitial lung disease, systemic lupus erythematosus associated lung disease, dermatomyositis/polymyositis associated lung disease, Sjogren's disease associated lung disease, ankylosing spondy litis associated lung disease, vasculitic diffuse lung disease, haemosiderosis associated lung disease, drug-induced interstitial lung disease, radiation fibrosis, bronchiolitis obliterans, chronic eosinophilic pneumonia, lymphocytic infiltrative lung disease, postinfectious interstitial lung disease, gouty arthritis, autoimmune hepatitis, type-1 autoimmune hepatitis (classical autoimmune or lupoid hepatitis), type-2 autoimmune hepatitis (anti-LKM antibody hepatitis), autoimmune mediated hypoglycemia, type B insulin resistance with acanthosis *nigricans*, hypoparathyroidism, acute immune disease associated with organ transplantation, chronic immune disease associated with organ transplantation, osteoarthrosis, primary sclerosing cholangitis, idiopathic leucopenia, autoimmune neutropenia, renal disease NOS, glomerulonephritides, microscopic vasulitis of the kidneys, discoid lupus, erythematosus, male infertility idiopathic or NOS, sperm autoimmunity, multiple sclerosis (all subtypes), insulindependent diabetes mellitus, sympathetic ophthalmia, pulmonary hypertension secondary to connective tissue disease, Goodpasture's syndrome, pulmonary manifestation of polyarteritis *nodosa*, acute rheumatio fever, rheumatoid spondylitis, Still's disease, systemic sclerosis, Takayasu's disease/arteritis, autoimmune thrombocytopenia, idiopathic thrombocytopenia, autoimmune thyroid disease, hyperthyroidism, goitrous autoimmune hypothyroidism (Hashimoto's disease), atrophic autoimmune hypothyroidism, primary myxoedema, phacogenic uveitis, primary vasculitis, vitiligo, allergic rhinitis (pollen allergies), anaphylaxis, pet allergies, latex allergies, drug allergies, allergic rhinoconjuctivitis, eosinophilic esophagitis, hypereosinophilic syndrome, eosinophilic gastroenteritis cutaneous lupus erythematosus, eosinophilic esophagitis, hypereosinophilic syndrome, and eosinophilic gastroenteritis.

The composition of the present invention can also be used as a pharmaceutical composition for preventing or treating infectious diseases in an individual whose resistance to the infectious diseases is impaired because of damage due to excessive inflammation caused by the immunity.

Example of infectious pathogens which impair maintenance or recovery of homeostasis of a host, and which eventually bring about such immunopathological tissue damage include *Salmonella, Shigella, Clostridium difficile, Mycobacterium* (which cause the disease tuberculosis), protozoa (which cause the disease malaria), filarial nematodes (which cause the disease filariasis), *Schistosoma* (which cause the disease schistosomiasis), *Toxoplasma* (which cause the disease toxoplasmosis), *Leishmania* (which cause the disease leishmaniasis), HCV and HBV (which cause the disease hepatitis C and hepatitis B), and herpes simplex viruses (which cause the disease herpes).

Pharmaceutical preparations can be formulated from the composition of the present invention by already known drug formulation methods. For example, the composition of the present invention can be used orally or parenterally in the forms of capsules, tablets, pills, liquids, powders, granules, fine granules, film-coated preparations, pellets, troches, sublingual preparations, chewables, buccal preparations, pastes, syrups, suspensions, elixirs, emulsions, liniments, ointments, plasters, cataplasms, transdermal absorption systems, lotions, inhalations, aerosols, injections, suppositories, and the like.

For formulating these preparations, the composition of the present invention can be used in appropriate combination with carriers acceptable pharmacologically or acceptable for a food or beverage, specifically, with sterile water, physiological saline, vegetable oil, solvent, a base material, an emulsifier, a suspending agent, a surfactant, a stabilizer, a flavoring agent, an aromatic, an excipient, a vehicle, a preservative, a binder, a diluent, a tonicity adjusting agent, a soothing agent, a bulking agent, a disintegrating agent, a buffer agent, a coating agent, a lubricant, a colorant, a sweetener, a thickening agent, a flavor corrigent, a solubilizer, other additives, or the like.

Meanwhile, for formulating a pharmaceutical preparation thereof, and particularly for formulating a pharmaceutical preparation for oral administration, it is preferable to use in combination a composition which enables an efficient delivery of the composition of the present invention to the colon, from the viewpoint of more efficiently inducing the proliferation or accumulation of regulatory T cells in the colon.

Such a composition or method which enables the delivery to the colon is not particularly limited, and known compositions or methods can be employed as appropriate. Examples thereof include pH sensitive compositions, more specifically, enteric polymers which release their contents when the pH becomes alkaline after the enteric polymers pass through the stomach. When a pH sensitive composition is used for formulating the pharmaceutical preparation, the pH sensitive composition is preferably a polymer whose pH threshold of the decomposition of the composition is 6.8 to 7.5. Such a numeric value range is a range where the pH shifts toward the alkaline side at a distal portion of the stomach, and hence is a suitable range for use in the delivery to the colon.

Moreover, another example of the composition enabling the delivery to the colon is a composition which ensures the delivery to the colon by delaying the release of the contents by approximately 3 to 5 hours, which corresponds to the small intestinal transit time. In an example of formulating a pharmaceutical preparation using the composition for delaying the release, a hydrogel is used as a shell. The hydrogel is hydrated and swells upon contact with gastrointestinal fluid, so that the contents are effectively released. Furthermore the delayed release dosage units include drug-containing compositions having a material which coats or selectively coats a drug. Examples of such a selective coating material include in vivo degradable polymers, gradually hydrolyzable polymers, gradually water-soluble polymers, and/or enzyme degradable polymers. A preferred coating material for efficiently delaying the release is not particularly limited, and examples thereof include cellulose-based polymers such as hydroxypropyl cellulose, acrylic acid polymers and copolymers such as methacrylic acid polymers and copolymers, and vinyl polymers and copolymers such as polyvinylpyrrolidone.

Examples of the composition enabling the delivery to the colon further include bioadhesive compositions which specifically adhere to the colonic mucosal membrane (for example, a polymer described in the specification of U.S. Pat. No. 6,368,586), and compositions into which a protease inhibitor is incorporated for protecting particularly a biopharmaceutical preparation in the gastrointestinal tracts from decomposition due to an activity of a protease.

An example of a system enabling the delivery to the colon is a system of delivering a composition to the colon by pressure change in such a way that the contents are released by utilizing pressure change caused by generation of gas in bacterial fermentation at a distal portion of the stomach. Such a system is not particularly limited, and a more specific example thereof is a capsule which has contents dispersed in a suppository base and which is coated with a hydrophobic polymer (for example, ethyl cellulose).

Another example of the system enabling the delivery to the colon is a system of delivering a composition to the colon, the system being specifically decomposed by an enzyme (for example, a carbohydrate hydrolase or a carbohydrate reductase) present in the colon. Such a system is not particularly limited, and more specific examples thereof include systems which use food components such as non-starch polysaccharides, amylose, xanthan gum, and azopolymers.

When used as a pharmaceutical composition, the composition of the present invention may be used in combination with an already known pharmaceutical composition for use in immunosuppression. Such a known pharmaceutical composition is not particularly limited, and may be at least one therapeutic composition selected from the group consisting of corticosteroids, mesalazine, mesalamine, sulfasalazine, sulfasalazine derivatives, immunosuppressive drugs, cyclosporin A, mercaptopurine, azathiopurine, prednisone, methotrexate, antihistamines, glucocorticoids, epinephrine, theophylline, cromolyn sodium, anti-leukotrienes, anti-cholinergic drugs for rhinitis, anti-cholinergic decongestants, mast-cell stabilizers, monoclonal anti-IgE antibodies, vaccines (preferably vaccines used for vaccination where the amount of an allergen is gradually increased), and combinations thereof. It is preferable to use these therapeutic compositions in combination with the composition of the present invention.

When the composition of the present invention is used as a food or beverage, the food or beverage can be, for example, a health food, a functional food, a food for specified health use, a dietary supplement, a food for patients, or an animal feed. The food or beverage of the present invention can be ingested in the forms of the compositions as described above, and also can be ingested in the forms of various foods and beverages. Specific examples of the foods and beverages include various beverages such as juices, refreshing beverages, tea beverages, drink preparations, jelly beverages, and functional beverages; alcoholic beverages such as beers; carbohydrate-containing foods such as rice food products, noodles, breads, and pastas; paste products such as fish hams, sausages, paste products of seafood; retort pouch products such as curries, food dressed with a thick starchy sauces, and Chinese soups; soups; dairy products such as milk, dairy beverages, ice creams, cheeses, and yogurts; fermented products such as fermented soybean pastes, yogurts, fermented beverages, and pickles; bean products; various confectionery products such as Western confectionery products including biscuits, cookies, and the like, Japanese confectionery products including steamed bean-jam buns, soft adzuki-bean jellies, and the like, candies, chewing gums, gummies, cold desserts including jellies, crème caramels, and frozen desserts; instant foods such as instant soups and instant soy-bean soups; microwavable foods; and the like. Further, the examples also include health foods and beverages prepared in the forms of powders, granules, tablets, capsules, liquids, pastes, and jellies. The composition of the present invention can be used for animals including humans. The animals, other than humans, are not particularly limited, and the composition can be used for various livestock, poultry, pets, experimental animals, and the like. Specific examples of the animals include pigs, cattle, horses, sheep, goats, chickens, wild ducks, ostriches, domestic ducks, dogs, cats, rabbits, hamsters, mice, rats, monkeys, and the like, but the animals are not limited thereto.

Without wishing to be bound by theory, in the present invention, individuals in which the relative abundance of bacteria belonging to the group Firmicutes (the group to which the *Clostridium* clusters IV and XIVa belong) is large gain more body weight than individuals in which the relative abundance of bacteria belonging to the group Bacteroidetes is large. Accordingly, the composition of the present invention is capable of conditioning absorption of nutrients and improving feed efficiency. From such a viewpoint, the composition of the present invention can be used for promoting body weight gain, or for an animal feed good in feed efficiency.

Moreover, the addition of the composition of the present invention to an antibiotic-free animal feed makes it possible to increase the body weight of a subject that ingests the animal feed to a level equal to or higher than those achieved by antibiotic-containing animal feeds, and also makes it possible to reduce pathogenic bacteria in the stomach to a level equal to those achieved by typical antibiotic-containing animal feeds. Accordingly, the composition of the present invention can be used for an animal feed which does not need the addition of antibiotics.

In addition, unlike conventional bacteria (*Lactobacillus* and Bifidobacteria) in commercial use which are not easy to incorporate into the livestock production, the composition of the present invention in the spore form can be pelletized, sprayed, or easily mixed with an animal feed, and also can be added to drinking water.

The feeding of such an animal feed using the composition of the present invention is not particularly limited, and the animal feed may be fed to a subject at regular intervals in a selective manner, or may be fed for a certain period (for example, at its birth, during weaning, or when the subject to be fed is relocated or shipped).

Moreover, from the above-described viewpoint, the composition of the present invention can be preferably used for malnourished humans. In other words, also when the subject who ingests the composition is a human, the composition of the present invention can preferably be used for promoting the body weight gain, and enhancing the energy absorption from foods.

The food or beverage of the present invention can be manufactured by a manufacturing technique which is well known in the technical field. To the food or beverage, one or more components (for example, a nutrient) which are effective for the improvement of an immune function by the immunosuppressive effect may be added. In addition, the food or beverage may be combined with another component or another functional food exhibiting a function other than the function of the improvement of an immune function to thereby serve as a multi-functional food or beverage.

Moreover, the composition of the present invention can be preferably incorporated into foods requiring a processing step which may destroy ordinary probiotic strains. Specifically, most commercially usable probiotic strains cannot be incorporated into foods which need to be processed by any one of a heat treatment, long term storage, a freezing treatment, a mechanical stress treatment, and a high-pressure treatment (for example, extrusion forming or roll forming). On the other hand, because of an advantageous nature of forming spores, the composition of the present invention can be easily incorporated into such processed foods.

For example, the composition of the present invention in the form of spore can survive even in a dried food, and can remain living even after being ingested. Likewise, the composition of the present invention can withstand low-temperature sterilization processes, typically processes at a temperature in a range from 70° C. to the boiling point, both inclusive. Thus, the composition of the present invention can be incorporated into all kinds of dairy products. Furthermore, the composition of the present invention can withstand long-term storage of many years; high-temperature processing such as baking and boiling; low-temperature processing such as freezing and cold storage; and high-pressure treatments such as extrusion forming and roll forming.

The foods which need to be processed under such harsh conditions are not particularly limited, and examples thereof include foods which need to be processed in a microwave oven to be edible (for example, oatmeal), foods which need to be baked to be edible (for example, muffin), foods which need to be subjected to a sterilization high-temperature treatment for a short period of time to be edible (for example, milk), and foods which need to be heated to be drinkable (for example, hot tea).

When the composition of the present invention is administered or ingested, the amount thereof for the administration or ingestion is selected as appropriate depending on the age, body weight, symptoms, health conditions, of a subject, the kind of the composition (a pharmaceutical product, a food or beverage, or the like), and the like. For example, the amount per administration or ingestion is generally 0.01 mg/kg body weight to 100 mg/kg body weight, and preferably 1 mg/kg body weight to 10 mg/kg body weight. The present invention also provides a method for suppressing the immunity of a subject, the method being characterized in that the bacteria belonging to the genus *Clostridium* or the physiologically active substance derived from the bacteria is administered into or ingested by the subject as described above.

A product of the composition of the present invention (a pharmaceutical product, a food or beverage, or a reagent) or a manual thereof may be provided with a note stating that the product can be used to suppress the immunity (including a note stating that the product has an immunosuppressive effect, and a note stating that the product has an effect of suppressing the proliferation or function of effector T-cells). Here, the "provision to the product or the manual thereof with the note" means that the note is provided to a main body, a container, a package, or the like of the product, or the note is provided to a manual, a package insert, a leaflet, or other printed matters, which disclose information on the product.

<Method for Inducing Proliferation or Accumulation of Regulatory T Cells>

As described above, and as will be shown in Examples, the administration of the composition of the present invention to an individual makes it possible to induce proliferation or accumulation of regulatory T cells in the individual. Thus, the present invention can provides a method for inducing proliferation or accumulation of regulatory T cells in an individual, the method comprising a step of administering, to the individual, at least one substance selected from the group consisting of the following (a) to (c):

(a) bacteria belonging to the genus *Clostridium* or a physiologically active substance derived from the bacteria;

(b) a spore-forming fraction of a fecal sample obtained from a mammal or a culture supernatant of the fraction; and (c) a chloroform-treated fraction of a fecal sample obtained from a mammal or a culture supernatant of the fraction.

Note that, the "individual" in the present invention is not particularly limited, and examples thereof include humans, various kinds of livestock, poultry, pets, experimental animals, and the like. The "individual" may be in a healthy state or a diseased state.

Moreover, as will be shown in Example 5 to be described later, Gram-positive commensal bacteria play principal roles in the proliferation or accumulation of regulatory T cells. Accordingly, the present invention can also provide a method for inducing proliferation or accumulation of regulatory T cells in an individual, the method comprising a step of administering an antibiotic against Gram-negative bacteria to the individual.

In the present invention, the "antibiotic against Gram-negative bacteria" is not particularly limited, and examples thereof include aminoglycoside antibiotics (amikacin, gentamicin, kanamycin, neomycin, netilmicin, tobramycin, and paromomycin), cephalosporin antibiotics (cefaclor, cefamandole, cefoxitin, cefprozil, cefuroxime, cefixime, cefdinir, cefditoren, cefoperazone, cefotaxime, ceftazidime, ceftibuten, ceftizoxime, ceftriaxone, and cefoxotin), sulfonamides, ampicillin, and streptomycin. Without wishing to be bound by theory, the "antibiotic against Gram-negative bacteria" according to the present invention is preferably one which reduces Gram-negative bacteria, and contributes to the colonization of Gram-positive bacteria.

Moreover, a prebiotic composition such as almond skin, inulin, oligofructose, raffinose, lactulose, pectin, hemicellulose (such as xyloglucan and alpha-glucans), amylopectin, and resistant starch which are not decomposed in the upper gastrointestinal tract and promote the growth of intestinal microbes in the intestinal tract, as well as growth factors such as acetyl-Co A, biotin, beet molasses, and yeast extracts, contribute to the proliferation of bacteria belonging to the genus *Clostridium*. Accordingly, the present invention can also provide a method for inducing proliferation or accumulation of regulatory T cells in an individual, the method comprising a step of administering, to the individual, at least one substance selected from the group consisting of these substances.

Meanwhile, in the "method for inducing proliferation or accumulation of regulatory T cells" of the present invention, the composition of the present invention, the above-described "antibiotic against Gram-negative bacteria," and the above-described "prebiotic composition or growth factor" may be used in combination. Such combined use is not particularly limited, and examples of the combined use are as follows: the "antibiotic against Gram-negative bacteria" is administered to an individual in advance, and then the composition of the present invention is administered; the "antibiotic against Gram-negative bacteria" and the composition of the present invention are simultaneously administered to an individual; the "prebiotic composition or growth factor" is administered to an individual in advance, and then the composition of the present invention is administered; the "prebiotic composition or growth factor" and the composition of the present invention are simultaneously administered to an individual; the composition of the present invention, the "antibiotic against Gram-negative bacteria," and the "prebiotic composition or growth factor" are administered to an individual simultaneously or individually at any appropriate time.

Moreover, a therapeutic composition may be administered to an individual together with at least one substance selected from the group consisting of the composition of the present invention, the "antibiotic against Gram-negative bacteria," and the "prebiotic composition or growth factor."

Such a therapeutic composition is not particularly limited, and may be at least one therapeutic composition selected from the group consisting of corticosteroids, mesalazine, mesalamine, sulfasalazine, sulfasalazine derivatives, immunosuppressive drugs, cyclosporin A, mercaptopurine, azathiopurine, prednisone, methotrexate, antihistamines, glucocorticoids, epinephrine, theophylline, cromolyn sodium, anti-leukotrienes, anti-cholinergic drugs for rhinitis, anti-cholinergic decongestants, mast-cell stabilizers, monoclonal anti-IgE antibodies, vaccines (preferably, vaccines used for vaccination where the amount of an allergen is gradually increased), and combinations thereof. It is preferable to use these therapeutic compositions in combination with the above-described substance.

Moreover, there is no particular limitation imposed on the combined use of the therapeutic composition with at least one substance selected from the group consisting of the composition of the present invention, the "antibiotic against Gram-negative bacteria," and the "prebiotic composition or growth factor". For example, the "one substance" and the therapeutic composition are administered orally or parenterally to an individual simultaneously or individually at any appropriate time.

Moreover, in the above-described "method for inducing proliferation or accumulation of regulatory T cells," whether or not the administration of the composition of the present invention or the like actually induces the proliferation or accumulation of regulatory T cells can be determined by using, as an index, increase or reinforcement of at least one selected from the group consisting of the number of regulatory T cells, the ratio of regulatory T cells in the T cell group of the colon, a function of regulatory T cells, and expression of a marker of regulatory T cells. It is preferable to use one measurement selected from the group consisting of promotion of IL-10 expression, promotion of CTLA4 expression, promotion of IDO expression, and suppression of IL-4 expression, as the index of the induction of proliferation or accumulation of regulatory T cells.

Note that examples of a method for detecting such expression include the northern blotting, the RT-PCR, and the dot blotting for detection of gene expression at the transcription level; and the ELISA, the radioimmunoassay, the immunoblotting, the immunoprecipitation, and the flow cytometry for detection of gene expression at the translation level.

Meanwhile, a sample used for measuring such an index is not particularly limited, and examples thereof include blood sampled from an individual and tissue pieces obtained in a biopsy.

<Method for Predicting Response of Individual to Composition of Present Invention and/or Prognosis of Individual>

The present invention can provide a method in which the absolute amount or the ratio of bacteria belonging to the genus *Clostridium* in a microbiota of an individual is determined, and, when the ratio or the absolute value of the bacteria belonging to the genus *Clostridium* is reduced in comparison with a base line value obtained by performing a similar determination on an individual in a typical health state, it is determined that the individual is possibly responsive to the composition of the present invention.

In one embodiment, a method to predict a subject's response to a substance and/or the subject's prognosis is provided. The method comprises measuring the percentage or absolute amounts of *Clostridium* clusters IV and XIV in the microbiota of the subject and comparing them to a baseline value of the same measurements in a prototypical healthy subject, wherein a decreased absolute amount or percentage level of *Clostridium* clusters IV and/or XIV indicates that the subject may respond favorably to the compositions of the invention.

In one embodiment, the method further comprises measuring the composition of the microbiota of the subject after administration of the substance, wherein an increase in the percentage or absolute number of *Clostridium* spp. belonging to clusters IV, XIV after administration of the compositions of the present invention relative to prior to the administering is a positive indicator of enhanced immunosuppression (or immunoregulation). The measurement of the composition of the subject's microbiota can be made with techniques known in the art, such as 16srRNA sequencing.

Note that, in these embodiments, the substance is at least one substance selected from the group consisting of the following (a) to (e):

(a) bacteria belonging to the genus *Clostridium* or a physiologically active substance derived from the bacteria;

(b) a spore-forming fraction of a fecal sample obtained from a mammal or a culture supernatant of the fraction;

(c) a chloroform-treated fraction of a fecal sample obtained from a mammal or a culture supernatant of the fraction;

(d) an antibiotic against Gram-negative bacteria according to the present invention; and (e) at least one substance selected from the group consisting of almond skin, inulin, oligofructose, raffinose, lactulose, pectin, hemicellulose (such as xyloglucan and alpha-glucans), amylopectin, acetyl-Co A, biotin, beet molasses, yeast extracts, and resistant starch.

<Method for Inhibiting Proliferation or Accumulation of Regulatory T Cells>

As will be shown in Example 5 to be described later, Gram-positive commensal bacteria have principal roles in the proliferation or accumulation of regulatory T cells. Accordingly, the present invention can also provide a method for inhibiting proliferation or accumulation of regulatory T cells in an individual, the method comprising a step of administering an antibiotic against Gram-positive bacteria to the individual.

In the present invention, the "antibiotic against Gram-positive bacteria" is not particularly limited, and examples thereof include cephalosporin antibiotics (cephalexin, cefuroxime, cefadroxil, cefazolin, cephalothin, cefaclor, cefamandole, cefoxitin, cefprozil, and ceftobiprole); fluoroquinolone antibiotics (cipro, Levaquin, floxin, tequin, avelox, and norflox); tetracycline antibiotics (tetracycline, minocycline, oxytetracycline, and doxycycline); penicillin antibiotics (amoxicillin, ampicillin, penicillin V, dicloxacillin, carbenicillin, vancomycin, and methicillin); and carbapenem antibiotics (ertapenem, doripenem, imipenem/cilastatin, and meropenem).

As described above, the "individual" in the present invention is not particularly limited, and examples thereof include humans, various kinds of livestock, poultry, pets, experimental animals, and the like. The "individual" may be in a healthy state or a diseased state. Such a diseased state is not particularly limited, and examples thereof include states of being subjected to cancer immunotherapy and of suffering from an infectious disease.

Moreover, as another mode of the "method for inhibiting proliferation or accumulation of regulatory T cells," the present invention can provide a method for inhibiting proliferation or accumulation of regulatory T cells in an individual, the method comprising a step of administering, to the individual, any one of an antibody, an antibody fragment, and a peptide, which are against an antigen that is at least one substance selected from the group consisting of the following (a) to (c):

(a) bacteria belonging to the genus *Clostridium* or a physiologically active substance derived from the bacteria;

(b) a spore-forming fraction of a fecal sample obtained from a mammal or a culture supernatant of the fraction; and (c) a chloroform-treated fraction of a fecal sample obtained from a mammal or a culture supernatant of the fraction.

<Vaccine Composition and Method for Treating or Preventing Infectious Disease or Autoimmune Disease by Using the Vaccine Composition>

As described above, and as will be shown in Example 15 to be described later, the induction of Treg cells in the colon by the *Clostridium* has an important role in local and systemic immune responses. Accordingly, the present invention can also provide a "vaccine composition comprising at least one substance selected from the group consisting of the following (a) to (c): (a) bacteria belonging to the genus *Clostridium*; (b) a spore of bacteria in a spore-forming fraction of a fecal sample obtained from a mammal; and (c) bacteria in a chloroform-treated fraction of a fecal sample obtained from a mammal" and a "method for treating, aiding in treating, reducing the severity of, or preventing at least one disease selected from infectious diseases and autoimmune diseases in an individual, the method comprising administering the vaccine composition to the individual."

Note that such "autoimmune diseases" are not particularly limited, and examples thereof include those described as the "specific examples of target diseases" in <Composition Having Effect of Inducing Proliferation or Accumulation of Regulatory T cells>. The "infectious diseases" are also not particularly limited, and examples thereof include infectious diseases associated with "infectious pathogens" described as the "example of infectious pathogens" in <Composition Having Effect of Inducing Proliferation or Accumulation of Regulatory T cells>.

<Method for Screening for Compound Having Activity to Promote Proliferation or Accumulation of Regulatory T Cells>

The present invention can also provide a method for screening for a compound having an activity to promote proliferation or accumulation of regulatory T cells, the method comprising:

(1) preparing a test substance from at least one substance selected from the group consisting of the following (a) to (c):

(a) bacteria belonging to the genus *Clostridium* or a physiologically active substance derived from the bacteria;

(b) a spore-forming fraction of a fecal sample obtained from a mammal or a culture supernatant of the fraction; and (c) a chloroform-treated fraction of a fecal sample obtained from a mammal or a culture supernatant of the fraction.

(2) preparing non-human mammals in which a reporter gene is to be expressed under control of IL-10 gene expression;

(3) bringing the test substance into contact with the non-human mammal;

(4) after the contact with the test substance, detecting cells expressing the reporter gene in a $CD4^+$ $Foxp3^+$ cell group of the non-human mammal, and determining the number of cells in the $CD4^+$ $Foxp3^+$ cell group expressing the reporter gene or a ratio of cells in the $CD4^+$ $Foxp3^+$ cell group expressing the reporter gene to cells in the $CD4^+$ $Foxp3^+$ cell group not expressing the reporter gene;

(5) detecting cells expressing the reporter gene in a $CD4^+$ $Foxp3^+$ cell group of the non-human mammal which has not been in contact with the test substance, and determining the number of cells in the $CD4^+$ $Foxp3^+$ cell group expressing the reporter gene or a ratio of cells in the $CD4^+$ $Foxp3^+$ cell group expressing the reporter gene to cells in the $CD4^+$ $Foxp3^+$ cell group not expressing the reporter gene; and (6) comparing the absolute numbers or the ratios determined in steps (4) with the number or the ratio determined in (5), and determining, when the number or the ratio determined in (4) is greater than that determined in (5), that the test substance is a compound that promotes proliferation or accumulation of Treg cells.

The "test substance" according to the present invention is not particularly limited, as long as the test substance is a substance prepared from at least one substance selected from the group consisting of the substances (a) to (c). Examples of the test substance include proteins, polysaccharides, lipids, and nucleic acids which are derived from at least one substance selected from the group consisting of the above described substances (a) to (c).

The "non-human mammal in which a reporter gene is to be expressed under control of IL-10 gene expression" according to the present invention is not particularly limited, as long as the non-human mammal is a non-human mammal having a reporter gene whose expression is controlled by an IL-10 gene expression control region (for example, a promoter, or an enhancer). Examples of such a reporter gene include genes encoding fluorescent proteins (for example, GFP), and genes encoding luciferase. As the "non-human mammal in which a reporter gene is to be expressed under control of IL-10 gene expression" according to the present invention, an $Il10^{venus}$ mouse to be shown later in Examples can be preferably used.

The "contact" according to the present invention is not particularly limited, and examples thereof include administration of the test substance to the non-human mammal orally or parenterally (for example, intraperitoneal injection, or intravenous injection).

The present invention can also provide a non-human mammal which is used for the method, and in which the reporter gene is to be expressed under the control of the IL-10 gene expression.

Furthermore, the present invention can also provide a method for isolating, from a sample of bacteria belonging to the genus *Clostridium*, a compound having an activity to promote proliferation or accumulation of regulatory T cells, the method comprising the following steps (1) to (3):

(1) preparing a genomic DNA from the sample of bacteria belonging to the genus *Clostridium;*

(2) inserting the genomic DNA into a cloning system, and preparing a gene library derived from the sample of bacteria belonging to the genus *Clostridium*; and (3) isolating a compound having an activity to promote proliferation or accumulation of regulatory T cells, by use of the gene library obtained in step (2).

In such steps, methods for the preparation and the isolation are not particularly limited, and known techniques for an in-vitro or in-vivo system can be used as appropriate. Moreover, the compound isolated by this method is not particularly limited, and examples thereof include nucleic acids (for example, a DNA, a mRNA, and a rRNA) derived from bacteria belonging to the genus *Clostridium*, as well as polypeptides and proteins derived from the bacteria belonging to the genus *Clostridium.*

Other Embodiment Modes According to Present Invention

In addition to the above-described embodiment modes, the present invention can also provide the following embodiment modes.

Specifically, the present invention can also provide a method for determining the composition of a microbiota in an individual, wherein the increase in the ratio or the absolute number of bacteria belonging to the genus *Clostridium* after the administration of the composition of the present invention to the individual with respect to the ratio or the absolute number before the administration is used as an index of increased immunosuppression. In such a method, the method for determining the composition of the microbiota is not particularly limited, and known techniques (for example, 16S rRNA sequencing) can be used as appropriate.

The present invention can also provide a method for measuring differentiation of Treg cells, wherein the increase in differentiation of Treg cells in an individual after administration of the composition of the present invention to the individual with respect to that before the administration is used as an index of increased immunosuppression (or immunoregulation).

Moreover, the composition of the present invention can also be administered to an individual under an antibiotic treatment. The timing of the administration is not particularly limited, and the composition of the present invention can be administered before or simultaneously with the antibiotic treatment, for example. Meanwhile, the composition of the present invention is preferably administered in the spore form from the viewpoint of resistance to antibiotics.

Moreover, in a preferred mode of such administration, the composition of the present invention is administered after or simultaneously with administration of an antibiotic against Gram-positive bacteria, for example. Note that such an "antibiotic against Gram-positive bacteria" is not particularly limited, and examples thereof include cephalosporin antibiotics (cephalexin, cefuroxime, cefadroxil, cefazolin, cephalothin, cefaclor, cefamandole, cefoxitin, cefprozil, and ceftobiprole); fluoroquinolone antibiotics (cipro, Levaquin, floxin, tequin, avelox, and norflox); tetracycline antibiotics (tetracycline, minocycline, oxytetracycline, and doxycycline); penicillin antibiotics (amoxicillin, ampicillin, penicillin V, dicloxacillin, carbenicillin, vancomycin, and methicillin); and carbapenem antibiotics (ertapenem, doripenem, imipenem/cilastatin, and meropenem).

Meanwhile, in another preferred mode of such administration, the composition of the present invention is administered after (or simultaneously with) a treatment using vancomycin, metronidazole, linezolid, ramoplanin, or fidaxomicin, for example.

EXAMPLES

Hereinafter, the present invention is described more specifically on the basis of Examples. However, the present invention is not limited to Examples below.

Note that mice used in Examples were prepared or produced as follows. In the following description, mice may be referred to with "SPF" or "GF" attached in front thereof. These "SPF" and "GF" indicate that the mice were maintained in the absence of specific pathogenic bacteria (specific pathogen-free, SPF), and that the mice were maintained under Germ-Free (GF) conditions, respectively.

<Mice>

C57BL/6, Balb/c, and IQI mice maintained under SPF or GF conditions were purchased from Sankyo Labo Service Corporation, Inc. (Japan), JAPAN SLC, INC. (Japan), CLEA Japan, Inc. (Japan), or The Jackson Laboratory (USA). GF mice and gnotobiotic mice were bread and maintained within the gnotobiotic facility of The University of Tokyo, Yakult Central Institute for Microbiological Research, or Sankyo Labo Service Corporation, Inc. $Myd88^{-/-}$, $Rip2^{-/-}$, and $Card9^{-/-}$ mice were produced as described in Non-Patent Documents 1 to 3, and backcrossed for 8 generations or more, so that a C57BL/6 genetic background was achieved. $Foxp3^{eGFP}$ mice were purchased from the Jackson Laboratory.

<$Il10^{venus}$ Mice>

To form a bicistronic locus encoding both Il10 and Venus under control of an Il10 promoter, a targeting construct was first created. Specifically, a cassette (IRES-Venus-SV40 polyA signal cassette, refer to Non-Patent Document 4) which was made of an internal ribosome entry site (IRES), a yellow fluorescent protein (Venus), and a SV40 polyA signal (SV40 polyA) and which was arranged next to a neomycin-resistant gene (neo), was inserted between a stop codon and a polyA signal (Exon 5) of a Il10 gene. Next, the obtained targeting construct was used to cause homologous recombination with the Il10 gene region in the genome of mice. Thus, $Il10^{venus}$ mice having an $Il10^{venus}$ alleles were produced (refer to FIG. 1). Note that in FIG. 1 "tk" represents a gene coding thymidine kinase, "neo" represents the neomycin-resistant gene, and "BamH1" represents a cleavage site by the restriction enzyme BamH1.

Figure 2:
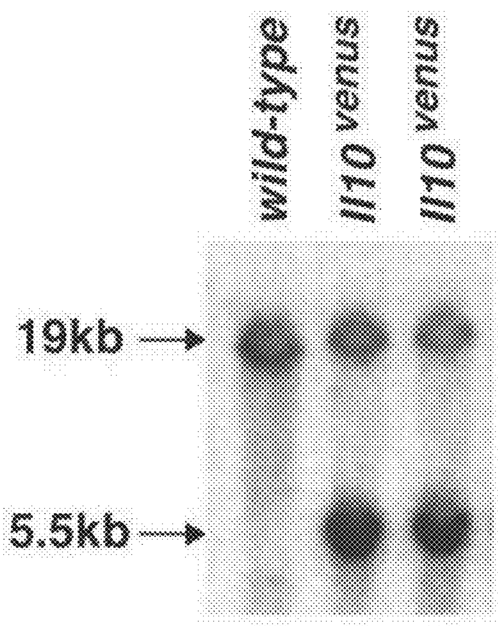
FIG. 2 is a diagram showing results of Southern blotting performed for analysis as to whether or not the Il10$^{venus}$ mice have an Il10$^{venus}$ allele.

Genomic DNAs were extracted from the $Il10^{venus}$ mice, treated with BamH1, and Southern blotted by use of a probe shown in FIG. 1. FIG. 2 shows the obtained results. Wild-type and $Il10^{venus}$ alleles were detected as bands having sizes of 19 kb and 5.5 kb, respectively. Hence, as is apparent from the results shown in FIG. 2, it was found that the homologous recombination shown in FIG. 1 occurred in the genome of the $Il10^{venus}$ mice.

Figure 3:
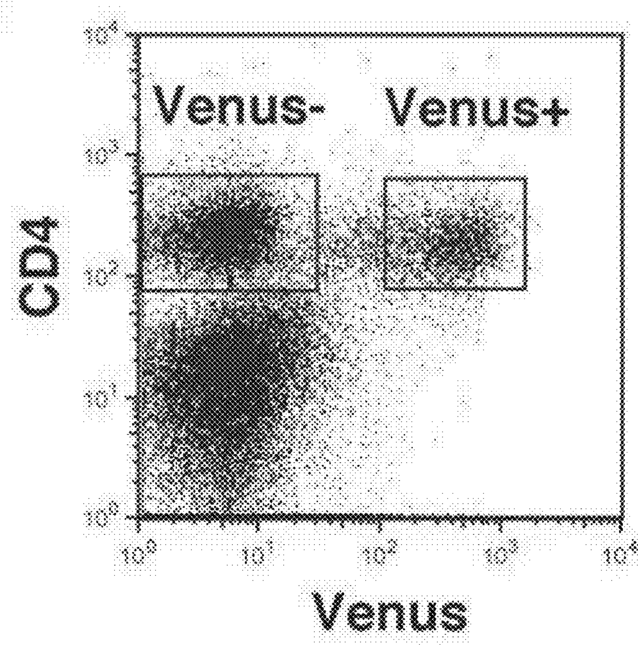
FIG. 3 is a FACS dot-plot diagram showing results obtained when Venus-positive cells and Venus-negative cells from the Il1$^{venus}$ mice were sorted.
Figure 4:
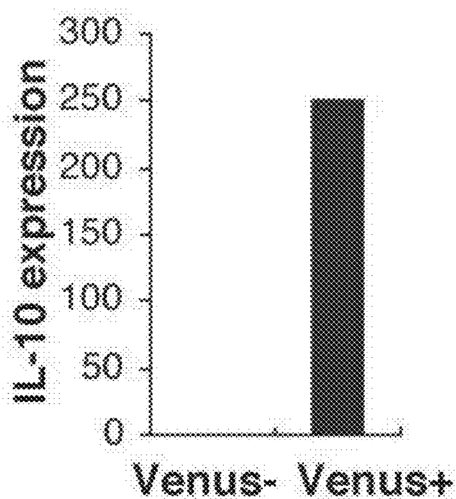
FIG. 4 is a graph showing the results obtained when the amounts of IL-10 mRNA expressed in Venus positive-cells and Venus-negative cells of the Il10$^{venus}$ mice were analyzed by real-time RT-PCR.

Further, $CD4^+$ $Venus^-$ cells or $CD4^+$ $Venus^+$ cells in the colonic lamina propria of the $Il10^{venus}$ mice were sorted by use of a FACSAria. Then, real-time RT-PCR was carried out on an ABI 7300 system by a method to be described later, to determine the amount of IL-10 mRNA expressed. FIGS. 3 and 4 show the obtained results. As is apparent from the results shown in FIGS. 3 and 4, it was found that, since the development of the IL-10 mRNA was detected only in the $CD4^+$ $Venus^+$ cells, the expression of IL-10 mRNA in the $Il10^{venus}$ mice was correctly reflected in the expression of Venus. Note that the germ-free states of such $Il10^{venus}$ mice were established in Central Institute for Experimental Animals (Kawasaki, Japan). The $Il10^{venus}$ mice in the germ-free states were maintained in vinyl isolators in Sankyo Labo Service Corporation, Inc. (Tokyo, Japan), and used in the following Examples.

Meanwhile, experiments and analyses in Examples were carried out as follows.

<Method for Colonization of Mice with Bacteria and Analysis Thereof>

According to the description in Non-Patent Documents 5 and 6, mice in which SFB or *Clostridium* were colonized were produced. Cecal contents or feces of the obtained gnotobiotic mice were dissolved in sterile water or an anaerobic dilution solution. The dissolved cecal contents or feces as they were or after a chloroform treatment were orally administered to GF mice. Three strains of the *Lactobacillus* and 16 strains of the *Bacteroides* were cultured separately from each other in a BL or EG agar medium in an anaerobic manner. The cultured bacteria were harvested, suspended in an anaerobic TS broth, and orally administrated forcibly to GF mice. The state of the colonization of the bacteria in the mice was assessed by microscopic observation conducted on a smear preparation of fecal pellets.

<Cell Separation and Flow Cytometry>

In order to isolate lymphocytes from the colonic lamina propria and the small intestinal lamina propria, the small intestine and the colon were collected, and cut open longitudinally. Then, fecal content and the like thereinside were washed to remove. Subsequently, the small intestine and the colon were shaken in HBSS containing 5 mM of EDTA at 37° C. for 20 minutes. After removal of epithelium and fat tissue, the intestinal tissues were cut into small pieces. To the small pieces, RPMI 1640 (4% fetal bovine serum (FBS), 1 mg/ml of collagenase D, 0.5 mg/ml of dispase, and 40 μg/ml of DNaseI (all of which were manufactured by Roche Diagnostics K.K.)) were added, and the mixture was shaken in a water bath kept at 37° C. for 1 hour. The digested tissues were washed with HBSS containing 5 mM of EDTA, and resuspended in 5 ml of 40% PERCOLL® (GE Healthcare). The suspension was overlayered on 2.5 ml of 80% PERCOLL® in a 15-ml Falcon tube. Then, centrifugation was carried out at room temperature and at 2000 rpm for 20 minutes to conduct cell separation by PERCOLL® density gradient centrifugation. Cells at the interface were collected, and used as lamina propria lymphocytes. The collected cells were suspend in a staining buffer (PBS, 2% FBS, 2 mM EDTA, and 0.09% $NaN_3$), and stained by use of an anti-CD4 antibody (RM4-5, BD Biosciences) labeled with PE or PE-Cy7. After the staining of CD4, Foxp3 in the cells were stained by use of CYTOFIX/CYTOPERM® Kit Plus with GOLGISTOP® (BD Biosciences) or Foxp3 Staining Buffer Set (eBioscience), as well as an anti-Foxp3 antibody (FJK-16s, eBioscience) labeled with Alexa647. Flow cytometry was performed by use of a FACScant II, and the data were analyzed by FLOWJO® software (TreeStar Inc.). The sorting of the cells were performed by use of a FACSARIA™.

<Real-Time RT-PCR>

From an RNA prepared by using RNeasy Mini Kit (Qiagen), a cDNA was synthesized by use of a MMV reverse transcriptase (Promega KK). The obtained cDNA was analyzed by real-time RT-PCR using Power SYBR Green PCR Master Mix (Applied Biosystems) and ABI 7300 real time PCR system (Applied Biosystems), or real-time RT-PCR using SYBR Premix Ex Tag (TAKARA) and Light Cycler 480. For each sample, a value obtained was normalized for the amount of GAPDH. A primer set was designed by using Primer Express Version 3.0 (Applied Biosystems), and those exhibiting a 90% or higher sequence identity at an initial evaluation were selected. The primer set used was as follows:

```
Foxp3
                                    (SEQ ID NO: 1)
5'-GGCAATAGTTCCTTCCCAGAGTT-3'

                                    (SEQ ID NO: 2)
5'-GGGTCGCATATTGTGGTACTTG-3'

CTLA4
                                    (SEQ ID NO: 3)
5'-CCTTTTGTAGCCCTGCTCACTCT-3'

                                    (SEQ ID NO: 4)
5'-GGGTCACCTGTATGGCTTCAG-3'

GITR
                                    (SEQ ID NO: 5)
5'-TCAGTGCAAGATCTGCAAGCA-3'

                                    (SEQ ID NO: 6)
5'-ACACCGGAAGCCAAACACA-3'

IL-10
                                    (SEQ ID NO: 7)
5'-GATTTTAATAAGCTCCAAGACCAAGGT-3'

                                    (SEQ ID NO: 8)
5'-CTTCTATGCAGTTGATGAAGATGTCAA-3'

GAPDH
                                    (SEQ ID NO: 9)
5'-CCTCGTCCCGTAGACAAAATG-3'

                                   (SEQ ID NO: 10)
5'-TCTCCACTTTGCCACTGCAA-3'

Mmp2
                                   (SEQ ID NO: 11)
5'-GGACATTGTCTTTGATGGCA-3'

                                   (SEQ ID NO: 12)
5'-CTTGTCACGTGGTGTCACTG-3'

Mmp9
                                   (SEQ ID NO: 13)
5'-TCTCTGGACGTCAAATGTGG-3'

                                   (SEQ ID NO: 14)
5'-GCTGAACAGCAGAGCCTTC-3'

Mmp13
                                   (SEQ ID NO: 15)
5'-AGGTCTGGATCACTCCAAGG-3'

                                   (SEQ ID NO: 16)
5'-TCGCCTGGACCATAAAGAA-3'
```

-continued

```
Idol
                                   (SEQ ID NO: 17)
5'-AGAGGATGCGTGACTTTGTG-3'

                                   (SEQ ID NO: 18)
5'-ATACAGCAGACCTTCTGGCA-3'.
```

<Preparation and Culturing of Large Intestinal Epithelial Cells (IECs)>

First, the colon was collected, cut open longitudinally, and rinsed with PBS. Subsequently, the colon was treated with 1 mM dithiothreitol (DTT) at 37° C. for 30 minutes on a shaker, and then vortexed for one minute to disrupt the epithelial integrity. The released IECs were collected, and suspended in 5 ml of 20% PERCOLL®. The suspension was overlayered on 2.5 ml of 80% PERCOLL® in a 15-ml Falcon tube. Then, the tube was centrifuged at 25° C. and 780 g for 20 minutes to conduct cell separation by PERCOLL® density gradient centrifugation. Cells at the interface were collected, and used as colonic IECs (purity: 90% or higher, viability: 95%). The obtained IECs thus collected were suspended in RPMI containing 10% FBS, and $1\times10^5$ cells of the IECs were cultured in a 24-well plate for 24 hours. Thereafter, the culture supernatant was collected, and measured for active TGF-β1 level by ELISA (Promega).

Meanwhile, for culturing T cells in vitro, $1.5\times10^5$ MACS-purified splenic $CD4^+$ T cells were cultured in each well of a round-bottomed 96-well plate, together with a 50% conditioned medium in which IECs isolated from GF mice or *Clostridium*-colonized mice were cultured, and with 25 ng/ml of hIL-2 (Peprotech), in the presence or absence of 25 μg/ml of an anti-TGF-β antibody (R&D). Note that 10 μg/ml of an anti-CD3 antibody and an anti-CD28 antibody (BD Bioscience) were bound to the round-bottomed plate. After a 5-day culture, the $CD4^+$ T cells were collected, and subjected to a real-time PCR.

<Colitis Experimental Model>

A fecal suspension of *Clostridium*-colonized mice was orally administered to C57BL/6 mice (2-week old), and grown in a conventional environment for six weeks.

For preparing a DSS-induced colitis model, 2% (wt/vol) DSS (reagent grade, DSS salt, molecular weight=36 to 50 kD, manufactured by MP Biomedicals), together with drinking water, was given to the mice for six days.

Meanwhile, for preparing an oxazolone-induced colitis model, the mice were presensitized by transdermally applying, onto the mice, 150 μl of a 3% oxazolone (4-ethoxymethylene-2-phenyl-2-oxazolin-5-one, Sigma-Aldrich)/100% ethanol solution. Five days after that, 150 μl of a 1% oxazolone/50% ethanol solution was intrarectally administered again to the presensitized mice under a light anesthesia. Note that the intrarectal administration was conducted by using a 3.5F catheter.

Each mouse was analyzed daily for body weight, occult blood, bleeding visible with the naked eyes (gross blood), and the hardness of stool. Moreover, the body weight loss percentage, intestinal bleeding (no bleeding, occult blood (hemoccult+), or bleeding visible with the naked eyes), and the hardness of stool (normal stool, loose stool, or diarrhea) were evaluated numerically, and the disease activity index (DAI) was calculated in accordance with the description in "S. Wirtz, C. Neufert, B. Weigmann, M. F. Neurath, Nat Protoc 2, 541 (2007)."

<OVA Specific IgE Reaction>

BALB/c SPF mice were inoculated with a fecal suspension of *Clostridium*-colonized mice (2-week old), and grown in a conventional environment. Then, 1 μg of OVA (grade V, Sigma) and 2 mg of alum (Thermo Scientific), 0.2 ml in total, were intraperitoneally injected to the mice (at their ages of 4 weeks and 6 weeks). Sera were collected every week from the mice at the root of their tail, and OVA-specific IgE was measured by ELISA (Chondrex). Then, at their ages of 8 weeks, splenic cells were collected, inoculated in a 96-well plate at $1\times10^6$ cells per well, and stimulated with OVA (100 μg/ml) for three days. Thereafter, the culture supernatant was collected, and measured for IL-4 and IL-10 levels by ELISA (R&D).

<Statistical Analysis>

The difference between control and experimental groups was evaluated by the Student's t-test.

Example 1

Figure 5:
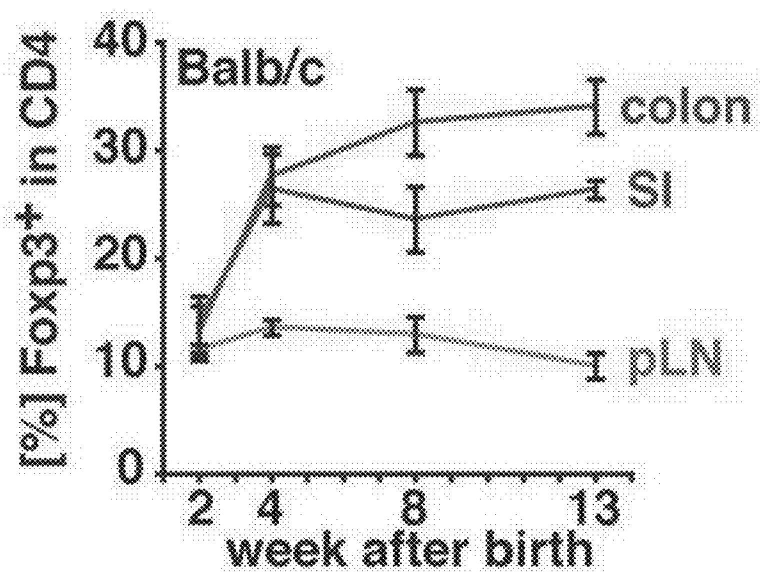
FIG. 5 is a graph showing change in the ratio of Foxp3$^{+}$ cells in CD4$^{+}$ lymphocytes of SPF mice.

First, it was investigated whether or not accumulation of regulatory T cells (Treg cells) in the colonic lamina propria was dependent on commensal bacteria. Specifically, lymphocytes were isolated from peripheral lymph nodes (pLN) of Balb/c mice bred in the absence of specific pathogenic bacteria (SPF) or from lamina propria of the colon or the small intestine (SI) of the mice. The CD4 and Foxp3 were stained by antibodies. Then, the ratio of $Foxp3^+$ cells in $CD4^+$ lymphocytes was analyzed by flow cytometry. FIG. 5 shows the obtained results. As is apparent from the results shown in FIG. 5, it was found that $Foxp3^+$ Treg cells were present at a high frequency in the lamina propria of the gastrointestinal tracts, especially in the colonic lamina propria, of the mice kept under the environment free from specific pathogenic microorganisms (SPF). In addition, it was also found that the number of the $Foxp3^+$ Treg cells in the colonic lamina propria gradually increased up to three months after their birth, whereas the number of the $Foxp3^+$ Treg cells in the peripheral lymph nodes was basically constant from the time of two weeks after their birth.

Example 2

Figure 6:
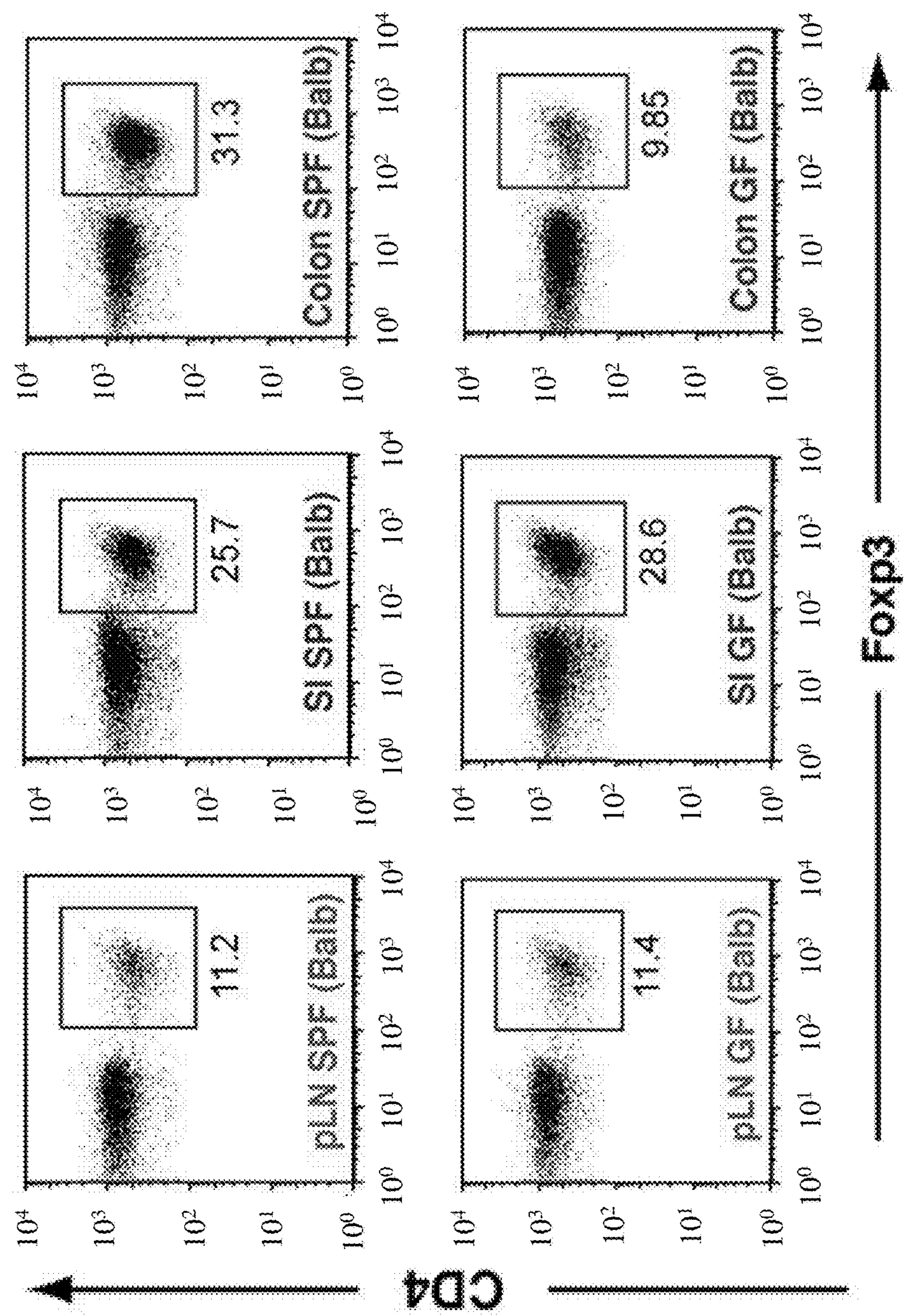
FIG. 6 shows FACS dot-plot diagrams showing analysis results of the ratios of Foxp3$^{+}$ cells in CD4$^{+}$ lymphocytes isolated from the small intestine, the colon, and the peripheral lymph nodes of GF mice and SPF mice.
Figure 7:
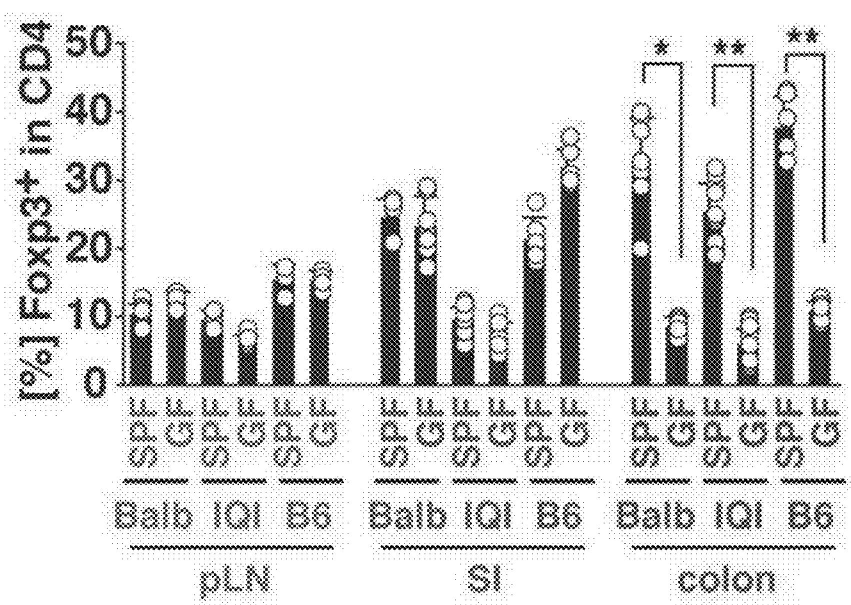
FIG. 7 is a graph showing analysis results of the ratios of Foxp3$^{+}$ cells in CD4$^{+}$ lymphocytes isolated from the small intestine, the colon, and the peripheral lymph nodes of GF mice and SPF mice.

Next, it was investigated whether or not the temporal accumulation of the Treg cells in the colon as found in Example 1 had a relationship with the colonization of intestinal commensal microbiota. Specifically, the expression of CD4 and the expression of Foxp3 in lymphocytes isolated from the small intestine, the colon, and the peripheral lymph nodes of mice bred under a germ-free (GF) or SPF environment (8 weeks old: Balb/c mice, IQI mice, and C57BL/6 mice) were analyzed. Similar results were obtained in three or more independent experiments. FIGS. 6 and 7 show the obtained results. Note that, in FIG. 7, each white circle represents the absolute number of $CD4^+$ $Foxp3^+$ cells in an individual mouse, and the error bars represent standard deviations (SDs).

Figure 8:
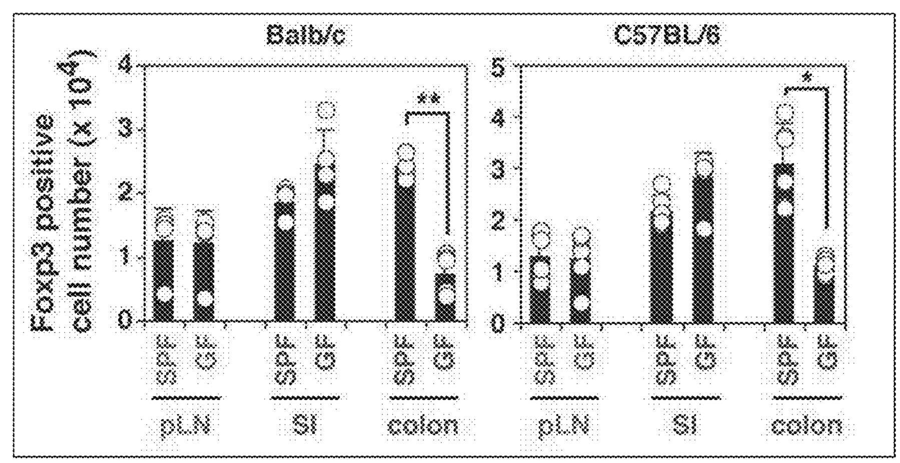
FIG. 8 shows graphs showing analysis results of the numbers of CD4$^{+}$ Foxp3$^{+}$ cells isolated from the small intestine, the colon, and the peripheral lymph nodes of GF mice and SPF mice.

In addition, lamina propria lymphocytes were collected from SPF mice and GF mice (Balb/c mice or C57BL/6 mice). CD4 and Foxp3 were stained with antibodies. Then, the lamina propria lymphocytes were analyzed by FACS. FIG. 8 shows the obtained results. Note that in FIG. 8 each white circle represents the absolute number of $CD4^+$ $Foxp3^+$ cells in an individual mouse, ** indicates that "P<0.001", and indicates that "P<0.01."

Figure 9:
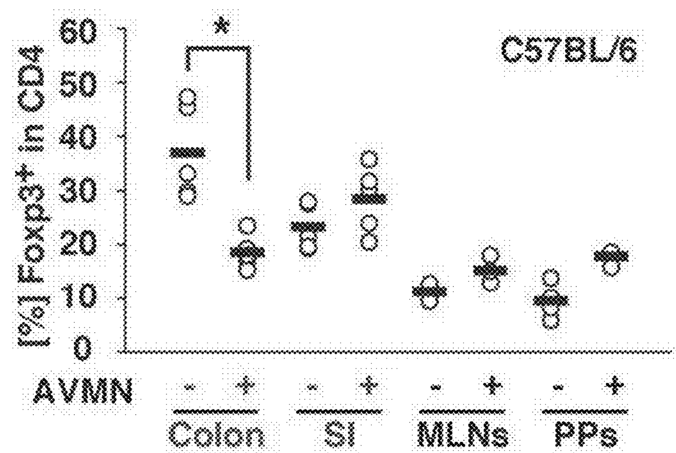
FIG. 9 is a plot diagram showing analysis results of the ratios of Venus$^{+}$ cells in CD4$^{+}$ cells in various tissues of SPF mice treated with antibiotics.

Further, lymphocytes were isolated from the lamina propria of the colon, the lamina propria of the small intestine (SI), Peyer's patches (PPs), and mesenteric lymph nodes (MLNs) of mice (SPF C57BL/6 mice) to which antibiotics were orally administered with water for eight weeks. CD4 and Foxp3 were stained with antibodies. Then, the lymphocytes were analyzed by FACS. Similar results were obtained in two or more independent experiments. FIG. 9 shows the obtained results (the ratio of the $Foxp3^+$ cells in the $CD4^+$ cells of an individual mouse). Note that the following antibiotics were used in combination in accordance with the description in the following document:

ampicillin (A; 500 mg/L, Sigma)
vancomycin (V; 500 mg/L, NACALAI TESQUE, INC.)
metronidazole (M; 1 g/L, NACALAI TESQUE, INC.)
neomycin (N; 1 g/L, NACALAI TESQUE, INC.)

Rakoff-Nahoum, J. Paglino, F. Eslami-Varzaneh, S. Edberg, R. Medzhitov, Cell 118, 229 (Jul. 23, 2004)

Fagarasan et al., Science 298, 1424 (Nov. 15, 2002)

In FIG. 9, each white circle represents the absolute number of the $CD4^+$ $Foxp3^+$ cells in an individual mouse, each horizontal bar represents the average value of the absolute numbers, * indicates that "P<0.01," and "AVMN" represents the kinds of the administered antibiotics by using the first letters of the antibiotics.

As is apparent from the results shown in FIGS. 6 to 9, the frequencies and the absolute numbers of $Foxp3^+$ $CD4^+$ cells in the small intestine and the peripheral lymph nodes of the GF mice were equal to or greater than those of the SPF mice (refer to FIGS. 6 to 8). In addition, the numbers of the Treg cells in the small intestinal lamina propria, Peyer's patches, and mesenteric lymph nodes of the SPF mice to which the antibiotics were orally administered for eight weeks were equal to or greater than those of the SPF mice (refer to FIG. 9). Meanwhile, the number of the $Foxp3^+$ $CD4^+$ cells in the colonic lamina propria of the GF mice was decreased significantly in comparison with that of the SPF mice (refer to FIGS. 6 and 7). This decrease was commonly observed among mice of different genetic backgrounds (Balb/c, IQI, and C57BL/6), as well as among mice bred in different animal facilities (refer to FIG. 7 for the data regarding the different genetic backgrounds, the data regarding the mice bred in the different animal facilities are not shown in the drawings). In addition, it was also shown that the number of Treg cells in the colonic lamina propria of the SPF C57BL/6 mice to which the antibiotics were administered was decreased significantly (refer to FIG. 9).

Example 3

Figure 10:
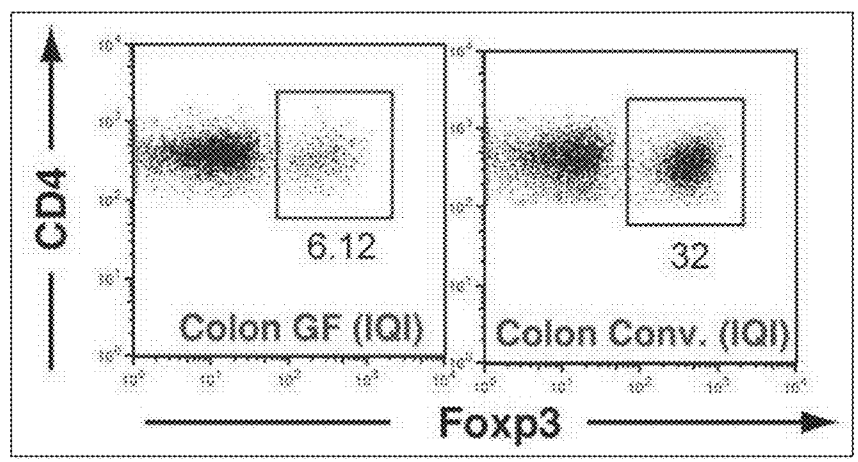
FIG. 10 shows FACS dot-plot diagrams showing analysis results of the ratio of Foxp3$^{+}$ cell in CD4$^{+}$ lymphocytes isolated from the colonic lamina propria of GF mice to which a fecal suspension of SPF mice was administered.
Figure 11:
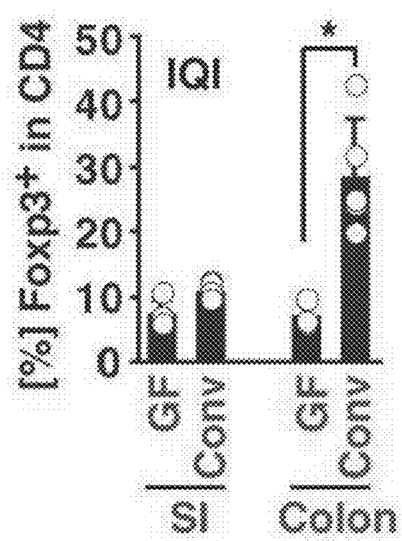
FIG. 11 is a graph showing analysis results of the ratios of Foxp3$^{+}$ cells in CD4$^{+}$ lymphocytes isolated from the lamina propria of the colon and the lamina propria of the small intestine of GF mice to which a fecal suspension of SPF mice was administered.

Next, it was directly checked whether or not the decrease in the number of the Treg cells in the colonic lamina propria of the GF mice shown in Example 2 was attributed to the absence of microbiota. Specifically, a fecal suspension of B6 SPF mice purchased from The Jackson Laboratory was orally administered to GF-IQI mice (conventionalization). Three weeks after the administration, lymphocytes were isolated from the colonic lamina propria, and the expression of Foxp3 in $CD4^+$ lymphocytes was analyzed. FIGS. 10 and 11 show the obtained results. Note that each white circle in FIG. 11 represents the absolute number of $CD4^+$ $Foxp3^+$ cells in an individual mouse, the error bars represent standard deviations (SD), * indicates that "P<0.01" in Student's t-test, and  indicates that "P<0.001." As is apparent from the results shown in FIGS. 10 and 11**, the number of Treg cells in the small intestinal lamina propria did not change. However, the number of the Treg cells in the colonic lamina propria increased significantly. Hence, it was shown that host-microbial interaction played an important role in the accumulation of $Foxp3^+$ Treg cells in the colonic lamina propria, while the accumulation of the Treg cells in the small intestinal lamina propria had a different mechanism.

Example 4

Figure 12:
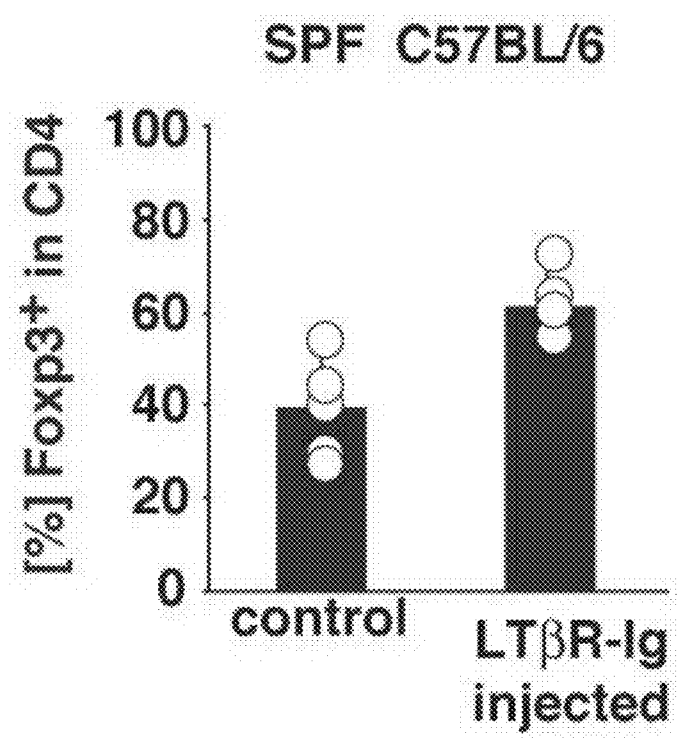
FIG. 12 is a graph showing analysis results of the ratio of Foxp3$^{+}$ cells in CD4$^{+}$ lymphocytes isolated from the lamina propria of mice deficient in ILFs, PPs, and colonic-patches.

Next, the relationship between the gut-associated lymphoid tissues of mice and the number of Foxp3$^+$ cells in the colonic lamina propria of the mice was investigated in accordance with the method described in M. N. Kweon et al., J Immunol 174, 4365 (Apr. 1, 2005). Specifically, 100 μg of an extracellular domain recombinant protein (a fusion protein (LTβR-Ig) between a lymphotoxin β receptor (LTβR) and a Fc region of human IgG1, refer to Honda et al., J Exp Med 193, 621 (Mar. 5, 2001)) was injected intraperitoneally into pregnant C57BL/6 mice 14 days after conception. The LTβR-Ig was again injected intraperitoneally into fetuses obtained from such mice, so that mice from which isolated lymphoid follicles (ILFs), Peyer's patches (PPs), and colonic-patches (CPs) were completely removed were produced. Then, the ratios of Foxp3$^+$ cells in CD4$^+$ cells in the colonic lamina propria of the mice treated with the LTβR-Ig, and mice treated with rat IgG (control) were analyzed by FACS. FIG. 12 shows the obtained results. Note that in FIG. 12 each white circle represents the ratio of Foxp3$^+$ cells in an individual mouse, and the error bars represent standard deviations. As is apparent from the results shown in FIG. 12, it was found that the ratio of the Foxp3$^+$ cells in the colonic lamina propria of the mice deficient in isolated lymphoid follicles, Peyer's patches, and the colonic-patches (the mice treated with the LTβR-Ig) rather increased. Accordingly, it was suggested that the decrease in the number of the Treg cells in the colonic lamina propria of the GF mice and the mice treated with the antibiotics was caused because the transmission of specific signals which promotes the accumulation of Treg cells in the colonic lamina propria and which is caused by the intestinal microbes did not occur, rather than simply because of a secondary effect of disorganized gut-associated lymphoid tissues.

Example 5

Figure 30:
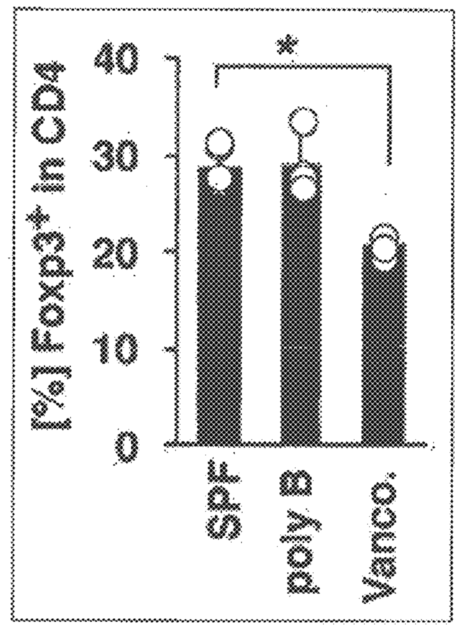
FIG. 30 is a graph showing the results obtained when SPF B6 mice were treated with polymyxin B or vancomycin for 4 weeks, and then analyzed for the ratio of Foxp3$^{+}$ cells in the CD4$^{+}$ cell group.

To investigate whether or not a specific intestinal flora induced the accumulation of colonic Treg cells, vancomycin as an antibiotic against Gram-positive bacteria or polymyxin B as an antibiotic against Gram-negative bacteria was administered to SPF mice (from 4 weeks of age) for four weeks, and analyzed for the ratio of Foxp3$^+$ cells in the CD4$^+$ cell group ([%] Foxp3$^+$ in CD4). FIG. 30 shows the obtained results. Note that, in FIG. 30, "SPF" indicates the result of SPF mice (control), "poly B" indicates the result of the SPF mice to which polymyxin B was administered, and "Vanco." indicates the result of the SPF mice to which vancomycin was administered. Meanwhile, * indicates that "P<0.01."

As is apparent from the results shown in FIG. 30, the number of Treg cells in the colon of the mice to which vancomycin was administered was markedly decreased in comparison with that of the control. In contrast, no influence was observed on the number of Treg cells of the mice to which polymyxin B was administered. Those facts suggested that Gram-positive commensal bacteria played a major role in accumulation of Treg cells.

Example 6

Figure 31:
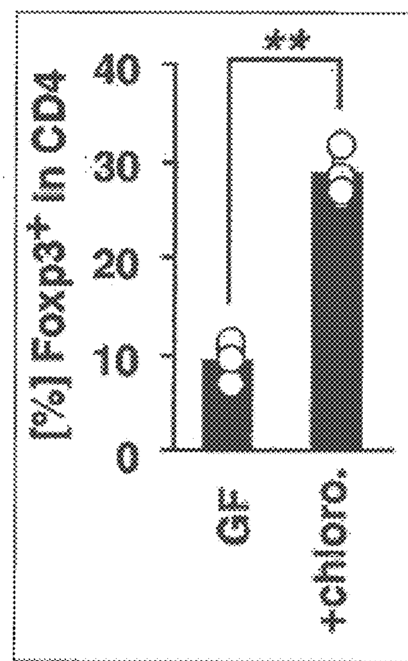
FIG. 31 is a graph showing the results obtained when SPF mice-derived chloroform-treated feces were orally administered to GF mice, and then the ratio of Foxp3$^{+}$ cells in the CD4$^{+}$ cell group was analyzed.

A recent report has suggested that spore-forming bacteria play an important role in intestinal T cells response (see V. Gaboriau-Routhiau et al., Immunity 31, 677 (Oct. 16, 2009)). In this respect, fecal microorganisms (spore-forming fraction) resistant to 3% chloroform were orally administered to GF mice, which were then analyzed for the ratio of Foxp3$^+$ cells in the CD4$^+$ cell group ([%] Foxp3$^+$ in CD4). FIG. 31 shows the obtained results. Note that, in FIG. 31, "GF" indicates the result of GF mice, and "+chloro" indicates the result of the GF mice to which the chloroform-treated feces were administered. Meanwhile, ** indicates that "P<0.001."

As is apparent from the results shown in FIG. 31, three weeks after the administration of the chloroform-treated feces, the number of Treg cells in the administered mice was markedly increased to the same level as those of the SPF mice and the GF mice to which the untreated feces was forcibly administered (see FIGS. 7 and 11).

Accordingly, considering the results shown in Example 5 in combination, it was revealed that the specific components of the indigenous microbiota were highly likely to belong to the Gram-positive group, and that the spore-forming fraction played an important role in the induction of Treg cells.

Example 7

Next, the species of the intestinal microbiota which induced the accumulation of Treg cells in the colon as suggested in Examples 4 to 6 were identified. Specifically, segmented filamentous bacteria (SFB), 16 strains of the *Bacteroides* spp. (Bactero. (6 strains of *B. vulgatus,* 7 of the *B. acidifaciens* group 1, and 3 of the *B. acidifaciens* group 2)), 3 strains of the *Lactobacillus* (Lacto. (*L. acidophilus, L. fermentum*, and *L. murinum*)), and 46 strains of *Clostridium* spp. (Clost., refer to "Itoh, K., and Mitsuoka, T. Characterization of clostridia isolated from faeces of limited flora mice and their effect on caecal size when associated with germ-free mice. Lab. Animals 19: 111-118 (1985))"), or microbiota collected from mice (SPF) bred under a conventional environment was orally administered to GF-Balb/c mice or GF-IQI mice. The mice were maintained in vinyl isolators for three weeks. Then, CD4 cells were isolated from the colon and the small intestine of these mice. The numbers of Treg cells in the colon and the small intestine were analyzed by flow cytometry.

Figure 13:
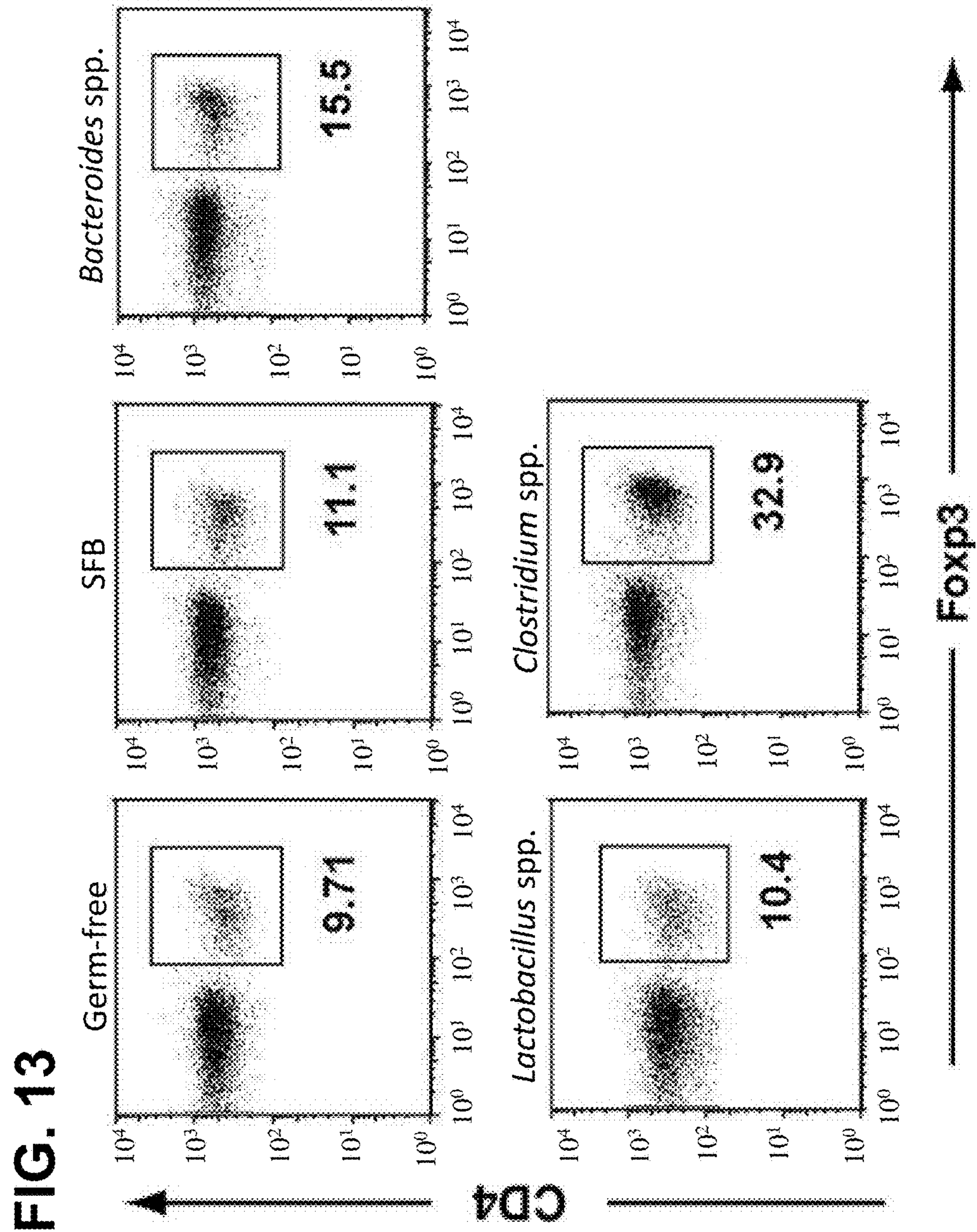
FIG. 13 shows FACS dot-plot diagrams showing analysis results of the ratios of Foxp3$^{+}$ cells in CD4$^{+}$ lymphocytes isolated from the colonic lamina propria of GF mice to which specific commensal bacteria were administered.
Figure 14:
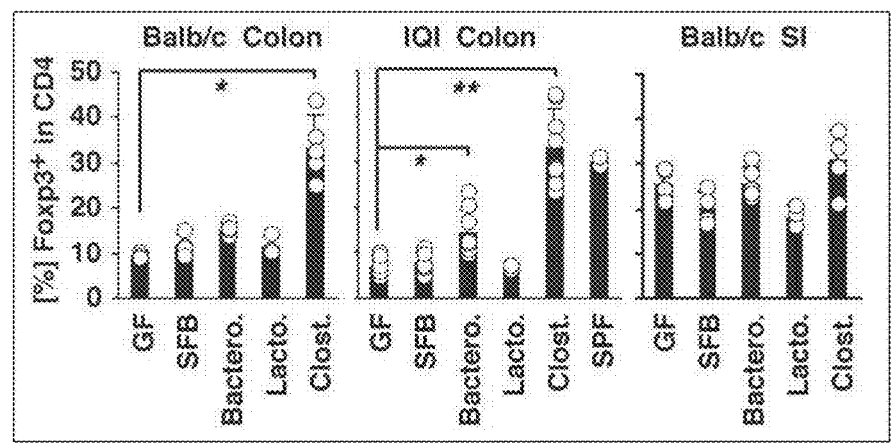
FIG. 14 shows graphs showing analysis results of the ratios of Foxp3$^{+}$ cells in CD4$^{+}$ lymphocytes isolated from the colonic lamina propria of GF mice to which specific commensal bacteria were administered.

FIG. 13 shows FACS dot-plots obtained when a gate was set on CD4$^+$ cells of the Balb/c mice. FIG. 14 shows the ratio of Foxp3$^+$ cells in CD4$^+$ cells of each mouse.

Note that, the bacteria belonging to the genus *Clostridium* are classified by sequencing of 16S rRNA gene, as follows. Specifically, the 16S rRNA genes of the bacteria were amplified by PCR using 16S rRNA gene-specific primer pairs: 5'-AGAGTTTGATCMTGGCTCAG-3' (SEQ ID NO: 19) and 5'-ATTACCGCGGCKGCTG-3' (SEQ ID NO: 20) (see T. Aebischer et al., Vaccination prevents *Helicobacter pylori*-induced alterations of the gastric flora in mice. FEMS Immunol. Med. Microbiol. 46, 221-229(2006)). The 1.5-kb PCR product was then introduced into pCR-Blunt Vector. The inserts were sequenced and aligned using the ClustalW software program. The resulting sequences of 16S rRNA genes derived from strain 1-41 of 46 strains of *Clostridium* spp. were shown in SEQ ID NO: 21-61. Phylogenetic tree which was constructed by the neighbor-joining method with the resulting sequences of the 41 strains of *Clostridium* and those of known bacteria obtained from Genbank database using Mega software was shown in FIG. 49.

As is apparent from the results shown in FIGS. 13 and 14, no effect on the number of the Treg cells in the colon was observed in the GF mice in which the segmented filamentous bacteria (SFB) were colonized (refer to FIG. 14). Moreover, mice in which the cocktail of three strains of *Lactobacillus* was colonized gave similar results (refer to FIG. 14). On the other hand, it was shown that the accumulation of Foxp3$^+$ cells in the colonic lamina propria was strongly induced in the mice in which 46 strains of *Clostridium* spp. were colonized. Importantly, such accumulation was promoted irrespective of the genetic backgrounds of the mice, and led to the increase in number similar to that in the SPF mice although intestinal microbiota of only a single genus were colonized. It was also shown that the colonization of the *Clostridium* did not change the number of Treg cells in the small intestinal lamina propria (refer to FIG. 14). Note that, when the 16 strains of Bactericides spp. were colonized, the number of Treg cells in the colon was increased significantly. However, the extent of the increase varied depending on the genetic background of the mice in which the bacteria were colonized (refer to FIGS. 13 and 14).

Example 8

Next, CD4 expression, Foxp3 expression, and Helios expression in LP lymphocytes of the thymuses and the colons of SPF mice, GF mice, *Lactobacillus*-colonized mice, and *Clostridium*-colonized mice were analyzed by flow cytometry.

Figure 32:
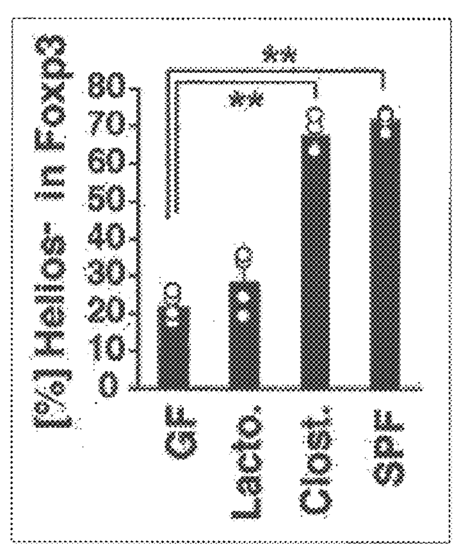
FIG. 32 is a graph showing the general results of flow cytometry analysis on Helios expression in LP lymphocytes in the thymuses or the colons of SPF mice, GF mice, *Lactobacillus*-colonized mice, or *Clostridium*-colonized mice.
Figure 33:
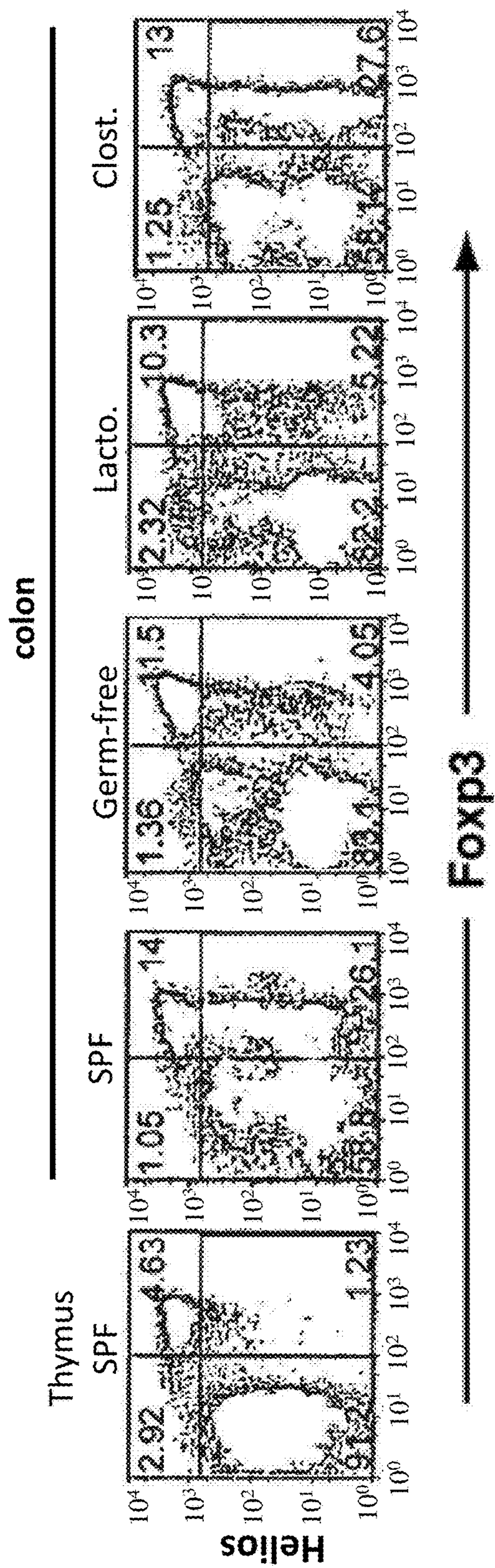
FIG. 33 shows plot diagrams showing representative results of flow cytometry analysis on CD4 expression, Foxp3 expression, and Helios expression in the LP lymphocytes in the thymuses or the colons of the SPF mice, the GF mice, the *Lactobacillus*-colonized mice, or the *Clostridium*-colonized mice.

FIGS. 32 and 33 show the obtained results. Note that, in FIGS. 32 and 33, "GF" or "Germ Free" indicates the results of the GF mice, "SPF" indicates the results of the SPF mice, "Lacto." indicates the results of the *Lactobacillus*-colonized mice, and "Clost." indicates the results of the *Clostridium*-colonized mice. In FIG. 32, the vertical axis represents the ratio of Helios$^-$ cells in the Foxp3$^+$ cell group ([%] Helios$^-$ in Foxp3$^+$), and ** indicates that "P<0.001."

As is apparent from the results shown in FIGS. 32 and 33, most Foxp3$^+$ cells found in the SPF mice or the *Clostridium*-colonized mice did not express Helios. Note that Helios is a transcription factor known to be expressed in thymic-derived natural Treg cells (see A. M. Thornton et al., J Immunol 184, 3433 (Apr. 1, 2010)). Accordingly, it was suggested that most of the Treg cells in the SPF mice and the *Clostridium*-colonized mice were Treg cells induced in peripheral portions, i.e., so-called iTreg cells.

Example 9

Figure 15:
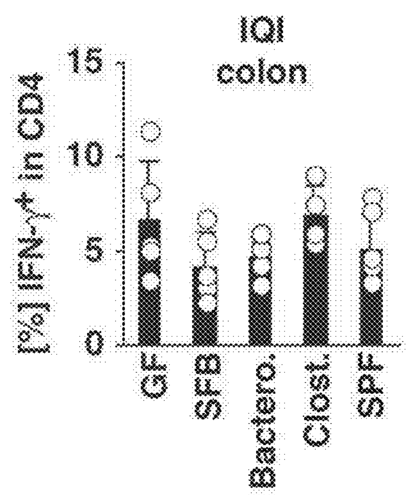
FIG. 15 is a graph showing analysis results of the ratios of IFN-γ$^{+}$ cells in CD4$^{+}$ lymphocytes isolated from the colonic lamina propria of mice in which specific commensal bacteria were colonized.
Figure 16:
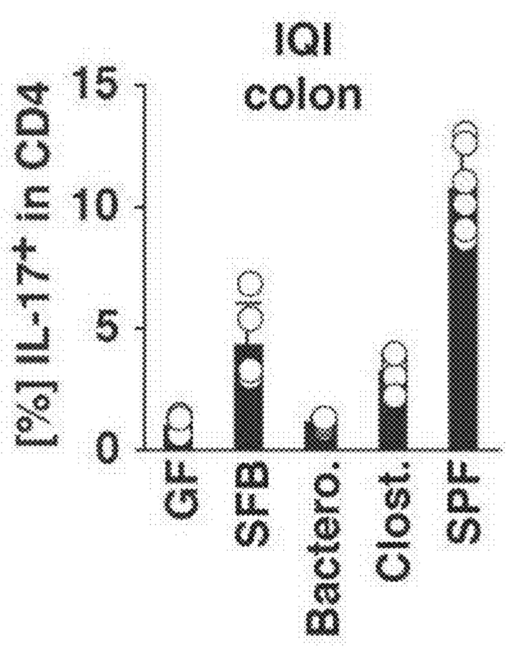
FIG. 16 is a graph showing analysis results of the ratios of IL-17$^{+}$ cells in CD4$^{+}$ lymphocytes isolated from the colonic lamina propria of mice in which specific commensal bacteria were colonized.

Next, it was investigated whether or not the colonization of the *Clostridium* or the like had an influence on other T cells. Specifically, SFB, 16 strains of *Bacteroides* spp. (Bactero.), 46 strains of *Clostridium* spp. (Clost.), or microbiota collected from mice bred under a conventional environment (SPF) was colonized in GF IQI mice. Three weeks later, lymphocytes in the colonic lamina propria were isolated from these mice, and stimulated with PMA (50 ng/ml) and ionomycin (1 μg/ml) for four hours in the presence of GOLGISTOP® (BD Bioscience). After the stimulation was given, intracellular cytokines were stained by using an anti-IL-17 PE antibody (TC11-18H10) and an anti-IFN-g FITC antibody (BD Bioscience) in accordance with the manual of a CYTOFIX/CYTOPERM® kit (BD Bioscience). Then, the ratio of IFN-γ$^+$ cells or IL-17$^+$ cells in CD4$^+$ leucocytes was analyzed by flow cytometry. FIGS. 15 and 16 show the obtained results. Note that, in FIGS. 15 and 16, each white circle represents the absolute number of CD4$^+$ IFN-γ$^+$ cells or the absolute number of CD4$^+$ IL-17$^+$ cells in each individual mouse, and the error bars represent standard deviations (SD). As is apparent from the results shown in FIGS. 15 and 16, the colonization of the *Clostridium* did not have any influence on Th1 cells (CD4$^+$ IFN-γ$^+$ cells) in the colon, and caused only a slight increase of Th17 cells (CD4$^+$ IL-17$^+$ cells). Accordingly, it was suggested that the genus *Clostridium* was a genus of bacteria which specifically induced Treg cells.

Example 10

It has been reported that 46 strains of *Clostridium* spp. exert an influence on the accumulation of CD8$^+$ intestinal tract intraepithelial lymphocytes (IELs) in the colon. Accordingly, it is conceivable that *Clostridium* regulates the immune system in various aspects, and that *Clostridium* exhibits a marked ability to induce and maintain Treg cells especially in the colon, as described above. In addition, a kind of cytokines, transforming growth factor-(3 (TGF-β), is known to play an important role in regulation of Treg cell generation.

Figure 34:
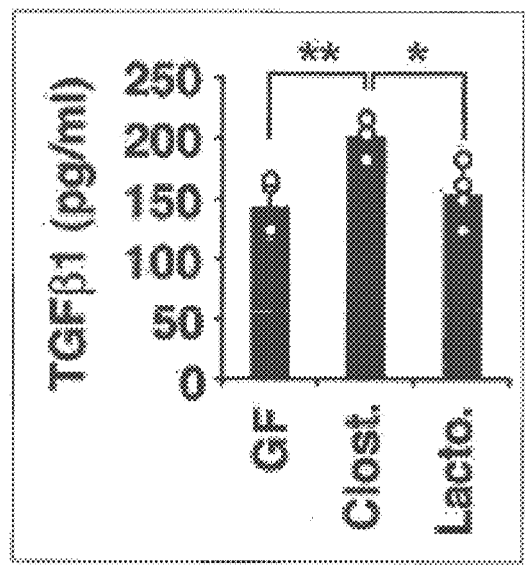
FIG. 34 is a graph showing the results obtained when the whole colons derived from GF mice, *Lactobacillus*-colonized mice, or *Clostridium*-colonized mice were cultured, and the culture supernatants thereof were analyzed for the TGF-β1 concentration by ELISA.

In this respect, it was examined whether or not the colonization of *Clostridium* provided a colonic environment rich in TGF-β. Specifically, first, the whole colons of GF mice, *Clostridium*-colonized mice, and *Lactobacillus*-colonized mice were cultured for 24 hours, and the culture supernatants thereof were measured for the concentration of active TGF-β (TGF-β1) by ELISA (the number of mice analyzed was four per group). FIG. 34 shows the obtained results. Note that, in FIG. 34, "GF" indicates the result of the GF mice, "Clost." indicates the result of the *Clostridium*-colonized mice, and "Lacto." indicates the result of *Lactobacillus*-colonized mice. Meanwhile, * indicates that "P<0.02," and ** indicates that "P<0.001."

As is apparent from the results shown in FIG. 34, the amount of TGF-β produced in the colons of the *Clostridium*-colonized mice was significantly larger than those of the GF mice and the *Lactobacillus*-colonized mice.

Figure 35:
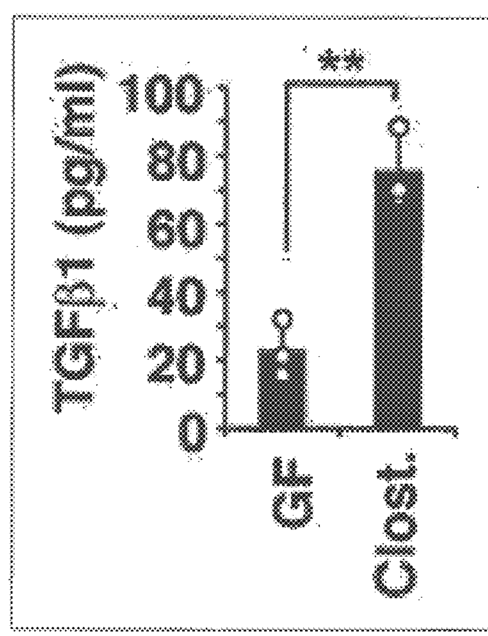
FIG. 35 is a graph showing the results obtained when intestinal epithelial cells (IECs) derived from GF mice or *Clostridium*-colonized mice were cultured, and the culture supernatants thereof were analyzed for the TGF-β1 concentration by ELISA.

Next, intestinal epithelial cells (IECs) of GF mice and *Clostridium*-colonized mice were cultured for 24 hours, and the culture supernatants thereof were measured for the concentration of active TGF-β (TGF-β1) by ELISA (the number of mice analyzed was four per group). FIG. 35 shows the obtained results. Note that, in FIG. 35, "GF" indicates the result of the GF mice, and "Clost." indicates the result of the *Clostridium*-colonized mice. Meanwhile, ** indicates that "P<0.001."

As is apparent from the results shown in FIG. 35, TGF-β was detected in the culture supernatant of the IECs isolated from the *Clostridium*-colonized mice, whereas no TGF-β was detected in the culture supernatant of the IECs isolated from the GF mice.

Figure 36:
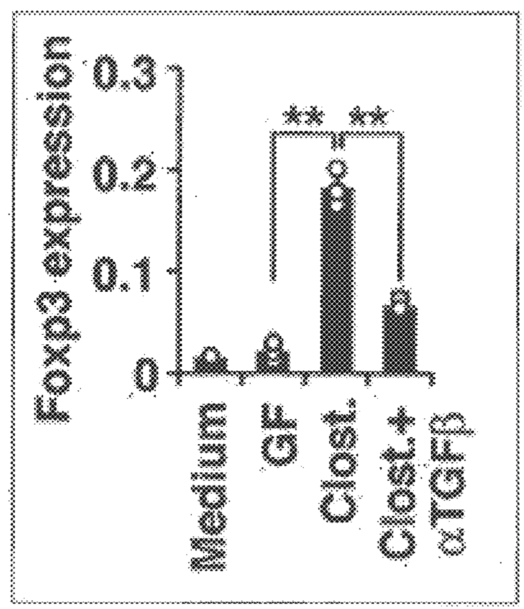
FIG. 36 is a graph showing the results obtained when splenic $CD4^+$ T cells were cultured together with an anti-CD3 antibody and with a culture supernatant of IECs isolated from GF mice or mice colonized with 46 bacterial strains of the genus *Clostridium* (Clost.) in the presence or absence of an anti-TGF-β antibody, and the T cells were collected on day 5 of the culture and analyzed for Foxp3 expression by real-time RT-PCR.

Next, as described above, splenic CD4$^+$ T cells were cultured for five days together with a 50% conditioned medium in which IECs isolated from the GF mice or the *Clostridium*-colonized mice were cultured, and with the anti-CD3 antibody, in the presence or absence of an anti-TGF-β antibody. Then, the T cells were collected, and analyzed for expression of Foxp3 by real-time RT-PCR. FIG. 36 shows the obtained results. Note that, in FIG. 36, "Medium" indicates the result of a medium in which no cells were cultured, "GF" indicates the result of the conditioned medium in which the IECs of the GF mice were cultured, "Clost." indicates the result of the conditioned medium in which the IECs of the *Clostridium*-colonized mice were cultured, and "Clost.+αTGFβ" indicates the result of the conditioned medium to which the anti-TGF-β antibody was added and in which the IECs of the *Clostridium*-colonized mice were cultured. Meanwhile, ** indicates that "P<0.001."

As is apparent from the results shown in FIG. 36, when the culture supernatant of the IECs derived from the *Clostridium*-colonized mice was added to the splenic $CD4^+$ T cells, the differentiation into Foxp3-expressing cells was accelerated. Meanwhile, the differentiation into the Treg cells was inhibited by the anti-TGF-β antibody.

Moreover, the expression of MMP2, MMP9, and MMP13, which are thought to contribute to the activation of latent TGF-β was investigated. The expression of indoleamine 2,3-dioxygenase (IDO), which is thought to be involved in the induction of Treg cells, was also investigated. Specifically, 46 bacterial strains of the genus *Clostridium* (Clost.), or three bacterial strains of the genus *Lactobacillus* (Lacto.) were orally administered to C57BL/6 germ-free mice. Three weeks after the administration, IECs were collected, and analyzed for relative mRNA expression levels of MMP2, MMP9, MMP13, and IDO genes by real-time RT-PCR (the number of mice analyzed was three per group). FIGS. 37 to 40 show the obtained results. Note that, in FIGS. 37 to 40, "GF#1 to 3" indicate the results of GF mice, "Clost.#1 to 3" indicate the results of the *Clostridium*-colonized mice, and "Lacto.#1 to 3" indicate the results of the *Lactobacillus*-colonized mice.

For the relationship between the activation of latent TGF-β and the above-describe MMP, see D'Angelo et al., J. Biol. Chem. 276, 11347-11353, 2001; Heidinger et al., Biol. Chem. 387, 69-78, 2006; Yu et al., Genes Dev. i4, 163-176, 2000. For the relationship between IDO and the induction of Treg cells, see G. Matteoli et al., Gut 59, 595 (May, 2010).

Figure 37:
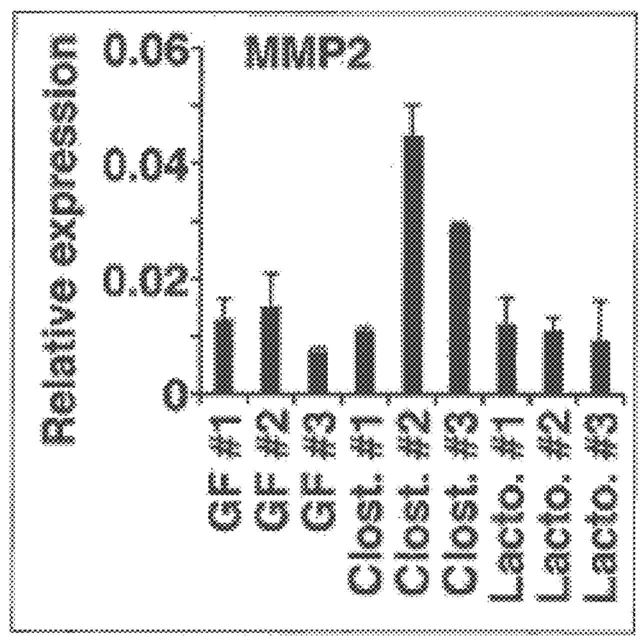
FIG. 37 is a graph showing the results obtained when C57BL/6 GF mice were orally inoculated with 46 bacterial strains of the genus *Clostridium* (Clost.) or three bacterial strains of the genus *Lactobacillus* (Lacto.), and IECs were collected three weeks after the inoculation and analyzed for the relative mRNA expression level of the MMP2 gene by real-time RT-PCR.
Figure 38:
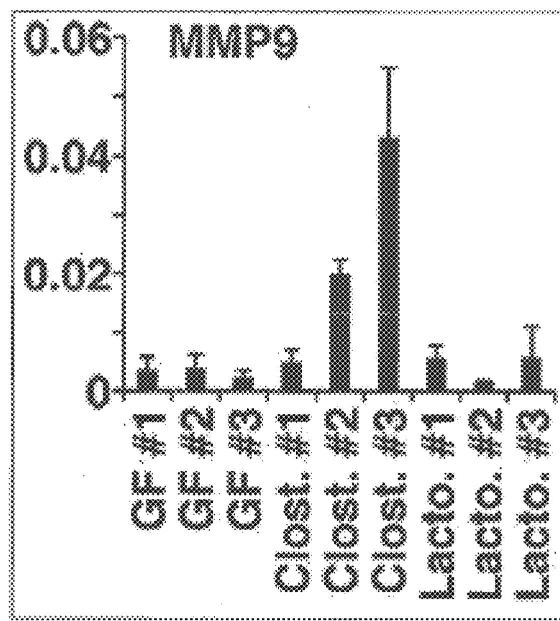
FIG. 38 is a graph showing the results obtained when C57BL/6 GF mice were orally inoculated with 46 bacterial strains of the genus *Clostridium* (Clost.) or three bacterial strains of the genus *Lactobacillus* (Lacto.), and IECs were collected three weeks after the inoculation and analyzed for the relative mRNA expression level of the MMP9 gene by real-time RT-PCR.
Figure 39:
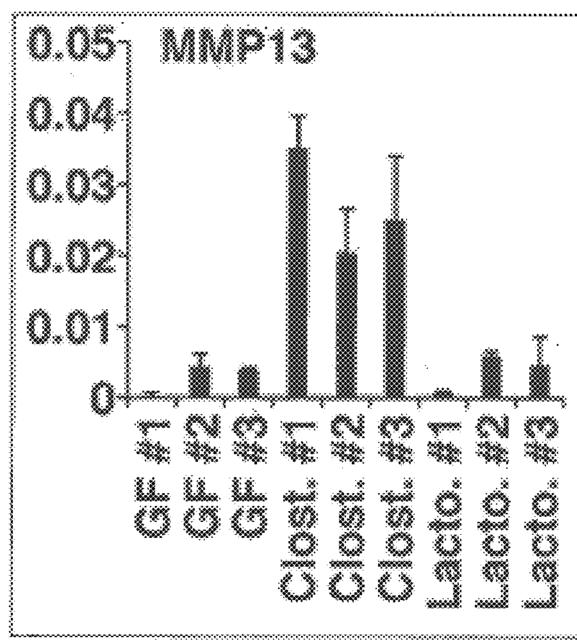
FIG. 39 is a graph showing the results obtained when C57BL/6 GF mice were orally inoculated with 46 bacterial strains of the genus *Clostridium* (Clost.) or three bacterial strains of the genus *Lactobacillus* (Lacto.), and IECs were collected three weeks after the inoculation and analyzed for the relative mRNA expression level of the MMP13 gene by real-time RT-PCR.

As is apparent from the results shown in FIGS. 37 to 39, in agreement with the production of TGF-β described above, transcription products of the genes encoding MMP2, MMP9, and MMP13 were expressed at higher levels in the IECs derived from the *Clostridium*-colonized mice than those in the GF mice and in the *Lactobacillus*-colonized mice.

Figure 40:
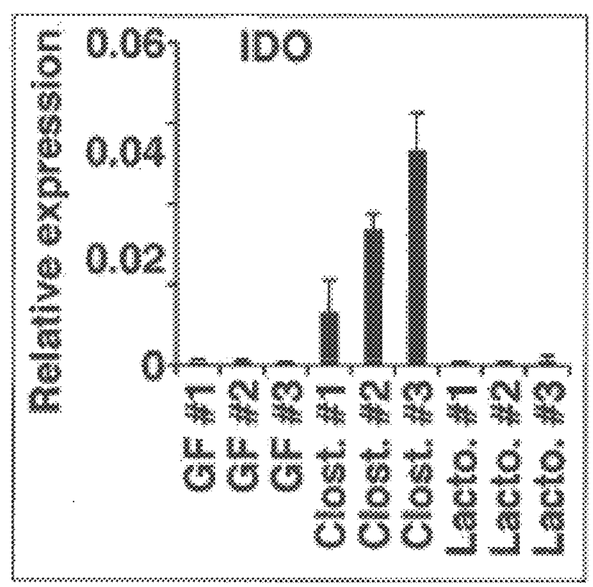
FIG. 40 is a graph showing the results obtained when C57BL/6 GF mice were orally inoculated with 46 bacterial strains of the genus *Clostridium* (Clost.) or three bacterial strains of the genus *Lactobacillus* (Lacto.), and IECs were collected three weeks after the inoculation and analyzed for the relative mRNA expression level of the IDO gene by real-time RT-PCR.

Moreover, as is apparent from the results shown in FIG. 40, IDO was expressed only in the *Clostridium*-colonized mice.

Accordingly, it was revealed that the *Clostridium* activated the IECs, and led to the production of TGF-β and other Treg cell-inducing molecules in the colon.

Example 11

Figure 17:
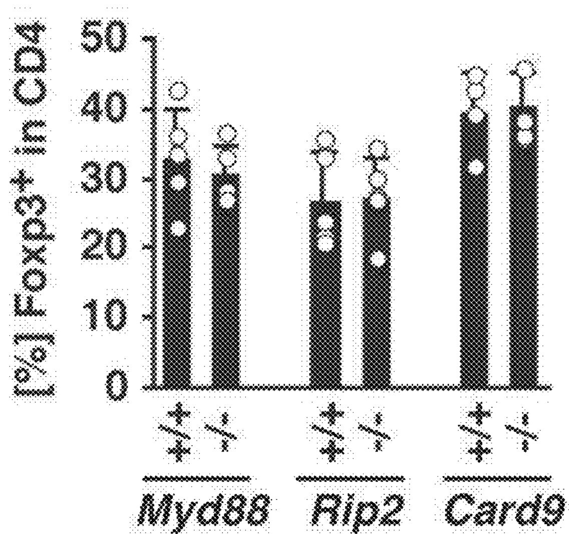
FIG. 17 is a graph showing analysis results of the ratios of Foxp3$^{+}$ cells in CD4$^{+}$ lymphocytes isolated from the colon of kinds of SPF mice each being deficient in a pathogen-associated molecular pattern recognition receptor-associated factor.
Figure 18:
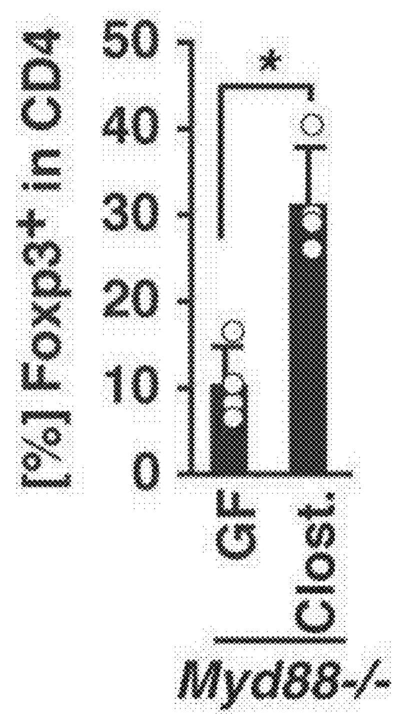
FIG. 18 is a graph showing analysis results of the ratios of Foxp3$^{+}$ cells in CD4$^{+}$ lymphocytes isolated from the colonic lamina propria of Myd88$^{-/-}$ mice in which the *Clostridium* was colonized.

Next, it was investigated whether or not the Treg cell accumulation induced by the colonization of the *Clostridium* was dependant on signal transmission by pathogen-associated molecular pattern recognition receptors. Specifically, the numbers of Treg cells in the colonic lamina propria of each of SPF mice of $Myd88^{-/-}$ (deficient in Myd88 (signaling adaptor for Toll-like receptor)), $Rip2^{-/-}$ (deficient in Rip2 (NOD receptor adaptor)), and $Card9^{-/-}$ (deficient in Card9 (essential signal transmission factor for Dectin-1 signal transmission)) were examined. In addition, *Clostridium* spp. were caused to be colonized in the $Myd88^{-/-}$ GF mice, and the change in the number of Treg cells was investigated. FIGS. 17 and 18 show the obtained results. As is apparent from the results shown in FIGS. 17 and 18, the number of Treg cells of each kind of the SPF mice deficient in the associated factors of the pathogen-associated molecular pattern recognition receptors did not change relative to that of wild-type mice of the same litter, which served as a control. In addition, it was found that also when *Clostridium* spp. were colonized in GF mice deficient in Myd88, the accumulation of Treg cells in the colonic lamina propria was induced. Accordingly, it has been suggested that the mechanism of inducing the accumulation of Treg cells in the colonic lamina propria relies not on activation of recognition pathway for major pathogen-associated molecular patterns as is caused by most of bacterium, but on specific commensal bacterial species.

Example 12

Figure 19:
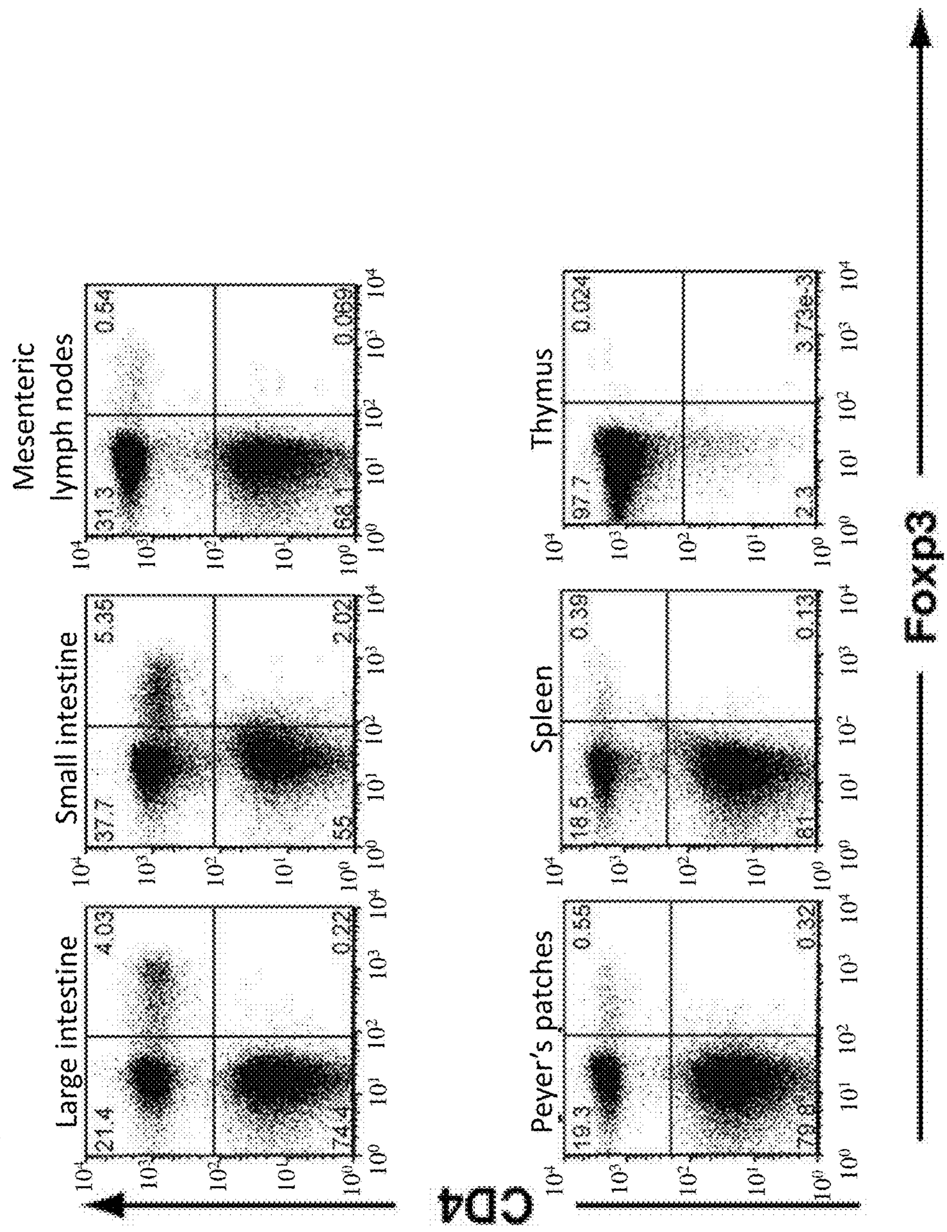
FIG. 19 shows FACS dot-plot diagrams showing analysis results of the ratios of Venus$^{+}$ cells in lymphocytes isolated from various tissues of Il10$^{venus}$ mice.
Figure 19:
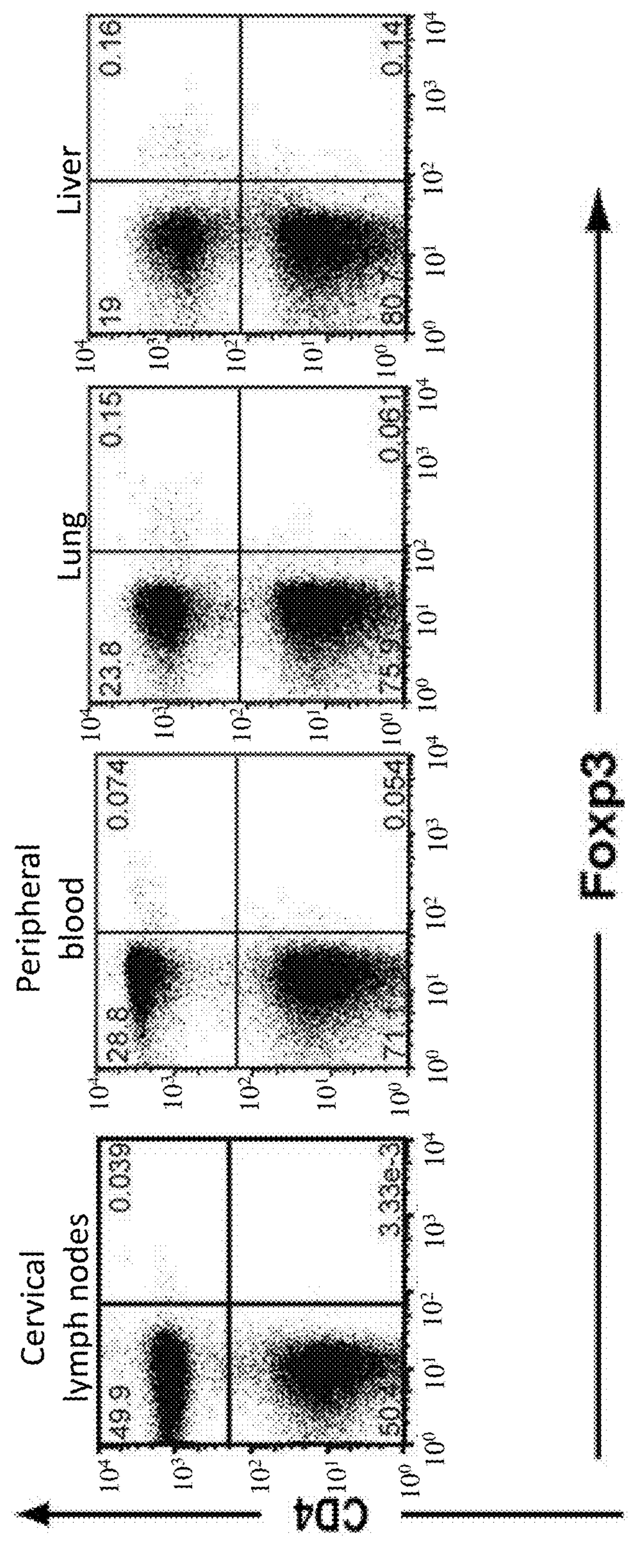

Intestinal tract $Foxp3^+$ Treg cells are known to exert some immunosuppressive functions through IL-10 production (refer to Non-Patent Document 9). Meanwhile, animals having $CD4^+$ $Foxp3^+$ cells from which IL-10 is specifically removed are known to develop inflammatory bowel disease (refer to Non-Patent Document 18). In this respect, first, the expression of IL-10 in lymphocytes of various tissues was examined. Specifically, lymphocytes were isolated from various tissues of SPF $Il10^{venus}$ mice, and the expression of CD4 and the expression of Venus were analyzed by flow cytometry. FIG. 19 shows the obtained results. Note that each numeric value in FIG. 19 represents the ratio of cells within the corresponding one of regions divided into four.

Figure 20:
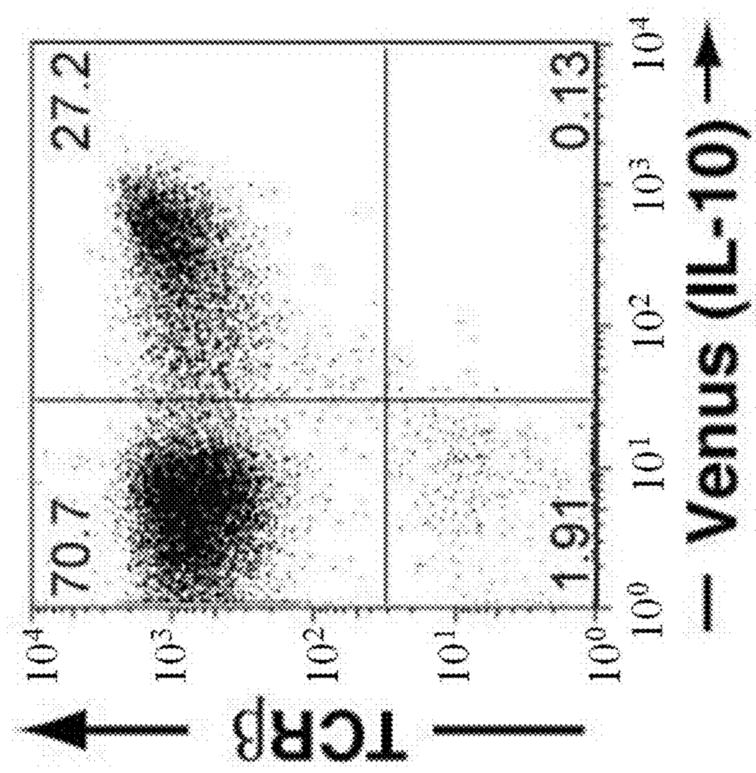
FIG. 20 is a FACS dot-plot diagram showing analysis results of the expression of a T cell receptor β chain on cell surfaces of lymphocytes isolated from the colonic lamina propria of Il10$^{venus}$ mice.

Moreover, lymphocytes in the colonic lamina propria were isolated from $Il10^{venus}$ mice, and the expression of T cell receptor β chain (TCRβ) on the surfaces of the cells was detected by FACS. FIG. 20 shows the obtained results (FACS dot-plots obtained when a gate was set on $CD4^+$ cells). Note that each numeric value in FIG. 20 represents the ratio of cells within the corresponding one of regions divided into four.

Figure 21:
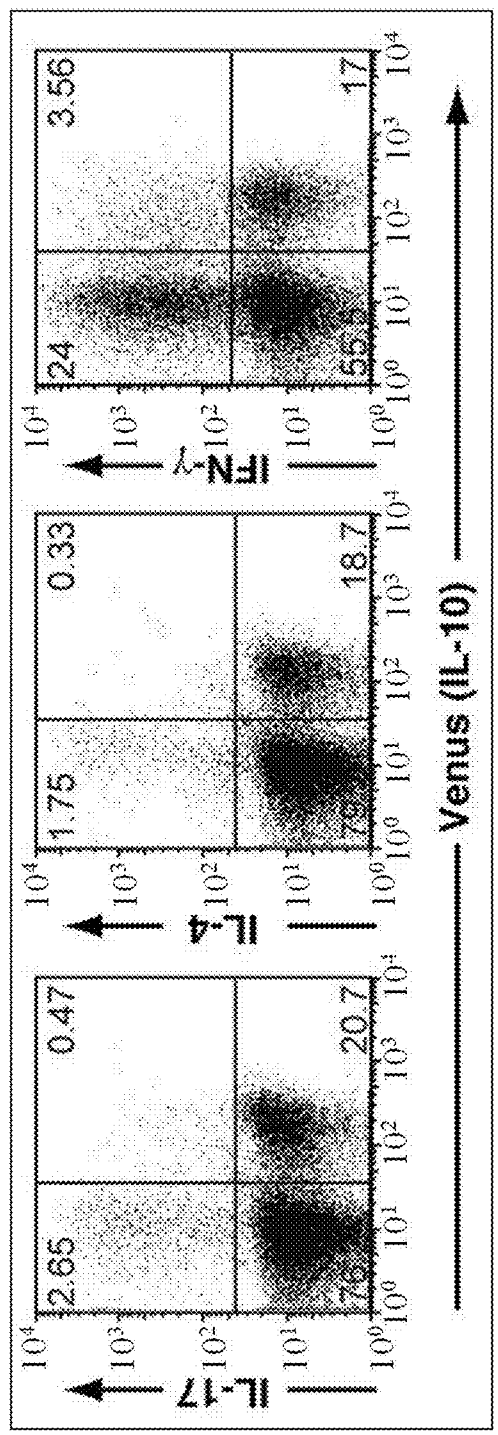
FIG. 21 shows FACS dot-plot diagrams showing analysis results of the expression of IL-17, IL-4, and IFN-γ in lymphocytes isolated from the colonic lamina propria of Il10$^{venus}$ mice.

Furthermore, lymphocytes in the colonic lamina propria were isolated from $Il10^{venus}$ Mice. The lymphocytes were stimulated with PMA (50 ng/ml) and ionomycin (1 μg/ml) for four hours in the presence of GOLGISTOP® (BD Bioscience). Then, after the stimulation was given, intracellular cytokines were stained by using an anti-IL-17 PE antibody, an anti-IL-4 APC antibody (11B11), and an anti-IFN-g FITC antibody (BD Bioscience) in accordance with the manual of a CYTOFIX/CYTOPERM® kit (BD Bioscience). FIG. 21 shows the obtained results (FACS dot-plots obtained when a gate was set on $CD4^+$ cells). Note that each numeric value in FIG. 21 represents the ratio of cells within the corresponding one of regions divided into four.

Figure 22:
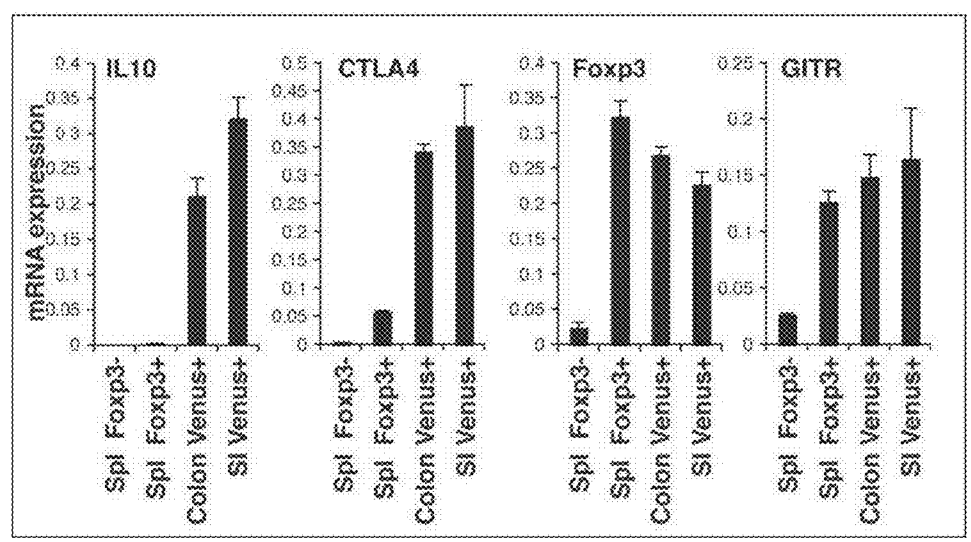
FIG. 22 shows graphs showing analysis results of the amounts of mRNAs of IL-10, CTLA4, Foxp3, and GITR expressed in spleen Foxp3$^{-}$ CD4$^{+}$ cells, spleen Foxp3$^{+}$ CD4$^{+}$ cells, colonic lamina propria Venus$^{+}$ cells, and small intestinal lamina propria Venus$^{+}$ cells.

In addition, $Foxp3^+$ $CD4^+$ cells and $Foxp3^-$ $CD4^+$ cells were isolated from the spleen (Spl) of $Foxp3^{eGFP}$ reporter mice, and $Venus^+$ cells were isolated from the colonic lamina propria and the small intestine (SI) lamina propria of $Il10^{venus}$ mice. Then, the obtained cells were analyzed in terms of the expression of predetermined genes. The gene expression was analyzed by real-time RT-PCR using a Power SYBR Green PCR Master Mix (Applied Biosystems) and an ABI 7300 real time PCR system (Applied Biosystems). Here, the value for each cell was normalized for the amount of GAPDH. FIG. 22 shows the obtained results. Note that in FIG. 22 the error bars represent standard deviations.

As is apparent from the results shown in FIGS. 19 to 22, almost no $Venus^+$ cells (IL-10-producing cells) were detected in the cervical lymph nodes (peripheral lymph nodes), thymus, peripheral blood, lung, and liver of mice kept under the SPF conditions. Meanwhile, in the spleen, Peyer's patches, and mesenteric lymph nodes thereof, $Venus^+$ cells were slightly detected (refer to FIG. 19). On the other hand, many $Venus^+$ cells were found in the lymphocytes in the small intestine lamina propria and colonic lamina propria. In addition, most of the Venus$^+$ cells in the intestines were positive for CD4, and also positive for T cell receptor β chain (TCRβ) (refer to FIGS. 19 and 20). Moreover, it was found that the Venus$^+$ CD4$^+$ T cells expressed Foxp3 and other Treg cell-associated factors such as a cytotoxic T-Lymphocyte antigen (CTLA-4) and a glucocorticoid-induced TNFR-associated protein (GITR) although the Venus$^+$ CD4$^+$ T cells showed none of the phenotypes of Th2 (IL-4-producing) and Th17 (IL-17-producing) (refer to FIGS. 21 and 22). In addition, it was shown that the expression level of CTLA-4 in the intestinal Venus$^+$ cells was higher than that in the splenic GFP$^+$ Treg cells isolated from the Foxp3$^{eGFP}$ reporter mice (refer to FIG. 22).

Example 13

Figure 23:
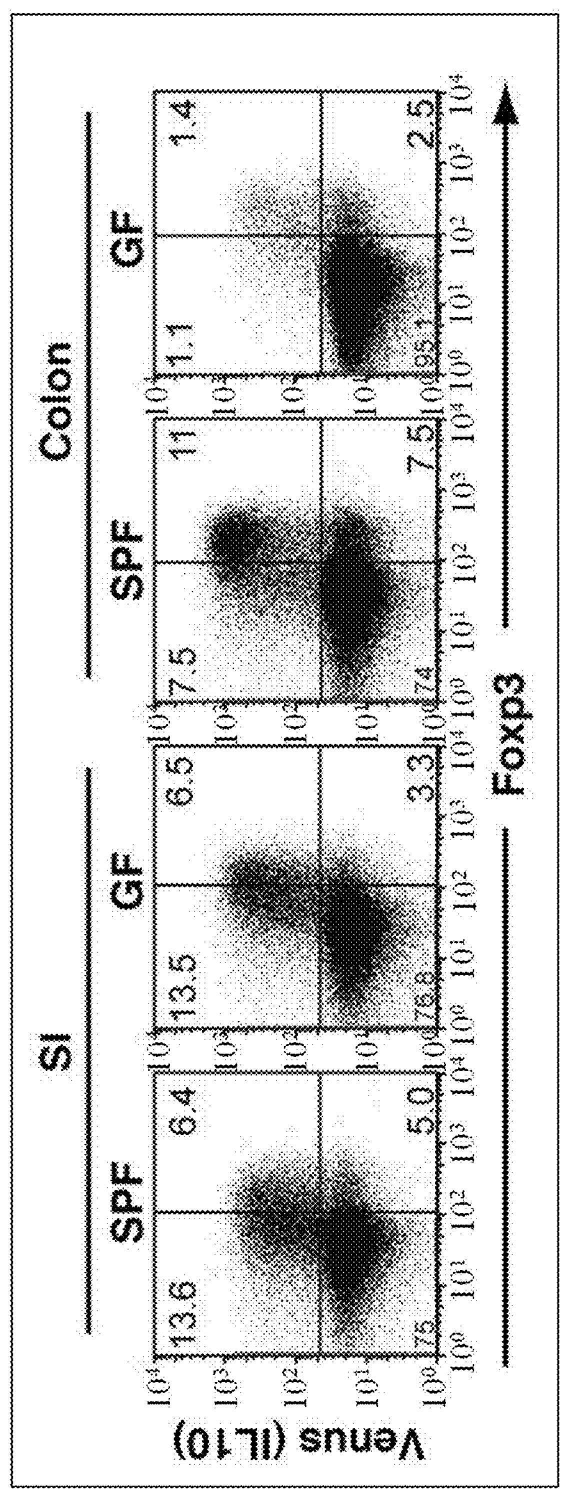
FIG. 23 shows FACS dot-plot diagrams showing analysis results of the expression of CD4, Foxp3, and Venus in the lamina propria of the small intestine and the lamina propria of the colon of GF Il10$^{venus}$ mice and SPF Il10$^{venus}$ mice.

Venus$^+$ cells can be classified into at least two subsets, namely, Venus$^+$ Foxp3$^+$ double positive (DP) Treg cells and Venus$^+$ Foxp3$^-$ Treg cells on the basis of intracellular Foxp3 expression. Cells of the latter subset correspond to type 1 regulatory T cells (Tr1) (refer to Non-Patent Documents 8 and 9). In this respect, the Venus$^+$ cells (IL-10-producing cells) observed in Example 8 were investigated in terms of the expression of Foxp3. Specifically, the expression of CD4, Foxp3, and Venus in the lamina propria of the colon and the lamina propria of the small intestine of Il10$^{venus}$ mice kept under GF or SPF conditions was analyzed by FACS, and the numbers of Venus$^+$ cells in the intestinal tract lamina propria were compared between SPF and GF Il10$^{venus}$ mice. FIG. 23 shows the obtained results (dot-plots obtained when a gate was set on CD4$^+$ cells).

Figure 24:
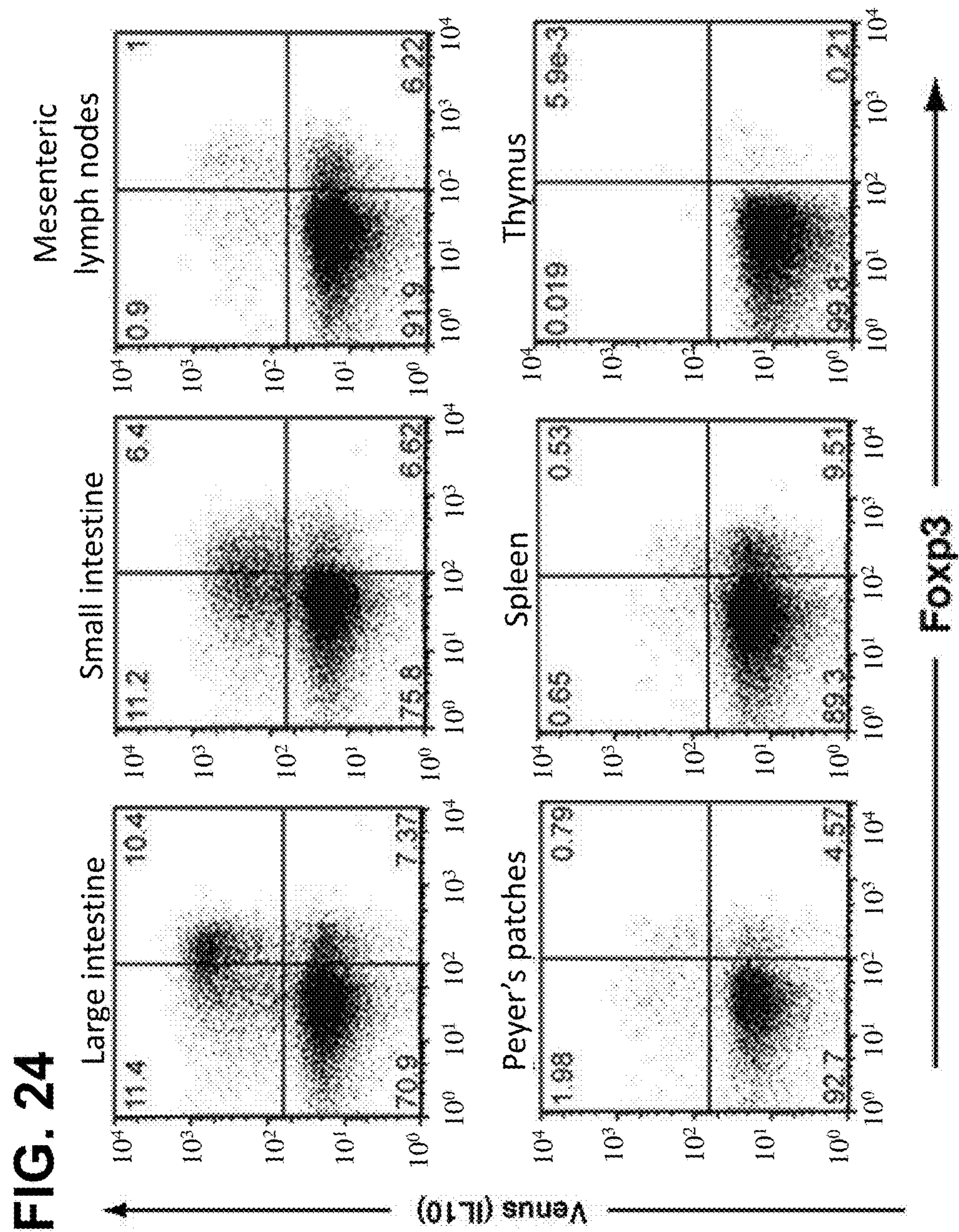
FIG. 24 shows FACS dot-plot diagrams showing analysis results of the expression of Venus and Foxp3 of CD4 cells in various tissues of SPF Il10$^{venus}$ mice.
Figure 24:
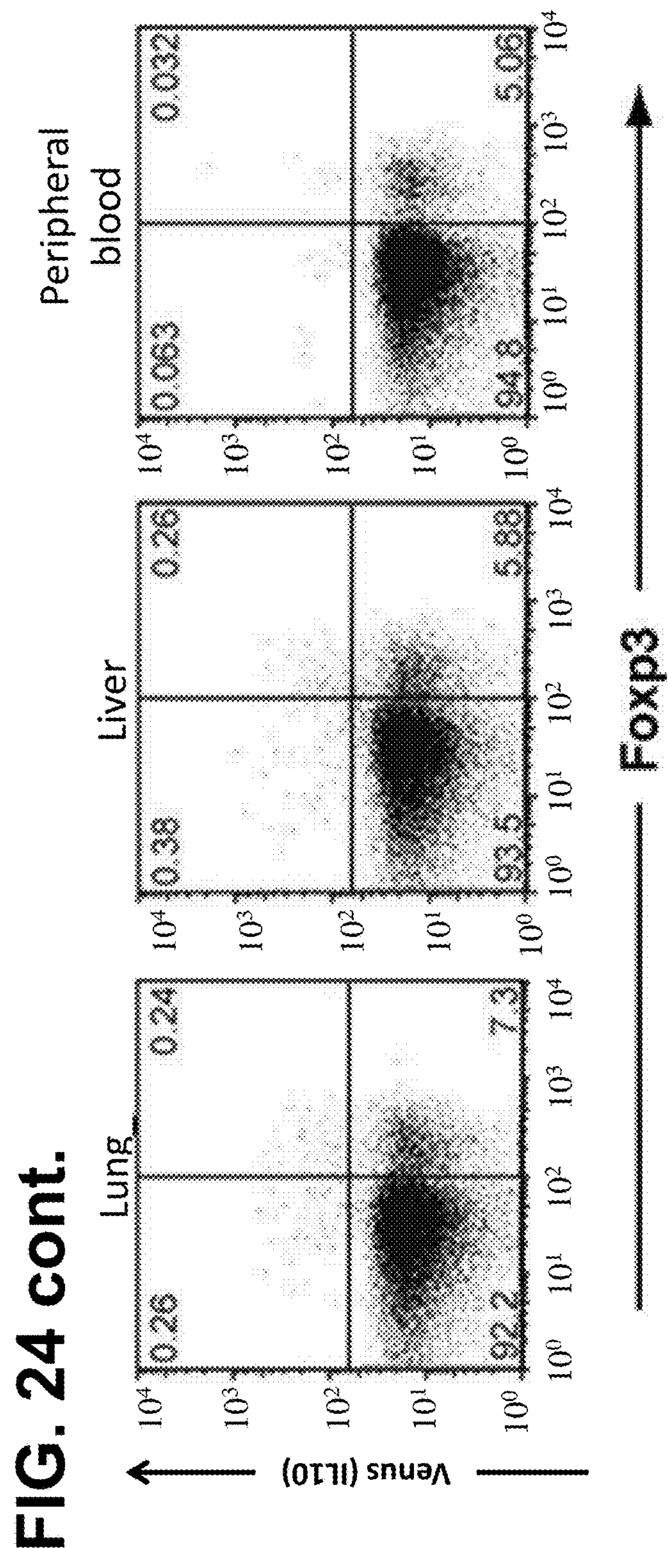

In addition, the intracellular expression of Venus and Foxp3 in CD4 cells in various tissues of SPF Il10$^{venus}$ mice was analyzed by flow cytometry. FIG. 24 shows the obtained results (dot-plots obtained when a gate was set on CD4$^+$ cells). Note that each numeric value in FIG. 24 represents the ratio of cells within the corresponding one of regions divided into four.

Figure 25:
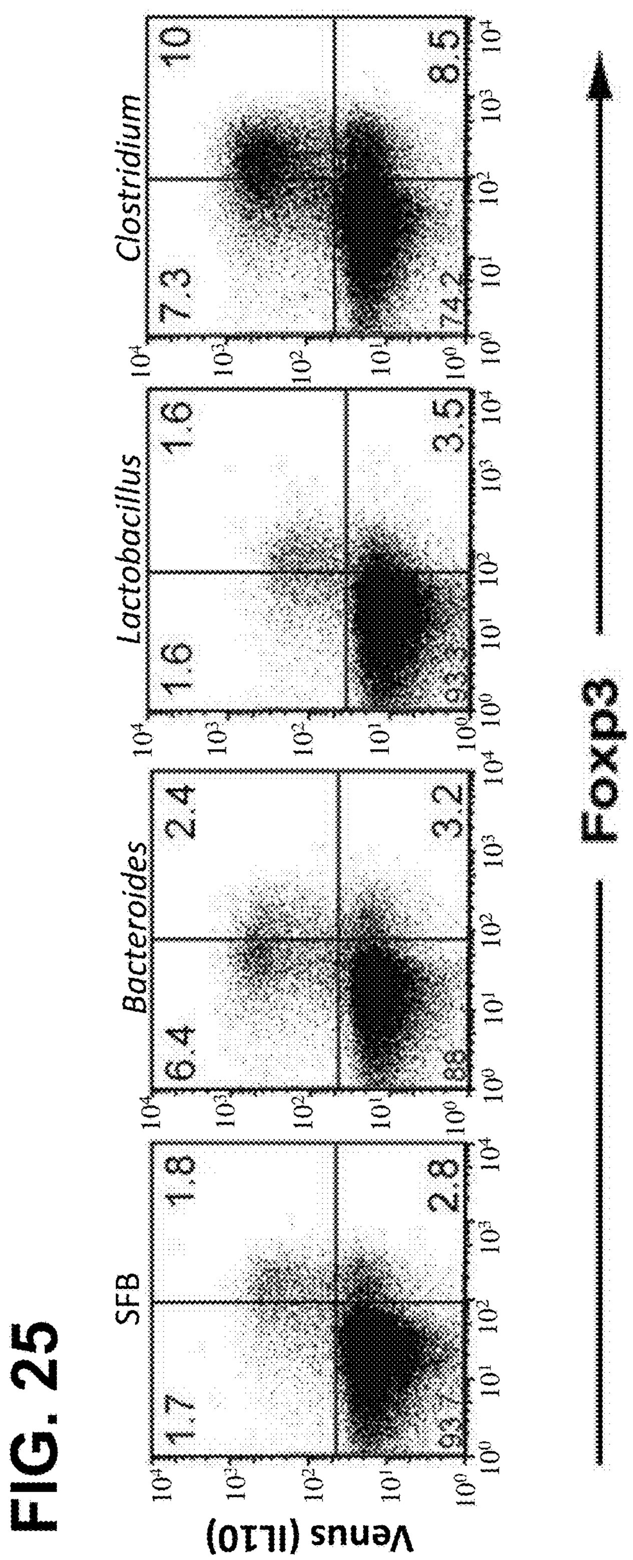
FIG. 25 shows FACS dot-plot diagrams showing analysis results of the expression of Foxp3 and Venus in Il10$^{venus}$ mice in which specific commensal bacteria were colonized.
Figure 26:
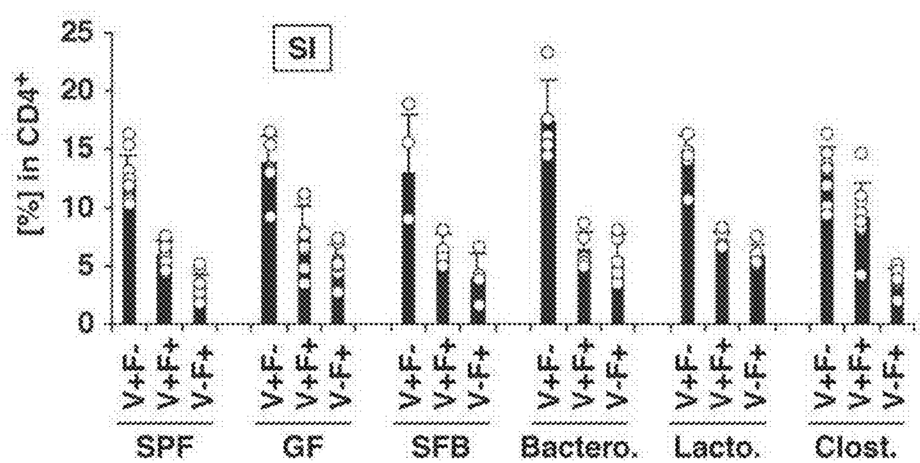
FIG. 26 is a graph showing analysis results of the expression of Foxp3 and/or Venus of CD4$^{+}$ cells in the small intestine of Il10$^{venus}$ mice in which specific commensal bacteria were colonized.
Figure 27:
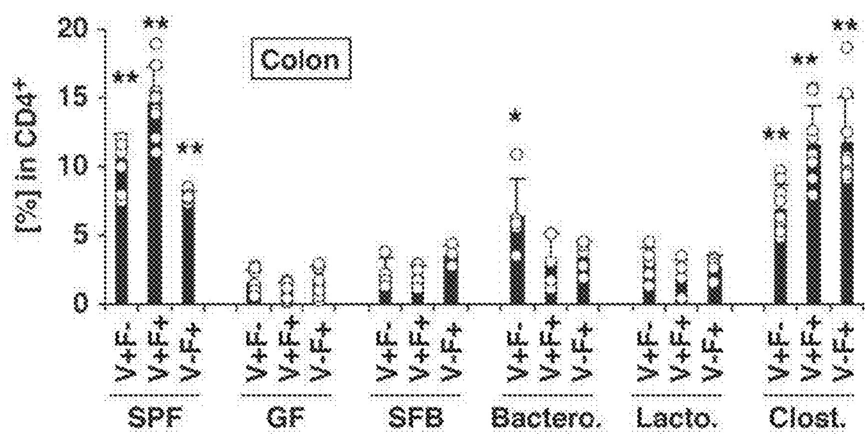
FIG. 27 is a graph showing analysis results of the expression of Foxp3 and/or Venus of CD4$^{+}$ cells in the colon of Il10$^{venus}$ mice in which specific commensal bacteria were colonized.

Moreover, in order to investigate whether or not the presence of commensal bacteria had any influence on the expression of IL-10 in regulatory cells in the gastrointestinal tracts, germ-free (GF) Il10$^{Venus}$ mice were prepared. Then, predetermined species of bacteria were caused to be colonized in the obtained GF Il10$^{venus}$ mice. Three weeks after the species of bacteria were colonized, a CD4$^+$ cell group (V$^+$F$^-$, Venus$^+$ Foxp3$^-$ cells; V$^+$F$^+$, Venus$^+$ Foxp3$^+$ cells; and V$^-$F$^+$, Venus$^-$ Foxp3$^+$ cells) in which Foxp3 and/or Venus were expressed in the colon and the small intestine was analyzed by flow cytometry. FIG. 25 shows dot-plots obtained when a gate was set on colonic CD4$^+$ cells, and FIGS. 26 and 27 show the ratios in the CD4$^+$ cell group of each mouse. Note that each numeric value in FIG. 25 represents the ratio of cells within the corresponding one of regions divided into four. Meanwhile, the error bars in FIGS. 26 and 27 represent standard deviations, indicates that "P<0.02," and ** indicates that "P<0.001."

Moreover, in order to check whether or not the presence of commensal bacteria had any influence on the expression of IL-10 in regulatory cells in the gastrointestinal tracts, antibiotics were orally given with water to five or six Il10$^{venus}$ mice per group for 10 weeks. The following antibiotics were used in combination.

ampicillin (A; 500 mg/L Sigma)
vancomycin (V; 500 mg/L NACALAI TESQUE, INC.)
metronidazole (M; 1 g/L NACALAI TESQUE, INC.)
neomycin (N; 1 g/L NACALAI TESQUE, INC.)

Figure 28:
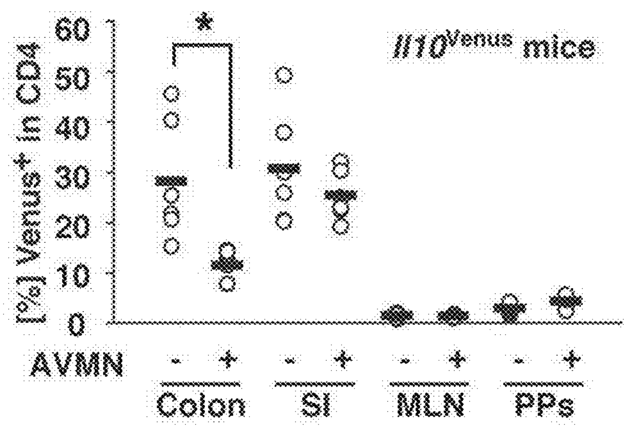
FIG. 28 is a plot diagram showing analysis results of the ratios of Venus$^{+}$ cells in CD4$^{+}$ cells isolated from various tissues of Il10$^{venus}$ mice treated with antibiotics.

Then, CD4 and Foxp3 of lymphocytes in the lamina propria of the colon, the lamina propria of the small intestine (SI), mesenteric lymph nodes (MLN), and Peyer's patches (PPs) were stained with antibodies, and analyzed by FACS. The results were obtained from two or more independent experiments which gave similar results. FIG. 28 shows the obtained results (the ratio of Venus$^+$ cells in CD4$^+$ cells in each sample). Note that each white circle in FIG. 28 represents an individual sample, each horizontal bar represents an average value, * indicates that "P<0.02," and "AVMN" represents the kinds of the administered antibiotics by using the first letters of the antibiotics.

As is apparent from the results shown in FIGS. 23 and 24, it was shown that the small intestinal lamina propria was rich in Venus$^+$ Foxp3$^-$ cells, namely, Tr1-like cells, and that the Venus$^+$ Foxp3$^+$ DP Treg cells were present at a high frequency in the colon of the SPF mice (refer to FIGS. 23 and 24). In contrast, although sufficient numbers of Foxp3$^+$ cells were observed also in other tissues, the expression of Venus was not observed in almost all of the cells (refer to FIG. 24).

In addition, as is apparent from the results shown in FIGS. 23 and 25 to 28, it was shown that all regulatory T cell fractions of Venus$^+$ Foxp3$^-$, Venus$^+$ Foxp3$^+$, and Venus$^-$ Foxp3$^+$ in the colon significantly decreased under the GF conditions (FIGS. 23 and 26 to 27). Moreover, similar decrease in Venus$^+$ cells was observed also in the SPF Il10$^{Venus}$ mice treated with the antibiotics (refer to FIG. 28).

Moreover, as is apparent from the results shown in FIGS. 25 to 27, the colonization of *Clostridium* spp. strongly induced all regulatory T cell fractions of Venus$^+$ Foxp3$^-$, Venus$^+$ Foxp3$^+$, and Venus$^-$ Foxp3$^+$ in the colon, and the degrees of the induction thereof were equal to those in the SPF mice (refer to FIGS. 25 and 27). In addition, it was found that the colonization of the three strains of *Lactobacillus* or the colonization of SFB had an extremely small influence on the number of Venus$^+$ and/or Foxp3$^+$ cells in the colon (refer to FIGS. 25 and 27). Moreover, the colonization of 16 strains of *Bacteroides* spp. also induced Venus$^+$ cells, but the influence of the colonization was specific to Venus$^+$ Foxp3$^-$ Tr1-like cells (refer to FIGS. 25 and 27). On the other hand, it was found that none of the bacterial species tested exerted any significant influence on the number of IL-10-producing cells in the small intestinal lamina propria (refer to FIG. 26).

Hence, it was shown that the genus *Clostridium* colonized in the colon or a physiologically active substance derived from the bacteria provided a signal for inducing the accumulation of IL-10$^+$ regulatory T cells in the colonic lamina propria or the expression of IL-10 in T cells. Meanwhile, it was shown that the number of Venus$^+$ cells in the small intestine was not significantly influenced by the situation where no commensal bacteria were present or commensal bacteria were decreased (refer to FIGS. 23 and 26 to 28), and that IL-10$^+$ regulatory cells (Tr1-like cells) accumulated in the small intestinal lamina propria independently of commensal bacteria.

Example 14

It was investigated whether or not Venus$^+$ cells induced by the genus *Clostridium* had an immunosuppressive function similar to that of Venus$^+$ cells in the colon of SPF mice. Specifically, CD4$^+$ CD25$^-$ cells (effector T cells, Teff cells) isolated from the spleen were seeded in a flat-bottomed 96-well plate at 2×10$^4$/well, and cultured for three days together with 2×10$^4$ splenic CD11c$^+$ cells (antigen-representing cells) subjected to 30 Gy radiation irradiation treatment, 0.5 μg/ml of an anti-CD3 antibody, and a lot of Treg cells. In addition, for the last six hours, the $CD4^+$ $CD25^-$ cells were cultured, with $[^3H]$-thymidine (1 μCi/well) was added thereto. Note that, Treg cells used in Example 14 were $CD4^+$ $GFP^+$ T cells isolated from the spleen of $Foxp3^{eGFP}$ reporter mice, or $CD4^+$ $Venus^+$ T cells in the colonic lamina propria of GF $Il10^{venus}$ mice in which *Clostridium* spp. were colonized or SPF $Il10^{venus}$ mice. Then, proliferation of the cells was determined based on the uptake amount of $[^3H]$-thymidine, and represented by a count per minute (cpm) value.

Figure 29:
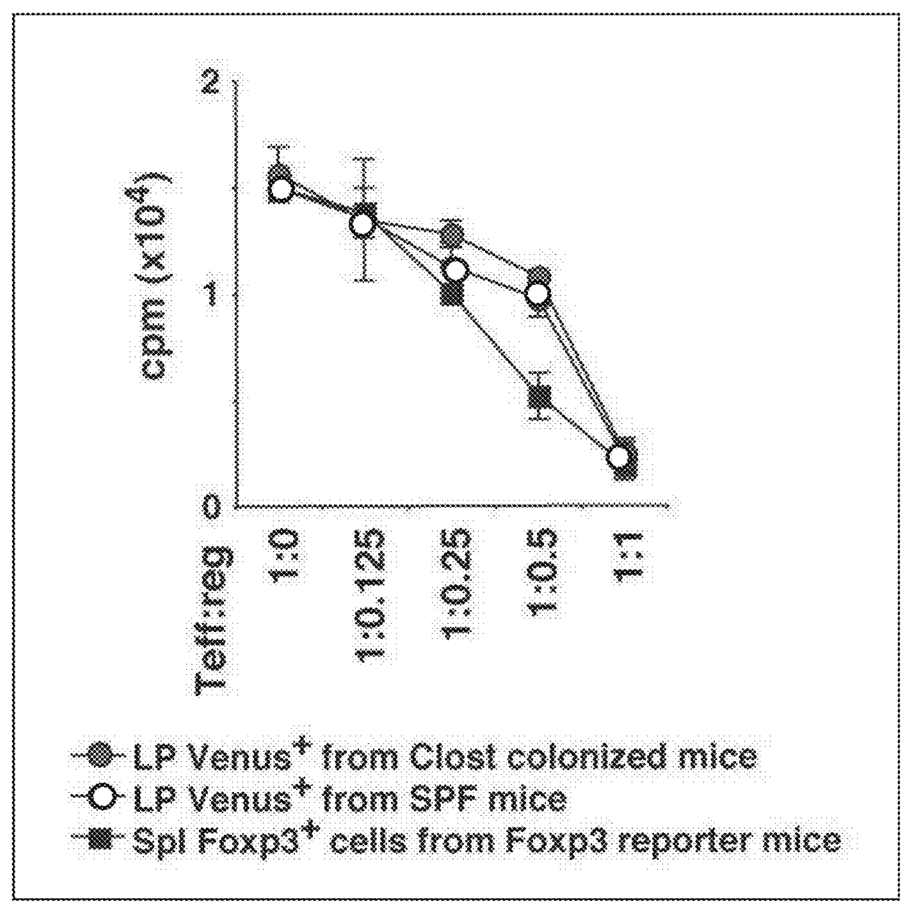
FIG. 29 is a graph showing analysis results of immunoregulatory functions of CD4$^{+}$ Venus$^{+}$ cells from the colonic lamina propria of GF Il10$^{venus}$ mice in which the genus *Clostridium* was colonized, CD4$^{+}$ Venus$^{+}$ cells from the colonic lamina propria of SPF Il10$^{venus}$ mice, and CD4+ GFP$^{+}$ cells from the spleen of Foxp3$^{eGFP}$ reporter mice.

As is apparent from the results shown in FIG. 29, $Venus^+$ $CD4^+$ cells of the mice in which the genus *Clostridium* was colonized suppressed in vitro proliferation of $CD25^-$ $CD4^+$ activated T cells. The suppression activity was slightly inferior to that of $GFP^+$ cells isolated from the $Foxp3^{eGFP}$ reporter mice, but equal to that of $Venus^+$ cells isolated from the SPF $Il10^{venus}$ mice. Accordingly, it has been shown that the genus *Clostridium* induces IL-10-expressing T cells having sufficient immunosuppressive activities, and thereby plays a critical role in maintaining immune homeostasis in the colon.

Example 15

Next, the influence, on the local immune response, of the colonization of a large number of *Clostridium* and the resultant proliferation of Treg cells was investigated.

<Dextran Sulfate Sodium (DSS)-Induced Colitis Model>

Figure 41:
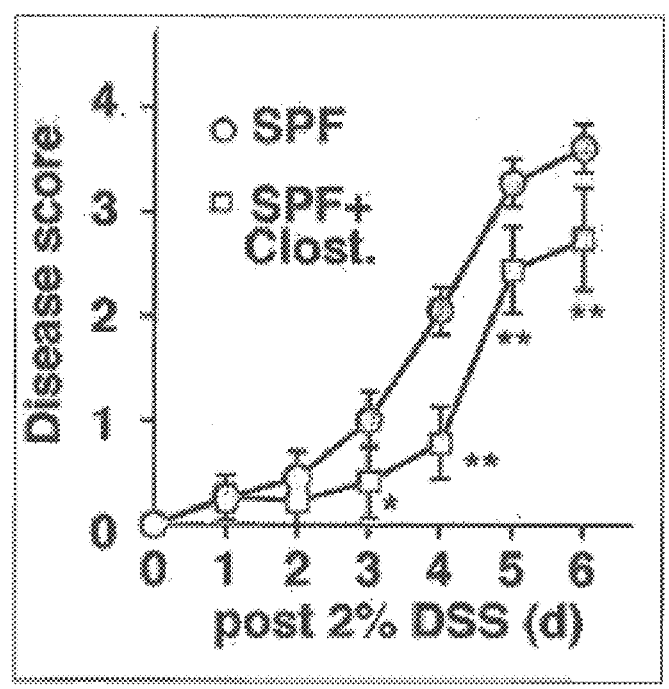
FIG. 41 is a graph showing the results obtained when control mice (SPF) and *Clostridium*-administered mice (SPF+Clost.) were treated with 2% DSS, observed and measured for the body weight loss, the hardness of stool, and bleeding for six days, and then evaluated numerically.
Figure 42:
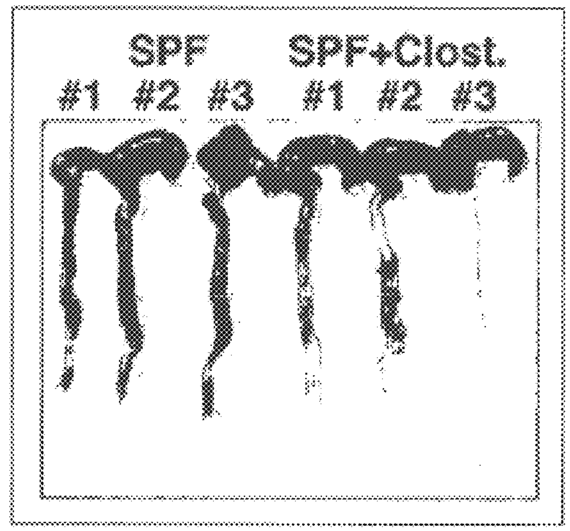
FIG. 42 is a photograph showing the state of the colons collected on day 6 after the control mice (SPF) and the *Clostridium*-administered mice (SPF+Clost.) were treated with 2% DSS.
Figure 43:
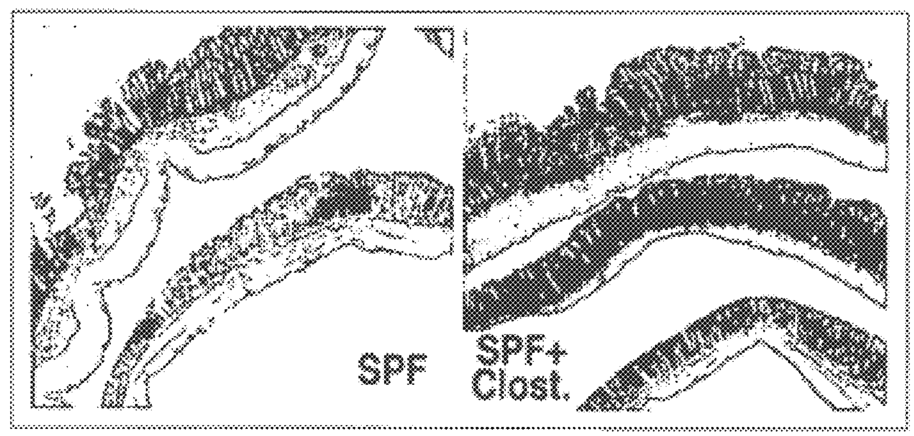
FIG. 43 shows photomicrographs showing the results obtained when the control mice (SPF) and the *Clostridium*-administered mice (SPF+Clost.) were treated with 2% DSS, and the colons thereof were collected on day 6 and analyzed histologically by HE staining.

First, the DSS-induced colitis model was prepared as described above, and the influence, on the model mice, of the inoculation of the *Clostridium* and the proliferation of Treg cells was investigated. Specifically, control mice and *Clostridium*-inoculated mice were treated with 2% DSS, then observed and measured for six days for the body weight loss, the hardness of stool, and bleeding, and then were evaluated numerically. In addition, on day 6, the colons were collected, dissected, and analyzed histologically by HE staining. FIGS. 41 to 43 show the obtained results. Note that, in FIGS. 41 to 43, "SPF+Clost." or "SPF+Clost.#1 to 3" indicate the results of C57BL/6 mice inoculated with a fecal suspension of *Clostridium*-colonized mice, and grown in a conventional environment for six weeks, and "SPF" or "SPF#1 to 3" indicate the results of C57BL/6 mice (control mice) grown in a conventional environment for six weeks without being inoculated with the fecal suspension. In addition, in FIG. 41, the vertical axis "Disease score" represents the disease activity index (DAI) described above, and the horizontal axis "post 2% DSS(d)" represents the days elapsed after the initial administration of 2% DSS to the mice. Moreover, in FIG. 41, * indicates that "P<0.02," and ** indicates that "P<0.001." Meanwhile, Treg cells induced by regulatory dendritic cells are known to play a preventive role in a DSS-induced colitis model (see S. Manicassamy et al., Science 329, 849 (Aug. 13, 2010)).

As is apparent from the results shown in FIGS. 41 to 43, the symptoms of the colitis such as body weight loss and rectal bleeding were significantly suppressed in the mice having a large number of *Clostridium* (hereinafter also referred to as "*Clostridium*-abundant mice") in comparison with the control mice (see FIG. 41). All the features typical for colonic inflammation, such as shortening of the colon, edema, and hemorrhage, were observed markedly in the control mice in comparison with the *Clostridium*-abundant mice (see FIG. 42). Moreover, histological features such as mucosal erosion, edema, cellular infiltration, and crypt loss were less severe in the DSS-treated *Clostridium*-abundant mice than in the control mice (see FIG. 43).

<Oxazolone-Induced Colitis Model>

Figure 44:
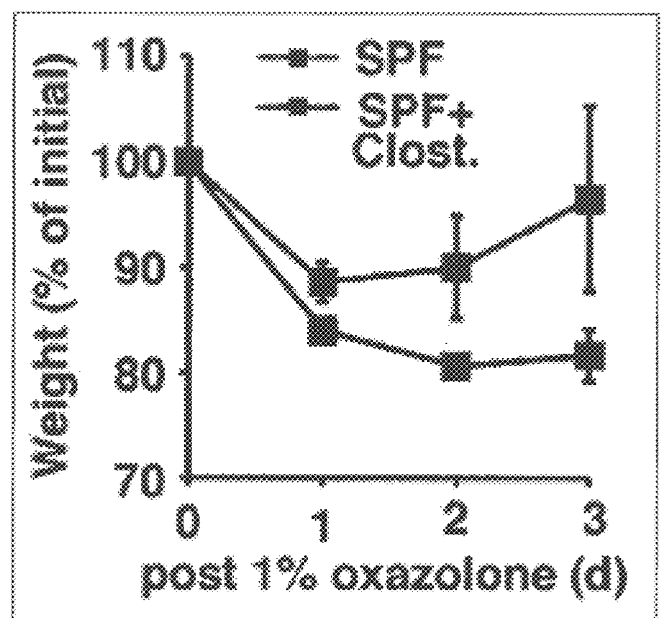
FIG. 44 is a graph showing the results obtained when control mice (SPF) and *Clostridium*-administered mice (SPF+Clost.) were sensitized with oxazolone, and subsequently the inside of each rectum was treated with a 1% oxazolone/50% ethanol solution, and the body weight loss was measured.
Figure 45:
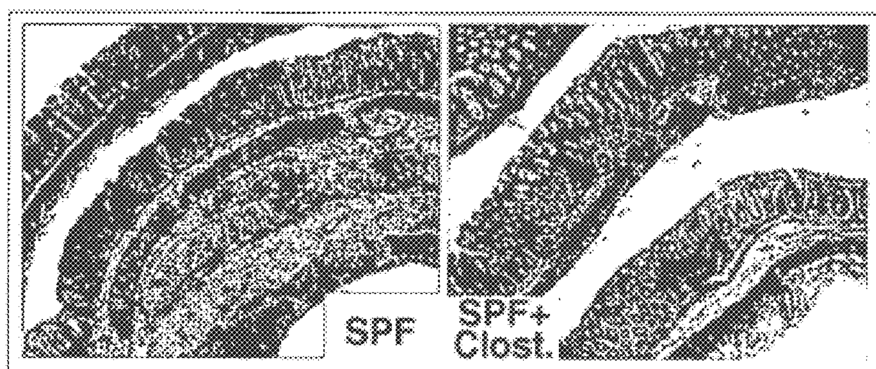
FIG. 45 shows photomicrographs showing the results obtained when the control mice (SPF) and the *Clostridium*-administered mice (SPF+Clost.) were sensitized with oxazolone, and subsequently the inside of each rectum was treated with a 1% oxazolone/50% ethanol solution, and the colons obtained by the treatment were analyzed histologically by HE staining.

Next, the oxazolone-induced colitis model was prepared as described above, and the influence, on the model mice, of the inoculation of *Clostridium* and the proliferation of Treg cells was investigated. Specifically, control mice and *Clostridium*-inoculated mice were sensitized with oxazolone, and subsequently the inside of the rectums thereof were treated with a 1% oxazolone/50% ethanol solution. Then, the body weight loss was observed and measured. In addition, the colons were dissected, and analyzed histologically by HE staining. FIGS. 44 and 45 show the obtained results. Note that, in FIGS. 44 and 45, "SPF+ Clost." indicates the results of C57BL/6 mice (*Clostridium*-abundant mice) inoculated with a fecal suspension of *Clostridium*-colonized mice, and grown in a conventional environment for six weeks, and "SPF" indicates the results of C57BL/6 mice (control mice) grown in a conventional environment for six weeks without being inoculated with the fecal suspension. In addition, in FIG. 44, the vertical axis "Weight (% of initial)" represents the body weight after the administration of 1% oxazolone where the body weight before the administration was taken as 100%, and the horizontal axis "post 1% oxazolone (d)" represents the days elapsed after the administration of 1% oxazolone to the mice. Meanwhile, it is known that Th2-type T cells are involved in colitis induced by oxazolone. (see M. Boirivant, I. J. Fuss, A. Chu, W. Strober, J Exp Med 188, 1929 (Nov. 16, 1998)).

As is apparent from the results shown in FIGS. 44 and 45, the colitis proceeded along with persistent body weight loss in the control mice. Meanwhile, the body weight loss of the *Clostridium*-abundant mice was reduced (see FIG. 44). In addition, it was also revealed that portions having histological diseases such as mucosal erosion, edema, cellular infiltration, and hemorrhage were reduced in the colon of the *Clostridium*-abundant mice (see FIG. 45).

Example 16

Figure 46:
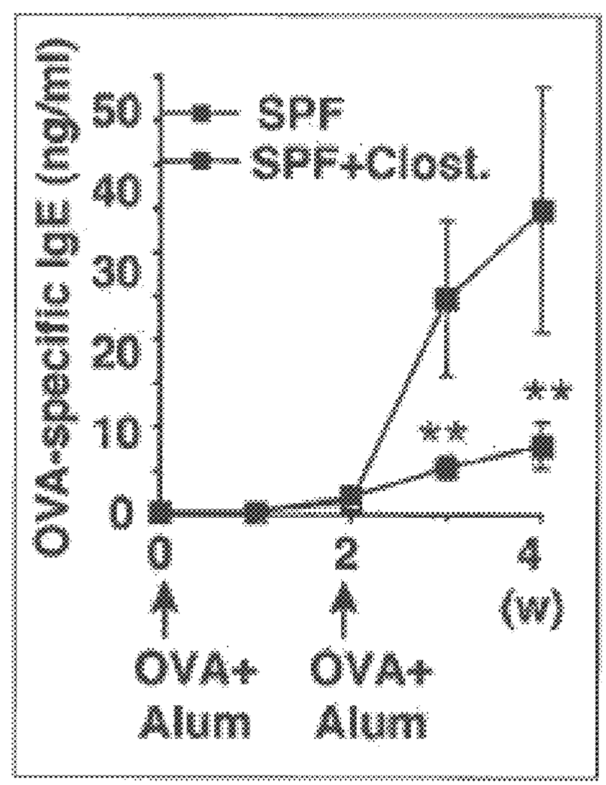
FIG. 46 is a graph showing the results obtained when control mice (SPF) and *Clostridium*-administered mice (SPF+Clost.) were immunized by administering alum-absorbed ovalbumin (OVA) twice at a 2-week interval, and the sera were collected therefrom and analyzed for the concentration of OVA-specific IgE in these sera by ELISA.
Figure 47:
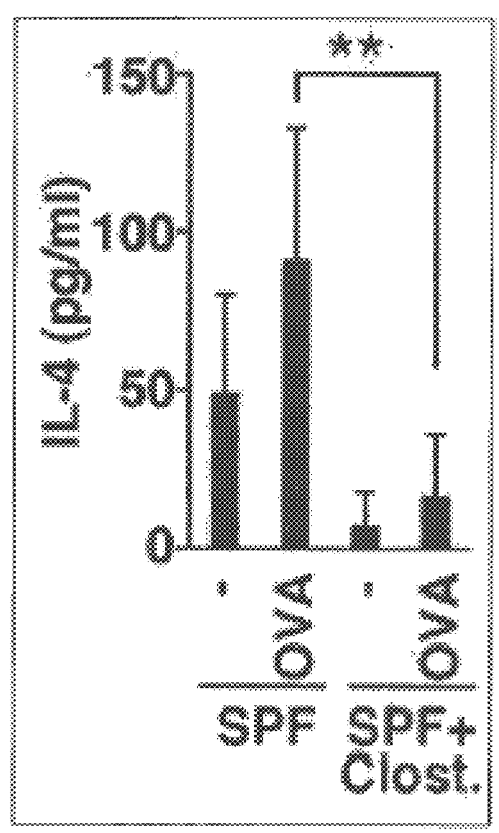
FIG. 47 is a graph showing the results obtained when the control mice (SPF) and the *Clostridium*-administered mice (SPF+Clost.) were immunized by administering the alum-absorbed OVA twice at a 2-week interval, and splenic cells were collected and analyzed for IL-4 production of these splenic cells by in-vitro OVA restimulation.
Figure 48:
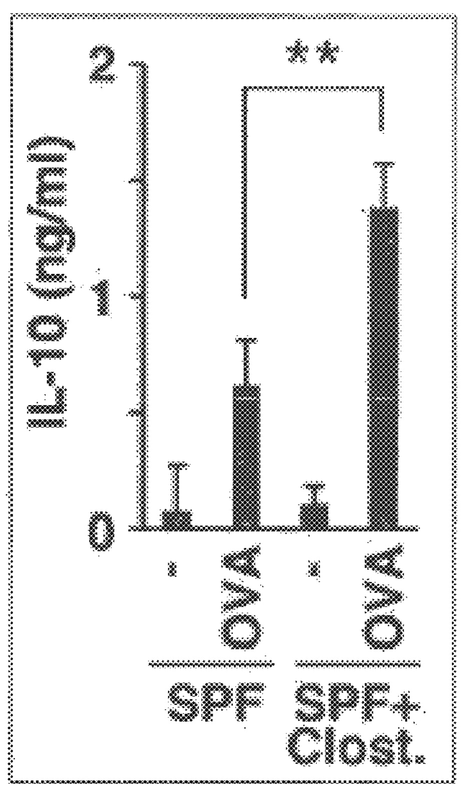
FIG. 48 is a graph showing the results obtained when the control mice (SPF) and the *Clostridium*-administered mice (SPF+Clost.) were immunized by administering the alum-absorbed OVA twice at a 2-week interval, and the splenic cells were collected and analyzed for IL-10 production of these splenic cells by the in-vitro OVA restimulation.

Next, the influence, on the systemic immune response (systemic IgE production), of the colonization of a large number of *Clostridium* and the resultant proliferation of Treg cells was investigated. Specifically, as described above, control mice and *Clostridium*-inoculated mice were immunized by administering alum-absorbed ovalbumin (OVA) twice at a 2-week interval. Then, sera were collected from these mice, and the OVA-specific IgE level thereof was investigated by ELISA. In addition, splenic cells were collected from the mice in each group, and IL-4 and IL-10 production by in-vitro OVA restimulation was investigated. FIGS. 46 to 48 show the obtained results. Note that, in FIGS. 46 to 48, "SPF+Clost." indicates the results of BALB/c SPF mice (*Clostridium*-abundant mice) inoculated with a fecal suspension of *Clostridium*-colonized mice, and grown in a conventional environment, "SPF" indicates the results of BALB/c SPF mice (control mice) grown in a conventional environment without being inoculated with the fecal suspension, and  indicates that "P<0.001." Meanwhile, in FIG. 46, the vertical axis "OVA-specific IgE (ng/ml)" represents the concentration of OVA-specific IgE in the sera. Moreover, in FIG. 46**, the horizontal axis represents the days elapsed after the initial administration of the alum-absorbed ovalbumin to the *Clostridium*-abundant mice or the control mice (4-week old), and "OVA+Alum" indicates the timing of the administration of the alum-absorbed ovalbumin. In addition, in FIGS. 47 and 48, "OVA" on the horizontal axis indicates the results in the case where the in-vitro OVA restimulation was performed, and "-" indicates the results in the case where no in-vitro OVA restimulation was performed. Moreover, in FIGS. 47 and 48, the vertical axes "IL-4 (pg/ml)" and "IL-10 (pg/ml)" show the IL-4 concentration and the IL-10 concentration in culture supernatants of splenic cells, respectively.

As is apparent from the results shown in FIGS. 46 to 48, the IgE level was significantly lower in the *Clostridium*-abundant mice than in the control mice (see FIG. 46). Moreover, the IL-4 production by the OVA restimulation was reduced (see FIG. 47) and the IL-10 production thereby was increased (see FIG. 48) in the splenic cells of the *Clostridium*-abundant mice sensitized with OVA and alum, in comparison with those of the control mice.

Accordingly, in consideration of the results shown in Example 15 in combination, it has been revealed that the induction of Treg cells by *Clostridium* in the colon plays an important role in local and systemic immune responses.

Example 17

Figure 49:
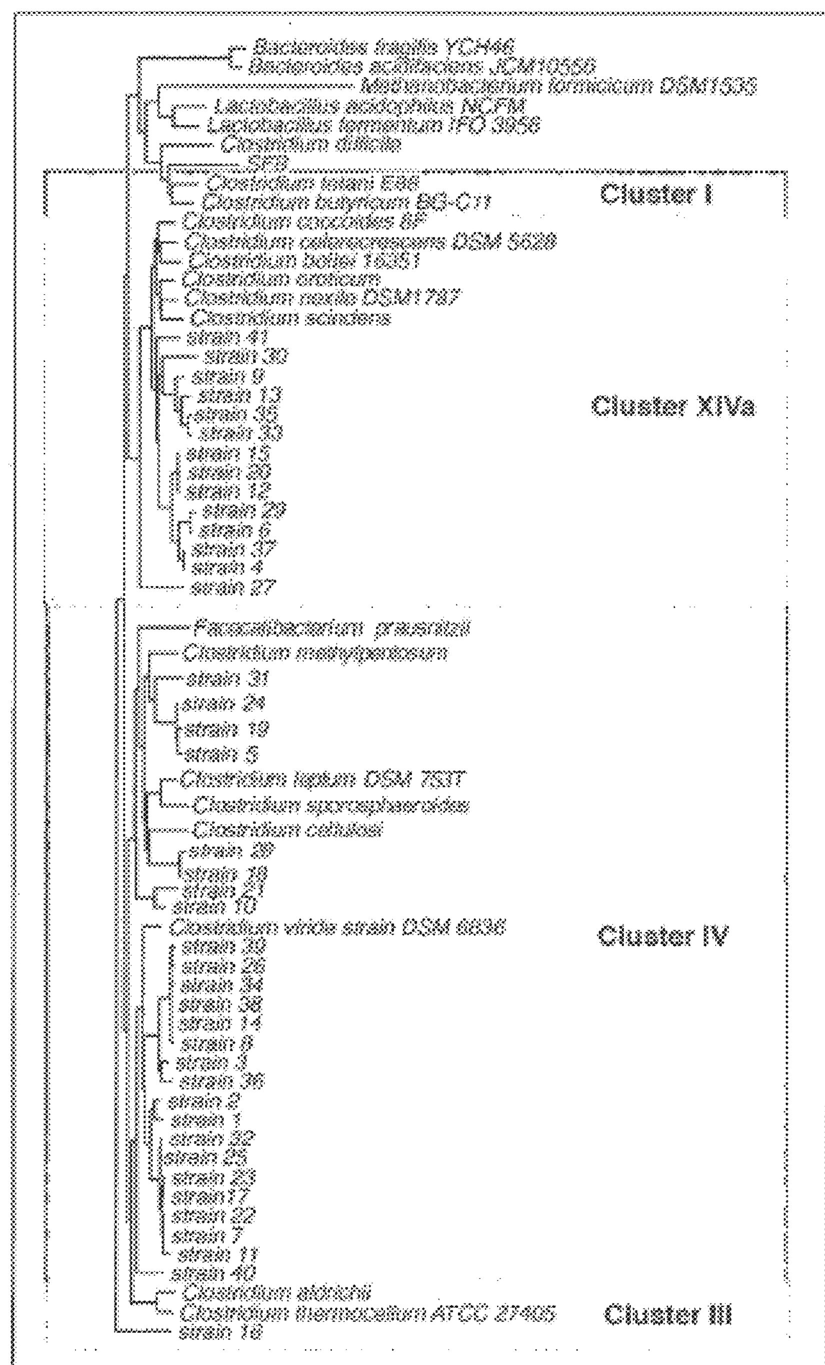
FIG. 49 is Phylogenetic tree constructed by the neighbor-joining method with the resulting sequences of the 41 strains of *Clostridium* and those of known bacteria obtained from Genbank database using Mega software.
Figure 50:
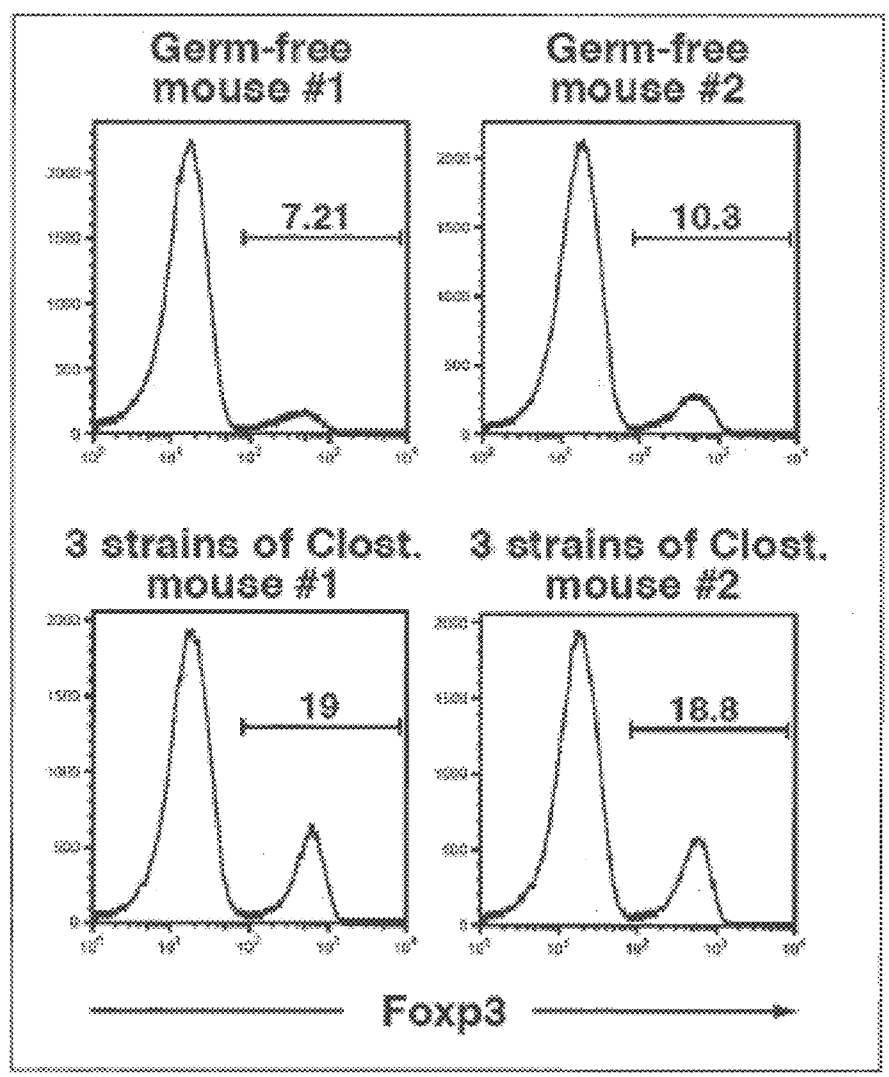
FIG. 50 is histograms showing Foxp3 expression gated CD4 cells from GF mice (Germ-free mouse #1 and #2) or GF mice colonized with three strains of *Clostridium* belonging to cluster IV (3 strains of Clost. mouse #1 and #2).

Next, GF Balb/c were colonized with three strains of *Clostridium* belonging to cluster IV (strains 22, 23 and 32 listed in FIG. 49). Three weeks later, colonic Foxp3$^+$ Treg cells were analyzed by FACS. FIG. 50 shows the obtained results. As is apparent from the results shown in FIG. 50, gnotobiotic mice colonized with three strains of *Clostridium* showed an intermediate pattern of Treg induction between GF mice and mice inoculated with all 46 strains.

Example 18

Next, it was investigated whether or not a spore-forming (for example, a chloroform resistant) fraction of a fecal sample obtained from humans had the effect of inducing proliferation or accumulation of regulatory T cells similar to the spore-forming fraction of the fecal sample obtained from mice.

Figure 51:
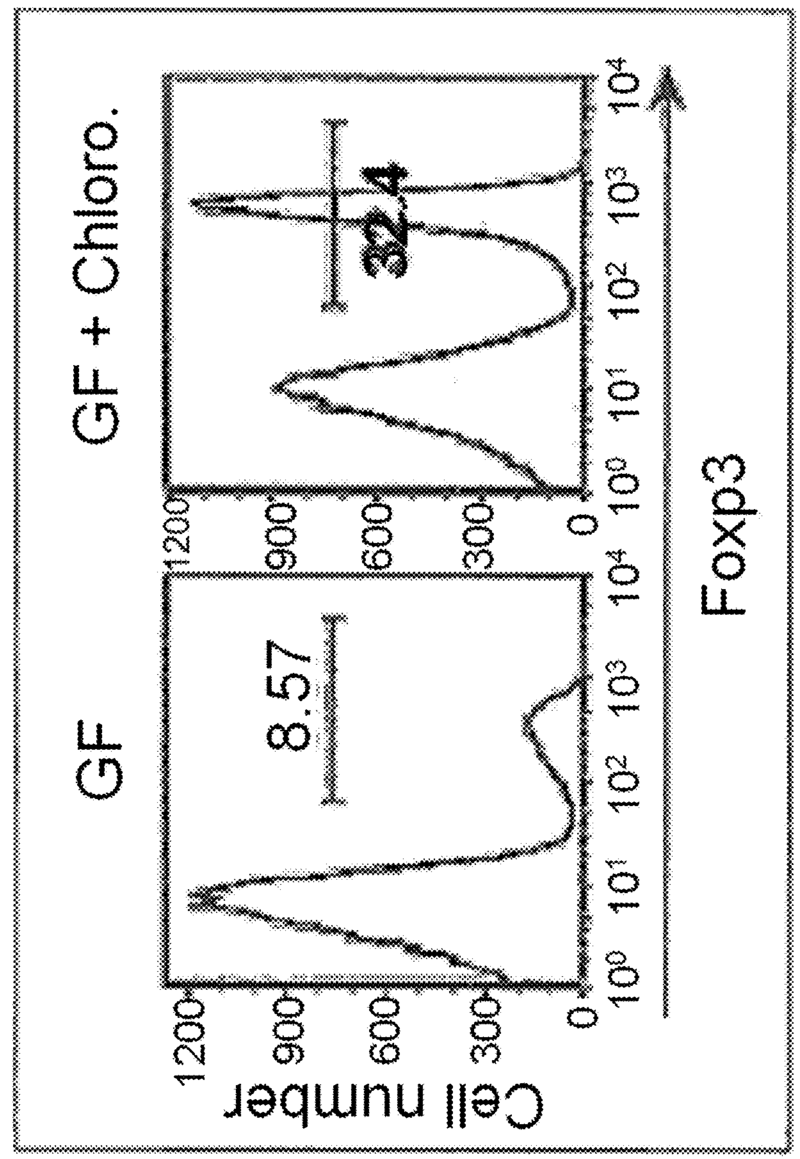
FIG. 51 is histograms showing Foxp3 expression by CD4 positive lymphocytes from GF mice (GF) or GF mice gavaged with chloroform-treated human stool (GF+Chloro.).
Figure 52:
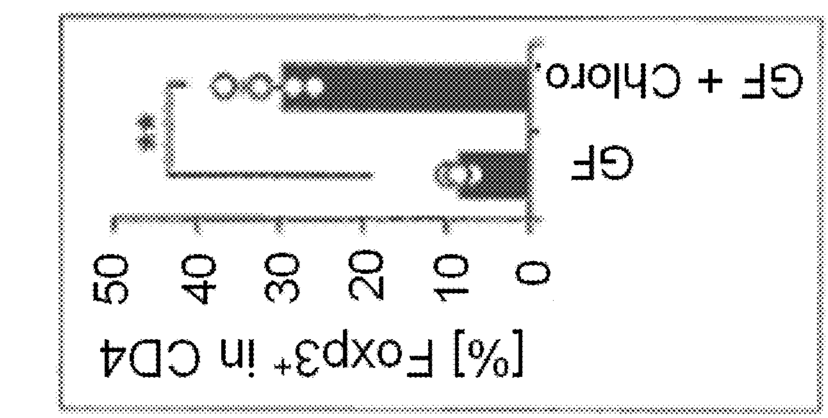
FIG. 52 is a graph showing Foxp3 expression by CD4 positive lymphocytes from GF mice (GF) or GF mice gavaged with chloroform-treated human stool (GF+Chloro.).

Specifically, human stool from a healthy volunteer (Japanese, male, 29 years old) was suspended with phosphate-buffered saline (PBS), mixed with chloroform (final concentration 3%), and then incubated in a shaking water bath for 60 min. After evaporation of chloroform by bubbling with $N_2$ gas, the aliquots containing chloroform-resistant (for example, spore-forming) fraction of human intestinal bacteria were orally inoculated into germ-free (GF) mice (IQI, 8 weeks old). The treated mice were kept in a vinyl isolator for 3 weeks. The colon was collected and opened longitudinally, washed to remove fecal content, and shaken in Hanks' balanced salt solution (HBSS) containing 5 mM EDTA for 20 min at 37° C. After removing epithelial cells and fat tissue, the colon was cut into small pieces and incubated with RPMI1640 containing 4% fetal bovine serum, 1 mg/ml collagenase D, 0.5 mg/ml dispase and 40 μg/ml DNase I (all manufactured by Roche Diagnostics) for 1 hour at 37° C. in a shaking water bath. The digested tissue was washed with HBSS containing mM EDTA, resuspended in 5 ml of 40% PERCOLL® (manufactured by GE Healthcare) and overlaid on 2.5 ml of 80% PERCOLL® in a 15-ml Falcon tube. PERCOLL® gradient separation was performed by centrifugation at 780 g for 20 min at 25° C. The interface cells were collected and suspended in staining buffer containing PBS, 2% FBS, 2 mM EDTA and 0.09% $NaN_3$ and stained for surface CD4 with Phycoerythrin-labeled anti-CD4 Ab (RM4-5, manufactured by BD Biosciences). Intracellular staining of Foxp3 was performed using the Alexa647-labeled anti-Foxp3 Ab (FJK-16s, manufactured by eBioscience) and Foxp3 Staining Buffer Set (manufactured by eBioscience). The percentage of Foxp3 positive cells within the CD4 positive lymphocyte population was analyzed by flow cytometry. FIGS. 51 and 52 show the obtained results.

In figures, representative histograms (FIG. 51) and combined data (FIG. 52) for Foxp3 expression by CD4 positive lymphocytes from GF mice (GF) or GF mice gavaged with chloroform-treated human stool (GF+Chloro.) are shown. In addition, numbers in FIG. 51 indicate the percentages of cells in the gate. Each circle in FIG. 52 represents a separate animal, error bars indicate the SD, and ** indicates that "P<0.001."

As is apparent from the results shown in FIGS. 51 and 52, it was found that also when the spore-forming (for example, the chloroform resistant) fraction of human intestinal bacteria was colonized in GF mice, the accumulation of Foxp3$^+$ regulatory (Treg) cells in the colonic lamina propria of the mice was induced.

Next, it was investigated what species of bacteria grew by gavaging with chloroform-treated human stool.

Specifically, using a QIAamp DNA Stool mini kit (manufactured by QIAGEN), bacterial genomic DNA was isolated from the human stool from a healthy volunteer as described above (human stool) or fecal pellets from GF mice gavaged with chloroform-treated human stool (GF+Chloro.). Quantitative PCR analysis was carried out using a LightCycler 480 (manufactured by Roche). Relative quantity was calculated by the ΔCt method and normalized to the amount of total bacteria, dilution, and weight of the sample. The following primer sets were used:

```
total bacteria
                                        (SEQ ID NO: 62)
5'-GGTGAATACGTTCCCGG-3'
and

                                        (SEQ ID NO: 63)
5'-TACGGCTACCTTGTTACGACTT-3'

Clostridium cluster XIVa (Clostridium coccoides
subgroup)
                                        (SEQ ID NO: 64)
5'-AAATGACGGTACCTGACTAA-3'
and

                                        (SEQ ID NO: 65)
5'-CTTTGAGTTTCATTCTTGCGAA-3'

Clostridium cluster IV (Clostridium leptum)
                                        (SEQ ID NO: 66)
5'-GCACAAGCAGTGGAGT-3'
and

                                        (SEQ ID NO: 24)
5'-CTTCCTCCGTTTTGTCAA-3'

Bacteroides
                                        (SEQ ID NO: 67)
5'-GAGAGGAAGGTCCCCCAC-3'
and

                                        (SEQ ID NO: 68)
5' -CGCTACTTGGCTGGTTCAG-3'.
```

Figure 53:
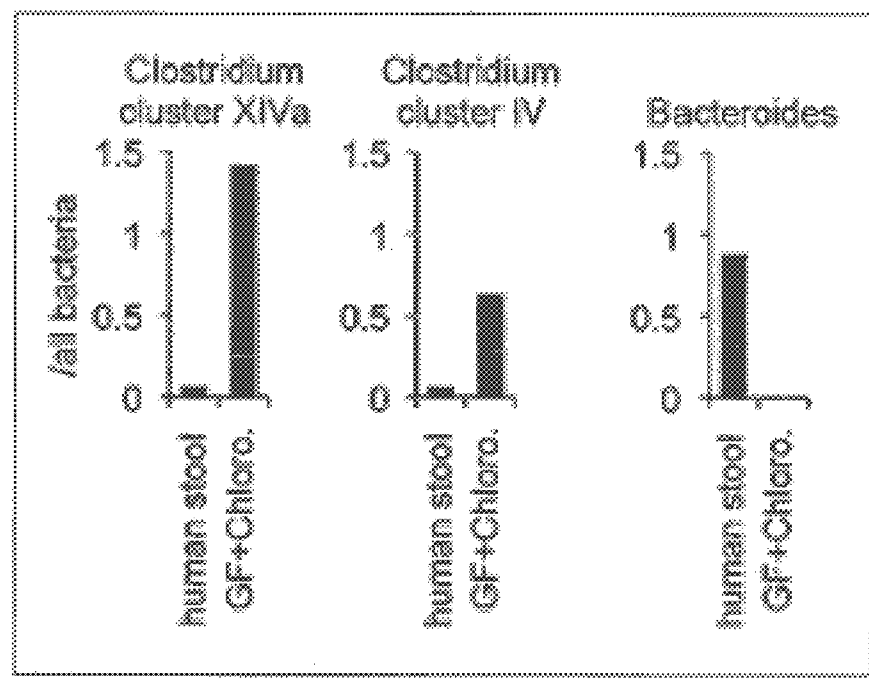
FIG. 53 is a graph showing amounts of *Clostridium* and *Bacteroides* in feces of mice gavaged with chloroform-treated human stool

FIG. 53 shows the obtained results.

As is apparent from the results shown in FIG. 53, mice gavaged with chloroform-treated human stool exhibited high amounts of spore-forming bacteria, such as *Clostridium* clusters XIVa and IV, and a severe decrease of non-sporeforming bacteria, such as *Bacteroides*, compared with the human stool before chloroform treatment.

INDUSTRIAL APPLICABILITY

As has been described above, the present invention makes it possible to provide an excellent composition for inducing proliferation or accumulation of regulatory T cells (Treg cells) by utilizing bacteria belonging to the genus *Clostridium* or a physiologically active substance or the like derived from the bacteria. Since the composition of the present invention has immunosuppressive effects, the composition can be used, for example, to prevent or treat autoimmune diseases or allergic diseases, as well as to suppress immunological rejection in organ transplantation or the like. In addition, healthy individuals can easily and routinely ingest the composition as a food or beverage, such as a health food, to improve their immune functions.

SEQUENCE LISTING

SEQ ID NO:1 to 20, 62 to 69
<223> Artificially synthesized primer sequence
SEQ ID NO:21 to 61
<223> 16S rRNA coding gene sequence of each *Clostridium* strain

The invention claimed is:

1. A pharmaceutical composition, comprising a purified bacterial mixture of at least two live bacterial strains belonging to *Clostridium* clusters IV and/or XIVa, wherein the bacterial mixture induces proliferation and/or accumulation of regulatory T cells, wherein the bacterial strains are spore forming bacteria and are human commensal bacteria, and wherein the pharmaceutical composition is formulated for delivery to the intestine.

2. The pharmaceutical composition of claim 1, wherein the at least two live bacterial strains belonging to *Clostridium* clusters IV and/or XIVa comprise two or more strains belonging to *Clostridium* cluster IV.

3. The pharmaceutical composition of claim 1, wherein the at least two live bacterial strains belonging to *Clostridium* clusters IV and/or XIVa comprise two or more strains belonging to *Clostridium* cluster XIVa.

4. The pharmaceutical composition of claim 1, wherein the at least two live bacterial strains belonging to *Clostridium* clusters IV and/or XIVa comprise one or more strains belonging to *Clostridium* cluster IV and one or more strains belonging to *Clostridium* cluster XIVa.

5. The pharmaceutical composition of claim 1, wherein the pharmaceutical composition further comprises one or more bacterial strains belonging to a *Clostridium* cluster other than *Clostridium* cluster IV or *Clostridium* cluster XIVa.

6. The pharmaceutical composition of claim 1, wherein the pharmaceutical composition further comprises a pharmacologically acceptable excipient.

7. The pharmaceutical composition of claim 1, wherein the pharmaceutical composition is formulated for oral administration.

8. The pharmaceutical composition of claim 1, wherein the pharmaceutical composition further comprises a pH sensitive composition comprising one or more enteric polymers.

9. The pharmaceutical composition of claim 1, wherein the pharmaceutical composition is in the form of a capsule.

10. The pharmaceutical composition of claim 1, wherein the bacteria are in the form of spores.

11. A method of treating a human subject having an autoimmune disease, the method comprising administering the composition of claim 1.

12. The method of claim 11, wherein the autoimmune disease is organ transplant rejection, inflammatory bowel disease (IBD), ulcerative colitis, Crohn's disease, sprue, rheumatoid arthritis, Type 1 diabetes, graft versus host disease, or multiple sclerosis.

13. A method of treating a human subject having an allergic disease, the method comprising administering the composition of claim 1.

14. A method of treating a human subject having an infectious disease, the method comprising administering the composition of claim 1.

15. The method of claim 14, wherein the infectious disease is *Clostridium difficile* infection.

16. A pharmaceutical composition, comprising a purified bacterial mixture of at least two live bacterial strains belonging to *Clostridium* clusters IV and/or XIVa, wherein the bacterial mixture induces proliferation and/or accumulation of regulatory T cells, wherein the bacterial strains are spore forming bacteria and are isolated from a human, and wherein the pharmaceutical composition further comprises a pH sensitive composition comprising one or more enteric polymers.

17. The pharmaceutical composition of claim 16, wherein the at least two live bacterial strains belonging to *Clostridium* clusters IV and/or XIVa comprise two or more strains belonging to *Clostridium* cluster IV.

18. The pharmaceutical composition of claim 16, wherein the at least two live bacterial strains belonging to *Clostridium* clusters IV and/or XIVa comprise two or more strains belonging to *Clostridium* cluster XIVa.

19. The pharmaceutical composition of claim 16, wherein the at least two live bacterial strains belonging to *Clostridium* clusters IV and/or XIVa comprise one or more strains belonging to *Clostridium* cluster IV and one or more strains belonging to *Clostridium* cluster XIVa.

20. The pharmaceutical composition of claim 16, wherein the pharmaceutical composition further comprises one or more bacterial strains belonging to a *Clostridium* cluster other than *Clostridium* cluster IV or *Clostridium* cluster XIVa.

21. The pharmaceutical composition of claim 16, wherein the pharmaceutical composition further comprises a pharmacologically acceptable excipient.

22. The pharmaceutical composition of claim 16, wherein the pharmaceutical composition is formulated for oral administration.

23. The pharmaceutical composition of claim 16, wherein the pharmaceutical composition is in the form of a capsule.

24. The pharmaceutical composition of claim 16, wherein the bacteria are in the form of spores.

25. A method of treating a human subject having an autoimmune disease, the method comprising administering the composition of claim 16.

26. The method of claim 25, wherein the autoimmune disease is organ transplant rejection, inflammatory bowel disease (IBD), ulcerative colitis, Crohn's disease, sprue, rheumatoid arthritis, Type 1 diabetes, graft versus host disease, or multiple sclerosis.

27. A method of treating a human subject having an allergic disease, the method comprising administering the composition of claim 16.

28. A method of treating a human subject having an infectious disease, the method comprising administering the composition of claim 16.

29. The method of claim 28, wherein the infectious disease is *Clostridium difficile* infection.

* * * * *